US012662517B2

(12) United States Patent
Wang et al.

(10) Patent No.: US 12,662,517 B2
(45) Date of Patent: Jun. 23, 2026

(54) METHODS AND COMPOSITIONS TO SPREAD PROTEIN CARGOES ACROSS MULTI-NUCLEATED CELLS

(71) Applicants: University of Florida Research Foundation, Incorporated, Gainesville, FL (US); University of Miami, Miami, FL (US)

(72) Inventors: Eric Tzy-shi Wang, Gainesville, FL (US); Keril K. Poukalov, Gainesville, FL (US); Zane Zeier, Miami, FL (US)

(73) Assignees: University of Florida Research Foundation, Incorporated, Gainesville, FL (US); University of Miami, Miami, FL (US)

( * ) Notice: Subject to any disclaimer, the term of this patent is extended or adjusted under 35 U.S.C. 154(b) by 725 days.

(21) Appl. No.: 17/927,337

(22) PCT Filed: May 21, 2021

(86) PCT No.: PCT/US2021/033680
§ 371 (c)(1),
(2) Date: Nov. 22, 2022

(87) PCT Pub. No.: WO2021/237104
PCT Pub. Date: Nov. 25, 2021

(65) Prior Publication Data
US 2024/0391969 A1 Nov. 28, 2024

Related U.S. Application Data

(60) Provisional application No. 63/029,303, filed on May 22, 2020.

(51) Int. Cl.
| | |
|---|---|
| *C07K 14/47* | (2006.01) |
| *A61K 48/00* | (2006.01) |
| *C07K 14/00* | (2006.01) |
| *C12N 15/62* | (2006.01) |
| *C12N 15/86* | (2006.01) |

(52) U.S. Cl.
CPC ...... *C07K 14/4707* (2013.01); *A61K 48/0058* (2013.01); *C12N 15/86* (2013.01); *C07K 2319/09* (2013.01); *C07K 2319/095* (2013.01); *C12N 2750/14122* (2013.01); *C12N 2750/14143* (2013.01)

(58) Field of Classification Search
None
See application file for complete search history.

(56) References Cited

U.S. PATENT DOCUMENTS

| | | |
|---|---|---|
| 2003/0049712 A1 | 3/2003 | Haugwitz |
| 2013/0288976 A1 | 10/2013 | Van Der Maarel et al. |
| 2014/0322169 A1 | 10/2014 | Harper et al. |
| 2020/0017842 A1 | 1/2020 | Jones et al. |

FOREIGN PATENT DOCUMENTS

| | | | | |
|---|---|---|---|---|
| EP | 2426203 B1 * | 7/2016 | .......... | C12N 15/111 |
| WO | WO 2020/232271 A1 | 11/2020 | | |

OTHER PUBLICATIONS

Extended European Search Report mailed May 14, 2024 for Application No. EP21809074.4.

International Search Report and Written Opinion mailed Oct. 19, 2021 in connection with Application No. PCT/US2021/033680.

International Preliminary Report on Patentability mailed Dec. 1, 2022 in connection with Application No. PCT/US2021/033680.

[No Author Listed] Database USPTO Proteins [Online], "Sequence 65 from U.S. Pat. No. 10,865,445.", retrieved from EBI accession No. USPOP:QRK99900, Database accession No. QRK99900, Feb. 10, 2021, 1 page.

Bernhofer et al., NLSdb-major update for database of nuclear localization signals and nuclear export signals. Nucleic Acids Res. Jan. 4, 2018;46(D1):D503-D508. doi: 10.1093/nar/gkx1021.

Carter, The growth cycle of adeno-associated virus. In: Handbook of parvoviruses. vol. I, P. Tijsser, ed. (CRC Press,. Boca Raton), 1990:155-68.

Choi et al., Effects of adeno-associated virus DNA hairpin structure on recombination. J Virol. Jun. 2005;79(11):6801-7. doi: 10.1128/JVI.79.11.6801-6807.2005.

Cutler et al., Non-equivalence of nuclear import among nuclei in multinucleated skeletal muscle cells. J Cell Sci. Feb. 5, 2018;131(3):jcs207670. doi: 10.1242/jcs.207670.

Fisher et al., Transduction with recombinant adeno-associated virus for gene therapy is limited by leading-strand synthesis. J Virol. Jan. 1996;70(1):520-32. doi: 10.1128/JVI.70.1.520-532.1996.

Flach et al., A yeast RNA-binding protein shuttles between the nucleus and the cytoplasm. Mol Cell Biol. Dec. 1994;14(12):8399-407. doi: 10.1128/mcb.14.12.8399-8407.1994.

(Continued)

*Primary Examiner* — Manjunath N Rao
*Assistant Examiner* — Jae W Lee
(74) *Attorney, Agent, or Firm* — Wolf, Greenfield & Sacks, P.C.

(57) ABSTRACT

Methods and compositions useful for delivering a protein to a plurality of nuclei in a cell. Fusion proteins comprising one or more signals useful for promoting delivery of the proteins to a plurality of nuclei in a multinucleate cell. Methods comprising administering isolated nucleic acids to a multinucleate cell, wherein the isolated nucleic acid comprises a sequence encoding a fusion protein, the fusion protein comprising, a protein of interest fused to at least the following migration signals: (a) at least one nuclear export signal (NFS); and (b) at least one nuclear localization signal (NLS) and/or at least one nucleolar localization signal (NoLS). Fusion proteins comprising: (a) a protein of interest; and (b) at least the following migration signals: (i) a nuclear export signal (NFS); (ii) a nuclear localization signal (NLS); and (iii) a nucleolar localization signal (NoLS). Methods of making and using the same. Methods of delivering recombinant genes and/or fusion proteins to multinucleate cells.

15 Claims, 22 Drawing Sheets

Specification includes a Sequence Listing.

(56)                    References Cited

OTHER PUBLICATIONS

Lischka et al., A novel transferable nuclear export signal mediates CRM1-independent nucleocytoplasmic shuttling of the human cytomegalovirus transactivator protein pUL69. EMBO J. Dec. 17, 2001;20(24):7271-83. doi: 10.1093/emboj/20.24.7271.

Marchand et al., The Jembrana disease virus Rev protein: Identification of nuclear and novel lentiviral nucleolar localization and nuclear export signals. PLoS One. Aug. 22, 2019;14(8):e0221505. doi: 10.1371/journal.pone.0221505.

Martin et al., Principles of protein targeting to the nucleolus. Nucleus. 2015;6(4):314-25. doi: 10.1080/19491034.2015.1079680.

Mccarty et al., Integration of adeno-associated virus (AAV) and recombinant AAV vectors. Annu Rev Genet. 2004;38:819-45. doi: 10.1146/annurev.genet.37.110801.143717.

Mccarty et al., Self-complementary recombinant adeno-associated virus (scAAV) vectors promote efficient transduction independently of DNA synthesis. Gene Ther. Aug. 2001;8(16):1248-54. doi: 10.1038/sj.gt.3301514.

Mccarty, Self-complementary AAV vectors; advances and applications. Mol Ther. Oct. 2008;16(10):1648-56. doi: 10.1038/mt.2008.171. Epub Aug. 5, 2008.

Mcnicoll et al., Quantitative Heterokaryon Assay to Measure the Nucleocytoplasmic Shuttling of Proteins. Bio Protoc. Sep. 5, 2018;8(17):e2472. doi: 10.21769/BioProtoc.2472.

Mitsuhashi et al., Functional domains of the FSHD-associated DUX4 protein. Biol Open. Apr. 26, 2018;7(4):bio033977. doi: 10.1242/bio.033977.

* cited by examiner

NCT_GFP_017
GFP Signal                    Brightfield Image
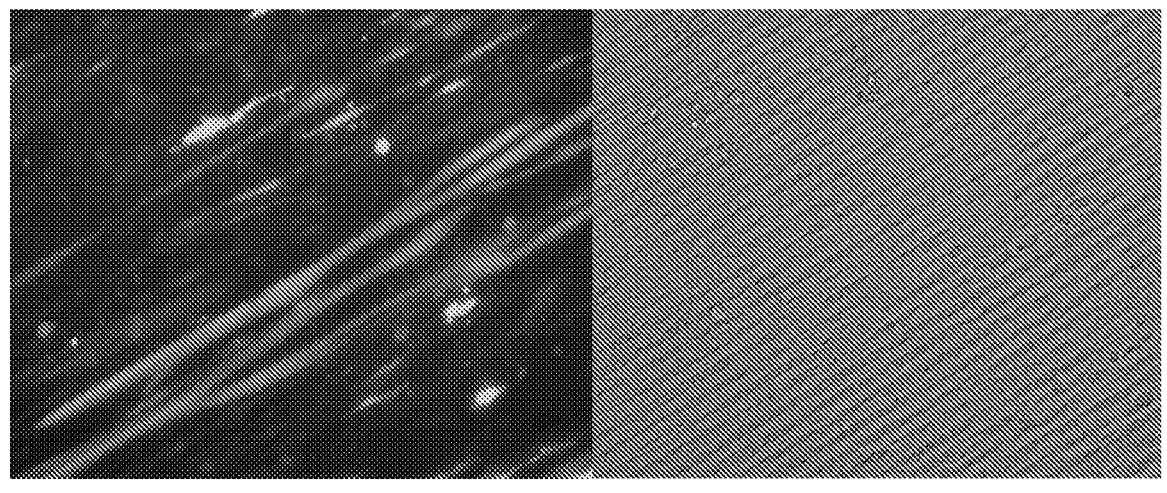
FIG. 1A                        FIG. 1B
NCT_GFP_017
GFP Signal                    Brightfield Image
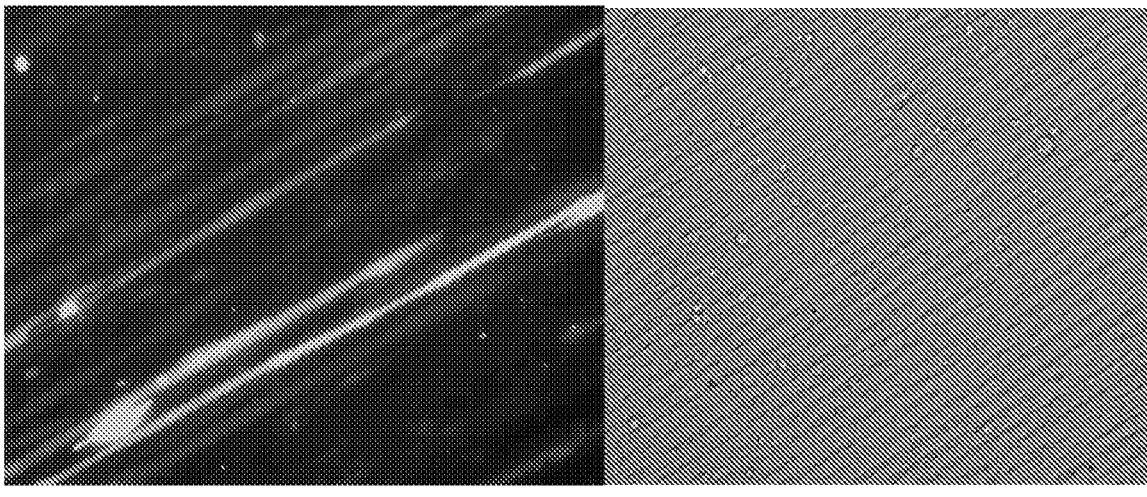
FIG. 1C                        FIG. 1D NCT_GFP_017
GFP Signal                        Brightfield Image
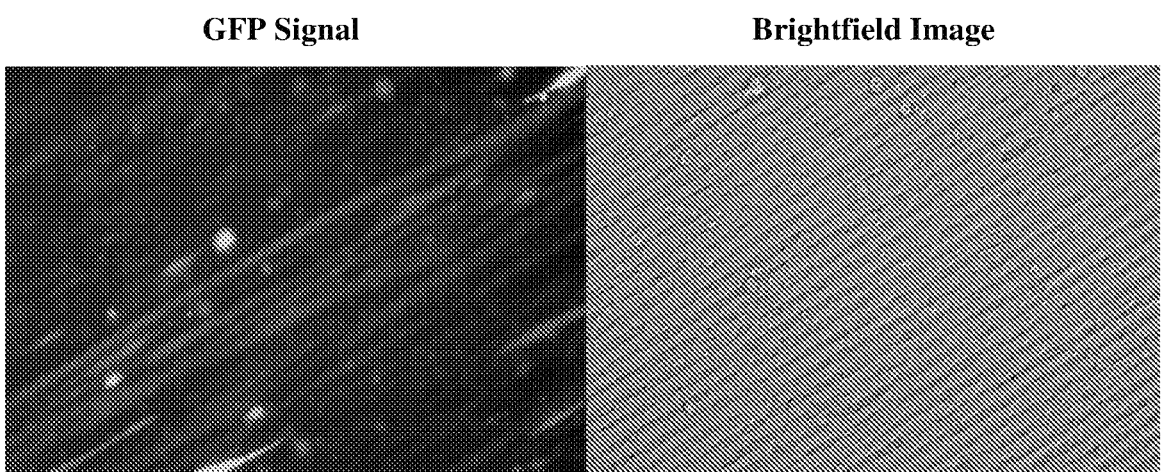
FIG. 1E                        FIG. 1F
NCT_GFP_018
GFP Signal                        Brightfield Image
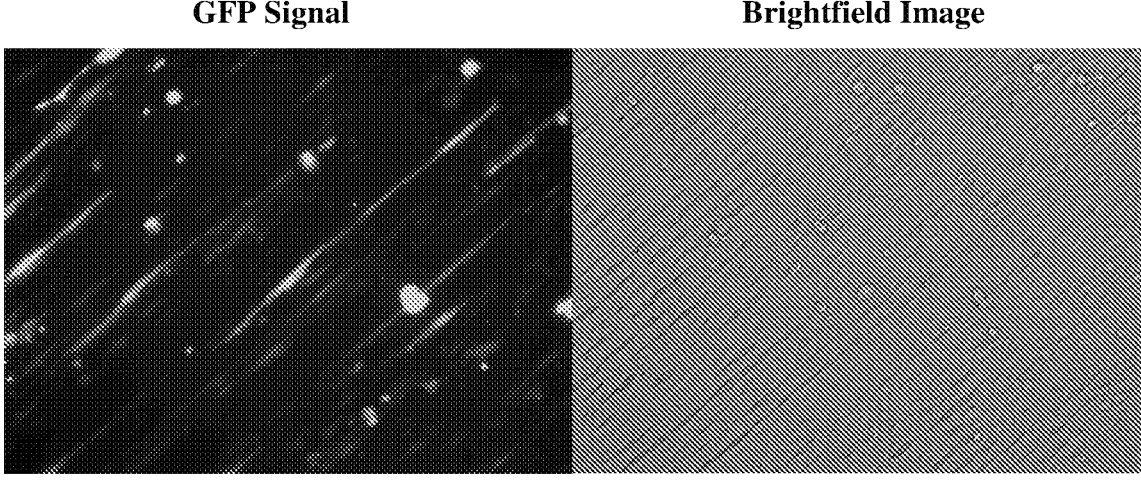
FIG. 2A                        FIG. 2B

NCT_GFP_018

GFP Signal　　　　　　　　　　　Brightfield Image

NCT_GFP_021

GFP Signal　　　　　　　　　　　Brightfield Image

NCT_GFP_021
GFP Signal                          Brightfield Image
FIG. 3C                              FIG. 3D
NCT_GFP_021
GFP Signal                          Brightfield Image
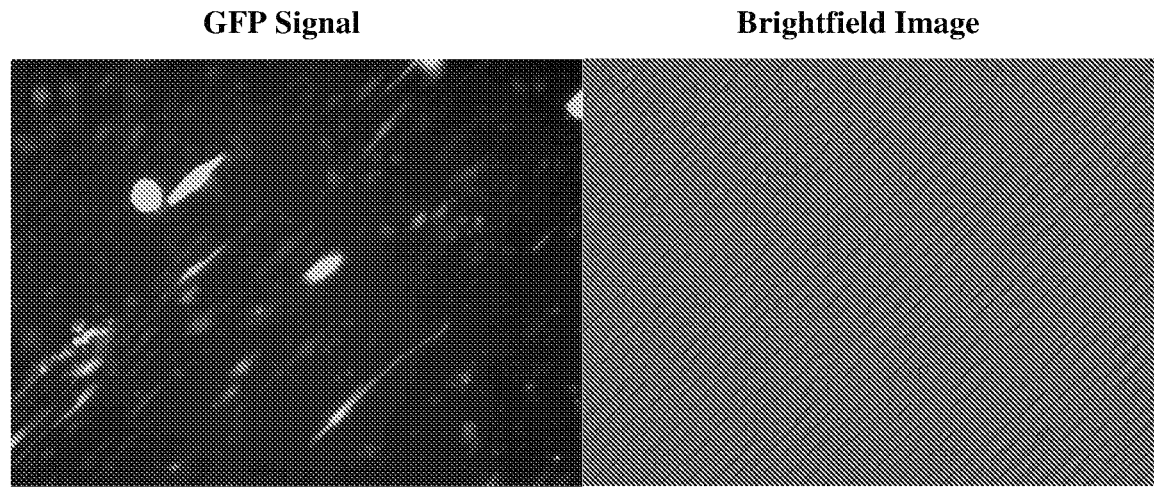
FIG. 3E                              FIG. 3F

NCT_GFP_020

GFP Signal           Brightfield Image

NCT_GFP_020

GFP Signal           Brightfield Image

NCT_GFP_020
GFP Signal                          Brightfield Image
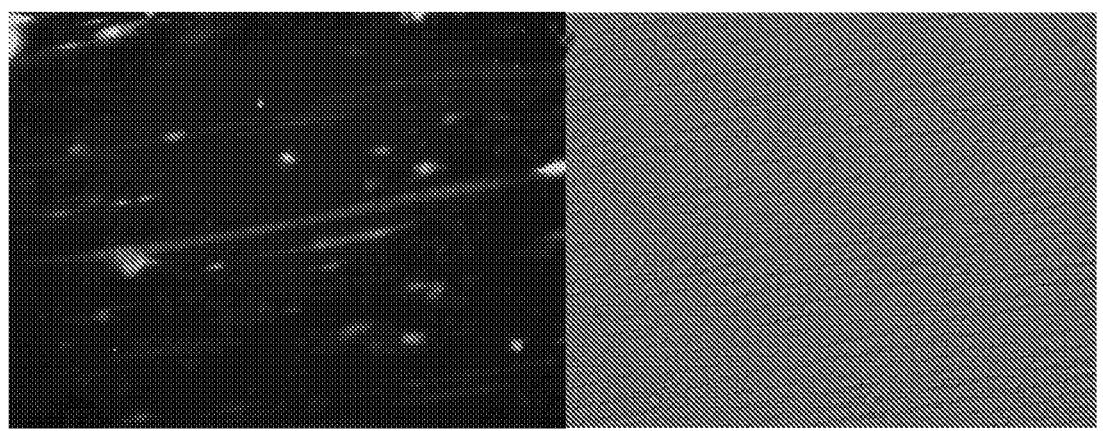
FIG. 4E                              FIG. 4F
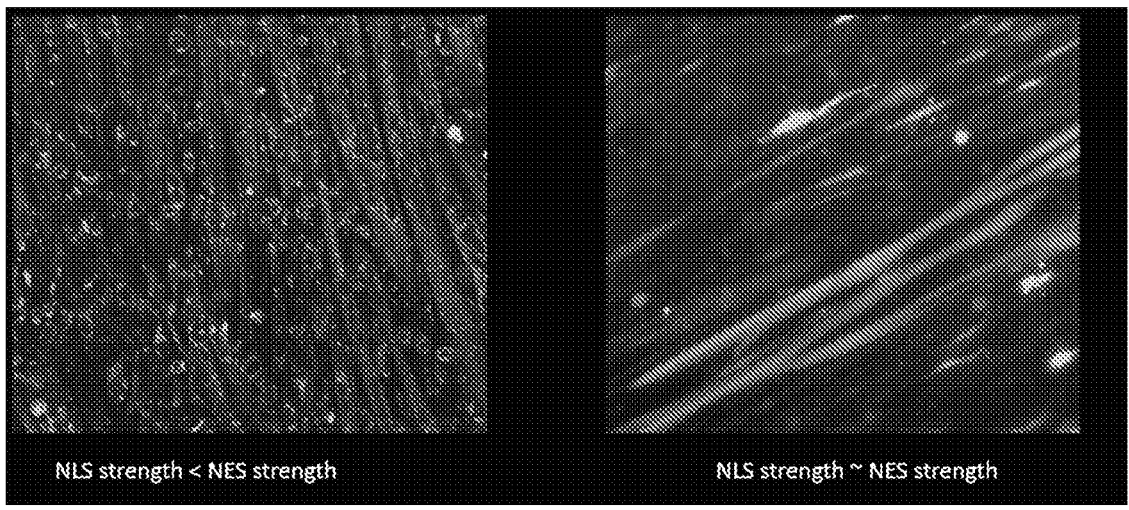
FIG. 5A                              FIG. 5B

FIG. 7H
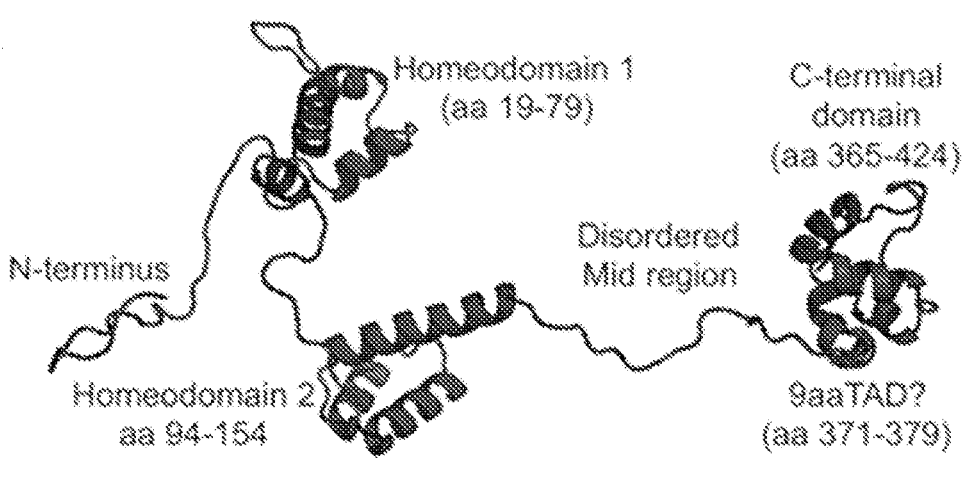
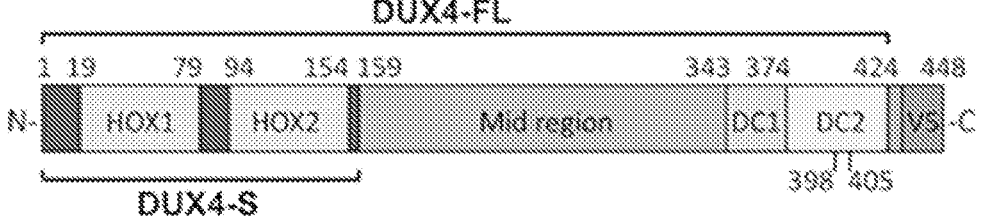
FIG. 8A

METHODS AND COMPOSITIONS TO SPREAD PROTEIN CARGOES ACROSS MULTI-NUCLEATED CELLS

CROSS-REFERENCE TO RELATED APPLICATIONS

This application is a national stage filing under 35 U.S.C. 371 of International Patent Application Serial No. PCT/US2021/033680, filed May 21, 2021, which claims the benefit under 35 U.S.C. § 119(e) of the filing date of U.S. Patent Application Ser. No. 63/029,303, filed May 22, 2020, the contents of which are hereby incorporated herein in its entirety by reference.

STATEMENT REGARDING FEDERALLY SPONSORED RESEARCH OR DEVELOPMENT

This invention was made with government support under Grant No(s) OD017865, R01 AG058636 and NS102829, awarded by the National Institutes of Health. The government has certain rights in the invention.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Aug. 13, 2023, is named U119670081US01-SUBSEQ-PRW and is 190, 610 bytes in size.

BACKGROUND OF THE INVENTION

Gene therapy has become an intense focus of research over the past decade. The focus of gene therapies has been to effect a change in an organism such that the organism itself produces a beneficial product, refrains from making a deleterious product, or a combination thereof. However, for such therapies to be successful, they should target the appropriate cellular machinery, including targeting relevant nucleic acids, and accomplish such targeting with a great enough efficiency to effectuate the change without causing toxicity or producing deleterious off-target effects. Various techniques have been employed to achieve this targeting of cellular reprogramming, with mixed results. Examples of some techniques are the inclusion of nuclear localization signals (NLS) and nuclear export signals (NES). However, while these signals may facilitate nuclear entry, they can inhibit and/or prevent the effective and efficient spread of such gene therapies across multiple nuclei, which is problematic, for example, in multinucleate cells. New directions and therapies that could improve understanding and treating of multinucleate cells are desperately needed.

SUMMARY OF THE INVENTION

In some aspects, the disclosure relates to methods and compositions for delivering recombinant genes and/or fusion proteins to multinucleate cells. In some embodiments, the method comprises administering an isolated nucleic acid to a multinucleate cell, wherein the isolated nucleic acid comprises a sequence encoding a fusion protein, the fusion protein comprising, a protein of interest fused to at least the following migration signals: (a) at least one nuclear export signal (NES); and (b) at least one nuclear localization signal (NLS) and/or at least one nucleolar localization signal (NoLS). In some embodiments, an isolated nucleic acid encodes an amino acid sequence comprising a sequence with at least 70% identity to SEQ ID NO: 13.

In some embodiments, fusion protein further comprises at least one additional migration signal, wherein the additional migration signal may be identical or distinct from the existing migration signals of the fusion protein. In some embodiments, the fusion protein further comprises at least two additional migration signals, wherein the additional migration signals may be identical or distinct from the existing migration of the fusion protein.

In some embodiments, the isolated nucleic acid encodes a fusion protein wherein at least one of the migration signals is positioned at the C-terminus of the protein of interest. In some embodiments, the isolated nucleic acid encodes a fusion protein wherein at least one of the migration signals is positioned at the N-terminus of the protein of interest. In some embodiments, a fusion protein comprises a sequence with at least 70% identity to SEQ ID NO: 13. In some embodiments, a fusion protein comprises a migration signal comprising a sequence with at least 70% identity to a sequence of any one of SEQ ID NO: 14-570. In some embodiments, a fusion protein comprises a migration signal comprising a sequence of any one of SEQ ID NO: 14-570.

In some embodiments, the protein of interest is a therapeutic protein. In some embodiments, the protein of interest is a nuclear protein. In some embodiments, the protein of interest is a transcriptional factor, transcriptional repressor, RNA binding protein. DNA modifying protein (e.g., enzyme), DNA editing protein (e.g., enzyme). Cas protein (e.g., Cas9. Cas13, etc . . . ). In some embodiments, the protein of interest is DUX4. In some embodiments the protein of interest may be used to treat Facioscapulohumeral dystrophy. In some embodiments, the protein of interest may carry RNA (e.g., mRNA, miRNA (microRNA), shRNA (short hairpin RNA, small hairpin RNA), gRNA (guide RNA)). In some embodiments, the protein of interest may carry RNA to multiple nuclei.

In some embodiments, the isolated nucleic acid is flanked by adeno-associated virus (AAV) inverted terminal repeats (ITRs).

In some embodiments, the multinucleate cell is a skeletal muscle cell.

In some embodiments, the nucleic acid is administered to a subject. In some embodiments, the subject is mammalian. In some embodiments, the subject is human.

In some aspects, the disclosure relates to a fusion protein comprising: (a) a protein of interest, and (b) at least the following migration signals: (i) a nuclear export signal (NES); (ii) a nuclear localization signal (NLS); and (iii) a nucleolar localization signal (NoLS). In some embodiments, the fusion protein further comprises at least one additional migration signal, wherein the additional migration signal may be identical or distinct from the existing migration signals of the fusion protein. In some embodiments, the fusion protein further comprises at least two additional migration signals, wherein the additional migration signals may be identical or distinct from the existing migration signals of the fusion protein.

In some embodiments, at least one of the migration signals is positioned at the C-terminus of the protein of interest. In some embodiments, at least one of the migration signals is positioned at the N-terminus of the protein of interest.

In some embodiments, at least one of the migration signals is linked to the protein of interest via a linker. In some embodiments, at least one of the migration signals is linked to at least one other migration signal via a linker.

In some embodiments, at least one of the migration signals comprises a sequence with at least 95% identity to SEQ ID NO: 1. In some embodiments, at least one of the migration signals comprises a sequence with at least 95% identity to SEQ ID NO: 3. In some embodiments, at least one of the migration signals comprises a sequence of SEQ ID NO: 1. In some embodiments, at least one of the migration signals comprises a sequence of SEQ ID NO: 3. In some embodiments, at least one of the migration signals comprises a sequence of SEQ ID NO: 1 and at least one of the migration signals comprises a sequence of SEQ ID NO: 3. In some embodiments, a migration signal comprises a sequence with at least 70% identity to a sequence of any one of SEQ ID NO: 14-570. In some embodiments, a migration signal comprises a sequence of any one of SEQ ID NO: 14-570.

In some embodiments, at least one of the migration signals is linked to at least one other migration signal via a linker.

In some aspects, the disclosure relates to an isolated nucleic acid comprising a nucleic acid sequence encoding at least one of the fusion proteins of the disclosure or of the methods of the disclosure.

In some embodiments, an isolated nucleic acid further comprises a promoter operably linked to a sequence encoding a fusion protein. In some embodiments, a promoter is a constitutive promoter, an inducible promoter, or a tissue specific promoter. In some embodiments, a promoter is a tissue specific promoter. In some embodiments, a tissue specific promoter is specific to skeletal muscle. In some embodiments, a tissue specific promoter is specific to liver tissue.

In some embodiments, an isolated nucleic acid further comprises at least one additional regulatory sequence.

In some aspects, the disclosure relates to a recombinant adeno-associated virus (rAAV), comprising: (a) an isolated nucleic acid as described herein flanked by adeno-associated virus (AAV) inverted terminal repeats (ITRs); and (b) an AAV capsid protein.

In some embodiments, AAV capsid protein exhibits a tropism for skeletal muscle. In some embodiments, an AAV capsid protein exhibits a tropism for liver tissue.

In some embodiments, an AAV capsid protein serotype is selected from: AAV1 and AAV6. In some embodiments, an AAV capsid protein serotype is AAV6. In some embodiments, an AAV capsid protein serotype is selected from: AAV7; AAV8; and AAV9.

In some aspects, the disclosure relates to a composition comprising any of the isolated nucleic acids of the disclosure, or any of the rAAVs of the disclosure, and a pharmaceutically acceptable excipient.

In some embodiments, a composition is formulated for intramuscular administration, intrathecal administration, intravenous administration, retrograde intravenous administration, intravascular administration, systemic administration, intra-arterial administration, intraportal administration, intratracheal administration, or direct injection.

In some aspects, the disclosure relates to a method of delivering a fusion protein to multinucleate cells, comprising, administering any of the fusion proteins of the disclosure, any of the isolated nucleic acids of the disclosure, any of the rAAVs of the disclosure, or any of the compositions of the disclosure to a subject.

In some embodiments, a protein of interest is a therapeutic protein in any of the fusion proteins of the disclosure, any of the isolated nucleic acids of the disclosure, any of the rAAVs of the disclosure, or any of the composition of the disclosure.

In some embodiments, a protein of interest is a transcriptional factor, transcriptional repressor, RNA binding protein, DNA modifying protein, DNA editing protein, Cas protein, DUX4, or variant thereof (e.g., dominant negative mutant), or an protein carrying an RNA in any of the fusion proteins of the disclosure, any of the isolated nucleic acids of the disclosure, any of the rAAVs of the disclosure, or any of the composition of the disclosure.

In some embodiments, a protein of interest is a nuclear protein in any of the fusion proteins of the disclosure, any of the isolated nucleic acids of the disclosure, any of the rAAVs of the disclosure, or any of the composition of the disclosure.

In some embodiments, a subject is mammalian. In some embodiments, a subject is human. In some embodiments, a subject has a disorder. In some embodiments, a disorder is Facioscapulohumeral dystrophy.

In some aspects, the disclosure relates to an isolated nucleic acid encoding at least one of the fusion proteins as disclosed herein.

In some embodiments, the isolated nucleic acid further comprises a promoter operably linked to the isolated nucleic acid encoding the fusion protein. In some embodiments, the promoter is a constitutive promoter, an inducible promoter, or a tissue specific promoter. In some embodiments, the promoter is a tissue specific promoter. In some embodiments, the tissue specific promoter is specific to skeletal muscle. In some embodiments, the tissue specific promoter is specific to liver tissue.

In some embodiments, the isolated nucleic acid further comprises at least one additional regulatory sequence.

In some aspects, the disclosure relates to a recombinant adeno-associated virus (rAAV), comprising: (a) at least one of the isolated nucleic acids as described herein flanked by adeno-associated virus (AAV) inverted terminal repeats (ITRs); and (b) an AAV capsid protein.

In some embodiments, the AAV capsid protein exhibits a tropism for skeletal muscle. In some embodiments, the AAV capsid protein serotype is selected from: AAV1. AAV6; AAV7; AAV8; and AAV9.

In some aspects, the disclosure relates to a composition comprising at least one of the isolated nucleic acids as described herein, or at least one of the rAAVs as disclosed herein, and a pharmaceutically acceptable excipient.

In some embodiments, the composition is formulated for intramuscular administration.

In some aspects, the disclosure relates to a method of delivering at least one of the fusion proteins as disclosed herein, to multinucleate cells. In some embodiments, the method comprises, administering at least one of the fusion proteins as disclosed herein, at least one of the isolated nucleic acids as disclosed herein, at least one of the rAAVs as disclosed herein, or at least one of the compositions as disclosed herein, to a subject (e.g., to one or more multinucleate cells in a subject).

In some embodiments, the protein of interest used in any of the fusion proteins as disclosed herein, any of the isolated nucleic acids as disclosed herein, any of the rAAVs as disclosed herein, or any of the compositions as disclosed herein, or as used in any of the methods as disclosed herein, may be a therapeutic protein.

In some embodiments, the protein of interest used in any of the fusion protein as disclosed herein, any of the isolated nucleic acids as disclosed herein, any of the rAAVs as disclosed herein, or any of the compositions as disclosed herein, or as used in any of the methods as disclosed herein, wherein the protein of interest is a nuclear protein.

In some embodiments, the protein of interest used in any of the fusion protein as disclosed herein, any of the isolated nucleic acids as disclosed herein, any of the rAAVs as disclosed herein, or any of the compositions as disclosed herein, or as used in any of the methods as disclosed herein, wherein the protein of interest is a transcriptional factor, transcriptional repressor. RNA binding protein. DNA modifying protein (e.g., enzyme). DNA editing protein (e.g., enzyme), Cas protein (e.g., Cas9, Cas13, etc. . . . ). In some embodiments, the protein of interest is DUX4 or variant thereof e.g., dominant negative form of DUX4). In some embodiments the protein of interest may be used to treat Facioscapulohumeral dystrophy. In some embodiments, the protein of interest may carry RNA (e.g., mRNA, miRNA (microRNA), shRNA (short hairpin RNA, small hairpin RNA), gRNA (guide RNA)). In some embodiments, the protein of interest may carry RNA to multiple nuclei.

In some embodiments, the subject in any of the methods as described herein is mammalian. In some embodiments, the subject is human.

These and other aspects and embodiments will be described in greater detail herein. The description of some exemplary embodiments of the disclosure are provided for illustration purposes only and not meant to be limiting. Additional compositions and methods are also embraced by this disclosure.

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description. Drawings, Examples, and Claims.

BRIEF DESCRIPTION OF THE DRAWINGS

Further aspects of the disclosure will be readily appreciated upon review of the Detailed Description of its various aspects and embodiments, described below, when taken in conjunction with the accompanying Drawings.

FIGS. 1A-1F show expression of GFP in C2C12 murine myoblasts transfected with NCT_GFP_017 plasmid. FIG. 1A. FIG. 1C, and FIG. 1E: GFP Signal of myoblasts post serum withdrawal to form myotubes. FIGS. 1B, FIG. 1D, and FIG. 1F: Brightfield Imaging of myoblasts post serum withdrawal to form myotubes.

FIGS. 2A-2D show expression of GFP in C2C12 murine myoblasts transfected with NCT_GFP_018 plasmid. FIG. 2A and FIG. 2C: GFP Signal of myoblasts post scrum withdrawal to form myotubes. FIG. 2B and FIG. 2D: Brightfield Imaging of myoblasts post serum withdrawal to form myotubes.

FIGS. 3A-3F show expression of GFP in C2C12 murine myoblasts transfected with NCT_GFP_021 plasmid. FIG. 3A, FIG. 3C, and FIG. 3E: GFP Signal of myoblasts post serum withdrawal to form myotubes. FIG. 3B, FIG. 3D, and FIG. 3F: Brightfield Imaging of myoblasts post serum withdrawal to form myotubes.

FIGS. 4A-4F show expression of GFP in C2C12 murine myoblasts transfected with NCT_GFP_020 plasmid. FIG. 4A. FIG. 4C, and FIG. 4E: GFP Signal of myoblasts post scrum withdrawal to form myotubes. FIGS. 4B, FIG. 4D, and FIG. 4F: Brightfield Imaging of myoblasts post serum withdrawal to form myotubes.

FIGS. 5A-SC show expression of enhanced green fluorescent protein (EGFP) in C2C12 murine myoblasts. Stable C2C12 cells were generated expressing EGFP and were mixed 50:50 with non-expressing C2C12 and fused on gelatin micro-molds to enhance fusion and alignment. Myotubes were imaged on day 8 post-serum withdrawal. FIG. 5A shows a construct in which the NLS is weaker as compared to the NES. FIG. 5B shows a construct in which the NLS is approximately the same strength as the NES.

FIGS. 7A-7H show the results of an in vivo study using either construct 1: CBh promoter driving SV40 NLS-EGFP (PKKKRKV; SEQ ID NO. 5) or construct 2: CBh promoter driving NLS-EGFP-NFS-NuLS (NCT20; SEQ ID NO: 11). Constructs were injected into tibialis anterior (TA) of C57BL6 mice at two different doses. TA fibers were harvested at either 3 or 8 weeks and imaged using fluorescence in sin hybridization against EGFP. Construct, dose, and time period are indicated on each figure. Imaging was performed using tile scans with 40× oil objective magnification.

FIGS. 8A-8J show DUX4 constructs and the results of in vitro experiments in C2C12 murine myoblasts cell lines. S+375-397 DUX4 construct contains HOX1 and HOX2 DNA binding domains but only part of the C-terminal domain (FIG. 8A). Identified by Mitsuhashi et al. as a potential inhibitory construct which can bind the DUX4 promoter without being toxic to cells (FIG. 8B). An S+375-397 dominant negative (SEQ ID NO: 12) and an S+375-397 dominant negative fused to ALYREF (S+375-397 dominant negative fused+ALYREF SEQ ID NO: 13) were used to inhibit a DUX4 promoter, greater inhibition was shown using the ALYREF sequence (FIGS. 8C-8J).

DETAILED DESCRIPTION OF CERTAIN EMBODIMENTS

Figures 2C, 2D:
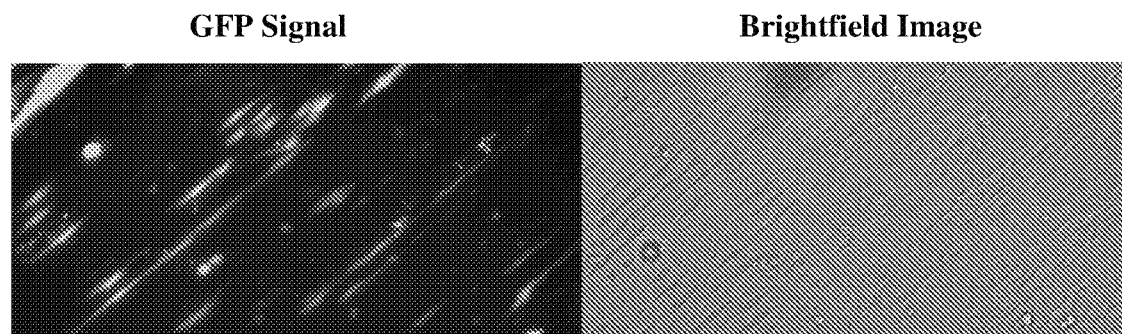
Figures 3A, 3B:
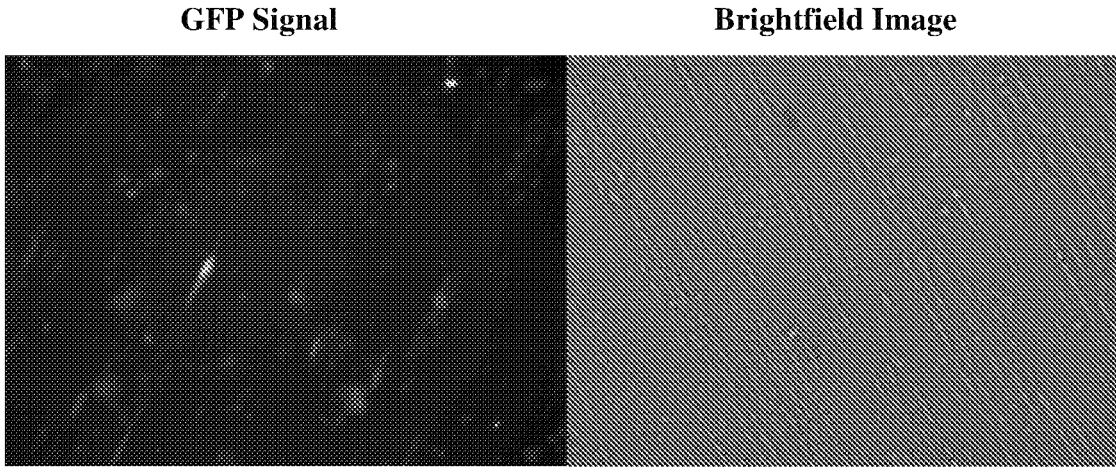
Figures 4A, 4B:
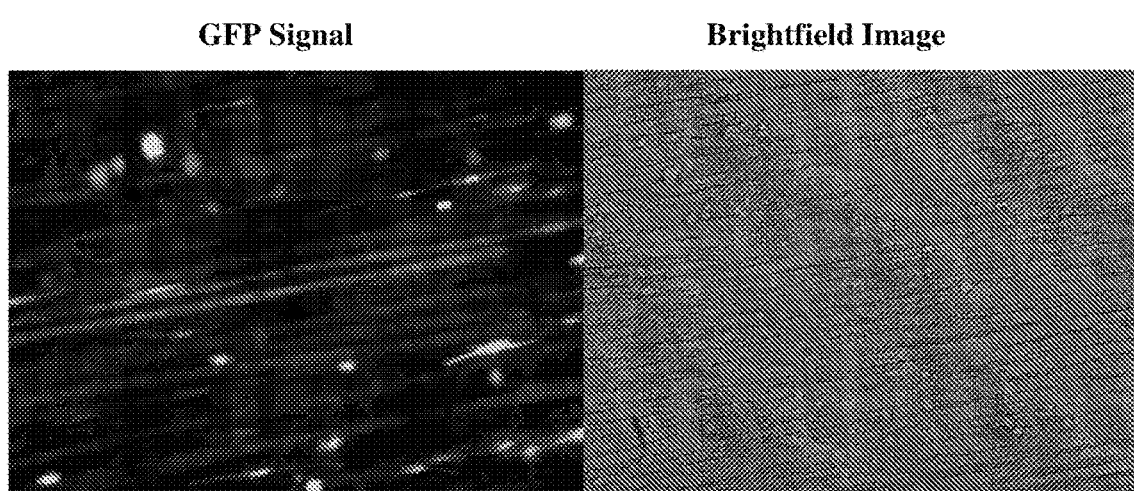
Figures 4C, 4D:
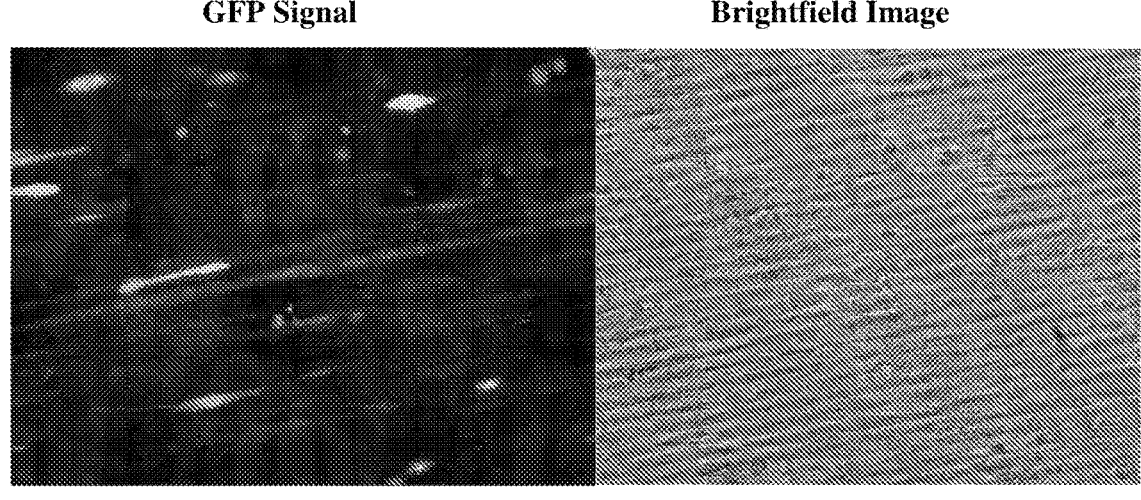

In some aspects, the disclosure relates to methods and compositions for delivering recombinant genes and/or fusion proteins to multinucleate cells. The terms "multinucleate," "multinucleated," and "polynuclear," as may be used interchangeably herein, refer to a eukaryotic cell which has at least two (e.g., more than one) nuclei per cell (e.g., multiple nuclei (e.g., 2 or mare)) sharing one common cytoplasm. In some embodiments, the methods and compositions are useful for delivering a protein to a plurality of nuclei in a cell. In some embodiments, the disclosure relates to fusion proteins comprising one or more signals useful for promoting d-livery of the proteins to a plurality of nuclei in a multinucleate cell.

Fusion Proteins

In some embodiments, a fusion protein comprises a protein of interest fused to one or more (e.g., 1, 2, 3, 4, 5, 6, 7, 8, 9, 10, or more) migration signals. The term "fusion protein," as may be used herein, refers to a hybrid (e.g., chimeric, recombinant) polypeptide which comprises protein domains from at least two different proteins. A protein may comprise different domains, for example, a migration signal (e.g., NES, NLS, NoLS) and a protein of interest. Any of the fusion proteins provided herein may be produced by any method known in the art. For example, the proteins provided herein may be produced via recombinant protein expression and purification, which is especially suited for fusion proteins comprising a peptide linker. Methods for fusion protein expression and purification are well known, and include those described by Green and Sambrook. Molecular Cloning: A Laboratory Manual (4th ed., Cold Spring Harbor Laboratory Press. Cold Spring Harbor, N.Y. (2012)), the entire contents of which are incorporated herein by reference. A fusion protein can be encoded by a recombinant nucleic acid (e.g., DNA, RNA). In some embodiments, a fusion protein comprises one or more migration signals at its N-terminus (N-terminal migration signal(s). In some embodiments, a fusion protein comprises one or more migration signals at its C-terminus (C-terminal migration signal(s)). In some embodiments, a fusion protein comprises a protein of interest that is fused to only N-terminal migration signal(s). In some embodiments, a fusion protein contains N-terminal migration signals and does not contain C-terminal migrations signals. In some embodiments, a fusion protein contains C-terminal migration signals and does not contain N-terminal migration signals. In some embodiments, a fusion protein contains both N-terminal migration signals and C-terminal migration signals. In some embodiment, a fusion protein comprises a protein of interest that is fused to only C-terminal migration signal(s). In some embodiments, a fusion protein comprises a protein of interest that is fused to both N-terminal and C-terminal migration signal(s). In some embodiments, a fusion protein comprises one or more migration signals at the N-terminus. In some embodiments, a fusion protein comprises one or more migration signals at its C-terminus. In some embodiments, a fusion protein comprises a protein of interest fused to migration signal(s) only at the N-terminus. In some embodiments, a fusion protein comprises a protein of interest that is fused to only to migration signal(s) at the C-terminus. In some embodiments, a fusion protein comprises a protein of interest that is fused to migration signal(s) at both its N-terminus and C-terminus.

The term "protein of interest." as may be used herein, refers to any protein (e.g., natural, synthetic, fragment, or variation thereof) which is the subject of (e.g., the target of) intervention. By this, the term is intended to represent the protein which is to be introduced into a system (e.g., organism, mammal, human, cell) to effect the environment into which it introduced (e.g., the system (e.g., organism, mammal, human, cell)). The protein of interest may be a naturally occurring protein. In such instances, the protein of interest may not be expressed by the subject, may be expressed in too little quantity, or a mutant may be expressed by the subject. Further, the protein may be a mutant or variant (e.g., non-naturally occurring, recombinant, engineered) of a protein. In such instances, the protein of interest may be not naturally found in the system (e.g., organism, mammal, human, cell) or may be introduced to alleviate a disease or disorder of the system (e.g., organism, mammal, human, cell). In some embodiments, the protein of interest is a naturally occurring protein. In some embodiments, the protein of interest is a mutant or variant (e.g., non-naturally occurring, recombinant, engineered) of a protein. In some embodiments, a protein of interest is a dominant negative variant (e.g., non-naturally occurring, recombinant, engineered) of a wild-type protein.

In some embodiments, the protein of interest may be a therapeutic protein. The term "therapeutic protein," as may be used herein, refers to a protein which is intended to be used as, used as, and/or is a, treatment. The terms "treatment," "treat," and "treating," as may be used interchangeably herein, refer to a clinical intervention aimed to reverse, alleviate, delay the onset of, or inhibit the progress of an, indication, disease, disorder, or one or more symptoms thereof. In some embodiments, treatment may be administered after one or more symptoms have developed and/or after a disease has been diagnosed. In other embodiments, treatment may be administered in the absence of symptoms (e.g., to prevent or delay onset of a symptom or inhibit onset or progression of a disease). For example, treatment may be administered to a susceptible individual (e.g., subject) prior to the onset of symptoms (e.g., in light of a history of symptoms and/or in light of genetic or other susceptibility factors). Treatment may also be continued after symptoms have resolved, for example, to prevent or delay their recurrence. In some embodiments, the therapeutic protein is intended to treat an indication, disease, or disorder of a multinucleate cell. In some embodiments, the therapeutic protein is intended to treat an indication, disease, or disorder of skeletal muscle. In some embodiments, the protein of interest is a nuclear protein. The term "nuclear protein." as may be used herein, is intended to have the meaning as commonly attributed to it in the art. Generally, a nuclear protein refers to a protein found in the cell nucleus. In some embodiments, the protein of interest is a transcriptional factor, transcriptional repressor, RNA binding protein, DNA modifying protein (e.g., enzyme), DNA editing protein (e.g., enzyme), Cas protein (e.g., Cas9, Cas13, etc . . . ). In some embodiments, the protein of interest is DUX4. In some embodiments, a protein of interest is a variant of a wild-type protein. In some embodiments, a protein of interest is a DUX4 variant. In some embodiments, a DUX4 variant is a dominant negative variant. In some embodiment, a DUX 4 variant is a S+375-397 variant. In some embodiments the protein of interest may be usec to treat Facioscapulohumeral dystrophy. In son embodiments, the protein of interest may carry RNA (e.g. mRNA, miRNA (microRNA), shRNA (short hairpin RNA, small hairpin RNA), gRNA (guide RNA)). In some embodiments, the protein of interest may carry RNA to multiple nuclei. In some embodiments, a fusion protein comprises a protein of interest fused to a migration signal. The term "migration signal," as may be used herein refers to peptides comprising amino acid sequences which facilitate migration of themselves (i.e., the peptide comprising the migration signal) and/or increase the residence time of a peptide or protein by means of affinity for an environment, non-affinity for another environment, or by the result of mechanical or chemical migration. Migration signals may also facilitate the migration of any peptide, protein, or other molecule (e.g., nucleic acid) they may be associated with (e.g., fused to: linked to; bound to by other mechanical, chemical, or biological interaction or bond). Generally, this is effectuated within a cell of an organism. The facilitation may occur as the result of recognition of the migration signal by import/export machinery within a cell or as the result of recognition and binding with other components which may be the target of migration (e.g., nucleic acids). In some embodiments, the migration signals facilitate nuclear export, nuclear localization, and/or nucleolar localization of a peptide. In some embodiments, the migration signals are nuclear export signals (NES), nuclear localization signals (NLS), and nucleolar localization signals (NoLS).

The terms "nuclear export signal," "nuclear export sequence," and "NES." as may be used interchangeably herein, refer to peptides (and their respective amino acid sequences) (generally 8-15 amino acid residues in length), usually attached to (e.g., part of) a protein, which promotes the protein for export from the cell nucleus to the cell cytoplasm through the nuclear pore complex using nuclear transport. In some embodiments, the NES peptide contains four hydrophobic residues. This is in contrast to the nuclear localization signal (NLS), which targets a protein located in the cytoplasm for import to the nucleus. The NES is recognized and bound by exportins. A common spacing of the hydrophobic residues found in an NES follows the following pattern LaaaLaaLaL, where "L" denotes a hydrophobic residue (often Leucine ("Leu" or "L")) and "x" denotes any other amino acid. The spacing and configuration is believed to facilitate the protein's interaction with exportin. Various NES motifs are in the art and would be apparent to the skilled artisan. The terms also include, where context implies or requires, the nucleic acid sequences encoding the NES.

The terms "nuclear localization signal." "nuclear localization sequence," and "NLS" as may be used interchangeably herein, refer to peptides (and their respective amino acid sequences), usually attached to (e.g., part of) a protein, which promotes the protein import into the cell nucleus from the cell cytoplasm through the nuclear pore complex using nuclear transport. In some embodiments, an NLS often consists of one or more short peptides of positively charged amino acid residues of Lysine ("Lys" or "K") or Arginine ("Arg" or "R") exposed on the protein surface. This is in contrast to the nuclear export signal (NES), which targets a protein located in the nucleus for export to the cell cytoplasm. The NLS is recognized and bound by importins. Various NLS motifs are in the art and would be apparent to the skilled artisan. The spacing and configuration is believed to facilitate the protein's interaction with importin. The terms also include, where context implies or requires, the nucleic acid sequences encoding the NLS.

NLS can be further classified as either monopartite (i.e., of "one" part) or bipartite (i.e., of "two" parts). The classification as monopartite or bipartite results from the presence of a short spacer between the basis amino acid of a bipartite NLS, which is absent in a monopartite NLS.

The terms "nucleolar localization signal," "NoLS," and "Nucleolar Targeting Signal," as may be used interchangeably herein, refer to peptides (and their respective amino acid sequences), usually attached to (e.g., part of) a protein, which promotes the protein localization to the cell nucleolus in the nucleus and promotes the protein's migration into the nucleolar compartment from the nucleoplasm. In some embodiments, an NoLS often comprises of primarily one or more short peptides of positively charged amino acid residues of Arginine ("Arg" or "R") exposed on the protein surface. In some embodiments, an NoLS is a positively charged peptide. In some embodiments, an NoLS may have an isoelectric point above 12.6. In some embodiments, an NoLS is composed entirely of arginine residues. In some embodiments, an NoLS comprises at least 4 residues. In some embodiments, an NoLS comprises at least 5 residues. In some embodiments, an NoLS comprises at least 6 residues. In some embodiments, an NoLS comprises at least 4 (e.g., 4 or more) arginine residues. In some embodiments, an NoLS comprises at least 5 (e.g., 5 or more) arginine residues. In some embodiments, an NoLS comprises at least 6 (e.g., 6 or more) arginine residues. In some embodiments, an NoLS comprises at least 7 (e.g., 7 or more) arginine residues. In some embodiments, an NoLS comprises at least 8 (e.g., 8 or more) arginine residues. In some embodiments, an NoLS comprises at least 9 (e.g., 9 or more) arginine residues. In some embodiments, an NoLS consists of 9 arginine residues. In some embodiments, an NoLS comprises at least 10 (e.g., 10 or more) arginine residues. In some embodiments, an NoLS comprises at least 11 (e.g., 11 or more) arginine residues. In some embodiments, an NoLS comprises at least 12 (e.g., 12 or more) arginine residues. In some embodiments, an NoLS comprises at least 4 (e.g., 4 or more) arginine residues fused to an NLS. In some embodiments, an NoLS comprises a strong basic charge. In some embodiments, an NoLS comprises both arginine and lysine. In some embodiments, an NoLS comprises at least 4 (e.g., 4, 5, 6, 7, 8, 9, 10, 11, 12, or more) residues of arginine and/or lysine. In some embodiments, the NoLS is fused to an NLS. Motifs (e.g., peptides, sequences) involved in regulating nucleolar localization are not well defined and are believed to result from direct or indirect interaction with one of the nucleolar building blocks (e.g., rDNA, its transcripts, protein components, which facilitates localization. This is in contrast to NLS and/or NES, which serve as recognition motifs for binding with import/export machinery (respectively). In some embodiments, the NoLS includes an RNA binding motif. Various NLS motifs are in the art and would be apparent to the skilled artisan (for a more detailed background see for example, Martin et al., Principals of protein targeting to the nucleolus. *Nucleus.* 2015; 6(4): 314-325 (2015)), some exemplary NoLS can be found in Table 2. The terms also include, where context implies or requires, the nucleic acid sequences encoding the NoLS.

NES, NLS, and NoLS signals are known in the art and the skilled artisan will readily be able to ascertain and locate a vast number of such migration signals (see for example, Michael Bernhofer, Tatyana Goldberg, Silvana Wolf, Mohamed Ahmed, Julian Zaugg, Mikael Boden, Burkhard Rost, *NLSdb—major update for database of nuclear localization signals and nuclear export signals, Nucleic Acids Research*, Volume 46, Issue D1, 4 Jan. 2018, Pages D503-D508, //doi.org/10.1093/nar/gkx1021). For example, without limitation, various publications and resources exist which provide information on such signals (e.g., databases), such as NLSdb (rostlab.org/services/nlsdb1/browse.php) and NESdb (prodata.swmed.edu/LRNes/IndexFiles/names-Good.php), which (in addition to those listed in Berhofer hereinabove) without limitation, are contemplated as encompassed in this disclosure.

In sane embodiments, a fusion protein comprises a protein of interest and migration signals comprising, an NES and at least one migration signal selected from: (1) an NLS; and (2) an NoLS. In some embodiments, the fusion protein comprises migration signals comprising an NES and at least two migration signals selected from: (1) an NLS; and (2) an NoLS, wherein the at least two migration signals are distinct from one another. In some embodiments, the fusion protein comprises migration signals comprising an NES and at least two migration signals selected from: (1) an NLS; and (2) an NoLS, wherein the at least two migration signals are identical from one another. In some embodiments, the fusion protein may comprise multiple migration signals of the same type (e.g., more than one NES, more than one NLS, more than one NoLS). In some embodiments, the fusion protein may comprise multiple migration signals of the same type, but fewer than 20 migration signals (e.g., more than one, but less than 20, NES, more than one, but less than 20, NLS, more than one, but less than 20, NoLS). In some embodiments, the multiple migration signals of the same type may be identical (e.g., the same sequence). In some embodiments, the multiple migration signals of the same type may be non-identical (e.g., different sequences).

In some embodiments, a fusion protein comprises a protein of interest, wherein the protein of interest has properties of an NES, NLS, and/or NoLS. In some embodiments, a fusion protein comprises a protein of interest, wherein the protein of interest has properties of an NES, NLS, and/or NoLS, wherein the fusion protein further comprises at least one migration signal comprising an NES, an NLS, and/or an NoLS, wherein the at least one migration signal has properties distinct from those of the protein of interest. For clarity, without limitation, if a protein of interest has properties of an NES, an at least one migration signal may comprise an NLS and/or NoLS, but as can be envisioned by the skilled artisan, each combination and permutation of such a fusion protein are contemplated herein. In structuring a fusion protein in this way it is contemplated to exploit a fusion protein's inherent migration signal properties (e.g., as an NES, NLS, and/or NoLS) without the inclusion of an additional migration signal to incorporate the same property. It is well-known to the skilled artisan how to assess such properties of a protein of interest. For example, without limitation, such properties may be observed as a result of sequences in a protein known to be part of, or a whole, NES, NLS, or NoLS. Additionally, charges or other protein properties analogous or similar to those of an NES, NLS, and/or NoLS may be observed or measured. One of skill in the art will readily be able to ascertain proteins of this type without undue experimentation. For example, various assays exist to measure the nuclear localization, nucleolar localization, or cytoplasmic localization (e.g., as in the case of NES signals) activity of molecular components (e.g., sequences, nucleic acids, proteins). For example, and without limitation, heterokaryon assays for measurement and quantification of nucleucytoplasmic shuttling of proteins (see for example, McNicoll, F. and Müller-McNicoll. M. (2018). *A Quantitative Heterokaryon Assay to Measure the Nucleocytoplasmic Shuttling of Proteins*. Bio-protocol 8 (17): e2472. DOI: 10.21769/BioProtoc.2472; and Flach J. Bossie M. Vogel J, et al. *A yeast RNA-binding protein shuttles between the nucleus and the cytoplasm*. Mol Cell Biol. 1994; 14 (12): 8399-8407. doi: 10.1128/mcb.14.12.8399).

In some embodiments, the disclosure relates to a method of selecting proteins of interest for use in a fusion protein of the present disclosure, comprising, selecting a protein of interest based on inherent activity analogous to an NES, NLS, and/or NoLS. In some embodiments, a protein of interest is selected for having inherent properties of an NES, NLS, or NoLS, or a gene encoding a recombinant protein encoding the fusion is produced, and then attached to a migration signal. In some embodiments, a migration signal is distinct from the inherent NES, NLS, or NoLS property exhibited by, or quantified from, a protein of interest. In some embodiments, a fusion protein comprises a protein of interest selected for having inherent properties of an NES, NLS, or NoLS, and a migration signal. In some embodiments, a fusion protein comprises a protein of interest selected for having inherent properties of an NES, NLS, or NoLS, and a migration signal distinct from the inherent NES, NLS, or NoLS property exhibited by, or quantified from, the protein of interest. In some embodiments, an isolated nucleic acid encodes the fusion protein.

In some embodiments, the fusion protein comprises a protein of interest and migration signals comprising, an NES, an NLS, and an NoLS. In some embodiments, the fusion protein may comprise multiple migration signals of the same type (e.g., more than one NES, more than one NLS, more than one NoLS). In some embodiments, the multiple migration signals of the same type may be identical (e.g., the same sequence). In some embodiments, the multiple migration signals of the same type may be non-identical (e.g., different sequence).

In some embodiments, the fusion protein comprises a protein of interest, more than one NES (e.g., 2, 3, 4, 5, or more), and at least one migration signal selected from: (1) an NES; and (2) an NoLS. In some embodiments, the fusion protein comprises a protein of interest, at least one NES (e.g., 1, 2, 3, 4, 5, or more), and more than one NLS (e.g., 2, 3, 4, 5, or more). In some embodiments, the fusion protein comprises a protein of interest, at least one NES (e.g., 1, 2, 3, 4, 5, or more), and more than one NoLS (e.g., 2, 3, 4, 5, or more). In some embodiments, the fusion protein comprises a protein of interest, at least one NES (e.g., 1, 2, 3, 4, 5, or more), more than one NLS (e.g., 2, 3, 4, 5, or more), and an NoLS. In some embodiments, the fusion protein comprises a protein of interest, at least one NES (e.g., 10, 2, 3, 4, 5, or more), more than one NoLS (e.g., 2, 3, 4, 5, or morel, and an NLS. In some embodiments, the fusion protein comprises a protein of interest, at least one NES (e.g., 1, 2, 3, 4, 5, or more), more than one NLS (e.g., 2, 3, 4, 5, or more), and more than one NoLS (e.g., 2, 3, 4, 5, or mom). In some embodiments, the fusion protein comprises a protein of interest, more than one NES (e.g., 2, 3, 4, 5, or more), more than one NLS (e.g., 2, 3, 4, 5, or more), and more than one NoLS (e.g., 2, 3, 4, 5, or more).

In some embodiments, at least one NES of the fusion protein comprises a sequence with at least 80% identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity) to a sequence selected from SEQ ID NO: 1-2 or 14-261. In some embodiments, at least one NES of the fusion protein comprises a sequence selected from SEQ ID NO: 1-2 or 14-261. In some embodiments, at least one NES of the fusion protein comprises a sequence of SEQ ID NO: 1, 2, or 14-261.

In some embodiments, at least one NLS of the fusion protein comprises a sequence with at least 80% identity (e.g., at least 80%, at least 81%, at least 82%, at least 83%, at least 4%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity) to a sequence selected from SEQ ID NO: 3-5 or 262-570. In some embodiments, at least one NLS of the fusion protein comprises a sequence selected from SEQ ID NO: 3-5 or 262-570. In some embodiments, at least one NLS of the fusion protein comprises a sequence of SEQ ID NO: 3-5 or 262-570.

In some embodiments, at least one NoLS of the fusion protein comprises a sequence with at least 80% identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity) to a sequence selected from SEQ ID NO: 6. In some embodiments, at least one NoLS of the fusion protein comprises a sequence selected from SEQ ID NO: 6.

In some embodiments, a fusion protein comprises a protein of interest and one or more of an NES, NLS, and/or NoLS of Table 2, or a variant of any one thereof (e.g., having one or more, for example 1, 2, 3, 4, 5, 6, 7, 8, 9, or 10 amino acid insertions, deletions, and/or substitutions relative to the sequences listed in Table 2).

The terms "percent identity," "sequence identity," "% identity," "% sequence identity," and % identical," as they may be interchangeably used herein, refer to a quantitative measurement of the similarity between two sequences (e.g., nucleic acid or amino acid). The percent identity of genomic DNA sequence, intron and exon sequence, and amino acid sequence between humans and other species varies by species type, with chimpanzee having the highest percent identity with humans of all species in each category. Percent identity can be determined using the algorithms of Karlin and Altschul. Proc. Natl. Acad. Sci. USA 87:2264-68, 1990, modified as in Karlin and Altschul, Proc. Natl. Acad. Sci. USA 90:5873-77, 1993. Such algorithms is incorporated into the NBLAST and XBLAST programs (version 2.0) of Altschul et al., J. Mol. Biol. 215:403-10, 1990. BLAST protein searches can be performed with the XBLAST program, score=50, word length=3, to obtain amino acid sequences homologous to the protein molecules of interest. Where gaps exist between two sequences. Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used. When a percent identity is stated, or a range thereof (e.g., at least, more than, etc.), unless otherwise specified, the endpoints shall be inclusive and the range (e.g., at least 70% identity) shall include all ranges within the cited range (e.g., at least 71%, at least 72%, at least 73%, at least 74%, at least 75%, at least 76%, at least 77%, at leas, 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity) and all increments thereof (e.g., tenths of a percent (i.e., 0.1%), hundredths of a percent (i.e., 0.01%), etc.).

In some embodiments, at least one of the migration signals is positioned at the C-terminus of the protein of interest. In some embodiments, at least one of the migration signals is positioned at the N-terminus of the protein of interest. In some embodiments, at least one migration signal is positioned at each the N-terminus of the protein of interest and the C-terminus of the protein of interest. In some embodiments, all of the migration signals of the fusion protein are position at the N-terminus of the protein of interest. In some embodiments, all of the migration signals of the fusion protein are position at the C-terminus of the protein of interest.

In some embodiments, at least one of the migration signals is linked to the protein of interest via a linker. The term "linker." as may be used herein, refers to a molecule linking two other molecules or moieties. Linkers are well known in the art and can comprise any suitable combination of nucleic acids or amino acids to facilitate the proper function of the structures they join. The linker can be a series of amino acids. The linker can be an amino acid sequence in the case of a linker joining two fusion proteins. For example, a protein (e.g., protein of interest) can be fused to a migration signal (e.g., NES, NLS, NoLS)(e.g., fusion protein as disclosed herein) by an amino acid linker sequence. The linker can also be a nucleotide sequence in the case of joining two nucleotide sequences together. In other embodiments, the linker is an organic molecule, group, polymer, or chemical moiety. In some embodiments, the linker is 1-100 amino acids in length, for example: 1; 2; 3; 4; 5; 6; 7; 8; 9; 10; 11; 12; 13; 14; 15; 16; 17; 18; 19; 20; 21; 22; 23; 24; 25; 26; 27; 28; 29; 30; 30-35; 35-40; 40-45; 45-50; 50-60; 60-70; 70-80; 80-90; 90-100; 100-150; or 150-200 amino acids in length. In some embodiments, the inker is 5-1,000 nucleotides in length, for example: 5; 6; 7; 8; 9; 10; 11; 12; 13; 14; 15; 16; 17; 18; 19; 20; 21; 22; 23; 24; 25; 26; 27; 28; 29; 30; 30-35; 35-40; 40-45; 45-50; 50-60; 60-70; 70-80: 80-90; 90-100; 100-150; 150-200; 200-300; 300-500; 500-1,000; 1,000-2,000; or 2,000-5,000 nucleotides. Longer or shorter linkers are also contemplated. In some embodiments, at least one of the migration signal, is linked to at least one other migration signal via a linker. In some embodiments, the fusion protein comprises a linker between the protein of interest, at least one migration signal, wherein at least one migration signal is linked to at least one other migration signal via a linker. In some embodiments, the fusion protein comprises a linker between the protein of interest, at least one migration signal, wherein each migration signal positioned next to another migration signal is linked to the migration signal via a linker. In some embodiments, where all of the migration signals are positioned at one end of the protein of interest (e.g., at either the N-terminus of the protein of interest or the C-terminus of the protein of interest), they are linked to the protein of interest via a linker at such terminus (e.g., either the N-terminus of the protein of interest or the C-terminus of the protein of interest). In some embodiments, where migration signals are positioned at both ends of the protein of interest (e.g., at least one at the N-terminus of the protein of interest and at least one at the C-terminus of the protein of interest), at least one migration signal is linked to the protein of interest via a linker at such terminus (e.g., either the N-terminus or the C-terminus of the protein of interest). In some embodiments, where migration signals are positioned at both ends of the protein of interest (e.g., at least one at the N-terminus of the protein of interest and at least one at the C-terminus of the protein of interest), the migration signals at either terminus are linked to the protein of interest via a linker at such terminus (e.g., either the N-terminus or the C-terminus of the protein of interest).

In some embodiments, a fusion protein comprises a DUX4 protein sequence, or variant thereof. In some embodiments, a fusion protein comprises a DUX4 protein sequence of an S+375-397 dominant negative. In some embodiments, a fusion protein comprises a sequence with an S+375-397 dominant negative DUX4 protein sequence and an ALYREF sequence. In some embodiments, a fusion protein comprises a DUX4 protein sequence with at least 70% (e.g., at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9%) identity to SEQ ID NO: 13. In some embodiments, a fusion protein comprises a DUX4 protein sequence of SEQ ID NO: 13.

Nucleic Acids

In some aspects, the disclosure relates to an isolated nucleic acid encoding at least one of the fusion proteins as disclosed herein. The term "isolated," as may be used herein, refers to a characteristic of a material as provided herein (e.g., nucleic acid (e.g., RNA, DNA, polynucleotide), amino acid, peptide (e.g., polypeptide, protein), vector (e.g., viral vector (e.g., adeno-associated viral vector))), as being altered or removed from its natural state (e.g., native or original environment if it is naturally occurring) such material would otherwise be found. Therefore, a naturally-occurring nucleic acid or peptide present in a living animal is not isolated, but the same nucleic acid or peptide, separated by human intervention from some or all of the coexisting materials in the natural system, is "isolated." For example, a nucleic acid or a peptide naturally present in a living animal is not "isolated," but the same nucleic acid or peptide partially or completely separated from the coexisting materials of its natural state or host is "isolated." An artificial, recombinant, or engineered material, for example, a non-naturally occurring nucleic acid construct or peptide construct, are, accordingly, also referred to as isolated. In some embodiments, an isolated nucleic acid is a recombinant nucleic acid in any environment. An isolated material can exist in substantially purified form, or can exist or; a non-native environment such as, for example, a vector or host cell, however, a material does not have to be purified in order to be isolated. Accordingly, a material may be part of a vector and/or part of a composition, and still be isolated in that such vector or composition is not part of the environment in which the material is found in its natural state.

In some embodiments, the isolated nucleic acid further comprises a promoter operably linked to the isolated nucleic acid encoding the fusion protein. The term "operably linked," as may be used herein, refers to an arrangement of sequences or regions wherein the components are configured so as to perform their usual or intended function. Thus, a regulatory or control sequence operably linked to a coding sequence is capable of affecting the expression of the coding sequence. The regulatory or control sequences need not be contiguous with the coding sequence, so long as they function to direct the proper expression or polypeptide production. Thus, as a non-limiting example, intervening untranslated but transcribed sequences can be present between a promoter sequence and the coding sequence and the promoter sequence can still be considered operably linked to the coding sequence. A promoter sequence, as described herein, is a DNA regulatory region a short distance from the 5' end of a gene that acts as the binding site for RNA polymerase. The promoter sequence may bind RNA polymerase in a cell and/or initiate transcription of a downstream 3' direction) coding sequence. The promoter sequence may be a promoter capable of initiating transcription in prokaryotes or eukaryotes. Some non-limiting examples of eukaryotic promoters include the cytomegalovirus (CMV) promoter, the chicken β-actin (CBA) promoter, and a hybrid form of the CBA promoter (CBh). In some embodiments, the promoter is a constitutive promoter, an inducible promoter, or a tissue specific promoter. In some embodiments, the promoter is a tissue specific promoter. In some embodiments, the tissue specific promoter is specific to skeletal muscle. In some embodiments, the tissue specific promoter is specific to liver tissue.

In some embodiments, the isolated nucleic acid further comprises at least one additional regulatory sequence. The terms "regulatory sequence," "regulatory signal," "control sequence," and "control signal," as may be used interchangeably herein, refer to sequences that are responsible for expressing a particular nucleic acid or may include other sequences, such as heterologous, synthetic, or partially synthetic sequences. The sequences can be of eukaryotic, prokaryotic, or viral origin that stimulate or repress transcription of a gene in a specific or non-specific manner and in an inducible or non-inducible manner. Regulatory or control regions may include origins of replication, RNA splice sites, introns, chimeric or hybrid introns, promoters, enhancers, transcriptional termination sequences, poly A sites, locus control regions, signal sequences that direct the polypeptide into the secretory pathways of the target cell, and introns. A heterologous regulatory region is not naturally associated with the expressed nucleic acid to which it is linked. Included among the heterologous regulatory regions are regulatory regions from a different species, regulatory regions from a different gene, hybrid regulatory sequences, and regulatory sequences that do not occur in nature, but which are designed by one of ordinary skill in the art.

In some embodiments, at least one NES of the fusion protein comprises a sequence with at least 80% identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity) to a sequence selected from SEQ ID NO: 1-2 or 14-261. In some embodiments, at least one NES of the fusion protein comprises a sequence selected from SEQ ID NO: 1-2 or 14-261. In some embodiments, at least one NES of the fusion protein comprises a sequence of SEQ ID NO: 1-2 or 14-161.

In some embodiments, at least one NLS of the fusion protein comprises a sequence with at least 80% identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity) to a sequence selected from SEQ ID NO: 3-5 or 262-570. In some embodiments, at least one NLS of the fusion protein comprises a sequence selected from SEQ ID NO: 3-5 or 262-570. In some embodiments, at least one NLS of the fusion protein comprises a sequence of SEQ ID NO: 3-5 or 262-570.

In some embodiments, at least one NoLS of the fusion protein comprises a sequence with at least 80% identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, a least 98%, at least 98.5%, at least 99%, at least 99.5%, at least 99.6%, at least 99.7%, at least 99.8%, at least 99.9% identity) to a sequence selected from SEQ ID NO: 6. In some embodiments, at least one NoLS of the fusion protein comprises a sequence selected from SEQ ID NO: 6.

In some embodiments, an isolated nucleic acid encodes a fusion protein comprising a DUX4 protein sequence, or variant thereof. In some embodiments, an isolated nucleic acid encodes a fusion protein comprising a DUX4 protein sequence of an S+375-397 dominant negative. In some embodiments, an isolated nucleic acid encodes a fusion protein comprising a sequence with an S+375-397 dominant negative DUX4 protein sequence and an ALYREF sequence. In some embodiments, an isolated nucleic acid encodes a fusion protein comprising a DUX4 protein sequence with at least 70% (e.g., at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least, 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9%) identity to SEQ In NO: 13. In some embodiments, an isolated nucleic acid encodes a fusion protein comprising a DUX4 protein sequence of SEQ ID NO: 13.

Viral Vectors

In some aspects, the disclosure relates to a viral vector comprising a recombinant virus and at least one of any of the isolated nucleic acids as described herein. In some embodiments, the recombinant virus is a recombinant adeno-associated virus (rAAV). In some embodiments, the recombinant virus is a recombinant lentivirus (rLV).

In same embodiments, the rAAV, comprises: (a) at least one of the isolated nucleic acids as described herein flanked by adeno-associated virus (AAV) inverted terminal repeats (ITRs); and (b) an AAV capsid protein.

Adeno-associated virus (AAV) is a small (20 nanometer (nm)) replication-defective, non-enveloped DNA virus, that depends on the presence of a second virus, for example, adenovirus or herpesvirus, for productive infection. AAV is not known to cause disease and induces a very mild immune response. AAV can infect both dividing and non-dividing cells and stably incorporates its genome into that of the host cell. AAV has a variety of different sub-types. e.g., scrotypes, and are known in the art. AAV vectors based on scrotype 2 (AAV2) provided a proof-of-concept for non-toxic and stable gene transfer in murine and large animal models. AAV vectors having distinct tissue targeting capabilities have been developed for gene therapy and research applications. AAV serotype affects tissue tropism of the respective viral particles and allows to target specific cell types or tissues, making AAV vectors attractive for in vivo gene delivery applications in which only a specific cell type or tissue is targeted and/or gene transfer into non-targeted cells or tissues is not desirable.

Wild-type (wt) AAV particles harbor a single-stranded DNA genome comprising two genes: the AAV rep gene and the AAV cap gene. The AAV rep gene encodes proteins controlling viral replication, structural gene expression, and integration into the host genome. The AAV cap gene encodes capsid structural proteins. The 5' and 3' termini of the AAV genome each comprise an inverted terminal repeat (ITR) region, which is involved in multiplication of the AAV genome. In some embodiments, an AAV ITR sequence comprises 145 nucleotides. In general, an AAV ITR sequence is a self-complementary nucleic acid structure that is able to form a hairpin, which plays a role in AAV self-priming for synthesis of the second DNA AAV strand during the viral life cycle. Recombinant AAV (rAAV) vectors am generally produced by replacing the viral genes, or parts thereof, with a heterologous expression cassettes. The term "expression cassette," as may be used herein, refers to a nucleic acid construct comprising nucleic acid elements sufficient for the expression of a gene product. Typically, an expression cassette comprises a nucleic acid encoding a gene product operably linked to a promoter sequence. In some embodiments, the expression cassette of the rAAVs described herein is any of the isolated nucleic acids of the present disclosure.

Typically, rAAV genomes up to about 5 kb in length can efficiently be packaged into infectious viral particles useful for gene transfer. In some embodiments, the rAAV construct is a single-stranded rAAV construct (ssAAV). That is, the rAAV construct contains two ITRs, a 5' ITR and a 3' ITR that comprise a functional terminal resolution sites (TRS) each. In some such embodiments, the AAV construct is a double-stranded, self-complementary AAV (scAAV) construct. For an overview of AAV biology. ITR function, and scAAV constructs, see McCarty D M. Self-complementary AAV vectors; advances and applications. Mol Thor. 2008 October; 16(10): at pages 1648-51, first full paragraph, incorporated herein by reference for disclosure of AAV and scAAV constructs. ITR function, and role of TRS ITR in scAAV constructs. An rAAV vector comprising a TRS ITR cannot correctly be nicked during the replication cycle and, accordingly, produces a self-complementary, double-stranded AAV (scAAV) genome, which can efficiently be packaged into infectious AAV particles. Various rAAV, ssAAV, and scAAV vectors, as well as the advantages and drawbacks of each class of vector for specific applications and methods of using such vectors in gene transfer applications are well known to those of skill in the art (see, for example. Choi V W, Samulski R J. McCarty D M. Effects of adeno-associated virus DNA hairpin structure on recombination. J Virol. 2005 June; 79(11):6801-7; McCarty D M. Young S M Jr. Samulski R J. Integration of adeno-associated 20 virus (AAV) and recombinant AAV vectors. Annu Rev Genet. 2004; 38:819-45: McCarty D M. Monahan P E. Samulski R J. Self-complementary recombinant adeno-associated virus (scAAV) vectors promote efficient transduction independently of DNA synthesis. Gene Ther. 2001 August; 8(16): 1248-54; and McCarty D M. Self-complementary AAV vectors: advances and applications. Mot Ther. 2008 October; 16(10):1648-56; all references cited in this application are incorporated herein by reference for disclosure of AAV, rAAV, and scAAV vectors).

In some embodiments, rAAV vectors are engineered to target specific cells, cell types, or tissues, for example, skeletal muscle or liver tissue. The AAV sequences of a rAAV construct provided herein typically comprise the cisacting 5' and 5' inverted terminal repeat sequences (See. e.g., B. J. Carter, in "Handbook of Parvoviruses", ed., P. Tijsser, CRC Press. pp. 155 168 (1990)). The ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J Virol., 70:520 532 (1996)). AAV ITR sequences may be obtained from any known AAV, including presently identified mammalian AAV types. In addition to the major elements identified above for the rAAV vectors and constructs, a rAAV vector may also include additional transcriptional control elements. Transcriptional control elements are known to those of skill in the art and exemplary elements include transcription initiation, termination, promoter and enhancer sequences. RNA processing signals such as splicing and polyadenylation (polyA) signals, sequences that stabilize cytoplasmic mRNA, sequences that enhance translation efficiency (e.g., Kozak consensus sequences), sequences that enhance protein stability, and, if appropriate, sequences that enhance secretion of the encoded product. A great number of expression control sequences, including promoters which are native, constitutive, inducible and/or tissue-specific, are known in die art and may be utilized. Adeno-associated viral ITR sequences may be obtained from any known AAV, including presently identified mammalian AAV types.

In some embodiments, the AAV capsid protein is selected from an AAV having a serotype of: AAV1, AAV2, AAV3, AAV3b, AAV4, AAV5, AAV6, AAV7, AAV8, AAVrh.8, AAV9, AAV10, AAVrh.10, AAVrh.39, AAVrh.43, AAV.PHPB, AAV.PHPB.e. AAVrh32.33, or a variant thereof. In some embodiments, the AAV capsid protein is of serotype AAV1. In some embodiments, the AAV capsid protein is of serotype AAV2. In some embodiments, the AAV capsid protein is of scrotype AAV3. In some embodiments, the AAV capsid protein is of serotype AAV3b. In some embodiments, the AAV capsid protein is of serotype AAV4. In some embodiments, the AAV capsid protein is of scrotype AAV5. In some embodiments, the AAV capsid protein is of serotype AAV6. In some embodiments, the AAV capsid protein is of serotype AAV7. In some embodiments, the AAV capsid protein is of serotype AAV8. In some embodiments, the AAV capsid protein is of serotype AAVrh.8. In some embodiments, the AAV capsid protein is of serotype AAV9. In some embodiments, the AAV capsid protein is of serotype AAV10. In some embodiments, the AAV capsid protein is of serotype AAVrh.10. In some embodiments, the AAV capsid protein is of serotype AAVrh.39. In some embodiments, the AAV capsid protein is of serotype AAVrh.43. In some embodiments, the AAV capsid protein is of serotype AAV.PHPB. In some embodiments, the AAV capsid protein is of serotype AAV.PHPB.e. In some embodiments, the AAV capsid protein is of serotype AAVrh32.33.

In some embodiments, the AAV capsid protein exhibits a tropism for tissue having multinucleate cells. In some embodiments, the AAV capsid protein exhibits a tropism for multinucleate cells. In some embodiments, the AAV capsid protein exhibits a tropism for skeletal muscle. In some embodiments, the AAV capsid protein serotype is selected from: AAV1; AAV6; AAV7; AAV8; and AAV9.

Compositions

In some aspects, the disclosure relates to a composition comprising at least one of the fusion proteins as described herein, at least one of the isolated nucleic acids as described herein, or at least one of the rAAVs as disclosed herein, and a pharmaceutically acceptable excipient.

In some embodiments, at least one of the fusion proteins as described herein, at least one of the isolated nucleic acids as described herein, or at least one of the rAAVs as disclosed herein can be formulated for administration to a subject as a composition, which, as used herein comprises at least one of the fusion proteins as described herein, at least one of the isolated nucleic acids as described herein, or at least one of the rAAVs as disclosed herein and a pharmaceutically acceptable carrier, diluent, or excipient. A carrier, diluent, or excipient that is "pharmaceutically acceptable" includes one that is sterile and pyrogen free. Suitable pharmaceutical carriers, diluents, and excipients are well known in the art. The carrier(s) should be "acceptable" in the sense of being compatible with the at least one of the fusion protein, at least one isolated nucleic acid, or at least one rAAV and not deleterious to the recipients thereof.

Formulations suitable for parenteral administration include aqueous and non-aqueous sterile injection solutions which may contain anti-oxidants, buffers, bacteriostats, and solutes which render the formulation isotonic with the blood of the intended recipient; and aqueous and non-aqueous sterile suspensions which may include suspending agents and thickening agents. Aqueous solutions may be suitably buffered (preferably to a pH of from about 3 to about 9). The preparation of suitable parenteral formulations under sterile conditions is readily accomplished by standard pharmaceutical techniques well-known to those skilled in the art.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the fusion protein, nucleic acid, rAAV and/or rLV and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the agents, can be dissolved and administered in a pharmaceutical excipient such as Water-for-Injection, 0.9% saline, or 5% glucose solution.

Any of the fusion proteins, nucleic acids, rAAVs, and/or rLVs disclosed herein may be administered by any administration route known in the art, such as parenteral administration, oral administration, buccal administration, sublingual administration (e.g., tablets, capsules, ovules, elixirs, solutions or suspensions, which may contain flavoring or coloring agents, for immediate-, delayed- or controlled-release applications) topical administration, or inhalation, in the form of a pharmaceutical formulation (e.g., comprising a composition) comprising the active ingredient, optionally in the form of a non-toxic organic, or inorganic, acid, or base, addition salt, in a pharmaceutically acceptable dosage form. Suitable tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the fusion proteins, nucleic acids, rAAVs, and/or rLVs of the disclosure may be combined with various sweetening or flavoring agents, coloring matter or dyes, with emulsifying and/or suspending agents and with diluents such as water, ethanol, propylene glycol and glycerin, and combinations thereof. Additionally, lubricating agents such as magnesium stearate, stearic acid, glyceryl behenate and tale may be included.

The formulations may be presented in unit-dose or multi-dose containers, for example scaled ampoules or vials, and may be stored in a freeze-dried (lyophilized) condition requiring only the addition of the sterile liquid carrier immediately prior to use.

In some embodiments, any of the fusion proteins, nucleic acids, rAAVs, and/or rLVs described herein can be administered to a subject in single or divided doses. In some embodiments, any of the fusion proteins, nucleic acids, rAAVs, and/or rLVs described herein is administered to a subject in a single dose. In some embodiments, any of the fusion proteins, nucleic acids, rAAVs, and/or rLVs described is administered to a subject in divided doses (e.g., multiple or sequential doses). In some embodiments, any of the fusion proteins, nucleic acids, rAAVs, and/or rLVs described herein can be administered to a subject at a dose of between 25 and 100 µg per subject or between 0.4 to 1.7 µg/kg per subject, administered in single or divided doses (e.g., multiple or sequential doses). A physician in any event may determine the actual dosage which will be most suitable for any subject, which will vary with the age, weight, and the particular indications (e.g., disease or disorder) to be treated or prevented.

Methods

In some aspects, the disclosure relates to a method of delivering at least one of the fusion proteins as disclosed herein, to multinucleate cells. Various examples of multinucleate cells exist throughout nature and are well known to the skilled artisan. Multinucleate cells can occur as part of a natural development, for example cells of the mammalian placenta, skeletal muscle, liver tissue, and osteoclasts of bone tissue.

In some embodiments, the multinucleate cells are mammalian. In some embodiments, the multinucleate cells are cells of the placenta. In some embodiments, the multinucleate cells are skeletal muscle cells. In some embodiments, the multinucleate cells are cells of the liver (e.g., hepatocytes). In some embodiments, the multinucleate cells are osteoclasts. In some embodiments, the multinucleate cells are human cells.

Multinucleate cells can also occur as the result of fusion of cells or as the result of exposure to a pathogen, for example Human Immuno-deficiency Virus (HIV). In some embodiments, the multinucleate cells are cells resulting from fusion of cells. In some embodiments, the multinucleate cells am cells resulting from exposure to a pathogen. In some embodiments, the multinucleate cells are cells resulting from exposure to IV.

In some aspects, the method comprises, administering at least one of the fusion protein as disclosed herein, at least one of the isolated nucleic acids as disclosed herein, at least one of the rAAVs as disclosed herein, at least one of the rLVs as disclosed herein, or at least one of the compositions as disclosed herein, to a subject.

In some aspects, the disclosure relates to a method of administering the fusion proteins, compositions, and/or isolated nucleic acids of the disclosure to a multinucleate tissue in a subject. In some embodiments, administration is directly to the tissue. In some embodiments, administration is by intravenous administration.

The term "subject," as used herein, refer to any organism in need of treatment or diagnosis using the subject matter herein. For example without limitation, subjects may include mammals and non-mammals. As used herein, a "mammal," refers to any animal constituting the class Mammalia (e.g., a human, mouse, rat, cat, dog, sheep, rabbit, horse, cow, goat, pig, guinea pig, hamster, chicken, turkey, or a non-human primate (e.g., Marmoset, Macaque)). In some embodiments, the subject in any of the methods as described herein is a mammal. In some embodiments, the subject is human.

In some embodiments, the subject has a disorder. In some embodiments, the disorder is a genetic disorder. In some embodiments, the disorder is muscular dystrophy. In some embodiments, the disorder is a genetically dominant muscle disorder. In some embodiments, the disorder is oculopharyngeal muscular dystrophy. In some embodiments, the disorder is Emery-Dreifuss muscular dystrophy. In some embodiments, the disorder is myotonic dystrophy. In some embodiments, the disorder is Facioscapulohumeral dystrophy. In some embodiments, the disorder is Charcot-Marie Tooth disease. In some embodiments, the disorder is Limb Girdle muscular dystrophy. In some embodiments, the disorder is Duchenne muscular dystrophy. In some embodiments, the disorder is a muscular dystrophy. To perform such a method, an effective amount of the fusion proteins, nucleic acids, rAAVs, and/or rLVs as described herein can be administered as described herein. The terms "effective amount," "therapeutically effective amount," and "pharmaceutically effective amount," as may be used interchangeably herein, refer to an amount of the fusion proteins, nucleic acids, rAAVs, and/or rLVs sufficient to elicit a desired biological response. For example, in some embodiments, an effective amount of a fusion protein, nucleic acid, rAAV, and/or rLV may refer to the amount of fusion proteins, nucleic acids, rAAVs, and/or rLVs sufficient to treat the disorder. The terms "treatment," "treat," and "treating." as may be used interchangeably herein, refer to a clinical intervention aimed to reverse, alleviate, delay the onset of, or inhibit the progress of a, indication, disease, disorder, or one or more symptoms thereof, as described herein. In some embodiments, treatment may be administered after one or more symptoms have developed and/or after a disease has been diagnosed. In other embodiments, treatment may be administered in the absence of symptoms (e.g., to prevent or delay onset of a symptom or inhibit onset or progression of a disease). For example, treatment may be administered to a susceptible individual (e.g., subject) prior to the onset of symptoms (e.g., in light of a history of symptoms and/or in light of genetic or other susceptibility factors). Treatment may also be continued after symptoms have resolved, for example, to prevent or delay their recurrence. As will be appreciated by the skilled artisan, the effective amount may vary depending on various factors as, for example, on the desired biological response (e.g., on the miRNA to be inhibited, the mRNA transcript to be promoted), on the cell or tissue being targeted, and on the agent, being used.

In some embodiments, any of the isolated nucleic acids of the disclosure, any of the fusion proteins of the disclosure, any of the vectors of the disclosure, and/or any of the compositions of the disclosure are administered intramuscularly. In some embodiments, any of the isolated nucleic acids of the disclosure, any of the fusion proteins of the disclosure, any of the vectors of the disclosure, and/or any of the compositions of the disclosure are administered intrathecally. In some embodiments, any of the isolated nucleic acids of the disclosure, any of the fusion proteins of the disclosure, any of the vectors of the disclosure, and/or any of the compositions of the disclosure are administered intravenously. In some embodiments, any of the isolated nucleic acids of the disclosure, any of the fusion proteins of the disclosure, any of the vectors of the disclosure, and/or any of the compositions of the disclosure are administered by retrograde intravenous administration. In some embodiments, the composition administered intravascularly. In some embodiments, any of the isolated nucleic acids of the disclosure, any of the fusion proteins of the disclosure, any of the vectors of the disclosure, and/or any of the compositions of the disclosure are administered systemically. In some embodiments, any of the isolated nucleic acids of the disclosure, any of the fusion proteins of the disclosure, any of the vectors of the disclosure, and/or any of the compositions of the disclosure are administered intra-arterially. In some embodiments, any of the isolated nucleic acids of the disclosure, any of the fusion proteins of the disclosure, any of the vectors of the disclosure, and/or any of the compositions of the disclosure are administered by intraportal administration. In some embodiments, any of the isolated nucleic acids of the disclosure, any of the fusion proteins of the disclosure, any of the vectors of the disclosure, and/or any of the compositions of the disclosure are administered by intratracheal administration. In some embodiments, any of the isolated nucleic acids of the disclosure, any of the fusion proteins of the disclosure, any of the vectors of the disclosure, and/or any of the compositions of the disclosure are administered by direct injection.

In some embodiments, the composition is formulated for intramuscular administration. In some embodiments, the composition is formulated for intrathecal administration. In some embodiments, the composition is formulated for intravenous administration. In some embodiments, the composition is formulated for retrograde intravenous administration. In some embodiments, the composition is formulated for intravascular administration. In some embodiments, the composition is formulated for systemic administration. In some embodiments, the composition is formulated for intraarterial administration. In some embodiments, the composition is formulated for intraportal administration. In some embodiments, the composition is formulated for intratracheal administration. In some embodiments, the composition is formulated for direct injection.

EXAMPLES

Example 1: Inclusion of a Nucleolar Localization Sequence (NoLS) Increases Transduction of Multiple Nuclei in Multi-Nucleated Cells C2C12 mouse myoblasts were transfected with the experimental GFP plasmid constructs and allowed to fuse. Due to the inefficient nature of transient transfection and the fact that many nuclei never receive the plasmid, imaging of GFP distribution within the fused tubes reveals the ability of each construct to spread throughout the myotubes. Myotubes were imaged after several days of fusion in culture.

TABLE 1

| | | Experimental Plasmid Constructs | | | |
| Plasmid ID | NLS Strength | NLS SEQ ID NO: | NES Strength | NES SEQ ID NO: | NoLS SEQ ID NO: |
| --- | --- | --- | --- | --- | --- |
| NCT_GFP_017 | Weak | 1 | ALYREF | 3 | N/A |
| NCT_GFP_018 | Strong | 2 | ALYREF | 3 | N/A |
| NCT_GFP_020 | Weak | 1 | ALYREF | 3 | 5 |
| NCT_GFP_021 | Strong | 2 | Weak P53 | 4 | N/A |

Example 2: Relative Strength of Signal Tags Affects Expression In Vitro

Figure 5C:
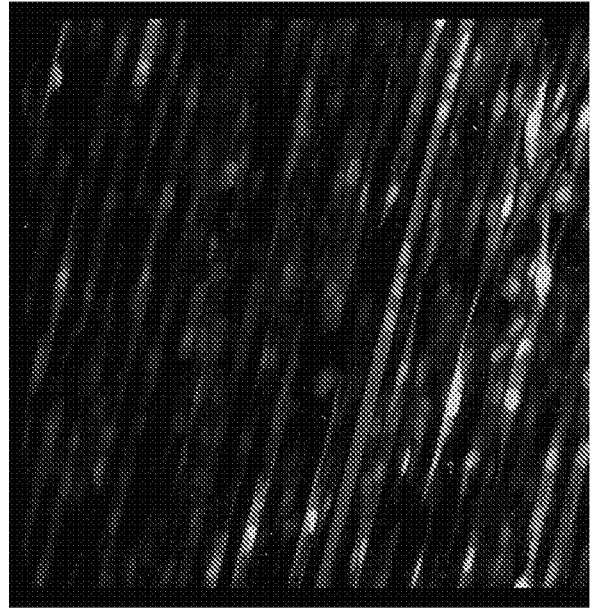
FIG. 5C shows a construct using NCT20, using a mutated SV40 NLS (SEQ ID NO: 3) and Alyref NES+Rev NuLS (SEQ ID NO: 1).
Figure 6A:
FIGS. 6A-6L show the results of an in vivo study using either construct 1: CBh promoter driving SV40 NLS-EGFP (PKKKRKV: SEQ ID NO: 5) or construct 2: CBh promoter driving NLS-EGFP-NES-NuLS (NCT20; SEQ ID NO: 11). Constructs were injected into tibialis anterior (TA) of C57BL6 mice at two different doses. TA fibers were harvested at either 3 or 8 weeks and imaged using fluorescence in situ hybridization against EGFP. Construct, dose, and time period are indicated on each figure. Imaging was performed using tile scans with 20× dry objective magnification.
Figure 6B:
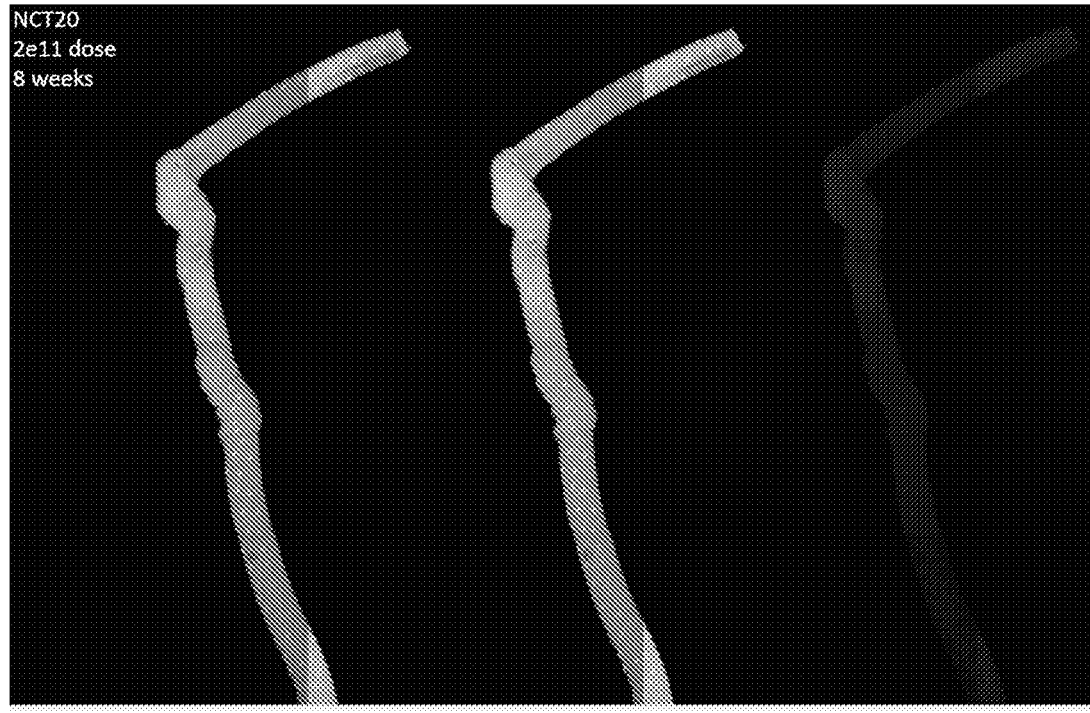
Figure 6C:
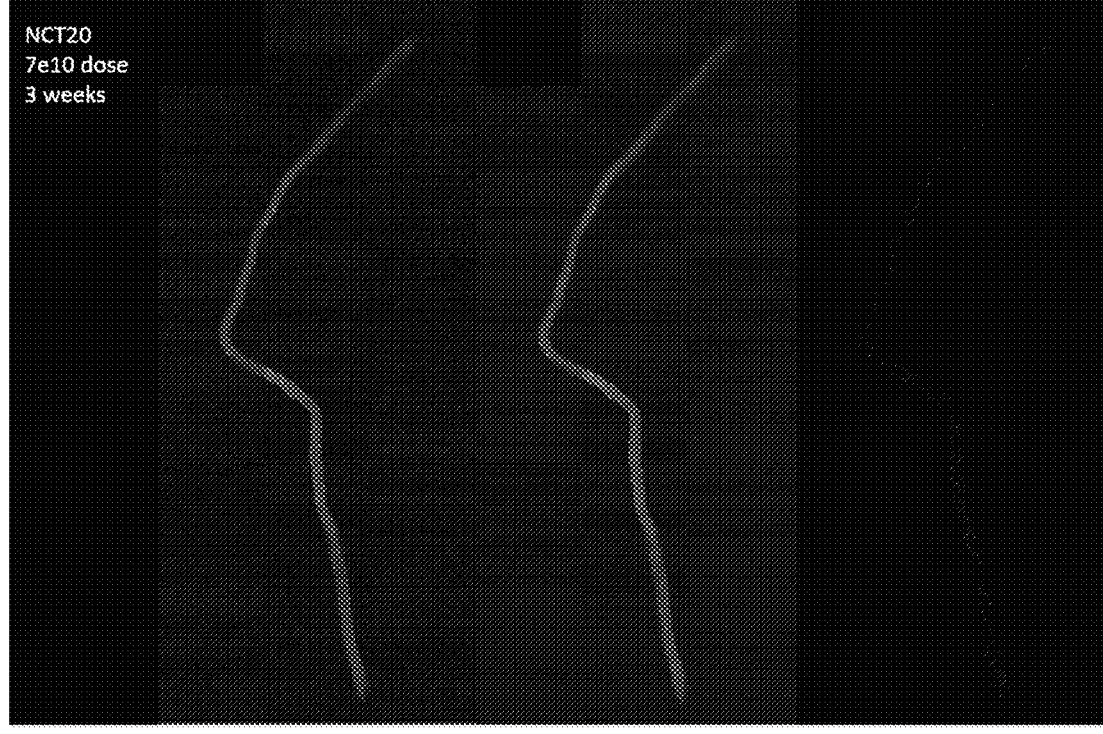
Figure 6D:
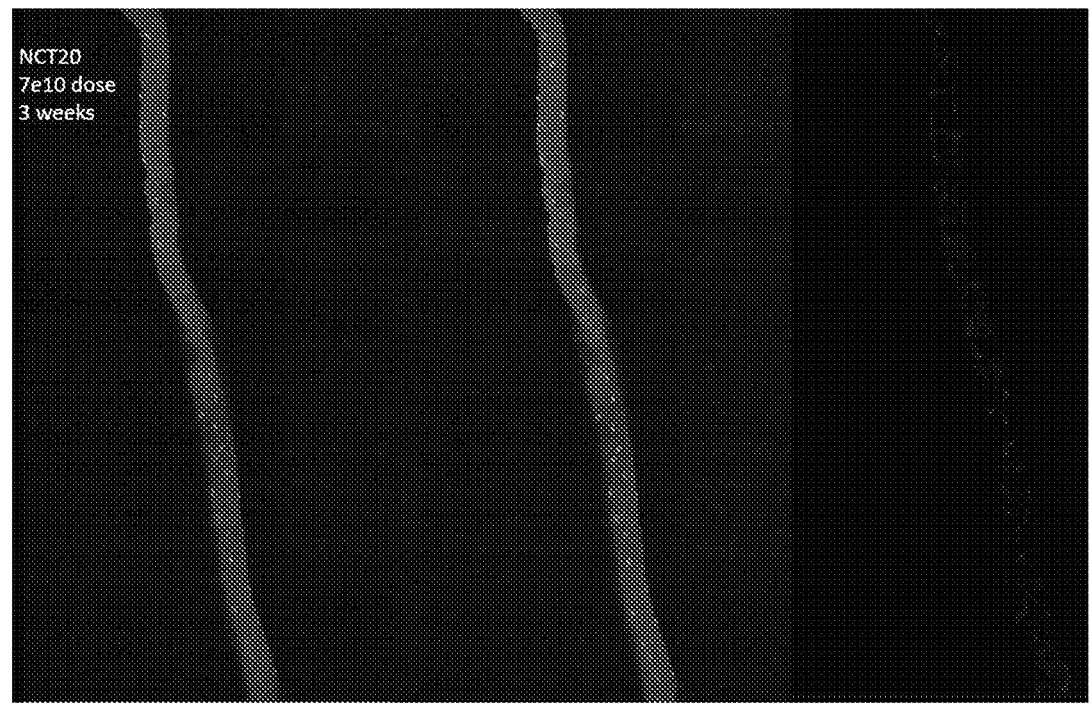
Figure 6E:
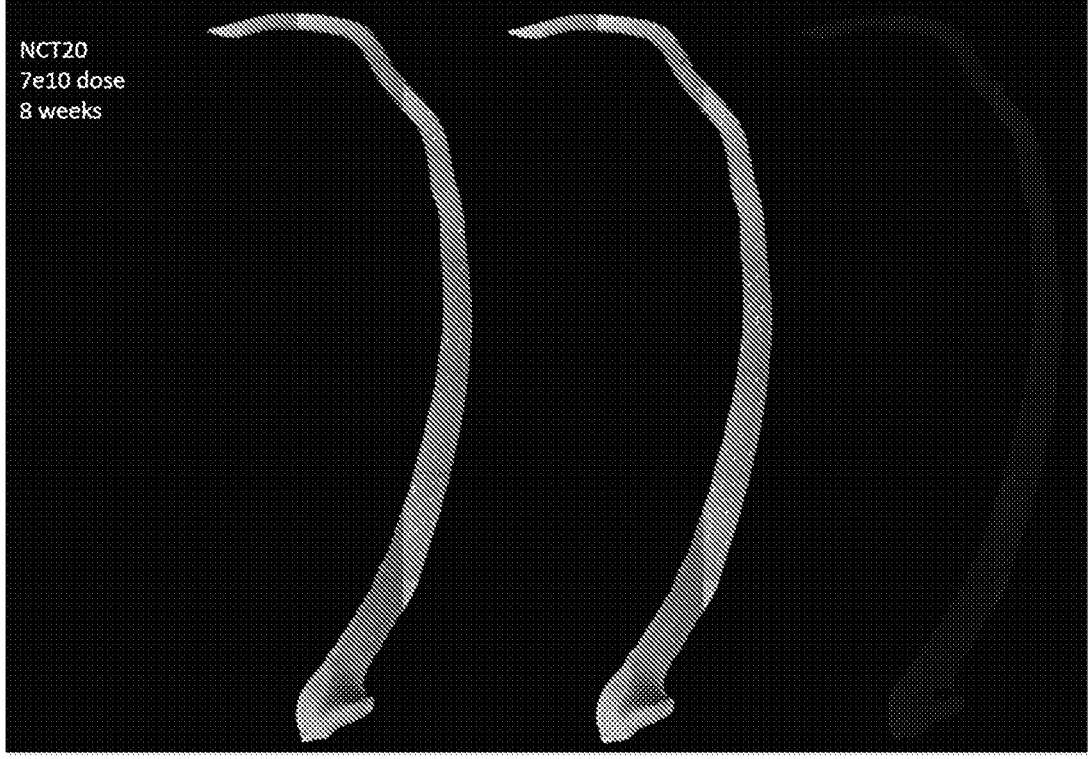
Figure 6F:
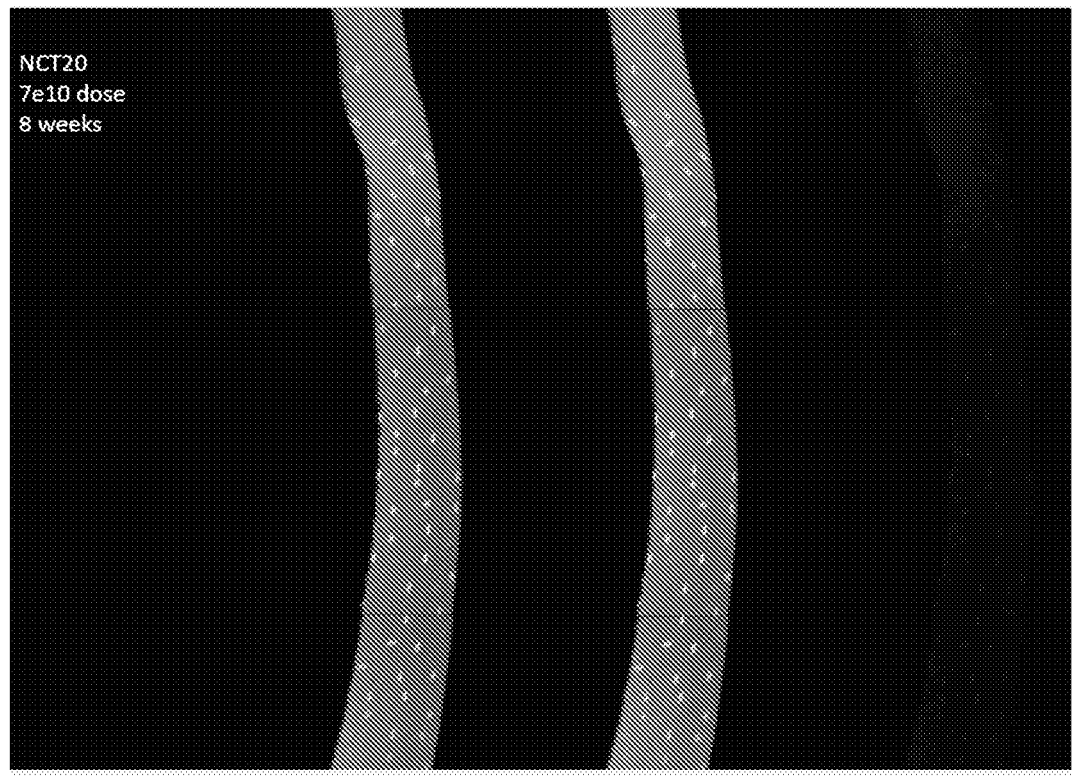
Figure 6G:
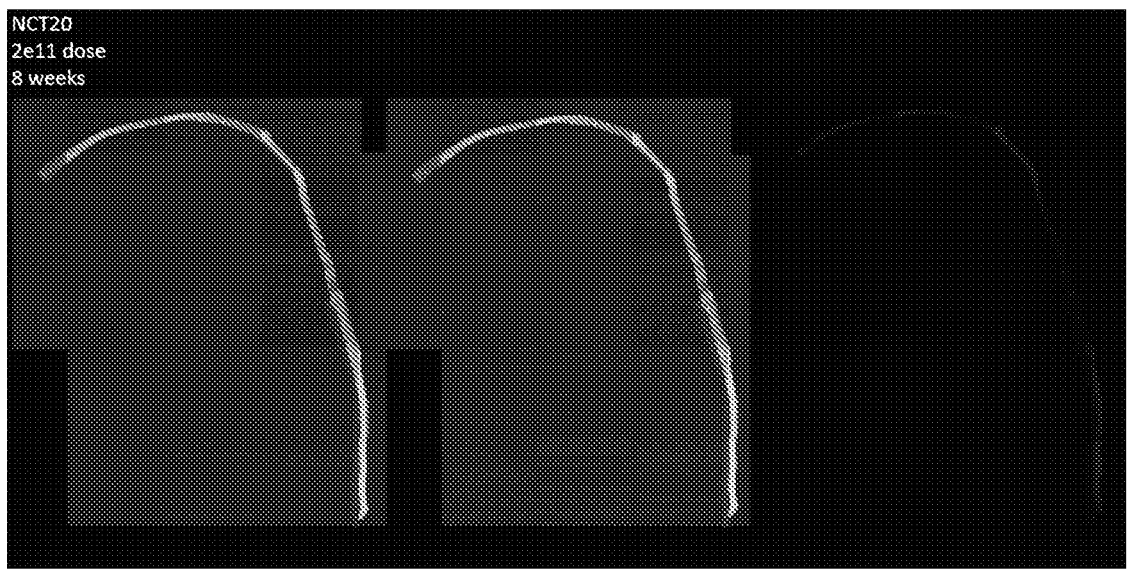
Figure 6H:
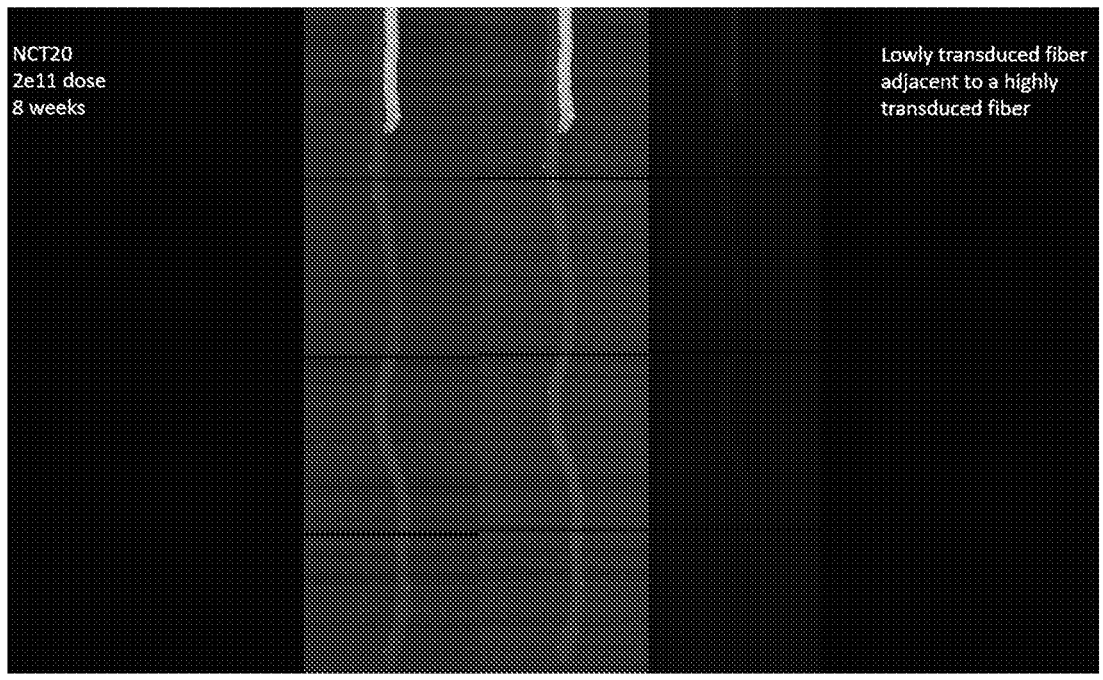
Figure 6I:
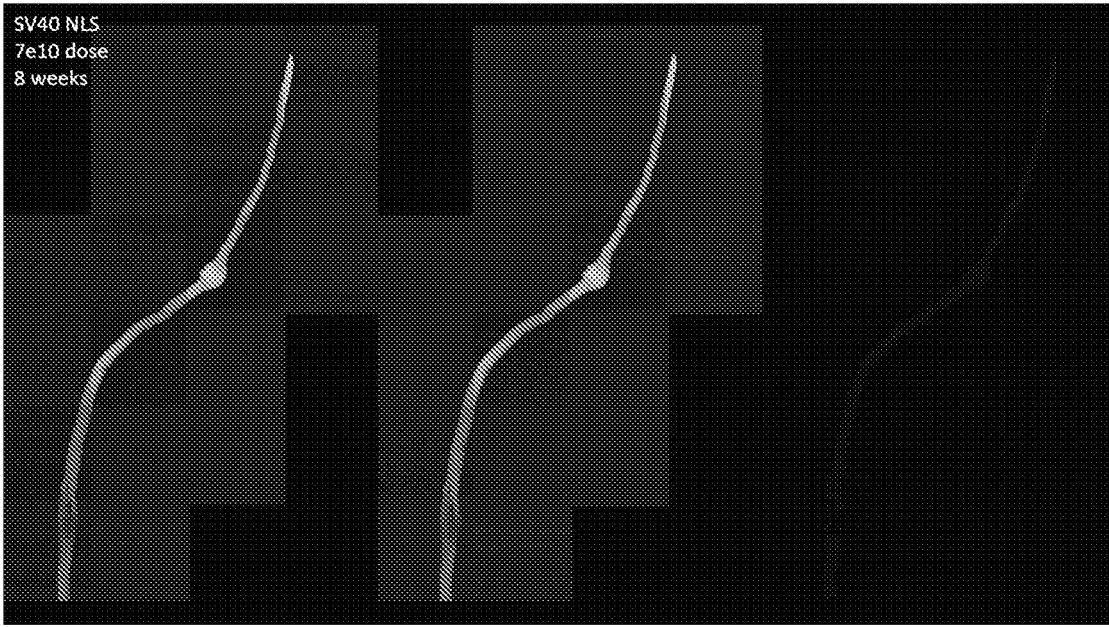
Figure 6J:
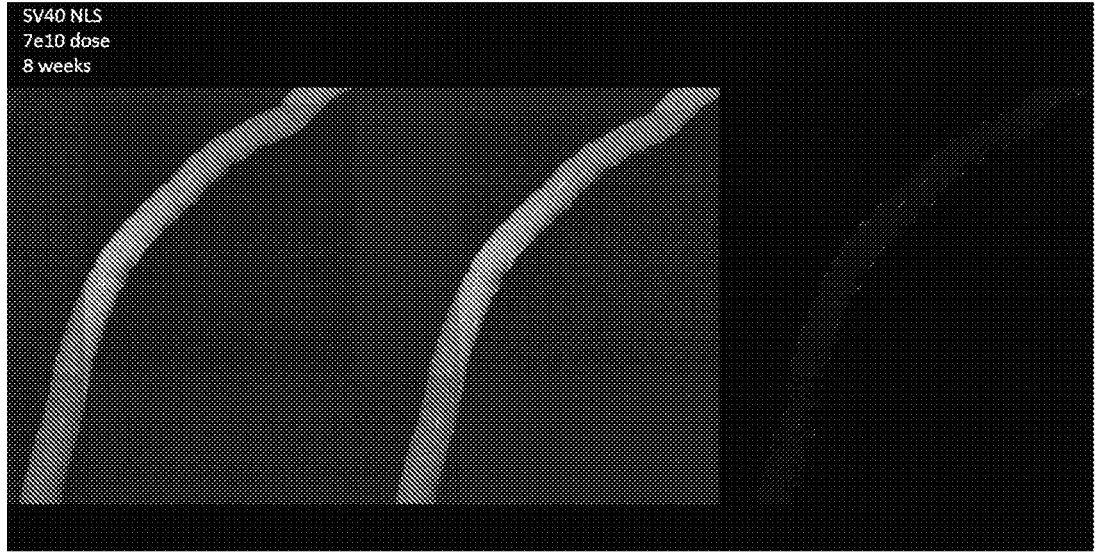
Figure 6K:
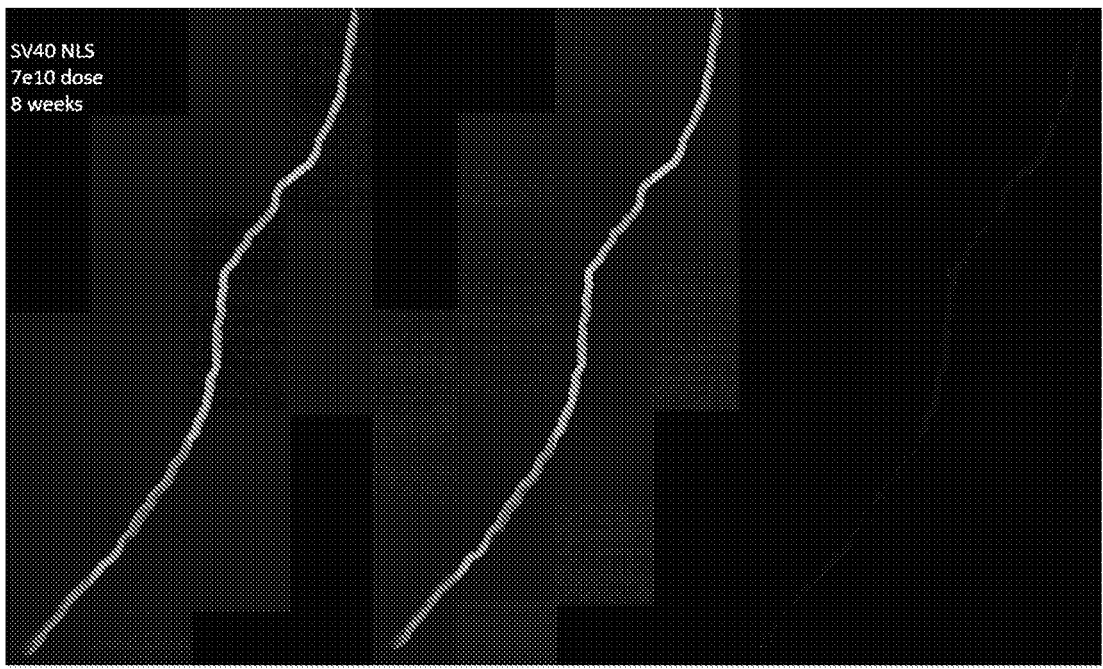
Figure 6L:
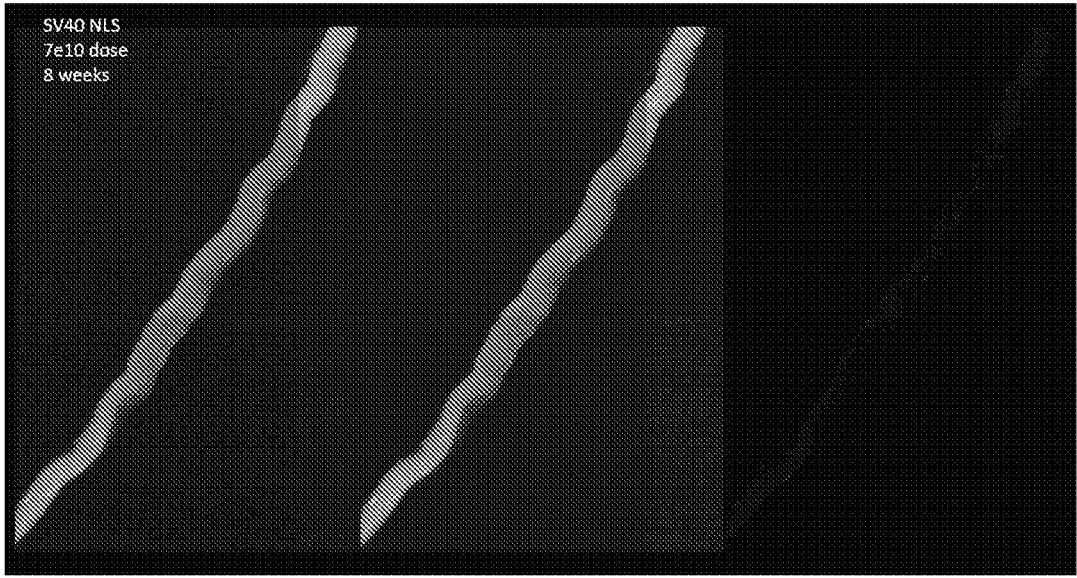
Figure 7A:
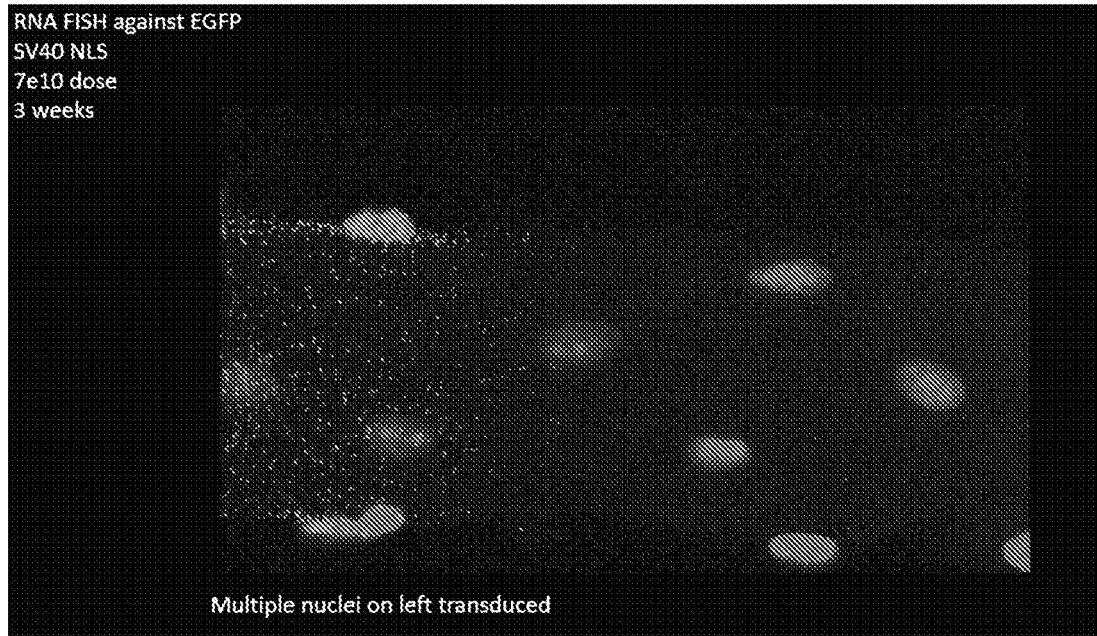
Figure 7B:
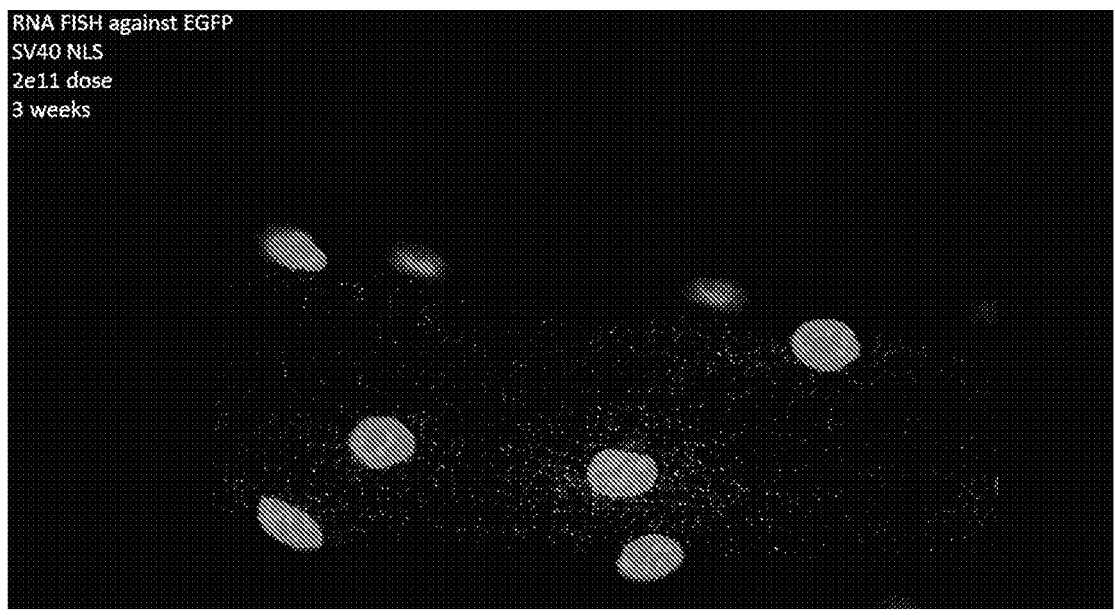
Figure 7C:
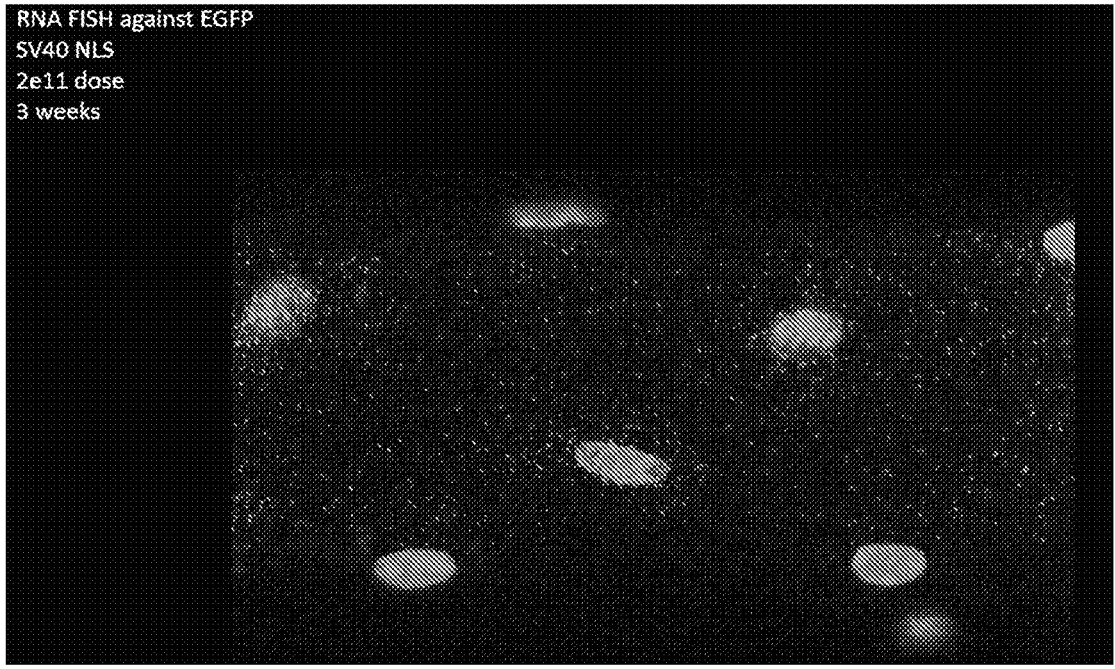
Figure 7D:
Figure 7E:
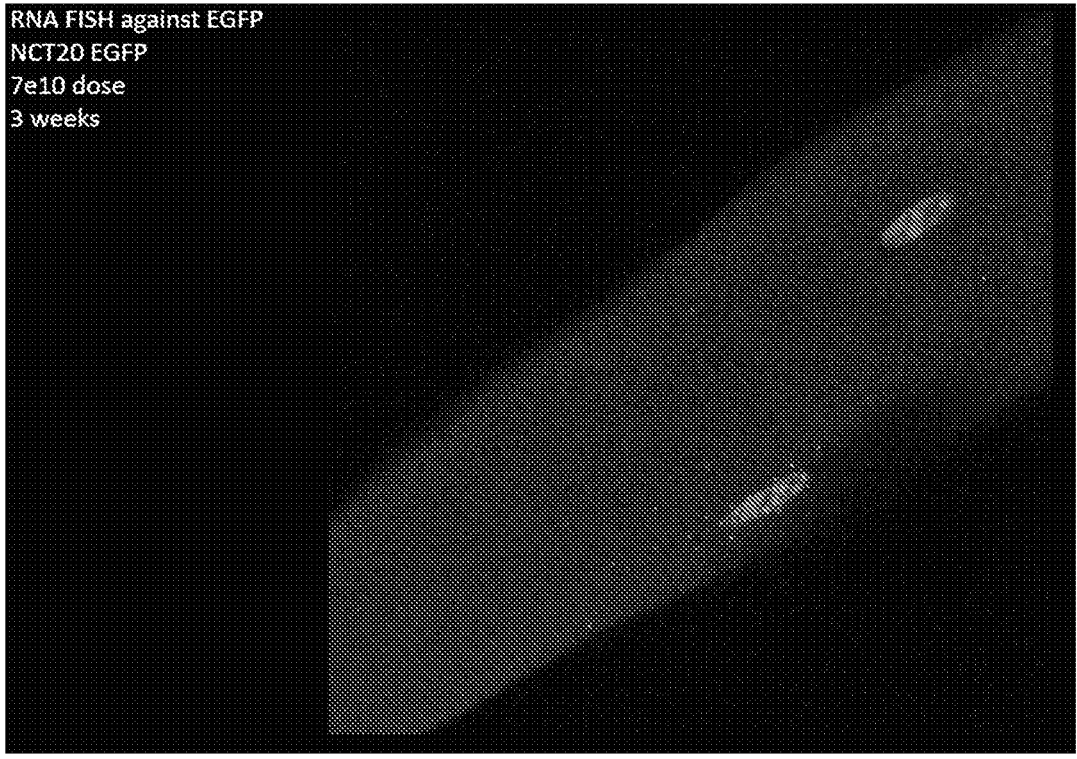
Figure 7F:
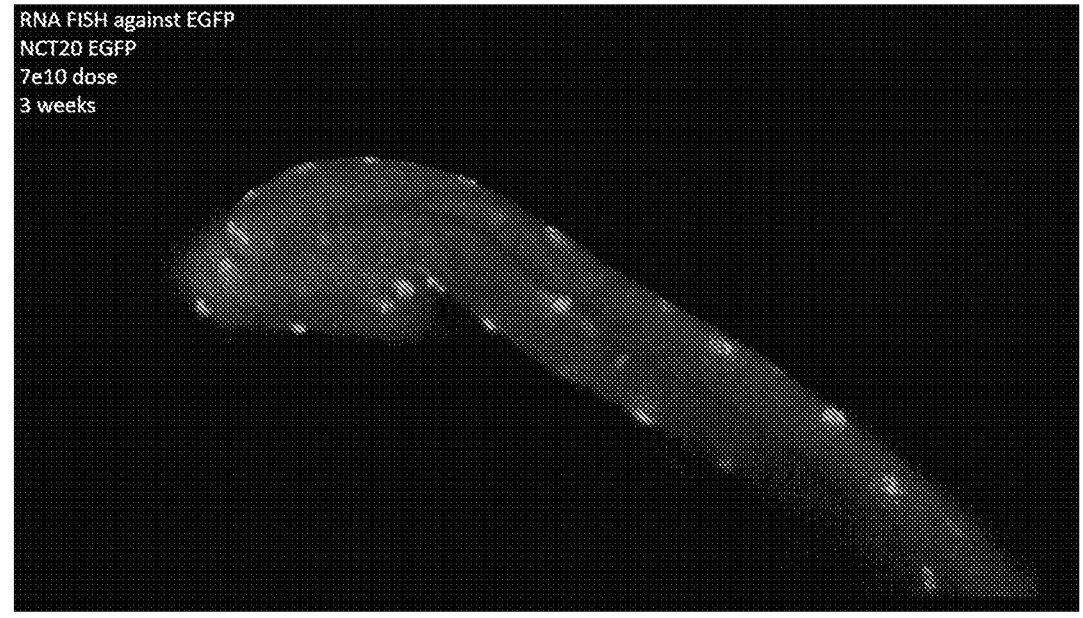
Figure 7G:

Stable C2C12 were generated in which EGFP is stably expressed. Various Nuclear Localization Sequences (NLS) or Nuclear Export Sequences (NES) were attached to EGFP (an EF1alpha promoter was used to drive EGFP expression). Cells were mixed 50:50 with non-expressing C2C12 cells and fused on gelatin micro-molds to enhance fusion and alignment Myotubes were imaged on day 8 post-serum withdrawal (FIGS. 5A-5C). Various constructs were imaged, constructs where the NLS was weaker than the NES (FIGS. 5A and 5C) and where the NLS was approximately equal strength to the NES (FIG. 5B). As is shown, where the NLS was weaker than the NES, increased proliferation of EGFP among the nuclei was observed (FIGS. 5A and 5C) relative to equal strength tags (FIG. 5B).

Example 3: Adeno-Associated Viral Constructs Transduce Multinucleated Cells In Vivo Two constructs were made: construct 1: CBh promoter driving SV40 NLS-EGFP (PKKKRKV (SEQ ID NO: 5)); and construct 2: CBh promoter driving NLS-EGFP-NES-NuLS (NCT20 (SEQ ID NO: 11)). Each used an AAV6 capsid protein.

The constructs were administered in two doses, either $7\times10^{10}$ viral genome (vg) total or $2\times10^{11}$ vg total. Doses were delivered via intramuscular injection into the tibialis anterior (TA) of C57BL6 mice. Tibialis Anterior fibers were harvested at two time periods, either 3 weeks or 8 weeks post injection. Fibers were analyzed using immunofluorescence and fluorescent in situ hybridization (FISH) using RNA ainst EGFP (FIGS. 6A-6L and FIGS. 7A-7H). Native EGFP was also imaged for some fibers. Fibers were assessed for EGFP expression and stained using DAPI (FIGS. 6A-6L, EGFP shown in leftmost panels/fibers; DAPI shown in rightmost panels/fibers: merged in center panels/fibers), as well as using FISH (FIGS. 7A-7H). Highly and lowly transduced fibers observed in both dosage groups.

Example 4. Application of Nuclear Spreading to Facioscapulohumeral Muscular Dystrophy (FSHD)

Facioscapulohumeral muscular dystrophy (FSHD) is a muscular dystrophy characterized by weakness of facial muscles, scapula, shoulder blades, upper arms, other muscles. Broad range of disease severity, with muscle weakness often presenting asymmetrically, which is caused by aberrant expression of DUX4 in muscle.

Figure 8B:
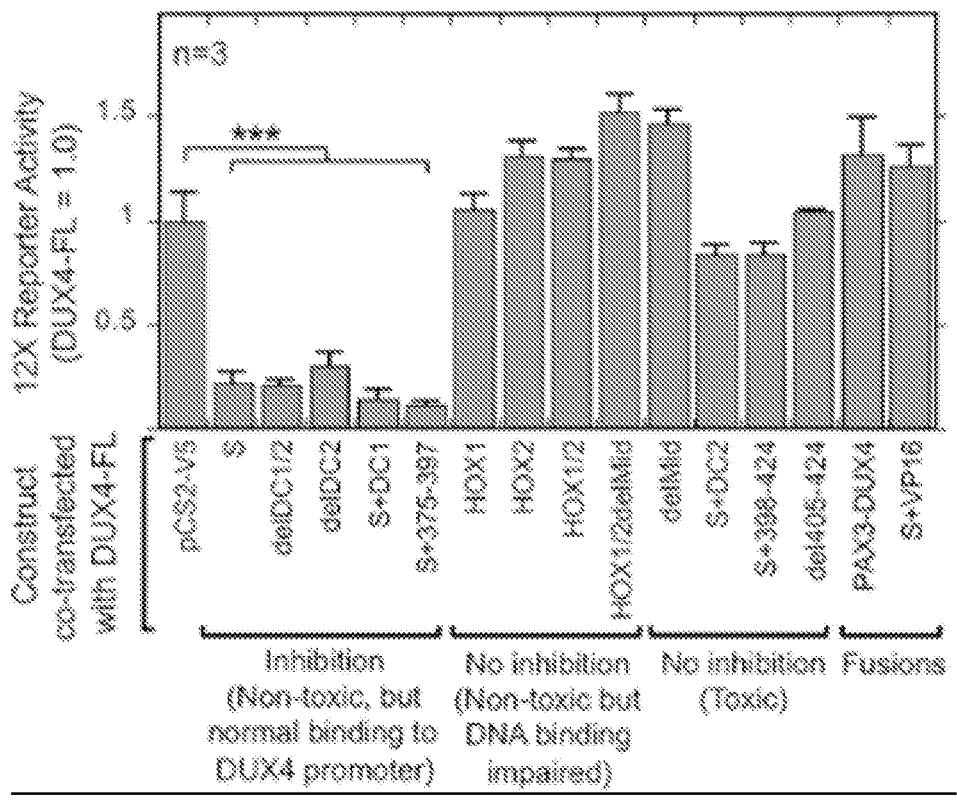
Figure 8C:
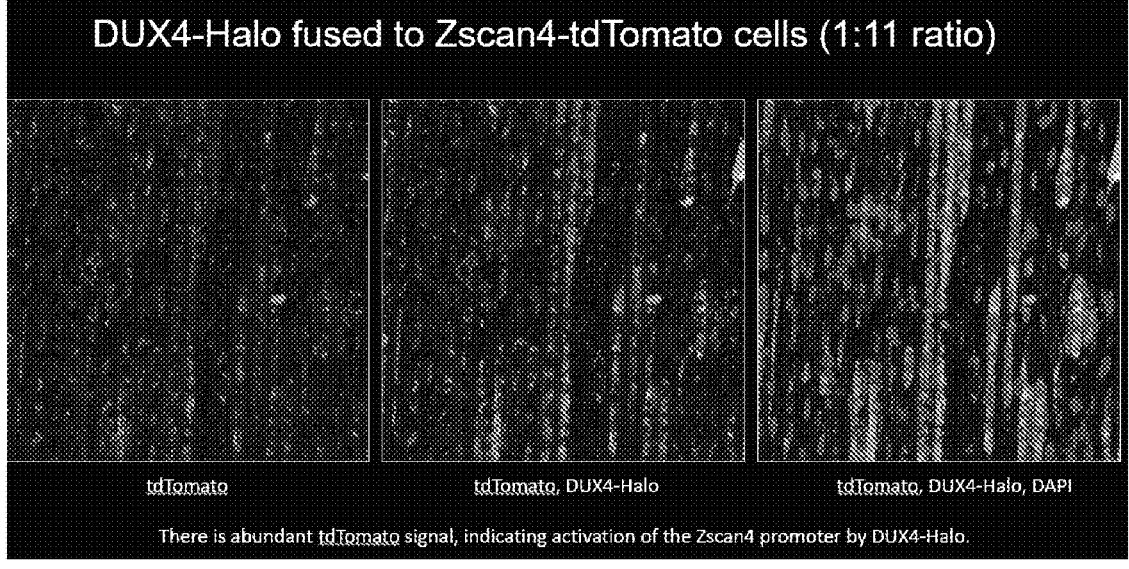
Figure 8D:
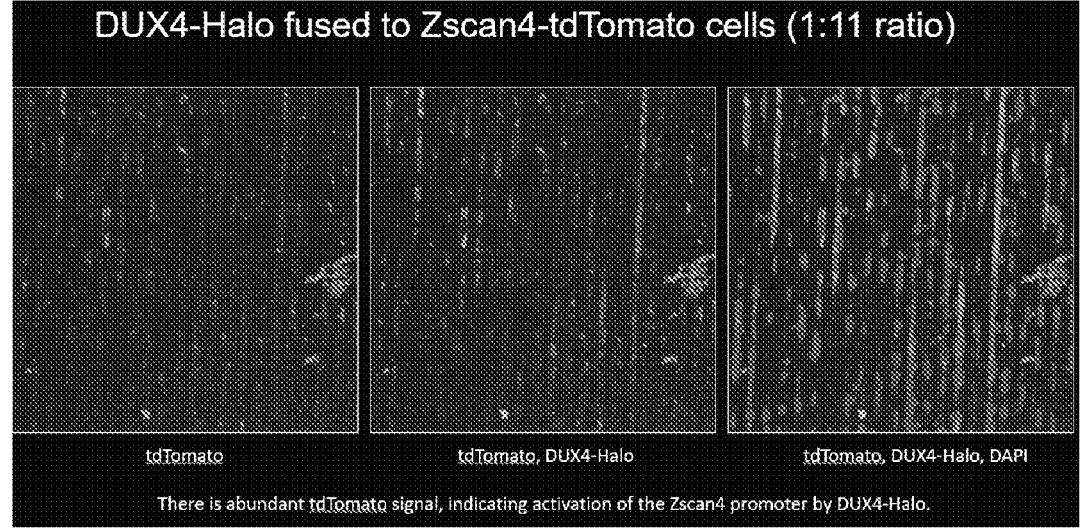
Figure 8E:
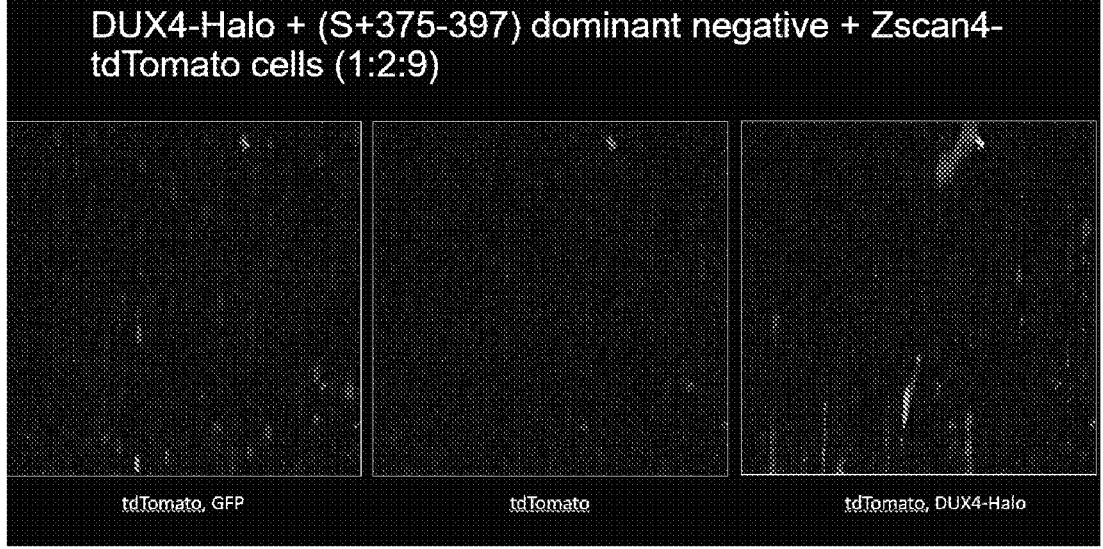
Figure 8F:
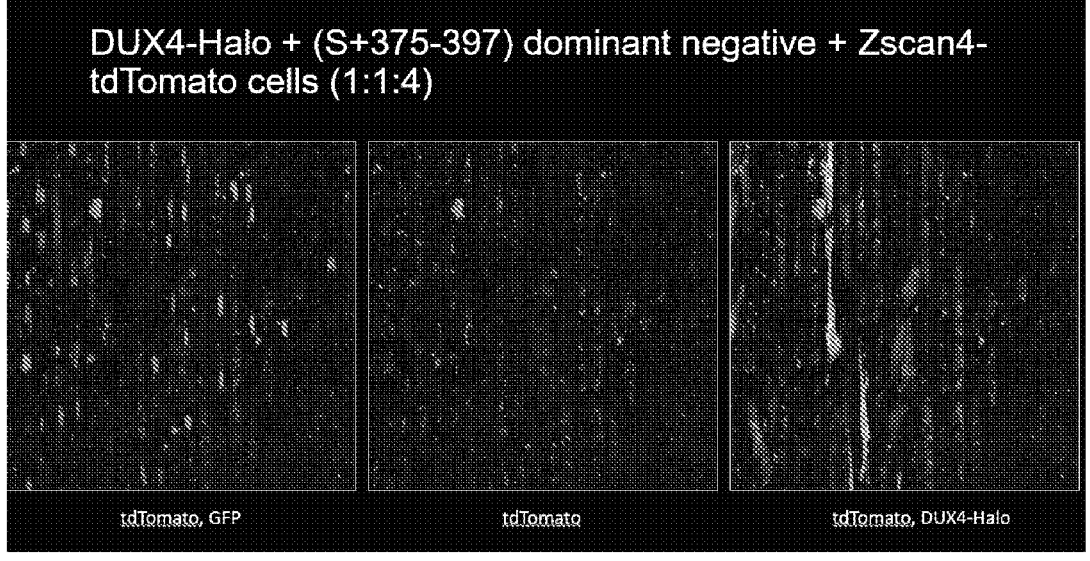
Figure 8G:
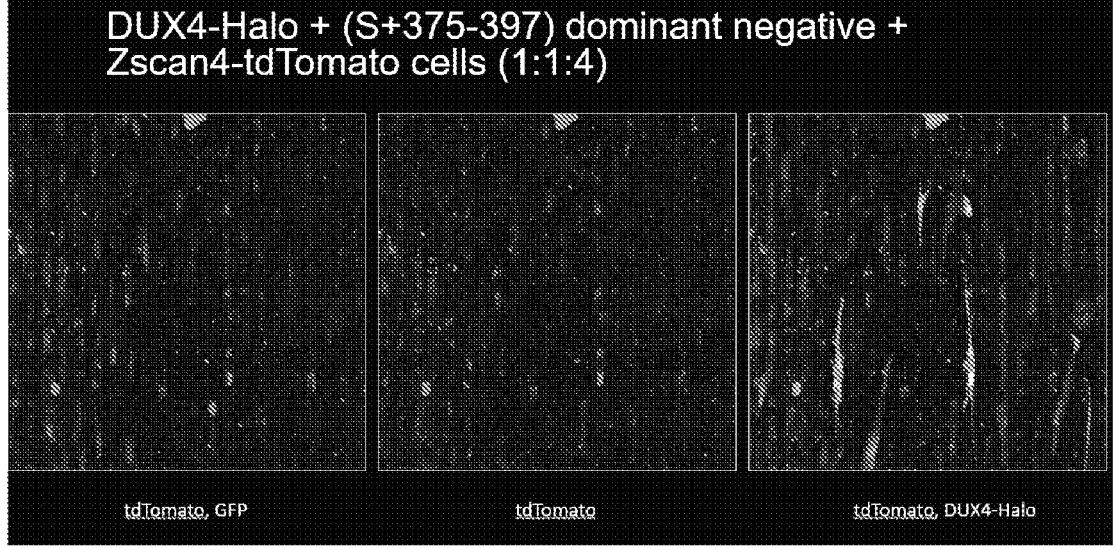
Figure 8H:
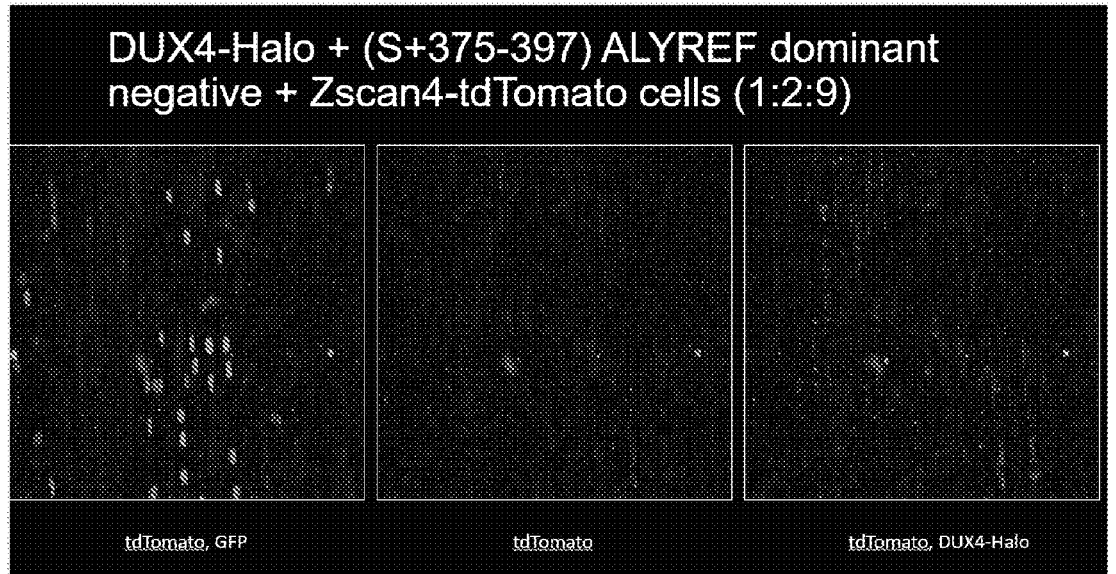
Figure 8I:
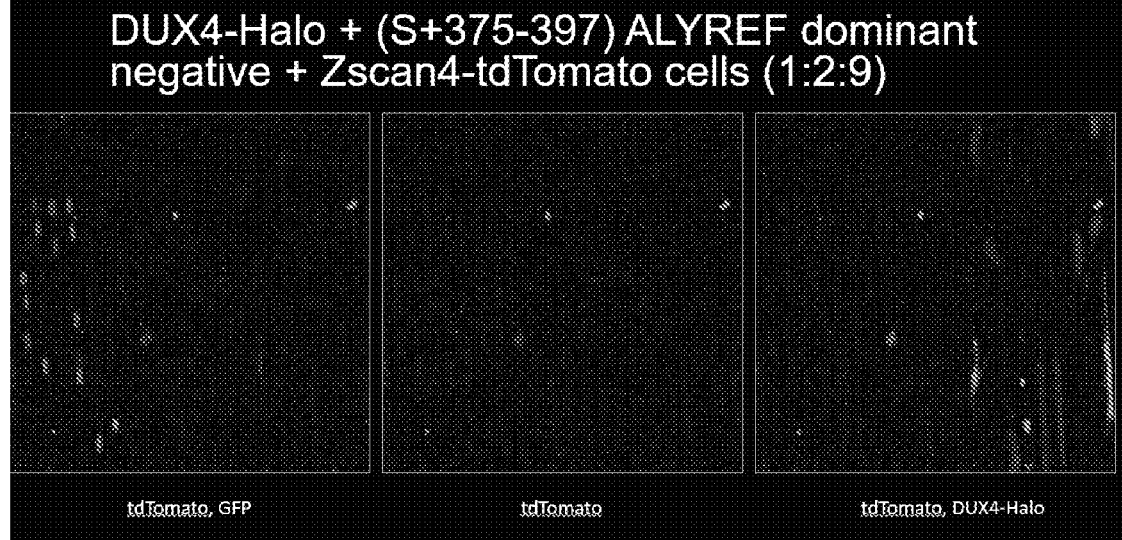
Figure 8J:
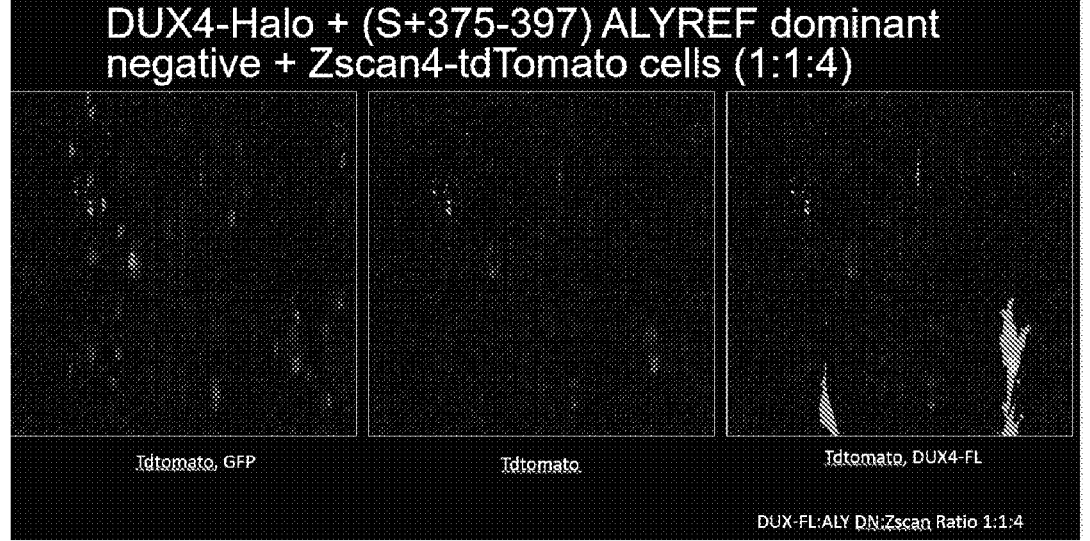

A DUX4 Dominant Negative can compete with full length DUX4 to prevent DUX4-mediated transcription. One such construct is S+375-397 DUX4, which contains HOX1 and HOX2 DNA binding domains, which but only part of the C-terminal domain (FIG. 8A). This construct was identified by Mitsuhashi et al. as a potential inhibitory construct which can bind the DUX4 promoter without being toxic to cells (FIG. 8B).

Muscle cells include cells including multiple nuclei, thus a DUX4 dominant negative may require efficient spreading to multiple myonuclei. Thus, if delivered by AAV, not all myonuclei will generate DUX4 dominant negative RNA, and if the DUX4 dominant negative has nuclear localization activity, then activity of the dominant negative will be limited to only a few nuclei. Addition of nuclear export sequences may enable the DUX4 dominant negative to spread across the myofiber.

Experimental Design

C2C12 mouse myoblast stable cell lines created and used: Reporter cell line containing Zscan4 promoter driving tdTomato (Zscan4 is a promoter activated by DUX4): cell line that contains tet-inducible DUX4-Halo (Halo is a fluorescent protein that can be visualized upon addition of a small molecule dye); cell line that stably expresses S+375-397 DUX4 dominant negative fused to GFP; and Cell line that stably expresses S+375-397 DUX4 dominant negative fused to GFP (SEQ ID NO: 12) and an ALYREF nuclear export signal (SEQ ID NO: 13).

Cells lines were plated at varying ratios onto a gelatin substrate that facilitates formation of myotubes. The cells were then differentiated into myotubes; each myotube contains a mixture of nuclei from all the different cell lines. Once differentiated (7 days post serum withdrawal), DUX4-Halo is induced with doxycycline-containing media (500 nanograms per milliliter (ng/ml))

Myotubes were imaged 72 hours following doxycycline induction (FIGS. 8C-8J). S+375-397 dominant negative prevents binding of DUX4-Halo to the Zscan promoter, limiting expression of tdTomato, with the ALYREF construct performing more efficiently.

Conclusions

The ALYREF dominant negative fusion prevents tdTomato expression more effectively than the dominant negative without the ALYREF sequence providing enhanced nuclear-cytoplasmic trafficking which is beneficial to limit DUX4 transcriptional activation (FIGS. 8A-8J).

Exemplary Sequences

This Table exhibits some exemplary sequences as disclosed by the instant Specification, but is not limiting. This Specification includes a Sequence Listing submitted concurrently herewith as a text file in ASCII format. The Sequence Listing and all of the information contained therein are expressly incorporated herein and constitute part of the instant Specification as filed.

TABLE 2

| Exemplary Sequences | | |
| --- | --- | --- |
| SEQ ID NO: | Sequence* | Description** |
| 1 | APPAQPPSQPQQHYSEGELEEDEDSDDA | NES (ALYREF)- NCT_GFP_017; NCT_GFP_018; NCT_GFP_020 (AA) ("Alyref NES + Rev NuLS") |
| 2 | RFEMFRELNEALELKDA | NES (weak P53) - NCT_GFP_021 (AA) |
| 3 | PKKKRAVE | NLS (weak) - NCT_GFP_017; NCT_GFP_020 (AA) "Mutated SV40 NLS" |
| 4 | MPKKKRAVE | NLS (weak) |
| 5 | PKKKRKV | NLS (strong) - NCT_GFP_018; NCT_GFP_021 (AA) |
| 6 | RKKRKKK | NoLS- NCT_GFP_020 (AA) |
| 7 | MVSKGEELFTGVVPILVELDGDVNGHKFSVSGEGE GDATYGKLTLKFICTTGKLPVPWPTLVTTLTYGVQ CFSRYPDHMKQHDFFKSAMPEGYVQERTIFFKDDG NYKTRAEVKFEGDTLVNRIELKGIDFKEDGNILGH KLEYNYNSHNVYIMADKQKNGIKVNFKIRHNIEDG SVQLADHYQQNTPIGDGPVLLPDNHYLSTQSALSK DPNEKRDHMVLLEFVTAAGITLGMDELYKGTAAA | eGFP (AA) |
| 8 | MIEQDGLHAGSPAAWVERLFGYDWAQQTIGCSDAA VFRLSAQGRPVLFVKTDLSGALNELQDEAARLSWL ATTGVPCAAVLDVVTEAGRDWLLLGEVPGQDLLSS HLAPAEKVSIMADAMRRLHTLDPATCPFDHQAKHR IERARTRMEAGLVDQDDLDEEHQGLAPAELFARLK ARMPDGEDLVVTHGDACLPNIMVENGRFSGFIDCG RLGVADRYQDIALATRDIAEELGGEWADRFLVLYG IAAPDSQRIAFYRLLDEFF | Aminoglycoside 3' phosphotransferase (AA) |
| 9 | MSIQHFRVALIPFFAAFCLPVFAHPETLVKVKDAE DQLGARVGYIELDLNSGKILESFRPEERFPMMSTF KVLLCGAVLSRIDAGQEQLGRRIHYSQNDLVEYSP VTEKHLTDGMTVRELCSAAITMSDNTAANLLLTTI GGPKELTAFLHNMGDHVTRLDRWEPELNEAIPNDE RDTTMPVAMATTERKLLTGELLTLASRQQLIDWME ADKVAGPLLRSALPAGWFIADKSGAGERGSRGIIA ALGPDGKPSRIVVIYTTGSQATMDERNRQIAEIGA SLIKHW | beta-lactamase (AA) |
| 10 | GACGGATCGGGAGATCTCCCGATCCCCTATGGTGC ACTCTCAGTACAATCTGCTCTGATGCCGCATAGTT AAGCCAGTATCTGCTCCCTGCTTGTGTGTTGGAGG TCGCTGAGTAGTGCGCGAGCAAAATTTAAGCTACA ACAAGGCAAGGCTTGACCGACAATTGCATGAAGAA TCTGCTTAGGGTTAGGCGTTTTGCGCTGCTTCGCG | /gene = "bla" /locus_tag = "AmpR promoter" /label = "AmpR promoter" /ApEinfo_label = "Amp |

TABLE 2-continued

Exemplary Sequences

| SEQ ID NO: | Sequence* | Description** |
|---|---|---|
| | ATGTACGGGCCAGATATACGCGTTGACATTGATTA<br>TTGACTAGTTATTAATAGTAATCAATTACGGGGTC<br>ATTAGTTCATAGCCCATATATGGAGTTCCGCGTTA<br>CATAACTTACGGTAAATGGCCCGCCTGGCTGACCG<br>CCCAACGACCCCCGCCCATTGACGTCAATAATGAC<br>GTATGTTCCCATAGTAACGCCAATAGGGACTTTCC<br>ATTGACGTCAATGGGTGGAGTATTTACGGTAAACT<br>GCCCACTTGGCAGTACATCAAGTGTATCATATGCC<br>AAGTACGCCCCCTATTGACGTCAATGACGGTAAAT<br>GGCCCGCCTGGCATTATGCCCAGTACATGACCTTA<br>TGGGACTTTCCTACTTGGCAGTACATCTACGTATT<br>AGTCATCGCTATTACCATGGTGATGCGGTTTTGGC<br>AGTACATCAATGGGCGTGGATAGCGGTTTGACTCA<br>CGGGGATTTCCAAGTCTCCACCCCATTGACGTCAA<br>TGGGAGTTTGTTTTGGCACCAAAATCAACGGGACT<br>TTCCAAAATGTCGTAACAACTCCGCCCCATTGACG<br>CAAATGGGGGGTAGGCGTGTACGGTGGGAGGTCTA<br>TATAAGCAGAGCTCTCTGGCTAACTAGAGAACCCA<br>CTGCTTACTGGCTTATCGAAATTAATACGACTCAC<br>TATAGGGAGACCCAAGCTGGCTAGCGTTTAAACTT<br>AAGCTTATGCCCAAAAAGAAAAGAGCCGTGGAAGG<br>ATCCGAATTCATGGTTTCTAAGGGGGAAGAGCTTT<br>TCACGGGAGTCGTCCCGATTCTGGTGGAGTTGGAC<br>GGGGATGTTAATGGTCACAAGTTCTCCGTCAGTGG<br>TGAGGGGGAGGGGGATGCGACCTACGGCAAACTGA<br>CTTTGAAGTTTATATGCACAACAGGCAAACTTCCC<br>GTACCCTGGCCTACTTTGGTGACTACGCTTACATA<br>CGGGGTCCAGTGCTTCAGTAGATATCCAGATCACA<br>TGAAGCAGCACGATTTTTTTAAAAGCGCCATGCCA<br>GAGGGCTATGTTCAAGAGAGGACAATTTTCTTCAA<br>GGATGACGGCAACTACAAAACTCGGGCTGAGGTCA<br>AATTTGAAGGAGATACGCTGGTGAACAGGATAGAA<br>CTGAAGGGAATTGACTTCAAGGAGGATGGAAATAT<br>TCTCGGGCATAAATTGGAGTATAACTACAATTCTC<br>ATAACGTTTACATTATGGCCGATAAACAAAAAAAT<br>GGTATAAAGGTTAACTTCAAAATTCGGCATAACAT<br>AGAGGACGGGTCAGTGCAGCTCGCAGACCATTACC<br>AGCAAAATACGCCGATAGGTGATGGGCCGGTTCTT<br>TTGCCTGATAATCACTACCTCAGCACACAGAGTGC<br>CCTCAGCAAAGACCCAAACGAAAAACGAGATCATA<br>TGGTGCTCCTGGAATTTGTTACAGCGGCAGGAATA<br>ACACTGGGAATGGACGAACTTTACAAGGGTACCGC<br>GGCCGCAGCTCCTCCGGCACAACCTCCCAGCCAAC<br>CTCAGCAGCATTATAGCGAAGGAGAGTTGGAGGAA<br>GATGAAGATTCTGATGACGCGCGCAAAAAACGCAA<br>AAAAAAATAAGTGACTCGAGTCTAGAGGGCCCGTT<br>TAAACCCGCTGATCAGCCTCGACTGTGCCTTCTAG<br>TTGCCAGCCATCTGTTGTTTGCCCCTCCCCCGTGC<br>CTTCCTTGACCCTGGAAGGTGCCACTCCCACTGTC<br>CTTTCCTAATAAAATGAGGAAATTGCATCGCATTG<br>TCTGAGTAGGTGTCATTCTATTCTGGGGGGTGGGG<br>TGGGGCAGGACAGCAAGGGGGAGGATTGGGAAGAC<br>AATAGCAGGCATGCTGGGGATGCGGTGGGCTCTAT<br>GGCTTCTGAGGCGGAAAGAACCAGCTGGGGCTCTA<br>GGGGGTATCCCCACGCGCCCTGTAGCGGCGCATTA<br>AGCGCGGGGGGTGTGGTGGTTACGCGCAGCGTGAC<br>CGCTACACTTGCCAGCGCCCTAGCGCCCGCTCCTT<br>TCGCTTTCTTCCCTTCCTTTCTCGCCACGTTCGCC<br>GGCTTTCCCCGTCAAGCTCTAAATCGGGGGCTCCC<br>TTTAGGGTTCCGATTTAGTGCTTTACGGCACCTCG<br>ACCCCAAAAAACTTGATTAGGGTGATGGTTCACGT<br>AGTGGGCCATCGCCCTGATAGACGGTTTTTCGCCC<br>TTTGACGTTGGAGTCCACGTTCTTTAATAGTGGAC<br>TCTTGTTCCAAACTGGAACAACACTCAACCCTATC<br>TCGGTCTATTCTTTTGATTTATAAGGGATTTTGCC<br>GATTTCGGCCTATTGGTTAAAAAATGAGCTGATTT<br>AACAAAAATTTAACGCGAATTAATTCTGTGGAATG<br>TGTGTCAGTTAGGGTGTGGAAAGTCCCCAGGCTCC<br>CCAGCAGGCAGAAGTATGCAAAGCATGCATCTCAA<br>TTAGTCAGCAACCAGGTGTGGAAAGTCCCCAGGCT<br>CCCCAGCAGGCAGAAGTATGCAAAGCATGCATCTC<br>AATTAGTCAGCAACCATAGTCCCGCCCCTAACTCC<br>GCCCATCCCGCCCCTAACTCCGCCCAGTTCCGCCC<br>ATTCTCCGCCCCATGGCTGACTAATTTTTTTTATT | R promoter"<br>/ApEinfo_fwdcolor = "pink"<br>/ApEinfo_revcolor = "pink"<br>/ApEinfo_graphicform<br>at = "arrow_data {[0 1 2<br>0 0 -1][]0}<br>width 5<br>offset 0" (NT) |

TABLE 2-continued

Exemplary Sequences

| SEQ ID NO: | Sequence* | Description** |
|---|---|---|

```
TATGCAGAGGCCGAGGCCGCCTCTGCCTCTGAGCT
ATTCCAGAAGTAGTGAGGAGGCTTTTTTGGAGGCC
TAGGCTTTTGCAAAAAGCTCCCGGGGAGCTTGTATA
TCCATTTTCGGATCTGATCAAGAGACAGGATGAGG
ATCGTTTCGCATGATTGAACAAGATGGATTGCACG
CAGGTTCTCCGGCCGCTTGGGTGGAGAGGCTATTC
GGCTATGACTGGGCACAACAGACAATCGGCTGCTC
TGATGCCGCCGTGTTCCGGCTGTCAGCGCAGGGGC
GCCCGGTTCTTTTTGTCAAGACCGACCTGTCCGGT
GCCCTGAATGAACTGCAGGACGAGGCAGCGCGGCT
ATCGTGGCTGGCCACGACGGGCGTTCCTTGCGCAG
CTGTGCTCGACGTTGTCACTGAAGCGGGAAGGGAC
TGGCTGCTATTGGGCGAAGTGCCGGGGCAGGATCT
CCTGTCATCTCACCTTGCTCCTGCCGAGAAAGTAT
CCATCATGGCTGATGCAATGCGGCGGCTGCATACG
CTTGATCCGGCTACCTGCCCATTCGACCACCAAGC
GAAACATCGCATCGAGCGAGCACGTACTCGGATGG
AAGCCGGTCTTGTCGATCAGGATGATCTGGACGAA
GAGCATCAGGGGCTCGCGCCAGCCGAACTGTTCGC
CAGGCTCAAGGCGCGCATGCCCGACGGCGAGGATC
TCGTCGTGACCCATGGCGATGCCTGCTTGCCGAAT
ATCATGGTGGAAAATGGCCGCTTTTCTGGATTCAT
CGACTGTGGCCGGCTGGGTGTGGCGGACCGCTATC
AGGACATAGCGTTGGCTACCCGTGATATTGCTGAA
GAGCTTGGCGGCGAATGGGCTGACCGCTTCCTCGT
GCTTTACGGTATCGCCGCTCCCGATTCGCAGCGCA
TCGCCTTCTATCGCCTTCTTGACGAGTTCTTCTGA
GCGGGACTCTGGGGTTCGAAATGACCGACCAAGCG
ACGCCCAACCTGCCATCACGAGATTTCGATTCCAC
CGCCGCCTTCTATGAAAGGTTGGGCTTCGGAATCG
TTTTCGGGACGCCGGCTGGATGATCCTCCAGCGC
GGGGATCTCATGCTGGAGTTCTTCGCCCACCCCAA
CTTGTTTATTGCAGCTTATAATGGTTACAAATAAA
GCAATAGCATCACAAATTTCACAAATAAAGCATTT
TTTTCACTGCATTCTAGTTGTGGTTTGTCCAAACT
CATCAATGTATOTTATCATGTCTGTATACCGTCGA
CCTCTAGCTAGAGCTTGGCGTAATCATGGTCATAG
CTGTTTCCTGTGTGAAATTGTTATCCGCTCACAAT
TCCACACAACATACGAGCCGGAAGCATAAAGTGTA
AAGCCTGGGGTGCCTAATGAGTGAGCTAACTCACA
TTAATTGCGTTGCGCTCACTGCCCGCTTTCCAGTC
GGGAAACCTGTCGTGCCAGCTGCATTAATGAATCG
GCCAACGCGCGGGGAGAGGCGGTTTGCGTATTGGG
CGCTCTTCCGCTTCCTCGCTCACTGACTCGCTGCG
CTCGGTCGTTCGGCTGCGGCGAGCGGTATCAGCTC
ACTCAAAGGCGGTAATACGGTTATCCACAGAATCA
GGGGATAACGCAGGAAAGAACATGTGAGCAAAAGG
CCAGCAAAAGGCCAGGAACCGTAAAAAGGCCGCGT
TGCTGGCGTTTTTCCATAGGCTCCGCCCCCCTGAC
GAGCATCACAAAAATCGACGCTCAAGTCAGAGGTG
GCGAAACCCGACAGGACTATAAAGATACCAGGCGT
TTCCCCCTGGAAGCTCCCTCGTGCGCTCTCCTGTT
CCGACCCTGCCGCTTACCGGATACCTGTCCGCCTT
TCTCCCTTCGGGAAGCGTGGCGCTTTCTCATAGCT
CACGCTGTAGGTATCTCAGTTCGGTGTAGGTCGTT
CGCTCCAAGCTGGGCTGTGTGCACGAACCCCCCGT
TCAGCCCGACCGCTGCGCCTTATCCGGTAACTATC
GTCTTGAGTCCAACCCGGTAAGACACGACTTATCG
CCACTGGCAGCAGCCACTGGTAACAGGATTAGCAG
AGCGAGGTATGTAGGCGGTGCTACAGAGTTCTTGA
AGTGGTGGCCTAACTACGGCTACACTAGAAGAACA
GTATTTGGTATCTGCGCTCTGCTGAAGCCAGTTAC
CTTCGGAAAAAGAGTTGGTAGCTCTTGATCCGGCA
AACAAACCACCGCTGGTAGCGGTGGTTTTTTTGTT
TGCAAGCAGCAGATTACGCGCAGAAAAAAAGGATC
TCAAGAAGATCCTTTGATCTTTTCTACGGGGTCTG
ACGCTCAGTGGAACGAAAACTCACGTTAAGGGATT
TTGGTCATGAGATTATCAAAAAGGATCTTCACCTA
GATCCTTTTAAATTAAAAATGAAGTITTAAATCAA
TCTAAAGTATATATGAGTAAACTTGGTCTGACAGT
TACCAATGOTTAATCAGTGAGGCACCTATCTCAGC
GATCTGTCTATTTCGTTCATCCATAGTTGCCTGAC
TCCCCGTCGTGTAGATAACTACGATACGGGAGGGC
TTACCATCTGGCCCCAGTGCTGCAATGATACCGCG
```

TABLE 2-continued

Exemplary Sequences

| SEQ ID NO: | Sequence* | Description** |
|---|---|---|
|  | AGACCCACGCTCACCGGCTCCAGATTTATCAGCAA TAAACCAGCCAGCCGGAAGGGCCGAGCGCAGAAGT GGTCCTGCAACTTTATCCGCCTCCATCCAGTCTAT TAATTGTTGCCGGGAAGCTAGAGTAAGTAGTTCGC CAGTTAATAGTTTGCGCAACGTTGTTGCCATTGCT ACAGGCATCGTGGTGTCACGCTCGTCGTTTGGTAT GGCTTCATTCAGCTCCGGTTCCCAACGATCAAGGC GAGTTACATGATCCCCCATGTTGTGCAAAAAGCG GTTAGCTCCTTCGGTCCTCCGATCGTTGTCAGAAG TAAGTTGGCCGCAGTGTTATCACTCATGGTTATGG CAGCACTGCATAATTCTCTTACTGTCATGCCATCC GTAAGATGCTTTTCTGTGACTGGTGAGTACTCAAC CAAGTCATTCTGAGAATAGTGTATGCGGCGACCGA GTTGCTCTTGCCCGGCGTCAATACGGGATAATACC GCGCCACATAGCAGAACTTTAAAAGTGCTCATCAT TGGAAAACGTTCTTCGGGGCGAAAACTCTCAAGGA TCTTACCGCTGTTGAGATCCAGTTCGATGTAACCC ACTCGTGCACCCAACTGATCTTCAGCATCTTTTAC TTTCACCAGCGTTTCTGGGTGAGCAAAAACAGGAA GGCAAAATGCCGCAAAAAAGGGAATAAGGGCGACA CGGAAATGTTGAATACTCATACTCTTCCTTTTTCA ATATTATTGAAGCATTTATCAGGGTTATTGTCTCA TGAGCGGATACATATTTGAATGTATTTAGAAAAAT AAACAAATAGGGGTTCCGCGCACATTTCCCCGAAA AGTGCCACCTGACGTC |  |
| 11 | MPKKKRAVEGSEFMVSKGEELFTGVVPILVELDGD VNGHKFSVSGEGEGDATYGKLTLKFICTTGKLPVP WPTLVTTLTYGVQCFSRYPDHMKQHDFFKSAMPEG YVQERTIFFKDDGNYKTRAEVKFEGDTLVNRIELK GIDFKEDGNILGHKLEYNYNSHNVYIMADKQKNGI KVNFKIRHNIEDGSVQLADHYQQNTPIGDGPVLLP DNHYLSTQSALSKDPNEKROHMVLLEFVTAAGITL GMDELYKGTAAAAPPAQPPSQPQQHYSEGELEEDE DSDDARKKRKKK* | NLS-EGFP-NES-NuLS |
| 12 | MALPTPSDSTLPAEARGRGRRRRLVWTPSQSEÅLR ACFERNPYPGIATRERLAQAIGIPEPRVQIWFQNE RSRQLRQHRRESRPWPGRRGPPEGRRKRTAVTGSQ TALLLRAFEKDRFPGIAAREELARETGLPESRIQI WFQNRRARHPGQGGRAPAQELLASPEFLQQAQPLL ETEAPG* | (S+375-397) dominant negative (EGFP was removed from the N-term) |
| 13 | MALPTPSDSTLPAEARGRGRRRRLVWTPSQSEALR ACFERNPYPGIATRERLAQAIGIPEPRVQIWFQNE RSRQLRQHRRESRPWPGRRGPPEGRRKRTAVTGSQ TALLLRAFEKDRFPGIAAREELARETGLPESRIQI WFQNRRARHPGQGGRAPAQELLASPEFLQQAQPLL ETEAPGLEGTRFEAPPAQPPSQPQQHYSEGELEED EDSDD* | (S+375-397) ALYREF dominant negative (EGFP was removed from the N-term) |
| 14 | DDIVFEDFARLRLKGM | NES - Beta-arrestin-2 |
| 15 | LIAGIIAMIC | NES - β-Dystroglycan |
| 16 | SLPPERMMPMDQTMHPDHTQTVIPYNPSSHESLDQ VGEEKEAMNTRESGKASSSLGLQDFDLL | NES - Protein kinase C type |
| 17 | MTLGMIWTIIL | NES - Alpha-actinin-4 |
| 18 | FEALMRMLDNLGYRT | NES - Alpha-adducin |
| 19 | LAQQFEQLSV | NES - argonaute 1 |
| 20 | PFPQDVINKLDKLSVLRLSVS | NES - Aryl hydrocarbon receptor |
| 21 | RLGSHTMDFFEMCASLITALAR | NES - AMPK subunit alpha-2 |
| 22 | MSHVAVENVLNLDQQFAGLDL | NES - Putative ATP-dependent RNA helicase an3 |

TABLE 2-continued

| | | Exemplary Sequences | |

| SEQ ID NO: | Sequence* | Description** |
|---|---|---|
| 23 | VIQQTLAAIVDAIKLDAI | NES - Ankyrin repeat domain-containing protein 11 |
| 24 | VGGELLDLLGDLNLS | NES - AP-1 complex subunit gamma |
| 25 | VLSAVKVLMKFLELLPKDS | NES - AP-2 complex subunit beta |
| 26 | LLERLKELNL | NES - denomatous polyposis coli protein |
| 27 | LTKRIDSLPL | NES - denomatous polyposis coli protein |
| 28 | ESTPDGFSCSSSLSALSLDEP | NES - denomatous polyposis coli protein |
| 29 | EGTPINFSTATSLSDLTIESP | NES - denomatous polyposis coll protein |
| 30 | EDTPVCFSRNSSLSSLSIDSE | NES - denomatous polyposis coli protein |
| 31 | LWVRLYVLELYCIIL | NES - C → U-editing enzyme APOBEC-1 |
| 32 | DVKSLESALKDLKIK | NES - Actin-related protein 2/3 complex subunit 1B-B |
| 33 | LLRNEVAQLKQLLLAH | NES - Cyclic AMP-dependent transcription factor ATF-2 |
| 34 | LEELCAARRLSL | NES - Bovine herpesvirus infected cell protein 27 |
| 35 | ELITFINALKL | NES - Replication protein E1 |
| 36 | QLVEELLKIICAFQLDTGL | NES - Breast cancer type 1 susceptibility protein |
| 37 | DLSDLTFLEVA | NES - Breast cancer type 2 susceptibility protein |
| 38 | RDLERAMTTLKLWES | NES - Protein C |
| 39 | AGDILALVFGLLFAVTSV | NES - Carbonic anhydrase 9 |
| 40 | LDSSLANLVGNLGIGNGT | NES - Clathrin assembly lymphoid myeloid leukemia protein |
| 41 | SSTSGLEQDVAQLNIAEQN | NES - Cancer susceptibility candidate gene 3 protein |
| 42 | ASSLRDYAASTMTEFLGMFGYDDQNTRDELARKIS FEKLHAGSTPEAATSSMLPTSEDTLSK | NES - Zinc finger protein castor homolog |
| 43 | LEMFGPEGAL | NES - Choline-phosphate cytidylyltransferase A |

TABLE 2-continued

| Exemplary Sequences | | |
| --- | --- | --- |

| SEQ ID NO: | Sequence* | Description** |
| --- | --- | --- |
| 44 | HLVLIG | NES - Cell division control protein 6 homolog |
| 45 | LRKLCERLRG | NES - Cell division cycle 7-related protein kinase |
| 46 | LLDKLLDLNP | NES - Cell division cycle 7-related protein kinase |
| 47 | EQCERA | NES - Cyclic GMP-AMP synthase |
| 48 | VLRMMVGVNI | NES - Calcineurin B homologous protein 1 |
| 49 | FVKVLEKVDV | NES - Calcineurin B homologous protein 1 |
| 50 | PNCPFLENSLETLRFSISNLSMQ | NES - Baculovimal IAP repeat-containing protein 2 |
| 51 | LGALWLAL | NES - MHC class II transactivator |
| 52 | IHTPVAIIELELGK | NES - COMM domain-containing protein 1 |
| 53 | EVKVNQILKTLSEVEES | NES - COMM domain-containing protein 1 |
| 54 | DLLGTDQDNLDLANVNLMLELLVQKKKQLEAESHA AQLQILMEFL | NES - E3 ubiquitin-protein ligase RFWD2 |
| 55 | LAALNHISAL | NES - Metal-binding regulatory protein Cuf1 |
| 56 | LKVIEENVCPKPAQVEPSSPSPMETSGCLPDELCQ AFSDVLIHVKDVDAD | NES - G2/mitotic-specific cyclin-B1 |
| 57 | DLCQAFSDVILA | NES - G2/MITOTIC-SPECIFIC CYCLIN B1 |
| 58 | NSHVAVENALGLDQQFAGLDLN | NES - ATP-dependent RNA helicase DDX3X |
| 59 | PFGQALRPLLDSIQI | NES - Desumoylating isopeptidase 1 |
| 60 | LSTLDQLRL | NES - diacylglycerol kinase zeta |
| 61 | SLEGAVSEISLRD | NES - Protein kinase dsk1 |
| 62 | LYPELRRILTI | NES - E1B protein, large T-antigen |
| 63 | YLAESSGPARGRGRHPGKGVKSPGEKS | NES - Transcription factor E2F1 |
| 64 | TPSAPRPALGRPPVKRRLDLETDHQY | NES - Transcription factor E2F1 |
| 65 | MVLTREELVI | NES - E4 34-kDa protein |

TABLE 2-continued

Exemplary Sequences

| SEQ ID NO: | Sequence* | Description** |
|---|---|---|
| 66 | VSQIFPDSVMLAVQEGIDLL | NES - Adenoviral E1A |
| 67 | FDIDEAEEGVKDLKIESDV | NES - Bukaryotic translation initiation factor 2 subunit 2 |
| 68 | RIDRDVQILNHILDDIEFFITKLQ | NES - Epidermal Growth Factor (EGF) receptor Pathway Substrate 8 |
| 69 | LCNCALEELRL | NES - ETS-related transcription factor Elf-3 |
| 70 | LWEFIRDILI | NES - ETS-related transcription factor Elf-3 |
| 71 | IHKKFSSIQM | NES - Hox cofactor Extradenticle |
| 72 | RLSHLRSEEVHWLHVDMGV | NES - Focal adhesion kinase 1 |
| 73 | FLQVRKYSLDLASLILYAYQL | NES - Focal adhesion kinase 1 |
| 74 | DLNALLLEVEGPLCKKLSLSKVIDCDS | NES - Fanconi anemia group A protein |
| 75 | PQVTVDVLQRMLIFALDALAAG | NES - Fanconi anemia group A protein |
| 76 | LADLKVSIENMGLYEDL | NES - Fanconi anemia group A protein |
| 77 | LSPGLIKKFQFLMFRLFSEAR | NES - Fanconi anemia group A protein |
| 78 | GNEDIISRLQEMVADLELQQDLIVPLGHTPS | NES - Fanconi anemia group A protein |
| 79 | LVVLPLELKL | NES - F-box only protein 7 |
| 80 | FVEKLQDIQQ | NES - Hypoxia-inducible factor 1-alpha inhibitor |
| 81 | EVDQLRLERLQIDEQLR | NES - Fragile X mental retardation 1 protein |
| 82 | LHGTMRPLSL | NES - Nitrogen regulatory protein GLN3 |
| 83 | QILPKVLHKRTLGLSAM | NES - Protein X |
| 84 | NVNFVSVGLFRCLPVPCPEDLLVEELVDGLLSL | NES - HTLV-1 basic leucine-zipper factor |
| 85 | EAQTCENEEAETVTAMASLSVGVKPA | NES - Histone deacetylase 4 (HD4) |
| 86 | EEAETVSAMALLSVGAEQAQAAAAREHSPRPAEEP NEQEPAL | NES - Histone deacetylase 5 |
| 87 | LSFDESLALCVIREI | NES - E3 ubiquitin-protein ligase MDM2 |

TABLE 2-continued

Exemplary Sequences

| SEQ ID NO: | Sequence* | Description** |
|---|---|---|
| 88 | LQLPPLERLTLD | NES - Protein Rev |
| 89 | LVDKFMKLDL | NES - MutS protein homolog 5 |
| 90 | DTDIQELSEQIHRLLLQPV | NES - Period circadian protein homolog 1 |
| 91 | ISPRLDAIKL | NES - Replication protein E1 |
| 92 | ARSFEMTEFNQALEEIKGQVVEN | NES - Serine/threonine-protein kinase R↓O2 |
| 93 | DIELTLRLN | NES - NmrA-like family domain-containing protein 1 |
| 94 | EELQDLVDQLGFL | NES - Heat shock factor protein HSF30 |
| 95 | IEAALSDALAALQI | NES - Heat shock protein SSB1 |
| 96 | MATLEKLMKAFESLKSF | NES - Huntingtin |
| 97 | NVAEMVESLQSVLALGHKRNSGVPAFLTPLLRNII ISLARLPLYNSYTRVP | NES - Huntingtin |
| 98 | MFQAAERPQEWAMEGPRDGLKKERLLDDRHDSGLD SMKDEEYEQMVKELQEIRLE | NES - NF-kappa-B inhibitor alpha |
| 99 | VIDYIRDLQLELNS | NES - DNA-binding protein inhibitor ID- 1 |
| 100 | LTTLNTDISILSLQASE | NES - DNA-binding protein inhibitor ID-2 |
| 101 | VSKYPLMEEIGFLVLGMRVYHVHSDS | NES - Inositol polyphosphate multikinase |
| 102 | QEDILDELLGNMVLA | NES - Interferon regulatory factor 3 |
| 103 | LQRMLPSLSLT | NES - Interferon regulatory factor S |
| 104 | LDRKLLELLW | NES - COP9 signalosome complex subunit 5 |
| 105 | RCHSLTPNFLQMQLQKCEILQSDSRCKDYLVKIFE ELTLHKPTQ | NES - Kelch-like ECH-associated protein 1 |
| 106 | IPYSINMNVFLPDITHLRTGLYKSQRPCVTQ | NES - Krueppel-like factor 5 |
| 107 | MDVLPMCSIFQELQIV | NES - Krüppel-like factor 6 |
| 108 | MVPLVIKLRL | NES - B-cell specific latent nuclear protein |
| 109 | FKPDMNPALREVLEALEDEAYVVND | NES - Protein LTV1 |
| 110 | ALREVLEALEDE | NES - Protein LTV1 |
| 111 | LEKVTNTLSSLKF | NES - Protein LTV1 |
| 112 | LEQELQQLSLEL | NES - Leucine zipper putative tumor suppressor 2 |

TABLE 2-continued

Exemplary Sequences

SEQ
ID
NO: Sequence*                                    Description**

113 LFGDTIAYLLSL                                 NES - M1 protein

114 LLYCLMVMYL                                   NES - M1 protein

115 QLLQEKLEKLTKLK                               NES - Spindle
                                                 assembly checkpoint
                                                 component MAD1

116 DKERWEDVKEEMTSALATMRVDYE                     NES - MAP Kinase-
                                                 activated protein kinase
                                                 2

117 ALQKKLEELELDE                                NES - Dual specificity
                                                 mitogen-activated
                                                 protein kinase kinase 1
                                                 (MAP kinase kinase 1)

118 VPEVEALLARLRAL                               NES - Protein
                                                 diaphanous homolog 3

119 DLVLLSLVL                                    NES - Menin

120 QLQQKLLWLL                                   NES - Menin

121 LVIAMDQLNL                                   NES - Microtubule
                                                 protein alp7

122 PLPVLGLGGLRISSDS                             NES - Mitogen-
                                                 activated protein kinase
                                                 phosphatase 3

123 LFDLAMLALD                                   NES - DNA mismatch
                                                 repair protein Mih1

124 LHLVGVNV                                     NES - Modulator of
                                                 KLF7 activity 125 ASLTKLFECMTLAYSGKLVS                         NES - MLX-interacting
                                                 protein 126 DIQELSEQIHRLLL                               NES - Period circadian
                                                 protein homolog 1

127 LEIALRNLNL                                   NES - Dual specificity
                                                 protein kinase TTK 128 DEMDSGTMVRAVGDEMGTVRVASTMTDGANTMIEH          NES -
    DDTLPSQLGTMVINAEDEEEEGTM                     Serine/threonine-
                                                 protein kinase 4

129 DGDYEFLKSWTVEDLQKRLLALDPMMEQEIE              NES -
                                                 Serine/threonine-
                                                 protein kinase 4

130 PVSKITFVTL                                   NES - mRNA export
                                                 factor EB2

131 LPSPLASLTL                                   NES - mRNA export
                                                 factor EB2

132 LCLSDLSLL                                    NES - Metal regulatory
                                                 transcription factor 1

133 IQDGLLKMLSLVL                                NES - Mammalian
                                                 target of rapamycin 134 ITFIFKSLGL                                   NES - Mammalian
                                                 target of rapamycin TABLE 2-continued Exemplary Sequences

| SEQ ID NO: | Sequence* | Description** |
|---|---|---|
| 135 | LEWLRRLSL | NES - Mammalian target of rapamycin |
| 136 | VQVVADVLSKLLVYGITDPD | NES - Mammalian target of rapamycin |
| 137 | LAPNVAALLFGGNVAVRELADSYEITYNYKMTVPK SDPNV | NES - Nucleoprotein |
| 138 | CTLSDSGRISYTVEFSLPTHHTVRLIRVTASPSÅ | NES - N nucleocapsid protein |
| 139 | GLPKNVKEKLLSLKTLQSELFEVEKEFQ | NES - Nucleosome assembly protein |
| 140 | KKTISPEHVIQALESLGFGSYISEVK | NES - Protein Dᴛ1 |
| 141 | ILMRMSKMQL | NES - Nuclear export protein |
| 142 | MVTRFESLKI | NES - Nuclear export protein |
| 143 | YIWALTQTLRIA | NES - Neurogenin-3 |
| 144 | SAIVAAINALTT | NES - Nuclear factor of activated T-cells |
| 145 | DÅERNRPLNGGSEPESNSALQEDEREKKDELQTES WSTKHEIANSDGLQDSSEELPRKLLLTEFRSLVVS NHNSTSRNLCVNECG | NES - Nibrin |
| 146 | KEHKDIDASLDYNSRAQKQEMERAEKDYELFLQEL EEDAELRQSVNLYKN | NES - 60S ribosomal export protein NMD3 |
| 147 | LDLPDALLPDLPKL | NES - Nitric oxide-associated protein 1 |
| 148 | LLPLAEADKVRLSYLHIMSLACIYT | NES - Neuronal PAS domain-containing protein 4 |
| 149 | DLCLAVEEVSL | NES - Nucleopbosmin |
| 150 | LKRRLSTLYL | NES - Nuclear factor erythroid 2-related factor 2 |
| 151 | LRNQLTALRI | NES - NS2 protein |
| 152 | LLLPLMRNLEM | NES - NS2 protein |
| 153 | LVSLIRLKSKL | NES - NS2 protein |
| 154 | DEMTKKFGTLTIHDTEKYASQPELCNN | NES - Marine minute virus |
| 155 | LCPDLPELDL | NES - N-truncated peroxisome proliferator-activated receptor gamma co-activator 1 alpha |
| 156 | LVDSLQQLRL | NES - Nuclear pore complex protein Nup214 |
| 157 | LELFVLRLA | NES - NUR-related factor 1 |
| 158 | LQRIFYLKL | NES - NUR-related factor 1 |

TABLE 2-continued

| SEQ ID NO: | Sequence* | Description** |
|---|---|---|
| 159 | LKSLGELGL | NES - Opioid growth factor receptor |
| 160 | LSKIATILL | NES - Oligodendrocyte transcription factor 1 |
| 161 | LLLAGLPLL | NES - Oligodendrocyte transcription factor 1 |
| 162 | HPSTPKRHTVLYISPPPEDLLDNSR | NES - Osmotic response element-binding protein |
| 163 | VLSQRIGLMDV | NES - Open reading frame 45 of Kaposi's sarcoma-associated herpesvirus 8 |
| 164 | LRHELVEDAVYENPL | NES - ORF9 protein |
| 165 | SLEEELDVLVLDDEGG | NES - Catenin delfa-1 |
| 166 | LTELEISSIFSHCCSLLI | NES - Nucleoprotein (N protein) |
| 167 | EMFRELNEALELKD | NES - Cellular tumor antigen p53 |
| 168 | NFEILMKLKESLELMELVP | NES - Tumor protein p73 |
| 169 | LTLLLDEFENMSV | NES - Serine/threonine-protein kinase PAK 4 |
| 170 | VVMEFLEGGALTDIV | NES - Serinc/threonine-protein kinase PAK 4 |
| 171 | LKGFLDRLLV | NES - Serine/threonine-protein kinase PAK 4 |
| 172 | VYNLVCVALGNLEIREIR | NES - Partner and localizer of BRCA2 |
| 173 | ESFDIDDLCSKLKNKAKCS | NES - AP-1-like transcription factor |
| 174 | MKPALFNVLCEIKEKTVL | NES - Pre-B-cell leukemia transcription factor 1 |
| 175 | ILKKVLEALKDLI | NES - Proliferating cell nuclear antigen |
| 176 | LLKDLPELALD | NES - Programmed cell death protein 4 |
| 177 | VAEMLRDLNLG | NES - Programmed cell death protein 4 |
| 178 | LELEALRLSL | NES - Pericentrin |
| 179 | LQDALRRLLGL | NES - Pericentrin |
| 180 | FGETLRAAVTL | NES - Pericentrin |
| 181 | LDEFNELAI | NES - Pericentrin |
| 182 | VIEKLQHELSL | NES - Pericentrin |

TABLE 2-continued

Exemplary Sequences

| SEQ ID NO: | Sequence* | Description** |
|---|---|---|
| 183 | RVREKQYQDTIGKLQKENNELLEQLEMLQAQLKNS TLDSPKEVEVNSEVV | NES - CCAAT-binding factor complex subunit Php4 |
| 184 | SLWGEHILALKNLKLDKM | NES - Serine/threonine-protein kinase PINK1, mitochondrial |
| 185 | NELALKLAGLDINKT | NES - CAMP-dependent Protein Kinase Inhibitor alpha |
| 186 | ELKDFLKELNIQVD | NES - 1-phosphatidylinositol-4,5-bisphosphate phosphodiesterase delta-1 |
| 187 | ISGFLAALPL | NES - Promyelocytic leukemia protein isoform I |
| 188 | REELWKKLEELKLKKÅLEK | NES - Serine/threonine-protein phosphatase 2A 56 kDa regulatory subunit alpha iscform |
| 189 | YEEQLVALFGSSMDLR | NES - Protein kinase, CAMP-dependent, regulatory subunit type Il alpha |
| 190 | IIELLKGLDL | NES - Human parainfluenza virus type 2 phosphoprotein |
| 191 | LSLNLFALRI | NES - 65 kDa carly nonstructural protein |
| 192 | LTLSSLTL | NES - 65 kDa early nonstructural protein |
| 193 | VEVLREIQL | NES - Nuclear protein UL4 |
| 194 | IMSQFRKLLM | NES - Tegument protein UL47 |
| 195 | EVDNLPEDMKRLHLDD | NES - Phosphoprotein |
| 196 | KVAEKLEALSVKEETKED | NES - Ran-specific GTPase-activating protein |
| 197 | EEILKLLMELVFRLVC | NES - Rap guanine nucleotide exchange factor 1 |
| 198 | LSEALLQLQF | NES - Transcription factor p65 |
| 199 | LEDLVRHMSL | NES - Protein Rev |
| 200 | ALSAQLYSSLSLDS | NES - Rex Protein |
| 201 | EKGNLPELEKLEINGNRLDEDSDALDLLQSKFDDL EVDDFEE | NES - Rnalp |
| 202 | GDVFGPELDTLLDSLSLVQGGLSGSGVPSELPQLI PV | NES - Zinc finger CCCH domain-containing protein 7B |

TABLE 2-continued

| Exemplary Sequences | | |
| --- | --- | --- |

| SEQ ID NO: | Sequence* | Description** |
| --- | --- | --- |
| 203 | DGFNELIPEDLVTVFDERELELLIGGIAEIDIEDW KKHTDYR | NES - E3 ubiquitin-protein ligase RSP5 |
| 204 | QMLSKEVDACVTDLLKELVRFQD | NES - Selenocysteine insertion sequence-binding protein 2 |
| 205 | QDQFHKMVELTVAAR | NES - Selenocysteine insertion sequence-binding protein 2 |
| 206 | QYESNENVVLVCSTIVCSFGKQVVEKVE | NES - Protein scalloped |
| 207 | LEPDLSEEVSARLRLG | NES - Sentrin-specific protease 2 |
| 208 | RRMQEMITRMQAQMQI | NES - Septin A |
| 209 | TGEQELESLVLKLSVLKDF | NES - SH2 domain-containing inositol 5'-phosphatase 2 |
| 210 | LESLVLKLSVLKDFLSGIQ | NES - SH2 domain-containing inositol 5'-phosphatase 2 |
| 211 | SRDAARCRRSKETEIFMELSAALPLKTDDVNQLDK ASVMRITIAFLKIREMLQF | NES - Protein similar |
| 212 | DMDFLRNLFSQTLSLGSQK | NES - NAD-dependent deacetylase sirtuin-2 |
| 213 | LTKMCTIRM | NES - Mothers against decapentaplegic homolog 1 |
| 214 | GIDLSGLTLQ | NES - Mothers against decapentaplegic homolog 4 |
| 215 | ELIIGGLDKIDL | NES - B3 ubiquitin-protein ligase SMURF1 |
| 216 | SPKAVELTSLSDEDSGKSSQPPSPPSPAPSSFSST SÅSSLEAEAFIAFPGLGQLPKQLARLSVAKDPQSR | NES - Zinc finger protein SNAI1 |
| 217 | MEELSQALASSFSVS | NES - Snurportia 1 |
| 218 | ESNGPVKVWGSIKGLTEGLHGFHVHEFGDNTA | NES - Superoxide dismutase |
| 219 | LSKTLGKLWRLL | NES - Transcription factor SOX-10 |
| 220 | EISKQLGKRWKNLTE | NES - SRY-box transcription factor SOX14A |
| 221 | EISKQLGRRWKMLTE | NES - SRY-box transcription factor SOX14B |
| 222 | ELSKTLGKLWRLLN | NES - Transcription factor SOX-9 |
| 223 | LEKQINDLQIDK | NES - Spindle pole component SPC72 |
| 224 | SASDDLEALGTLSLGTTEE | NES - NCK-interacting protein with SH3 domain |

TABLE 2-continued

Exemplary Sequences

| SEQ ID NO: | Sequence* | Description** |
|---|---|---|
| 225 | IYPWMKRVHL | NES - Homeotic protein Sex combs reduced |
| 226 | LLLKKMYLM | NES - Signal transducer and activator of transcription 1-alpha/beta |
| 227 | WDRTESLFQQLIQ | NES - Signal transducer and activator of transcription 1-alpha/beta |
| 228 | MEESTNGSLAAEFRHLQLKEQK | NES - Signal transducer and activator of transcription 1-alpha/beta |
| 229 | EERIVELFRNLMK | NES - Signal transducer and activator of transcription 3 |
| 230 | LSAEFKHLTLR | NES - Signal transducer and activator of transcription 3 |
| 231 | QLTTLAEKLLGPGV | NES - Signal transducer and activator of transcription 3 |
| 232 | INQMFSVQLSL | NES - Double-stranded RNA-binding protein Staufen homolog 2 |
| 233 | EATEAQLNNSMAALNVN | NES - Sup35 protcin |
| 234 | VKKQFEELTLGEFLKL | NES - Apoptosis inhibitor survivin |
| 235 | YKRIEELLYKISLTT | NES - Protein Tax-1 |
| 236 | NPASAPPPLPPPGQQVIHVTQDLDTDLEÅLFNSVM NPKP | NES - NPASAPPPLPPPGQQ VIHVTQDLDTDLEA LFNSVMNPKP |
| 237 | HVLSSSAGNSAPNSPMAMLHIGSN | NES - Transcription Factor EB |
| 238 | MANSANTNTVPKLYRSVIEDVINDVRDIFLDDGVD EQVLM | NES - Transcription initiation factor IIA subunit 1 |
| 239 | QPDASKADPLPVLENLTLK | NES - Transcription factor IIIA |
| 240 | ILRDFFELRLK | NES ~ DNA topoisomerase II, alpha isozyme |
| 241 | FILEKIDGKIIIE | NES - DNA topoisomerase IL, alpha isozyme |
| 242 | ETVQDILKEFF | NES - DNA topoisomerase II, beta isozyme |

TABLE 2-continued

Exemplary Sequences

| SEQ ID NO: | Sequence* | Description** |
|---|---|---|
| 243 | RISYQPENIQPNRHVANIVEKLREVKLSPEEGQK | NES - Tripartite motif-containing protein 5 |
| 244 | QRLQGLPPDRGIIRPGSLDAEIDSLTSMLADLDGG RSHAP | NES - Thyroid receptor-interacting protein 6 |
| 245 | WMAIAGKIRSDL | NES - Homeotic protein Ultrabithorax |
| 246 | CILCQLLLLY | NES - Capsid-binding protein UL94 |
| 247 | TTEELELELETLDIN | NES - MGC115246 protein |
| 248 | TDPFLAMQVQELTRSMANLTFKQRRDAPPEGPSAK KPKK | NES - VEEV Capsid protein |
| 249 | ELDTNFFTLYVAQG | NES - Nucleocapsid protein VP1 |
| 250 | LERLFGRLRI | NES - Triplex capsid protein VP19C |
| 251 | MDGAIASGVSKFATLSLHD | NES - WD repeat-containing protein 20 |
| 252 | IEVEASDLSLSL | NES - DDB1- and CUL4-associated factor 8 |
| 253 | SSLQELVQQFEALPGDLVG | NES - Amyloid beta A4 precursor protein-binding family A member 3 |
| 254 | EQLERLRKDMGSVAL | NES - GPN-loop GTPase 1 |
| 255 | LRLGSQIFI | NES - Tight junction protein ZO-2 |
| 256 | LQLVVLRDSK | NES - Tight junction protein ZO-3 |
| 257 | LFGPIADIAL | NES - Tight junction protein ZO-4 |
| 258 | LEKLANELPDL | NES - Tight junction protein ZO-5 |
| 259 | LTMKEVEELELLTQKLM | NES - Zyxin |
| 260 | APPAQPPSQPQQHYSEGELEEDEDSDDA | NES - ALYREF |
| 261 | RFEMFRELNEALELKDA | NES - weak P53 |
| 262 | KRx{10}KKKL | NLS - Nucleoplasmin |
| 263 | PKKKRKV | NLS - SV40, LrgT |
| 264 | PKKNRLRRP | NLS - BRCA1 |
| 265 | PKRPRDRHDGELGGRKRARG | NLS - VirD2-Cterm |
| 266 | PLLKKIKQ | NLS - c-myb |
| 267 | PNKKKRK | NLS - SV40(VP2) |
| 268 | PPQKKIKS | NLS - N-myc |
| 269 | PPRIYPQLPSAPT | NLS - BDV-P |

TABLE 2-continued

Exemplary Sequences

| SEQ ID NO: | Sequence* | Description** |
|---|---|---|
| 270 | PPRKKRTVV | NLS - NS5A |
| 271 | PPVKRERTS | NLS - RanBP3 |
| 272 | PQPKKKP | NLS - p53 |
| 273 | PQSRKKLR | NLS - Max |
| 274 | PRGRRQPIPKARQP | NLS - HCV |
| 275 | PRPRKIPR | NLS - BDV-P |
| 276 | PRRGPR | NLS - HCV |
| 277 | PRRRK | NLS - SOX9 |
| 278 | PYLNKRKGKP | NLS - Pho4p |
| 279 | PKKARED | NLS - polyoma |
| 280 | PAKRARRGYK | NLS - CPVcapsid |
| 281 | KRx{7,9}PQPKKKP | NLS - p53-NLS1 |
| 282 | KSKKKAQ | NLS - HIV1423 |
| 283 | KTRKHRG | NLS - L29 |
| 284 | KVNSRKRRKEVPGPNGATEED | NLS - CTP |
| 285 | KVTKRKHDNEGSGSKRPK | NLS - hum-Ku70 |
| 286 | K[RK]{3,5}x{11,18}[RK]Kx{2,3}K | NLS - |
| 287 | LEKKVKKKFDWCA | NLS - prot.Hsci |
| 288 | LKDVRKRKLGPGH | NLS - DNAseBBV |
| 289 | LKRKLQR | NLS - Pax-QNR |
| 290 | LKRPRSPSS | NLS - EBNA1 |
| 291 | MAPSAKATAAKKAVVKGTNGKKALKVRTSATFRLP KTLKLAR | NLS - L25 |
| 292 | MNKIPIKDLLNPG | NLS - Mat-alpha |
| 293 | MPKTRRRPRRSQRKRPPT | NLS - Rex |
| 294 | MPTEERVRKRKESNRESARRSRYRKAAHLK | NLS - opaque2 |
| 295 | NQSSNFGPMKGGNFGGRSSGPYGGGGQYFAKPRNQ GGY | NLS - M9 |
| 296 | PÅAKRVKLD | NLS - IscMyc |
| 297 | QRKRQK | NLS - NF-KB |
| 298 | RAIKRRPGLDFDDDGEGNSKFLR | NLS - hARNT |
| 299 | REKKEKEQKEKCA | NLS - prot.Hsc9 |
| 300 | RRPSx{22}RRKRQ | NLS - PK-A |
| 301 | RRRx{11}KRRK | NLS - CBP80 |
| 302 | RRSMKRK | NLS - hVDR |
| 303 | RVHPYQR | NLS - QKI-5 |
| 304 | SÅNKVTKNKSNSSPYLNKRGKPGPDS | NLS - Pho4 |
| 305 | SDKKVRSRLIECA | NLS - Ta.alpha |

TABLE 2-continued

Exemplary Sequences

| SEQ ID NO: | Sequence* | Description** |
|---|---|---|
| 306 | SKRVAKRKL | NLS - c-erb-A |
| 307 | SxGTKRSYxxM | NLS - FluA |
| 308 | TEKK[QG]KSILYDCÅ | NLS - prot.Hsc3 |
| 309 | TKRSxxxM | NLS - influenzaNP |
| 310 | VNEAFETLKRC | NLS - MyoD |
| 311 | VSRKRPR | NLS - polyoma |
| 312 | VKRPCKRSFIRFI | NLS - DNAseEBV |
| 313 | YLTQETNKVETYKEQPLKTPGKKKKGKP | NLS - PTHrP |
| 314 | YNNQSSNFGPMKGGN | NLS - M9 |
| 315 | [KAR]TPIQKHWRPTVLTEGPPVKIRIETGEWE[KA] | NLS - ASVintegrase |
| 316 | RRMKWKK | NLS - PDX-1 |
| 317 | RRKGKEK | NLS - Hunt.Dis.pro |
| 318 | RGRRRRQR | NLS - Amida |
| 319 | RIRKKLR | NLS - p54 |
| 320 | RKCLQAGMNLEARKTKK | NLS - hGlu.cort. |
| 321 | RKEWLTNFMEDRRQRKL | NLS - hDNAtopoII |
| 322 | RKKRKx{9}KAKKSK | NLS - N1N2 |
| 323 | RKKRRQRRR | NLS - HIV-1Tat |
| 324 | RKRAFHGDDPFGEGPPDKK | NLS - ICP-8 |
| 325 | RKRIREDRKATTAQKVQQMKQRLNENERKRKR | NLS - TCPTP |
| 326 | RKRKK | NLS - ystDNApolalpha |
| 327 | RKRKKMPASQRSKRRKT | NLS - hBLM |
| 328 | RKRRR | NLS - Amida |
| 329 | RLKKLKCSKx{19}KTKR | NLS - GAL4 |
| 330 | RPRRK | NLS - SRY |
| 331 | RQARRNRRRWR | NLS - HIV-1Rev |
| 332 | RRERNKMAAAKCRNRRR | NLS - cFOS |
| 333 | RRERx{4}RPRKIPR | NLS - BDV-P |
| 334 | [KR]{4}x{20,24}K{1,4}xK | NLS - |
| 335 | KKKRERLD | NLS - RCP |
| 336 | KRKRRP | NLS - BRCA1 |
| 337 | IKYFKKFPKD | NLS - yeast, SK13 |
| 338 | HRKYEAPRHx{6}PRKR | NLS - L3 |
| 339 | KRKx{11}KKKSKK | NLS - hpoly(ADP)poly |
| 340 | HRIEEKRKRTYETFKSI | NLS - NF-kB |
| 341 | KRKx{22}KELQKQITK | NLS - HIV-1 |

TABLE 2-continued

Exemplary Sequences

| SEQ ID NO: | Sequence* | Description** |
|---|---|---|
| 342 | KRMRNRIAASKCRKRKL | NLS - cJUN |
| 343 | KRPAATKKAGQAKKKK | NLS - Nucloplasmin |
| 344 | EEDGPQKKKRRL | NLS - polyomaVP2 |
| 345 | KRPACTLKPECVQQLLVCSQEAKK | NLS - HCDA |
| 346 | KRPAEDMEEEQAFKRSR | NLS - humKprotein |
| 347 | KRPMNAFIVWSRDQRRK | NLS - SRY |
| 348 | KRPMNAFMVWAQAARRK | NLS - SOX9 |
| 349 | KRKKEMANKSAPEAKKKK | NLS - Nucleolin |
| 350 | APKRKSGVSKC | NLS - polyomaVP1 |
| 351 | KRAAEDDEDDDVDTKKQK | NLS - hProTalpha |
| 352 | KKKRRSREK | NLS - TCF-1 |
| 353 | KKKKKEEEGEGKKK | NLS - act/inh, betaA |
| 354 | KKKYKLK | NLS - HIV1422 |
| 335 | KKQTTLAFKPIKKGKKR | NLS - hDNAtopoII |
| 356 | CKRKTTNADRRKA | NLS - MyoD |
| 357 | KKEKKKSKK | NLS - dyskerin |
| 358 | KHRKHPG | NLS - L29 |
| 359 | KRx{9}KTKK | NLS - THOV |
| 360 | CYGSKNTGAKRKIDDA | NLS - |
| 361 | KKSKKGRQEALERLKKA | NLS - hDNApolalpha |
| 362 | KDCVINKHHRNRCQYCRLQR | NLS - TR2 |
| 363 | KAKRQR | NLS - v-Rel |
| 364 | KKx{15}KKRK | NLS - DNAhelicaseQ1 |
| 365 | EYLSRKGKLEL | NLS - VirD2-Nterm |
| 366 | KRQRx{20}KKSKK | NLS - Mitosin |
| 367 | KRSAEGGNPPKPLKKLR | NLS - p110RB1 |
| 368 | APTKRKGS | NLS - SV400VP1 |
| 369 | KKKKRKREK | NLS - LBF-1 |
| 370 | KRPRP | NLS - adenovE1a |
| 371 | GRKRKKRT | NLS - Tst1/Oct6 |
| 372 | HKKKKIRTSPTFTTPKTLRLRRQPKYPRKSAPRRN KLDHY | NLS - BIB |
| 373 | GGGx{3}KNRRx{6}RGGRN | NLS - Nab2 |
| 374 | GKKRSKA | NLS - H2B |
| 375 | GKKKYKLKH | NLS - HIV-1 |
| 376 | [DE]K[NIF]RR[DEK][STMNQ] | NLS - |
| 377 | [DE]KR[MQN]R[MQN]R | NLS - |
| 378 | [DE]KK[PL][GL]K[GL] | NLS - |

TABLE 2-continued

Exemplary Sequences

| SEQ ID NO: | Sequence* | Description** |
|---|---|---|
| 379 | R[RK]x{4,6}[RK][RK]x[RK]x{1,3}[RK][RK][PLQ] | NLS - |
| 380 | R[RK]{2,4}[PL][RK][MNQ]R | NLS - |
| 381 | \|R[RK]{2,4}x{15,19}[RK]{2,4}[QLM]K | NLS - |
| 382 | R[RK]{3,)?[DE]K | NLS - |
| 383 | [DE]KxRRK[MNQ] | NLS - |
| 384 | [DE]RKRR[DEPLQ] | NLS - |
| 385 | [DE]RxKKKK | NLS - |
| 386 | [DE][RK]{2,4}[GA]R[PL][GA] | NLS - |
| 387 | R[PL]xx[KR]{2,}?xx[KR]V | NLS - |
| 388 | [DE][KR]RR[KR][FYW] | NLS - |
| 389 | R[QMPL]RR[DE]R | NLS - |
| 390 | R[RK]K[RK]KR | NLS - |
| 391 | R[RK]x[KR]x[RK]{2 ,}?[DE] | NLS - |
| 392 | R[STCMNQ]R[STCMNQ]KR | NLS - |
| 393 | [DE]R{2,4}xRK[PL] | NLS - |
| 394 | RxKKKK[DE] | NLS - |
| 395 | R{2,}?PR{3,)? | NLS - |
| 396 | T[PLV]KRC | NLS - |
| 397 | R{2,3}xK{2,3}R[ST] | NLS - |
| 398 | D[KR]x{0,1}[QL][RK]{2,3}R | NLS - |
| 399 | R{2,3}K{3,4}[PLRKE] | NLS - |
| 400 | Rx{2,3}RRRRR | NLS - |
| 401 | Rx{2,3}Hx{3,5}RRRR | NLS - |
| 402 | DR[MN]KKKKE | NLS - |
| 403 | WKQ[KR]RKF | NLS - |
| 404 | Rx[KR][KR][KR]xxRKKR | NLS - |
| 405 | RX[KR][KR]K[PLQM]R | NLS - |
| 406 | RxR{2,}?[QL]x[ST]R | NLS - |
| 407 | RxRxRxRxRxRxK | NLS - |
| 408 | RxRxRxRxRxR | NLS - |
| 409 | RxRSRSx{0,1}RxR | NLS - |
| 410 | DK[QL]KK[QL] | NLS - |
| 411 | RxRRx{4,6}RKK | NLS - |
| 412 | R{2,)}[QMN]R{3,)? | NLS - |
| 413 | [TS][RK]KK[VLI]R[PL] | NLS - |
| 414 | [QL]xKRxKxKK | NLS - |

TABLE 2-continued

Exemplary Sequences

| SEQ ID NO: | Sequence* | Description** |
|---|---|---|
| 415 | [QL]K{2,4}x{8,12}[RK][QL][RK][QL]KR | NLS - |
| 416 | [PVLI][RK][RK][RK][RK][QMN]K | NLS - |
| 417 | [PL]xxKR[IV]K[PL][DE] | NLS - |
| 418 | [PL][RK]{2,3}K[PLI][RK]x[PLI]xK | NLS - |
| 419 | [PL][RK][RK][KR][GAPL][RK][STQM] | NLS - |
| 420 | [PL][RK][RK][DEP]R[RK][FYW] | NLS - |
| 421 | [PL][PL]x[KR]R[DE][KR][QST] | NLS - |
| 422 | [PL][KR]{5,7}[PL] | NLS - |
| 423 | [PL]R[DE]K[DE]R | NLS - |
| 424 | [PL]RKRK[PL] | NLS - |
| 425 | [RK]H[RK]xxx[RK]{2,4}xR | NLS - |
| 426 | [RK]K{2,4}x[RK][QL][RK][PL] | NLS - |
| 427 | [RK]R[MS]KxK[KR] | NLS - |
| 428 | [ST]Gx{1,3}G{3,}?x{1,2}G{3,}?[ST] | NLS - |
| 429 | [STQM]RRRK[STQM] | NLS - |
| 430 | [STQM]RKRR[STQM] | NLS - |
| 431 | [STQM]RKRK[STQM] | NLS - |
| 432 | [RK]{4,}?[QMNPL][RK]x{3,4}[RK]{2} | NLS - |
| 433 | [RK]{3,}?x(8,16)[RK]{4,}? | NLS - |
| 434 | [RK]{3,}?x[RK]x[RK]x{4,9}[RK]{3,}? | NLS - |
| 435 | [RK]{2,4}x{2,4}[QLM][RK]x{2,3}[RK]KR | NLS - |
| 436 | [RK]{2,4}x{1,2}[RK]x{0,2}[RK]x{3,5} [RK]x{0,2}[AK][RK]{2,4}[PL] | NLS - |
| 437 | [RK]x[RK]x[KR]x{4,6}RKK | NLS - |
| 438 | [RK][PLIV][KR][RK]{2,4}[PLVI]R | NLS - |
| 439 | [PL]KxxKRR | NLS - |
| 440 | [PLV]RK[ST]R[DE]K | NLS - |
| 441 | [YFW]RRRR[PL] | NLS - |
| 442 | [KR][DE][KR][DE]xx[KR]{4,)? | NLS - |
| 443 | [KR]XXKNKX{6,8}K[KR] | NLS - |
| 444 | [KR]KRKK | NLS - |
| 445 | [KR]G{2,}?xxG{3,}?[RK] | NLS - |
| 446 | [QMN]R[RK]xXx[RK][RK] | NLS - |
| 447 | [GA][KR]KRX[KR][GA] | NLS - |
| 448 | [GA]Rx[RK]x[RK][R]x[QM] | NLS - |
| 449 | [GA]KxKKK[MNQ] | NLS - |
| 450 | [GAPLV]RKRKKR | NLS - |
| 451 | [ED]R{4,}?[ED] | NLS - |

TABLE 2-continued

Exemplary Sequences

| SEQ ID NO: | Sequence* | Description** |
|---|---|---|
| 452 | [DE][ST][PL]KR[STC] | NLS - |
| 453 | [KR][KR][KR][KR][KR][KR][KR] | NLS - |
| 454 | [KR][KR][QMN]R[RK][QMN]R | NLS - |
| 455 | [KR][KR]x[KR][KR][KR]x[KR][KR] | NLS - |
| 456 | [PLV]K[RK]x[RK][RK][RK][PL] | NLS - |
| 457 | [PLV]K[RK]x[QMN][RK]R | NLS - |
| 458 | [PLQ][KR]x{3,4}KKRK | NLS - |
| 459 | [PLQ]K[RK]x{1,2}[RK]x{3,6}[RK][RK]x{1,2}[RK]x{1,2)[RK][RK] | NLS - |
| 460 | [PLQMNKR]K[KR][KR]RxK[PLQMNKR] | NLS - |
| 461 | [PLQMKR]R[KR][QM][KR]RxK | NLS - |
| 462 | [MI]VWSRD[HEQ]RRK | NLS - |
| 463 | [LF][STK][VIQM][KR]R[QMVI][STK]L | NLS - |
| 464 | [KR]{2}x{0,1}[KR]{2,4}x{25,34}K{2,4}x{1,2}K | NLS . |
| 465 | [KR]{2,}?[PL]x{1,4}[KR]{2,}?x{1,5}K{3,}? | NLS - |
| 466 | [KR]{2,3}xxKR[KR][QLM] | NLS - |
| 467 | [DE][RK]{3,}?x[KR]{2,}?[PL] | NLS - |
| 468 | KKRKRT | NLS - |
| 469 | KRKx{10,14}[KR]{3,}?x[KR]K | NLS - |
| 470 | PK[KR][KRP][RAK][KT][VSE] | NLS - |
| 471 | PKRPx{5,8}Lx{2,4}RxKxK | NLS - |
| 472 | KRKx{2,4}DRRK | NLS - |
| 473 | PKKKxRK | NLS - |
| 474 | KRKX{5,10}KK[PL]K | NLS - |
| 475 | N[QR]RQ[RK][EG]KR[IVLS] | NLS - |
| 476 | LKKIKQ | NLS - |
| 473 | KR[GPL]R[GPL]R[GLP]RK | NLS - |
| 478 | KR[MNSQ]R[MNSQ]R | NLS - |
| 479 | KRKx{0,8}KR[PL]K | NLS - |
| 480 | KRGRGRPRK | NLS - |
| 481 | KKx{1,7}K[PL][PLIV]KK | NLS - |
| 482 | RER[MNQ]Kx{4,8}R[MNQ]RR | NLS - |
| 483 | KKRKR[KR] | NLS - |
| 484 | KKRKR[ST] | NLS - |
| 485 | Q[RK][HRK][RK]xRR | NLS - |
| 486 | KKRRK | NLS - |

TABLE 2-continued

Exemplary Sequences

| SEQ ID NO: | Sequence* | Description** |
|---|---|---|
| 487 | QNRRxKx[RK][RK][DQE] | NLS - |
| 488 | Px[PQLVMN][KR]{2,3}xKQ | NLS - |
| 489 | KKRRxK | NLS - |
| 490 | KK[MNQSTC]R[MNQSTC]K[MNQSTC] | NLS - |
| 491 | KKxRx{3,5}R[PVL]K | NLS - |
| 492 | K{3,4}R{2,3} | NLS - |
| 493 | K{1,}?R{2,}?[QM]R{2,} | NLS - |
| 494 | KxxKxKxKxxxxxRKK | NLS - |
| 495 | K[GA]K[AG]KK[AG] | NLS - |
| 496 | KR[RK][RK]x{2,4}[RK]x{0,2}Rx{3,5}[RK]x{0,2}[RK]x{0,2}[RK][RK]K | NLS - |
| 497 | KR[ST]RxxR{2,4}[QL]K | NLS - |
| 498 | KRxRxRx{2,6]RKRK | NLS - |
| 499 | KRxRxxRRLK | NLS - |
| 500 | KR{3,}?[LVI] | NLS - |
| 501 | KR{2,4}x{3,6}[RK]{2,4}x{0,2}KR | NLS - |
| 502 | KKRR[DE]K | NLS - |
| 503 | KRx[DE][KR][KR]xK | NLS - |
| 504 | KRxxKKxK[DE] | NLS - |
| 505 | K[IVQM]RR[VI][STK]L | NLS - |
| 506 | K[KR][KR]RR[KR] | NLS - |
| 507 | K[KR][QMN][RK]R[QMN]R | NLS - |
| 508 | Kx[PLV][RK][RK]RK | NLS ~ |
| 509 | KxKxKxxxxxRKK | NLS - |
| 510 | KxKRQR | NLS - |
| 511 | KR[PLV][GA]KRK[PL] | NLS - |
| 512 | K[RK]{2,}?[QL]x{3,8}R{3} | NLS ~ |
| 513 | K[RK]{2,4}[ST]H | NLS - |
| 514 | K[PL]K{3,}?xKK | NLS - |
| 515 | K[PL]K{2,3}x{1,3}[RK]{2,4}x{6,9}K[KR] | NLS - |
| 516 | K[PLMN]RRK[MNQ] | NLS - |
| 517 | K[MNQ]RR[PLVI]K[PL] | NLS - |
| 518 | KRx{1,3}Hx{3,5}R[LQ]RR | NLS - |
| 519 | R[PL]xGx[KR][KR]xK | NLS - |
| 520 | RRxRxKxKQ | NLS - |
| 521 | RRxR[PVL]RK | NLS - |
| 522 | RRxRRRRR | NLS - |
| 523 | RRxKRxK[PLV] | NLS - |

TABLE 2-continued

Exemplary Sequences

| SEQ ID NO: | Sequence* | Description** |
|---|---|---|
| 524 | RR[TS]x[QK][KR][KN] | NLS - |
| 525 | RR[TS]x[QK][KR][KNS] | NLS - |
| 526 | RR[PLQMN]xRRRR | NLS - |
| 527 | RR[PLIV]RKxK | NLS - |
| 528 | G{2,4}[RK]x{1,3}G{3} | NLS - |
| 529 | RRR{3,5}T | NLS - |
| 530 | RRxRxRKQ | NLS - |
| 531 | RRxxKRK | NLS - |
| 532 | RRx{0,1}RRRRR | NLS - |
| 533 | R[MNQ]x{4,8}R[MNQ]RR | NLS - |
| 534 | R[MNQ]RRRRxR | NLS - |
| 535 | R[KR]{3,4}K[DE] | NLS - |
| 536 | R[KR][RK]x{0,2}[RK]x{0,2}[RK]x{3,5} [RK]x{0,2}[AK][RK][RK][RK][PMQL] | NLS - |
| 537 | R[KR]RRRRxR | NLS - |
| 538 | R[IVLP][IVLP]KRR | NLS - |
| 539 | R[GVLIP]RRRRxR | NLS - |
| 540 | R[GA]x{0,2}[GA]R[GA]x[GA]R[GA] | NLS - |
| 541 | R[GA][IVLP]KRR | NLS - |
| 542 | GR[RK]{2,4}xx[RK][QL] | NLS - |
| 543 | RRR[PL]RK | NLS - |
| 544 | RRR[LP]xxR[PLQ] | NLS - |
| 545 | RRRRRxRR | NLS - |
| 546 | RKR{3,5}[ST] | NLS - |
| 547 | RKRx{12,16}RRKK | NLS - |
| 548 | RKR[PLQMN]R[PLQMN]R | NLS - |
| 549 | RKRKR[KR] | NLS - |
| 550 | KKKKKx{3,6}KK | NLS - |
| 551 | KKKKR[KR] | NLS - |
| 552 | RKKRRxR | NLS - |
| 553 | KKKR[KR][VPL] | NLS - |
| 554 | RKKRKR | NLS - |
| 555 | KKPx{6,9}Kx{1,3}RK | NLS - |
| 556 | RK[IVE]W[ML][TQR]N[HF] | NLS - |
| 557 | RK[PL][PLV]KK[RKH] | NLS - |
| 558 | RK[RK][QML][RK]xR | NLS - |
| 559 | RRRRRRx{0,2}R | NLS - |

TABLE 2-continued

Exemplary Sequences

| SEQ ID NO: | Sequence* | Description** |
|---|---|---|
| 560 | RRRRRR | NLS - |
| 561 | RRRK[STC]K | NLS - |
| 562 | RRRKKR | NLS - |
| 563 | RRKx{5,7}RRR | NLS - |
| 564 | RRKX{3,5}R[DE]R{3,}?[PLV] | NLS - |
| 565 | RRER[MNQ]Kx{4,8}R[MNQ]RRR | NLS - |
| 566 | KHLKGR | NLS - |
| 567 | RKx{7,12}RK[STMNQ]KK | NLS - |
| 568 | RK]{2,4}[PL][RK]x{7,11}[RK][QL]KH | NLS - |
| 569 | RH[RK]Hx{2,4}[RK]{2,4}}[PL]R | NLS - |
| 570 | PKKKRAVE | NLS - weak sv40 |

*Unless otherwise specified, nucleic acid sequences are described 5' to 3' and amino acid sequences are described N-terminus to C-terminus
**'NT' denotes a nucleic acid sequence; 'AA' denotes an amino acid sequence.

Other Embodiments

Embodiment 1. A method comprising administering an isolated nucleic acid to a multinucleate cell, wherein the isolated nucleic acid comprises a sequence encoding a fusion protein, the fusion protein comprising, a protein of interest fused to at least the following migration signals: (a) at least one nuclear export signal (NES); and (b) at least one nuclear localization signal (NLS) and/or at least one nucleolar localization signal (NoLS), optionally, wherein the isolated nucleic acid encodes an amino acid sequence comprising a sequence with at least 70% identity to SEQ ID NO: 13.

Embodiment 2. The method of embodiment 1, wherein the fusion protein further comprises at least one additional migration signal, wherein the additional migration signal may be identical or distinct from the migration signals used in embodiment 1.

Embodiment 3. The method of any one of embodiments 1-2, wherein the fusion protein further comprises at least two additional migration signals, wherein the additional migration signals may be identical or distinct from the migration signals used in any one of embodiments 1-2.

Embodiment 4. The method of any one of embodiments 1-3, wherein the isolated nucleic acid encode a fusion protein wherein at least one of the migration signals is positioned at the C-terminus of the protein of interest.

Embodiment 5. The method of any one of embodiments 1-3, wherein the isolated nucleic acid encodes a fusion protein wherein at least one of the migration signals is positioned at the N-terminus of the protein of interest.

Embodiment 6. The method of any one of embodiments 1-5, wherein the protein of interest is a therapeutic protein.

Embodiment 7. The method of any one of embodiments 1-5, wherein the protein of interest is a nuclear protein.

Embodiment 8. The method of any one of embodiments 1-5, wherein the protein of interest is at least uric of the following: a transcriptional factor, a transcriptional repressor, an RNA binding protein, a DNA modifying protein, a DNA editing protein, and a Cas protein.

Embodiment 9. The method of any one of embodiments 1-5, wherein the protein of interest is DUX4, or variant thereof.

Embodiment 10. The method of any one of embodiments 1-5, wherein the protein of interest carries RNA.

Embodiment 11. The method of any one of embodiments 1-5, wherein the protein of interest be used to treat Facioscapulohumeral dystrophy.

Embodiment 12. The method of any one of embodiments 1-11, wherein the isolated nucleic acid is flanked by adeno-associated virus (AAV) inverted terminal repeats (ITRs).

Embodiment 13. The method of any one of embodiments 1-12, wherein the multinucleate cell is a skeletal muscle cell.

Embodiment 14. The method of any one of embodiments 1-12, wherein the multinucleate cell is a liver cell.

Embodiment 15. The method of any one of embodiments 1-14, wherein the nucleic acid is administered to a subject.

Embodiment 16. The method of any one of embodiments 1-15, wherein the subject has a disorder.

Embodiment 17. The method of embodiment 16, wherein the protein of interest treats the disorder.

Embodiment 18. The method of any one of embodiments 16-17, wherein the disorder is Facioscapulohumeral dystrophy.

Embodiment 19. The method of any one of embodiments 16-18, wherein the protein of interest treats Facioscapulohumeral dystrophy.

Embodiment 20. The method of any one of embodiments 15-19, wherein the subject is mammalian.

Embodiment 21. The method of any one of embodiments 15-20, wherein the subject is human.

Embodiment 22. A fusion protein comprising: (a) a protein of interest; and (b) at least the following migration signals: (i) a nuclear export signal (NES); (ii) a nuclear localization signal (NLS); and (iii) a nucleolar localization signal (NoLS), optionally, wherein the fusion protein comprises a sequence with at least 70% identity to SEQ ID NO: 13.

Embodiment 23. The fusion protein of embodiment 22, further comprising at least one additional migration signal, wherein the additional migration signal may be identical or distinct from the migration signals used in embodiment 22.

Embodiment 24. The fusion protein of any one of embodiments 22-23, further comprising at least two additional migration signals, wherein the additional migration signals may be identical or distinct from the migration signals used in any one of embodiments 22-23.

Embodiment 25. The fusion protein of any one of embodiments 22-24, wherein the at least one of the migration signals is positioned at the C-terminus of the protein of interest.

Embodiment 26. The fusion protein of any one of embodiments 22-24, wherein at least one of the migration signals is positioned at the N-terminus of the protein of interest. .embodiment Embodiment 27. The fusion protein of any one of embodiments 22-26, wherein at least one of the migration signals is linked to the protein of interest via a linker.

Embodiment 28. The fusion protein of any one of embodiments 22-27, wherein at least one of the migration signals comprises a sequence with at least 95% identity to SEQ ID NO: 1-6 or 14-570.

Embodiment 29. The fusion protein of any one of embodiments 22-28, wherein at least one of the migration signals comprises a sequence with at least 95% identity to SEQ ID NO: 3.

Embodiment 30. The fusion protein of any one of embodiments 22-29, wherein at least one of the migration signals comprises a sequence of SEQ ID NO: 1.

Embodiment 31. The fusion protein of any one of embodiments 22-30, wherein at least one of the migration signals comprises a sequence of SEQ ID NO: 3.

Embodiment 32. The fusion protein of any one of embodiments 22-31, wherein at least one of the migration signals comprises a sequence of SEQ ID NO: 1 and at least one of the migration signals comprises a sequence of SEQ ID NO: 3.

Embodiment 33. The fusion protein of the method of any one of embodiments 1-21, or the fusion protein of any one of embodiments 22-31, wherein at least one of the migration signals is linked to at least one other migration signal via a linker.

Embodiment 34. An isolated nucleic acid comprising a nucleic acid sequence encoding the fusion protein of the method of any one of embodiments 1-21, or the fusion protein of any one of embodiments 22-31.

Embodiment 35. The isolated nucleic acid of embodiment 34, further comprising a promoter operably linked to the sequence encoding the fusion protein.

Embodiment 36. The isolated nucleic acid of embodiment 35, wherein the promoter is a constitutive promoter, an inducible promoter, or a tissue specific promoter.

Embodiment 37. The isolated nucleic acid of any one of embodiments 35-36, wherein the promoter is a tissue specific promoter.

Embodiment 38. The isolated nucleic acid of embodiment 37, wherein the tissue specific promoter is specific to skeletal muscle.

Embodiment 39. The isolated nucleic acid of embodiment 37, wherein the tissue specific promoter is specific to liver tissue.

Embodiment 40. The isolated nucleic acid of any one of embodiments 34-39, further comprising at least one additional regulatory sequence.

Embodiment 41. A recombinant adeno-associated virus (rAAV), comprising: (a) the isolated nucleic acid of any one of embodiments 34-40 flanked by adeno-associated virus (AAV) inverted terminal repeats (ITRs); and (b) an AAV capsid protein.

Embodiment 42. The rAAV of embodiment 41, wherein the AAV capsid protein exhibits a tropism for skeletal muscle.

Embodiment 43. The rAAV of embodiment 41, wherein the AAV capsid protein exhibits a tropism for liver tissue.

Embodiment 44. The rAAV of any one of embodiments 41-42, wherein the AAV capsid protein serotype is selected from: AAV1 and AAV6.

Embodiment 45. The rAAV of any one of embodiments 44, wherein the AAV capsid protein serotype is AAV6.

Embodiment 46. The rAAV of any one of embodiments 41-43, wherein the AAV capsid protein serotype is selected from: AAV7; AAV8; and AAV9.

Embodiment 47. A composition comprising the isolated nucleic acid of any one of embodiments 34-40, or the rAAV of any one of embodiments 41-46, and a pharmaceutically acceptable excipient.

Embodiments 48. The composition of embodiment 47, wherein the composition is formulated for intramuscular administration, intrathecal administration, intravenous administration, retrograde intravenous administration, intravascular administration, systemic administration, intra-arterial administration, intraportal administration, intratracheal administration, or direct injection.

Embodiment 49. A method of delivering a fusion protein to multinucleate cells, comprising, administering the fusion protein of any one of embodiments 22-32, the isolated nucleic acid of any one of embodiments 34-40, the rAAV of any one of embodiments 41-46, or the composition of any one of embodiments 47-48 to a subject.

Embodiment 50. The fusion protein of any one of embodiments 22-32, the isolated nucleic acid of any one of embodiments 34-40, the rAAV of any one of embodiments 41-46, or the composition of any one of embodiments 47-48, or the fusion protein of the method of embodiment 49, wherein the protein of interest is a therapeutic protein.

Embodiment 51. The fusion protein of any one of embodiments 22-32, the isolated nucleic acid of any one of embodiments 34-40, the rAAV of any one of embodiments 4146, or the composition of any one of embodiments 47-48, or the fusion protein of the method of embodiment 49, wherein the protein of interest is a transcriptional factor, transcriptional repressor. RNA binding protein. DNA modifying protein, DNA editing protein. Cas protein, DUX4, or an protein carrying an RNA.

Embodiment 52. The fusion protein of any one of embodiments 22-32, the isolated nucleic acid of any one of embodiment, 34-40, the rAAV of any one of embodiments 4146, or the composition of any one of embodiments 47-4841-42, or the fusion protein of the method of embodiment 49, wherein the protein of interest is a nuclear protein.

Embodiment 53. The method of embodiment 49, wherein the subject is mammalian.

Embodiment 54. The method of any one of embodiments 49 or 53, wherein the subject is human.

Embodiment 55. The method of any one of embodiments 49 or 53-54, wherein the subject has a disorder.

Embodiment 56. The method of embodiment 55, wherein the disorder is Facioscapulohumeral dystrophy.

General Techniques

The practice of the subject matter of the disclosure will employ, unless otherwise indicated, conventional techniques of molecular biology (including recombinant techniques), microbiology, cell biology, biochemistry and immunology, which are within the skill of the art. Such techniques are explained fully in the literature, such as, but without limiting. Molecular Cloning: A Laboratory Manual, second edition (Sambrook, et al., 1989) Cold Spring Harbor Press; Oligonucleotide Synthesis (M. J. Gait, ed., 1984): Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press: Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds. 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999): Immunobiology C. A. Janeway and P. Travers, 1997); Antibodies (P. Finch, 1997); Antibodies: a practical approach (D. Catty, ed., IRL Press, 1988-1989); Monoclonal antibodies: a practical approach (P. Shepherd and C. Dean, eds., Oxford University Press, 2000): Using antibodies: r laboratory manual (E. Harlow and D. Lane (Cold Spring Harbor Laboratory Press, 1999); The Antibodies (M. Zanetti and J. D. Capra, eds., Harwood Academic Publishers, 1995).

EQUIVALENTS AND SCOPE

It is to be understood that this disclosure is not limited to any or all of the particular embodiments described expressly herein, and as such may, of course, vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents (i.e., any lexicographical definition in the publications and patents cited that is not also expressly repeated in the disclosure should not be treated as such and should not be read as defining any terms appearing in the accompanying claims). If there is a conflict between any of the incorporated references and this disclosure, this disclosure shall control. In addition, any particular embodiment of this disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the disclosure can be excluded from any claim, for any reason, whether or not related to the existence of prior art.

The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

In the claims articles such as "a," "an," and "the" may mean one or more than one unless indicated to the contrary or otherwise evident from the context. Wherever used herein, a pronoun in a gender (e.g., masculine, feminine, neuter, other, etc. . . . ) the pronoun shall be construed as gender neutral (e.g., construed to refer to all genders equally) regardless of the implied gender unless the context clearly indicates or requires otherwise. Wherever used herein, words used in the singular include the plural, and words used in the plural includes the singular, unless the context clearly indicates or requires otherwise. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permulations in which one or more limitations, elements, clauses, and descriptive term from one or more of the listed claims is introduced into another claim. For example, any claim that is dependent on another claim can be modified to include one or mom limitations found in any other claim that is dependent on the same base claim. Where elements are presented as lists (e.g., in Markush group format), each subgroup of the elements is also disclosed, and any element(s) can be removed from the group. It should it be understood that, in general, where the disclosure, or aspects of the disclosure, is/are referred to as comprising particular elements and/or features, certain embodiments of the disclosure or aspects of the disclosure consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included in such ranges unless otherwise specified. Furthermore, unless otherwise indicated or otherwise evident from the context and understanding of one of ordinary skill in the art, values that are expressed as ranges can assume any specific value or sub-range within the stated ranges in different embodiments of the disclosure, to the tenth of the unit of the lower limit of the range, unless the context clearly dictates otherwise.

Those skilled in the art will recognize or be able to ascertain using no more than routine experimentation many equivalents to the specific embodiments described herein. 5 The scope of the present embodiments described wherein is not intended to be limited to the above Description, but rather is as set forth in the appended claims. Those of ordinary skill in the art will appreciate that various changes and modifications to this description may be made without departing from the spirit or scope of the disclosure, as defined in the following claims.

---

The invention claimed is:

1. A method comprising administering an isolated nucleic acid to a multinucleate cell, wherein the isolated nucleic acid comprises a sequence encoding a fusion protein, the fusion protein comprising, a protein of interest fused to at least the following migration signals:

(a) at least one nuclear export signal (NES); and
   (b) at least one nuclear localization signal (NLS) and/or at least one nucleolar localization signal (NoLS),
   wherein the protein of interest comprises an amino acid sequence having at least 90% identity to SEQ ID NO: 13.

2. The method of claim 1, wherein the fusion protein further comprises at least one additional migration signal, wherein the additional migration signal may be identical or distinct from the migration signals used in claim 1, or wherein the fusion protein further comprises at least two additional migration signals, wherein the additional migration signals may be identical or distinct from the migration signals used in claim 1.

3. The method of claim 1, wherein the isolated nucleic acid encodes a fusion protein wherein at least one of the migration signals is positioned at the C-terminus of the protein of interest or at the N-terminus of the protein of interest.

4. The method of claim 1, wherein the protein of interest carries RNA.

5. The method of claim 1, wherein the protein of interest is used to treat Facioscapulohumeral dystrophy.

6. The method of claim 1, wherein the isolated nucleic acid is flanked by adeno-associated virus (AAV) inverted terminal repeats (ITRs).

7. The method of claim 1, wherein the multinucleate cell is a skeletal muscle cell.

8. The method of claim 1, wherein the multinucleate cell is a liver cell.

9. The method of claim 1, wherein the nucleic acid is administered to a subject, optionally wherein the subject is mammalian.

10. The method of claim 1, wherein the subject has a disorder, optionally wherein the disorder is Facioscapulohumeral dystrophy.

11. The method of claim 1, wherein at least one of the migration signals is linked to the protein of interest via a linker.

12. The method of claim 1, wherein at least one of the migration signals comprises an amino acid sequence with at least 95% identity to any one of SEQ ID NO: 1-6 or 14-570.

13. The method of claim 1, wherein at least one of the migration signals comprises an amino acid sequence with at least 95% identity to SEQ ID NO: 3.

14. The method of claim 1, wherein at least one of the migration signals comprises an amino acid sequence of SEQ ID NO: 1.

15. The method of claim 1, wherein at least one of the migration signals comprises an amino acid sequence of SEQ ID NO: 3.

* * * * *

SEQUENCE LISTING

```
<160> NUMBER OF SEQ ID NOS: 570

<210> SEQ ID NO 1
<211> LENGTH: 28
<212> TYPE: PRT
<213> ORGANISM: Artificial Sequence
<220> FEATURE:
<223> OTHER INFORMATION: Synthetic polypeptide

<400> SEQUENCE: 1

Ala Pro Pro Ala Gln Pro Pro Ser Gln Pro Gln Gln His Tyr Ser Glu
1               5               10              15

Gly Glu Leu Glu Glu Asp Glu Asp Ser Asp Asp Ala
            20              25

<210> SEQ ID NO 2
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 2

Arg Phe Glu Met Phe Arg Glu Leu Asn Glu Ala Leu Glu Leu Lys Asp
1               5               10              15

Ala

<210> SEQ ID NO 3
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 3

Pro Lys Lys Lys Arg Ala Val Glu
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 4

Met Pro Lys Lys Lys Arg Ala Val Glu
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 5

Pro Lys Lys Lys Arg Lys Val
1               5
```

```
<210> SEQ ID NO 6
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 6

Arg Lys Lys Arg Lys Lys Lys
1               5

<210> SEQ ID NO 7
<211> LENGTH: 244
<212> TYPE: PRT
<213> ORGANISM: Artificial Sequence
<220> FEATURE:
<223> OTHER INFORMATION: Synthetic

<400> SEQUENCE: 7

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
        130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
        210                 215                 220

Val Thr Ala Ala Gly Ile Thr Leu Gly Met Asp Glu Leu Tyr Lys Gly
225                 230                 235                 240

Thr Ala Ala Ala

<210> SEQ ID NO 8
<211> LENGTH: 264
<212> TYPE: PRT
<213> ORGANISM: Artificial Sequence
<220> FEATURE:
<223> OTHER INFORMATION: Synthetic
```

<400> SEQUENCE: 8

```
Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
            20                  25                  30

Asp Ala Ala Val Phe Arg Leu Ser Ala Gln Gly Arg Pro Val Leu Phe
        35                  40                  45

Val Lys Thr Asp Leu Ser Gly Ala Leu Asn Glu Leu Gln Asp Glu Ala
    50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Leu Gly Glu
                85                  90                  95

Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
            115                 120                 125

Ala Thr Cys Pro Phe Asp His Gln Ala Lys His Arg Ile Glu Arg Ala
    130                 135                 140

Arg Thr Arg Met Glu Ala Gly Leu Val Asp Gln Asp Asp Leu Asp Glu
145                 150                 155                 160

Glu His Gln Gly Leu Ala Pro Ala Glu Leu Phe Ala Arg Leu Lys Ala
            165                 170                 175

Arg Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
            195                 200                 205

Cys Gly Arg Leu Gly Val Ala Asp Arg Tyr Gln Asp Ile Ala Leu Ala
            210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
            260
```

<210> SEQ ID NO 9
<211> LENGTH: 286
<212> TYPE: PRT
<213> ORGANISM: Artificial Sequence
<220> FEATURE:
<223> OTHER INFORMATION: Synthetic

<400> SEQUENCE: 9

```
Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
```

-continued

```
                         85                    90                    95

Gln Asn Asp Leu Val Glu Tyr Ser Pro Val Thr Glu Lys His Leu Thr
            100                   105                   110

Asp Gly Met Thr Val Arg Glu Leu Cys Ser Ala Ala Ile Thr Met Ser
            115                   120                   125

Asp Asn Thr Ala Ala Asn Leu Leu Leu Thr Thr Ile Gly Gly Pro Lys
        130                   135                   140

Glu Leu Thr Ala Phe Leu His Asn Met Gly Asp His Val Thr Arg Leu
145                   150                   155                   160

Asp Arg Trp Glu Pro Glu Leu Asn Glu Ala Ile Pro Asn Asp Glu Arg
                165                   170                   175

Asp Thr Thr Met Pro Val Ala Met Ala Thr Thr Leu Arg Lys Leu Leu
            180                   185                   190

Thr Gly Glu Leu Leu Thr Leu Ala Ser Arg Gln Gln Leu Ile Asp Trp
            195                   200                   205

Met Glu Ala Asp Lys Val Ala Gly Pro Leu Leu Arg Ser Ala Leu Pro
        210                   215                   220

Ala Gly Trp Phe Ile Ala Asp Lys Ser Gly Ala Gly Glu Arg Gly Ser
225                   230                   235                   240

Arg Gly Ile Ile Ala Ala Leu Gly Pro Asp Gly Lys Pro Ser Arg Ile
                245                   250                   255

Val Val Ile Tyr Thr Thr Gly Ser Gln Ala Thr Met Asp Glu Arg Asn
            260                   265                   270

Arg Gln Ile Ala Glu Ile Gly Ala Ser Leu Ile Lys His Trp
        275                   280                   285
```

<210> SEQ ID NO 10
<211> LENGTH: 6246
<212> TYPE: DNA
<213> ORGANISM: Artificial Sequence
<220> FEATURE:
<223> OTHER INFORMATION: Synthetic

<400> SEQUENCE: 10

```
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca caaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagc     900
gtttaaactt aagcttatgc ccaaaaagaa aagagccgtg gaaggatccg aattcatggt     960
```

```
ttctaagggg gaagagcttt tcacgggagt cgtcccgatt ctggtggagt tggacgggga   1020
tgttaatggt cacaagttct ccgtcagtgg tgaggggggag ggggatgcga cctacggcaa   1080
actgactttg aagtttatat gcacaacagg caaacttccc gtaccctggc ctactttggt   1140
gactacgctt acatacgggg tccagtgctt cagtagatat ccagatcaca tgaagcagca   1200
cgattttttt aaaagcgcca tgccagaggg ctatgttcaa gagaggacaa ttttcttcaa   1260
ggatgacggc aactacaaaa ctcgggctga ggtcaaattt gaaggagata cgctggtgaa   1320
caggatagaa ctgaagggaa ttgacttcaa ggaggatgga aatattctcg ggcataaatt   1380
ggagtataac tacaattctc ataacgttta cattatggcc gataaacaaa aaaatggtat   1440
aaaggttaac ttcaaaattc ggcataacat agaggacggg tcagtgcagc tcgcagacca   1500
ttaccagcaa aatacgccga taggtgatgg gccggttctt ttgcctgata atcactacct   1560
cagcacacag agtgccctca gcaaagaccc aaacgaaaaa cgagatcata tggtgctcct   1620
ggaatttgtt acagcggcag gaataacact gggaatggac gaactttaca agggtaccgc   1680
ggccgcagct cctccggcac aacctcccag ccaacctcag cagcattata gcgaaggaga   1740
gttggaggaa gatgaagatt ctgatgacgc gcgcaaaaaa cgcaaaaaaa aataagtgac   1800
tcgagtctag agggcccgtt taaacccgct gatcagcctc gactgtgcct tctagttgcc   1860
agccatctgt tgtttgcccc tccccgtgc cttccttgac cctggaaggt gccactccca   1920
ctgtcctttc ctaataaaat gaggaaattg catcgcattg tctgagtagg tgtcattcta   1980
ttctgggggg tggggtgggg caggacagca aggggggagga ttgggaagac aatagcaggc   2040
atgctgggga tgcggtgggc tctatggctt ctgaggcgga aagaaccagc tggggctcta   2100
gggggtatcc ccacgcgccc tgtagcggcg cattaagcgc ggcgggtgtg gtggttacgc   2160
gcagcgtgac cgctacactt gccagcgccc tagcgcccgc tcctttcgct ttcttccctt   2220
cctttctcgc cacgttcgcc ggctttcccc gtcaagctct aaatcggggg ctccctttag   2280
ggttccgatt tagtgcttta cggcacctcg accccaaaaa acttgattag ggtgatggtt   2340
cacgtagtgg gccatcgccc tgatagacgg ttttttcgcc tttgacgttg gagtccacgt   2400
tctttaatag tggactcttg ttccaaactg gaacaacact caaccctatc tcggtctatt   2460
cttttgattt ataagggatt ttgccgattt cggcctattg gttaaaaaat gagctgattt   2520
aacaaaaatt taacgcgaat taattctgtg gaatgtgtgt cagttagggt gtggaaagtc   2580
cccaggctcc ccagcaggca gaagtatgca aagcatgcat ctcaattagt cagcaaccag   2640
gtgtggaaag tccccaggct ccccagcagg cagaagtatg caaagcatgc atctcaatta   2700
gtcagcaacc atagtcccgc ccctaactcc gcccatcccg cccctaactc cgcccagttc   2760
cgcccattct ccgccccatg ctgactaat ttttttttatt tatgcagagg ccgaggccgc   2820
ctctgcctct gagctattcc agaagtagtg aggaggcttt tttggaggcc taggcttttg   2880
caaaaagctc ccgggagctt gtatatccat tttcggatct gatcaagaga caggatgagg   2940
atcgtttcgc atgattgaac aagatggatt gcacgcaggt tctccggccg cttgggtgga   3000
gaggctattc ggctatgact gggcacaaca gacaatcggc tgctctgatg ccgccgtgtt   3060
ccggctgtca gcgcagggggc gcccggttct ttttgtcaag accgacctgt ccggtgccct   3120
gaatgaactg caggacgagg cagcgcggct atcgtggctg gccacgacgg gcgttccttg   3180
cgcagctgtg ctcgacgttg tcactgaagc gggaagggac tggctgctat tgggcgaagt   3240
gccggggcag gatctcctgt catctcacct tgctcctgcc gagaaagtat ccatcatggc   3300
```

-continued

```
tgatgcaatg cggcggctgc atacgcttga tccggctacc tgcccattcg accaccaagc   3360
gaaacatcgc atcgagcgag cacgtactcg gatggaagcc ggtcttgtcg atcaggatga   3420
tctggacgaa gagcatcagg ggctcgcgcc agccgaactg ttcgccaggc tcaaggcgcg   3480
catgcccgac ggcgaggatc tcgtcgtgac ccatggcgat gcctgcttgc cgaatatcat   3540
ggtggaaaat ggccgctttt ctggattcat cgactgtggc cggctgggtg tggcggaccg   3600
ctatcaggac atagcgttgg ctacccgtga tattgctgaa gagcttggcg gcgaatgggc   3660
tgaccgcttc ctcgtgcttt acggtatcgc cgctcccgat tcgcagcgca tcgccttcta   3720
tcgccttctt gacgagttct tctgagcggg actctgggt tcgaaatgac cgaccaagcg   3780
acgcccaacc tgccatcacg agatttcgat tccaccgccg ccttctatga aaggttgggc   3840
ttcggaatcg ttttccggga cgccggctgg atgatcctcc agcgcgggga tctcatgctg   3900
gagttcttcg cccaccccaa cttgtttatt gcagcttata atggttacaa ataaagcaat   3960
agcatcacaa atttcacaaa taaagcattt ttttcactgc attctagttg tggtttgtcc   4020
aaactcatca atgtatctta tcatgtctgt ataccgtcga cctctagcta gagcttggcg   4080
taatcatggt catagctgtt tcctgtgtga aattgttatc cgctcacaat tccacacaac   4140
atacgagccg gaagcataaa gtgtaaagcc tggggtgcct aatgagtgag ctaactcaca   4200
ttaattgcgt tgcgctcact gcccgctttc cagtcgggaa acctgtcgtg ccagctgcat   4260
taatgaatcg gccaacgcgc ggggagaggc ggtttgcgta ttgggcgctc ttccgcttcc   4320
tcgctcactg actcgctgcg ctcggtcgtt cggctgcggc gagcggtatc agctcactca   4380
aaggcggtaa tacggttatc cacagaatca ggggataacg caggaaagaa catgtgagca   4440
aaaggccagc aaaaggccag gaaccgtaaa aaggccgcgt tgctggcgtt tttccatagg   4500
ctccgccccc ctgacgagca tcacaaaaat cgacgctcaa gtcagaggtg gcgaaacccg   4560
acaggactat aaagatacca ggcgtttccc cctggaagct ccctcgtgcg ctctcctgtt   4620
ccgaccctgc cgcttaccgg atacctgtcc gcctttctcc cttcgggaag cgtggcgctt   4680
tctcatagct cacgctgtag gtatctcagt tcggtgtagg tcgttcgctc caagctgggc   4740
tgtgtgcacg aaccccccgt tcagcccgac cgctgcgcct tatccggtaa ctatcgtctt   4800
gagtccaacc cggtaagaca cgacttatcg ccactggcag cagccactgg taacaggatt   4860
agcagagcga ggtatgtagg cggtgctaca gagttcttga agtggtggcc taactacggc   4920
tacactagaa gaacagtatt tggtatctgc gctctgctga agccagttac cttcggaaaa   4980
agagttggta gctcttgatc cggcaaacaa accaccgctg gtagcggtgg tttttttgtt   5040
tgcaagcagc agattacgcg cagaaaaaaa ggatctcaag aagatccttt gatcttttct   5100
acggggtctg acgctcagtg gaacgaaaac tcacgttaag ggattttggt catgagatta   5160
tcaaaaagga tcttcaccta gatccttta aattaaaaat gaagttttaa atcaatctaa   5220
agtatatatg agtaaacttg gtctgacagt taccaatgct taatcagtga ggcacctatc   5280
tcagcgatct gtctatttcg ttcatccata gttgcctgac tccccgtcgt gtagataact   5340
acgatacggg agggcttacc atctggcccc agtgctgcaa tgataccgcg agacccacgc   5400
tcaccggctc cagatttatc agcaataaac cagccagccg gaagggccga gcgcagaagt   5460
ggtcctgcaa ctttatccgc ctccatccag tctattaatt gttgccggga agctagagta   5520
agtagttcgc cagttaatag tttgcgcaac gttgttgcca ttgctacagg catcgtggtg   5580
tcacgctcgt cgtttggtat ggcttcattc agctccggtt cccaacgatc aaggcgagtt   5640
acatgatccc ccatgttgtg caaaaaagcg gttagctcct tcggtcctcc gatcgttgtc   5700
```

```
agaagtaagt tggccgcagt gttatcactc atggttatgg cagcactgca taattctctt      5760
actgtcatgc catccgtaag atgctttct gtgactggtg agtactcaac caagtcattc       5820
tgagaatagt gtatgcggcg accgagttgc tcttgcccgg cgtcaatacg ggataatacc      5880
gcgccacata gcagaacttt aaaagtgctc atcattggaa aacgttcttc ggggcgaaaa      5940
ctctcaagga tcttaccgct gttgagatcc agttcgatgt aacccactcg tgcacccaac      6000
tgatcttcag catcttttac tttcaccagc gtttctgggt gagcaaaaac aggaaggcaa      6060
aatgccgcaa aaaagggaat aagggcgaca cggaaatgtt gaatactcat actcttcctt      6120
tttcaatatt attgaagcat ttatcagggt tattgtctca tgagcggata catatttgaa      6180
tgtatttaga aaaataaaca aatagggggtt ccgcgcacat ttccccgaaa agtgccacct     6240
gacgtc                                                                6246
```

<210> SEQ ID NO 11
<211> LENGTH: 292
<212> TYPE: PRT
<213> ORGANISM: Artificial Sequence
<220> FEATURE:
<223> OTHER INFORMATION: Synthetic

<400> SEQUENCE: 11

```
Met Pro Lys Lys Lys Arg Ala Val Glu Gly Ser Glu Phe Met Val Ser
1               5                   10                  15

Lys Gly Glu Glu Leu Phe Thr Gly Val Val Pro Ile Leu Val Glu Leu
            20                  25                  30

Asp Gly Asp Val Asn Gly His Lys Phe Ser Val Ser Gly Glu Gly Glu
        35                  40                  45

Gly Asp Ala Thr Tyr Gly Lys Leu Thr Leu Lys Phe Ile Cys Thr Thr
    50                  55                  60

Gly Lys Leu Pro Val Pro Trp Pro Thr Leu Val Thr Thr Leu Thr Tyr
65                  70                  75                  80

Gly Val Gln Cys Phe Ser Arg Tyr Pro Asp His Met Lys Gln His Asp
                85                  90                  95

Phe Phe Lys Ser Ala Met Pro Glu Gly Tyr Val Gln Glu Arg Thr Ile
            100                 105                 110

Phe Phe Lys Asp Asp Gly Asn Tyr Lys Thr Arg Ala Glu Val Lys Phe
            115                 120                 125

Glu Gly Asp Thr Leu Val Asn Arg Ile Glu Leu Lys Gly Ile Asp Phe
        130                 135                 140

Lys Glu Asp Gly Asn Ile Leu Gly His Lys Leu Glu Tyr Asn Tyr Asn
145                 150                 155                 160

Ser His Asn Val Tyr Ile Met Ala Asp Lys Gln Lys Asn Gly Ile Lys
                165                 170                 175

Val Asn Phe Lys Ile Arg His Asn Ile Glu Asp Gly Ser Val Gln Leu
            180                 185                 190

Ala Asp His Tyr Gln Gln Asn Thr Pro Ile Gly Asp Gly Pro Val Leu
            195                 200                 205

Leu Pro Asp Asn His Tyr Leu Ser Thr Gln Ser Ala Leu Ser Lys Asp
        210                 215                 220

Pro Asn Glu Lys Arg Asp His Met Val Leu Leu Glu Phe Val Thr Ala
225                 230                 235                 240

Ala Gly Ile Thr Leu Gly Met Asp Glu Leu Tyr Lys Gly Thr Ala Ala
                245                 250                 255
```

Ala Ala Pro Pro Ala Gln Pro Pro Ser Gln Pro Gln Gln His Tyr Ser
            260                 265                 270

Glu Gly Glu Leu Glu Glu Asp Glu Asp Ser Asp Asp Ala Arg Lys Lys
        275                 280                 285

Arg Lys Lys Lys
    290

<210> SEQ ID NO 12
<211> LENGTH: 181
<212> TYPE: PRT
<213> ORGANISM: Artificial Sequence
<220> FEATURE:
<223> OTHER INFORMATION: Synthetic

<400> SEQUENCE: 12

Met Ala Leu Pro Thr Pro Ser Asp Ser Thr Leu Pro Ala Glu Ala Arg
1               5                   10                  15

Gly Arg Gly Arg Arg Arg Leu Val Trp Thr Pro Ser Gln Ser Glu
            20                  25                  30

Ala Leu Arg Ala Cys Phe Glu Arg Asn Pro Tyr Pro Gly Ile Ala Thr
        35                  40                  45

Arg Glu Arg Leu Ala Gln Ala Ile Gly Ile Pro Glu Pro Arg Val Gln
    50                  55                  60

Ile Trp Phe Gln Asn Glu Arg Ser Arg Gln Leu Arg Gln His Arg Arg
65                  70                  75                  80

Glu Ser Arg Pro Trp Pro Gly Arg Arg Gly Pro Pro Glu Gly Arg Arg
            85                  90                  95

Lys Arg Thr Ala Val Thr Gly Ser Gln Thr Ala Leu Leu Leu Arg Ala
            100                 105                 110

Phe Glu Lys Asp Arg Phe Pro Gly Ile Ala Ala Arg Glu Glu Leu Ala
        115                 120                 125

Arg Glu Thr Gly Leu Pro Glu Ser Arg Ile Gln Ile Trp Phe Gln Asn
    130                 135                 140

Arg Arg Ala Arg His Pro Gly Gln Gly Gly Arg Ala Pro Ala Gln Glu
145                 150                 155                 160

Leu Leu Ala Ser Pro Glu Phe Leu Gln Gln Ala Gln Pro Leu Leu Glu
            165                 170                 175

Thr Glu Ala Pro Gly
            180

<210> SEQ ID NO 13
<211> LENGTH: 215
<212> TYPE: PRT
<213> ORGANISM: Artificial Sequence
<220> FEATURE:
<223> OTHER INFORMATION: Synthetic

<400> SEQUENCE: 13

Met Ala Leu Pro Thr Pro Ser Asp Ser Thr Leu Pro Ala Glu Ala Arg
1               5                   10                  15

Gly Arg Gly Arg Arg Arg Leu Val Trp Thr Pro Ser Gln Ser Glu
            20                  25                  30

Ala Leu Arg Ala Cys Phe Glu Arg Asn Pro Tyr Pro Gly Ile Ala Thr
        35                  40                  45

Arg Glu Arg Leu Ala Gln Ala Ile Gly Ile Pro Glu Pro Arg Val Gln
    50                  55                  60

Ile Trp Phe Gln Asn Glu Arg Ser Arg Gln Leu Arg Gln His Arg Arg
65                  70                  75                  80

```
Glu Ser Arg Pro Trp Pro Gly Arg Arg Gly Pro Pro Glu Gly Arg Arg
            85              90              95

Lys Arg Thr Ala Val Thr Gly Ser Gln Thr Ala Leu Leu Leu Arg Ala
            100             105             110

Phe Glu Lys Asp Arg Phe Pro Gly Ile Ala Ala Arg Glu Glu Leu Ala
            115             120             125

Arg Glu Thr Gly Leu Pro Glu Ser Arg Ile Gln Ile Trp Phe Gln Asn
    130             135             140

Arg Arg Ala Arg His Pro Gly Gln Gly Gly Arg Ala Pro Ala Gln Glu
145             150             155             160

Leu Leu Ala Ser Pro Glu Phe Leu Gln Gln Ala Gln Pro Leu Leu Glu
            165             170             175

Thr Glu Ala Pro Gly Leu Glu Gly Thr Arg Phe Glu Ala Pro Pro Ala
            180             185             190

Gln Pro Pro Ser Gln Pro Gln Gln His Tyr Ser Glu Gly Glu Leu Glu
    195             200             205

Glu Asp Glu Asp Ser Asp Asp
    210             215

<210> SEQ ID NO 14
<211> LENGTH: 16
<212> TYPE: PRT
<213> ORGANISM: Artificial Sequence
<220> FEATURE:
<223> OTHER INFORMATION: Synthetic

<400> SEQUENCE: 14

Asp Asp Ile Val Phe Glu Asp Phe Ala Arg Leu Arg Leu Lys Gly Met
1               5               10              15

<210> SEQ ID NO 15
<211> LENGTH: 10
<212> TYPE: PRT
<213> ORGANISM: Artificial Sequence
<220> FEATURE:
<223> OTHER INFORMATION: Synthetic

<400> SEQUENCE: 15

Leu Ile Ala Gly Ile Ile Ala Met Ile Cys
1               5               10

<210> SEQ ID NO 16
<211> LENGTH: 63
<212> TYPE: PRT
<213> ORGANISM: Artificial Sequence
<220> FEATURE:
<223> OTHER INFORMATION: Synthetic

<400> SEQUENCE: 16

Ser Leu Pro Pro Glu Pro Met Met Pro Met Asp Gln Thr Met His Pro
1               5               10              15

Asp His Thr Gln Thr Val Ile Pro Tyr Asn Pro Ser Ser His Glu Ser
            20              25              30

Leu Asp Gln Val Gly Glu Glu Lys Glu Ala Met Asn Thr Arg Glu Ser
        35              40              45

Gly Lys Ala Ser Ser Ser Leu Gly Leu Gln Asp Phe Asp Leu Leu
    50              55              60

<210> SEQ ID NO 17
<211> LENGTH: 11
```

```
<212> TYPE: PRT
<213> ORGANISM: Artificial Sequence
<220> FEATURE:
<223> OTHER INFORMATION: Synthetic

<400> SEQUENCE: 17

Met Thr Leu Gly Met Ile Trp Thr Ile Ile Leu
1               5                   10

<210> SEQ ID NO 18
<211> LENGTH: 15
<212> TYPE: PRT
<213> ORGANISM: Artificial Sequence
<220> FEATURE:
<223> OTHER INFORMATION: Synthetic

<400> SEQUENCE: 18

Phe Glu Ala Leu Met Arg Met Leu Asp Asn Leu Gly Tyr Arg Thr
1               5                   10                  15

<210> SEQ ID NO 19
<211> LENGTH: 10
<212> TYPE: PRT
<213> ORGANISM: Artificial Sequence
<220> FEATURE:
<223> OTHER INFORMATION: Synthetic

<400> SEQUENCE: 19

Leu Ala Gln Gln Phe Glu Gln Leu Ser Val
1               5                   10

<210> SEQ ID NO 20
<211> LENGTH: 21
<212> TYPE: PRT
<213> ORGANISM: Artificial Sequence
<220> FEATURE:
<223> OTHER INFORMATION: Synthetic

<400> SEQUENCE: 20

Pro Phe Pro Gln Asp Val Ile Asn Lys Leu Asp Lys Leu Ser Val Leu
1               5                   10                  15

Arg Leu Ser Val Ser
            20

<210> SEQ ID NO 21
<211> LENGTH: 22
<212> TYPE: PRT
<213> ORGANISM: Artificial Sequence
<220> FEATURE:
<223> OTHER INFORMATION: Synthetic

<400> SEQUENCE: 21

Arg Leu Gly Ser His Thr Met Asp Phe Phe Glu Met Cys Ala Ser Leu
1               5                   10                  15

Ile Thr Ala Leu Ala Arg
            20

<210> SEQ ID NO 22
<211> LENGTH: 21
<212> TYPE: PRT
<213> ORGANISM: Artificial Sequence
<220> FEATURE:
<223> OTHER INFORMATION: Synthetic

<400> SEQUENCE: 22

Met Ser His Val Ala Val Glu Asn Val Leu Asn Leu Asp Gln Gln Phe
```

-continued

```
1               5              10              15

Ala Gly Leu Asp Leu
          20

<210> SEQ ID NO 23
<211> LENGTH: 18
<212> TYPE: PRT
<213> ORGANISM: Artificial Sequence
<220> FEATURE:
<223> OTHER INFORMATION: Synthetic

<400> SEQUENCE: 23

Val Ile Gln Gln Thr Leu Ala Ala Ile Val Asp Ala Ile Lys Leu Asp
1               5              10              15

Ala Ile

<210> SEQ ID NO 24
<211> LENGTH: 15
<212> TYPE: PRT
<213> ORGANISM: Artificial Sequence
<220> FEATURE:
<223> OTHER INFORMATION: Synthetic

<400> SEQUENCE: 24

Val Gly Gly Glu Leu Leu Asp Leu Leu Gly Asp Leu Asn Leu Ser
1               5              10              15

<210> SEQ ID NO 25
<211> LENGTH: 19
<212> TYPE: PRT
<213> ORGANISM: Artificial Sequence
<220> FEATURE:
<223> OTHER INFORMATION: Synthetic

<400> SEQUENCE: 25

Val Leu Ser Ala Val Lys Val Leu Met Lys Phe Leu Glu Leu Leu Pro
1               5              10              15

Lys Asp Ser

<210> SEQ ID NO 26
<211> LENGTH: 10
<212> TYPE: PRT
<213> ORGANISM: Artificial Sequence
<220> FEATURE:
<223> OTHER INFORMATION: Synthetic

<400> SEQUENCE: 26

Leu Leu Glu Arg Leu Lys Glu Leu Asn Leu
1               5              10

<210> SEQ ID NO 27
<211> LENGTH: 10
<212> TYPE: PRT
<213> ORGANISM: Artificial Sequence
<220> FEATURE:
<223> OTHER INFORMATION: Synthetic

<400> SEQUENCE: 27

Leu Thr Lys Arg Ile Asp Ser Leu Pro Leu
1               5              10

<210> SEQ ID NO 28
<211> LENGTH: 21
<212> TYPE: PRT
<213> ORGANISM: Artificial Sequence
```

```
<220> FEATURE:
<223> OTHER INFORMATION: Synthetic

<400> SEQUENCE: 28

Glu Ser Thr Pro Asp Gly Phe Ser Cys Ser Ser Ser Leu Ser Ala Leu
1               5                   10                  15

Ser Leu Asp Glu Pro
            20

<210> SEQ ID NO 29
<211> LENGTH: 21
<212> TYPE: PRT
<213> ORGANISM: Artificial Sequence
<220> FEATURE:
<223> OTHER INFORMATION: Synthetic

<400> SEQUENCE: 29

Glu Gly Thr Pro Ile Asn Phe Ser Thr Ala Thr Ser Leu Ser Asp Leu
1               5                   10                  15

Thr Ile Glu Ser Pro
            20

<210> SEQ ID NO 30
<211> LENGTH: 21
<212> TYPE: PRT
<213> ORGANISM: Artificial Sequence
<220> FEATURE:
<223> OTHER INFORMATION: Synthetic

<400> SEQUENCE: 30

Glu Asp Thr Pro Val Cys Phe Ser Arg Asn Ser Ser Leu Ser Ser Leu
1               5                   10                  15

Ser Ile Asp Ser Glu
            20

<210> SEQ ID NO 31
<211> LENGTH: 15
<212> TYPE: PRT
<213> ORGANISM: Artificial Sequence
<220> FEATURE:
<223> OTHER INFORMATION: Synthetic

<400> SEQUENCE: 31

Leu Trp Val Arg Leu Tyr Val Leu Glu Leu Tyr Cys Ile Ile Leu
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Synthetic

<400> SEQUENCE: 32

Asp Val Lys Ser Leu Glu Ser Ala Leu Lys Asp Leu Lys Ile Lys
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Synthetic

<400> SEQUENCE: 33
```

-continued

```
Leu Leu Arg Asn Glu Val Ala Gln Leu Lys Gln Leu Leu Leu Ala His
1               5                  10                  15

<210> SEQ ID NO 34
<211> LENGTH: 12
<212> TYPE: PRT
<213> ORGANISM: Artificial Sequence
<220> FEATURE:
<223> OTHER INFORMATION: Synthetic

<400> SEQUENCE: 34

Leu Glu Glu Leu Cys Ala Ala Arg Arg Leu Ser Leu
1               5                  10

<210> SEQ ID NO 35
<211> LENGTH: 11
<212> TYPE: PRT
<213> ORGANISM: Artificial Sequence
<220> FEATURE:
<223> OTHER INFORMATION: Synthetic

<400> SEQUENCE: 35

Glu Leu Ile Thr Phe Ile Asn Ala Leu Lys Leu
1               5                  10

<210> SEQ ID NO 36
<211> LENGTH: 19
<212> TYPE: PRT
<213> ORGANISM: Artificial Sequence
<220> FEATURE:
<223> OTHER INFORMATION: Synthetic

<400> SEQUENCE: 36

Gln Leu Val Glu Glu Leu Leu Lys Ile Ile Cys Ala Phe Gln Leu Asp
1               5                  10                  15

Thr Gly Leu

<210> SEQ ID NO 37
<211> LENGTH: 11
<212> TYPE: PRT
<213> ORGANISM: Artificial Sequence
<220> FEATURE:
<223> OTHER INFORMATION: Synthetic

<400> SEQUENCE: 37

Asp Leu Ser Asp Leu Thr Phe Leu Glu Val Ala
1               5                  10

<210> SEQ ID NO 38
<211> LENGTH: 15
<212> TYPE: PRT
<213> ORGANISM: Artificial Sequence
<220> FEATURE:
<223> OTHER INFORMATION: Synthetic

<400> SEQUENCE: 38

Arg Asp Leu Glu Arg Ala Met Thr Thr Leu Lys Leu Trp Glu Ser
1               5                  10                  15

<210> SEQ ID NO 39
<211> LENGTH: 18
<212> TYPE: PRT
<213> ORGANISM: Artificial Sequence
<220> FEATURE:
<223> OTHER INFORMATION: Synthetic

<400> SEQUENCE: 39
```

```
Ala Gly Asp Ile Leu Ala Leu Val Phe Gly Leu Leu Phe Ala Val Thr
1               5               10              15

Ser Val

<210> SEQ ID NO 40
<211> LENGTH: 18
<212> TYPE: PRT
<213> ORGANISM: Artificial Sequence
<220> FEATURE:
<223> OTHER INFORMATION: Synthetic

<400> SEQUENCE: 40

Leu Asp Ser Ser Leu Ala Asn Leu Val Gly Asn Leu Gly Ile Gly Asn
1               5               10              15

Gly Thr

<210> SEQ ID NO 41
<211> LENGTH: 19
<212> TYPE: PRT
<213> ORGANISM: Artificial Sequence
<220> FEATURE:
<223> OTHER INFORMATION: Synthetic

<400> SEQUENCE: 41

Ser Ser Thr Ser Gly Leu Glu Gln Asp Val Ala Gln Leu Asn Ile Ala
1               5               10              15

Glu Gln Asn

<210> SEQ ID NO 42
<211> LENGTH: 62
<212> TYPE: PRT
<213> ORGANISM: Artificial Sequence
<220> FEATURE:
<223> OTHER INFORMATION: Synthetic

<400> SEQUENCE: 42

Ala Ser Ser Leu Arg Asp Tyr Ala Ala Ser Thr Met Thr Glu Phe Leu
1               5               10              15

Gly Met Phe Gly Tyr Asp Asp Gln Asn Thr Arg Asp Glu Leu Ala Arg
            20              25              30

Lys Ile Ser Phe Glu Lys Leu His Ala Gly Ser Thr Pro Glu Ala Ala
        35              40              45

Thr Ser Ser Met Leu Pro Thr Ser Glu Asp Thr Leu Ser Lys
    50              55              60

<210> SEQ ID NO 43
<211> LENGTH: 10
<212> TYPE: PRT
<213> ORGANISM: Artificial Sequence
<220> FEATURE:
<223> OTHER INFORMATION: Synthetic

<400> SEQUENCE: 43

Leu Glu Met Phe Gly Pro Glu Gly Ala Leu
1               5               10

<210> SEQ ID NO 44
<211> LENGTH: 6
<212> TYPE: PRT
<213> ORGANISM: Artificial Sequence
<220> FEATURE:
<223> OTHER INFORMATION: Synthetic
```

```
<400> SEQUENCE: 44

His Leu Val Leu Ile Gly
1               5

<210> SEQ ID NO 45
<211> LENGTH: 10
<212> TYPE: PRT
<213> ORGANISM: Artificial Sequence
<220> FEATURE:
<223> OTHER INFORMATION: Synthetic

<400> SEQUENCE: 45

Leu Arg Lys Leu Cys Glu Arg Leu Arg Gly
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Synthetic

<400> SEQUENCE: 46

Leu Leu Asp Lys Leu Leu Asp Leu Asn Pro
1               5                   10

<210> SEQ ID NO 47
<211> LENGTH: 6
<212> TYPE: PRT
<213> ORGANISM: Artificial Sequence
<220> FEATURE:
<223> OTHER INFORMATION: Synthetic

<400> SEQUENCE: 47

Glu Gln Cys Glu Arg Ala
1               5

<210> SEQ ID NO 48
<211> LENGTH: 10
<212> TYPE: PRT
<213> ORGANISM: Artificial Sequence
<220> FEATURE:
<223> OTHER INFORMATION: Synthetic

<400> SEQUENCE: 48

Val Leu Arg Met Met Val Gly Val Asn Ile
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Synthetic

<400> SEQUENCE: 49

Phe Val Lys Val Leu Glu Lys Val Asp Val
1               5                   10

<210> SEQ ID NO 50
<211> LENGTH: 23
<212> TYPE: PRT
<213> ORGANISM: Artificial Sequence
<220> FEATURE:
<223> OTHER INFORMATION: Synthetic

<400> SEQUENCE: 50
```

```
Pro Asn Cys Pro Phe Leu Glu Asn Ser Leu Glu Thr Leu Arg Phe Ser
1               5                   10                  15

Ile Ser Asn Leu Ser Met Gln
            20
```

<210> SEQ ID NO 51
<211> LENGTH: 8
<212> TYPE: PRT
<213> ORGANISM: Artificial Sequence
<220> FEATURE:
<223> OTHER INFORMATION: Synthetic

<400> SEQUENCE: 51

```
Leu Gly Ala Leu Trp Leu Ala Leu
1               5
```

<210> SEQ ID NO 52
<211> LENGTH: 14
<212> TYPE: PRT
<213> ORGANISM: Artificial Sequence
<220> FEATURE:
<223> OTHER INFORMATION: Synthetic

<400> SEQUENCE: 52

```
Ile His Thr Pro Val Ala Ile Ile Glu Leu Glu Leu Gly Lys
1               5                   10
```

<210> SEQ ID NO 53
<211> LENGTH: 17
<212> TYPE: PRT
<213> ORGANISM: Artificial Sequence
<220> FEATURE:
<223> OTHER INFORMATION: Synthetic

<400> SEQUENCE: 53

```
Glu Val Lys Val Asn Gln Ile Leu Lys Thr Leu Ser Glu Val Glu Glu
1               5                   10                  15

Ser
```

<210> SEQ ID NO 54
<211> LENGTH: 45
<212> TYPE: PRT
<213> ORGANISM: Artificial Sequence
<220> FEATURE:
<223> OTHER INFORMATION: Synthetic

<400> SEQUENCE: 54

```
Asp Leu Leu Gly Thr Asp Gln Asp Asn Leu Asp Leu Ala Asn Val Asn
1               5                   10                  15

Leu Met Leu Glu Leu Leu Val Gln Lys Lys Lys Gln Leu Glu Ala Glu
            20                  25                  30

Ser His Ala Ala Gln Leu Gln Ile Leu Met Glu Phe Leu
        35                  40                  45
```

<210> SEQ ID NO 55
<211> LENGTH: 10
<212> TYPE: PRT
<213> ORGANISM: Artificial Sequence
<220> FEATURE:
<223> OTHER INFORMATION: Synthetic

<400> SEQUENCE: 55

```
Leu Ala Ala Leu Asn His Ile Ser Ala Leu
1               5                   10
```

<210> SEQ ID NO 56
<211> LENGTH: 50
<212> TYPE: PRT
<213> ORGANISM: Artificial Sequence
<220> FEATURE:
<223> OTHER INFORMATION: Synthetic

<400> SEQUENCE: 56

Leu Lys Val Ile Glu Glu Asn Val Cys Pro Lys Pro Ala Gln Val Glu
1               5                   10                  15

Pro Ser Ser Pro Ser Pro Met Glu Thr Ser Gly Cys Leu Pro Asp Glu
            20                  25                  30

Leu Cys Gln Ala Phe Ser Asp Val Leu Ile His Val Lys Asp Val Asp
        35                  40                  45

Ala Asp
    50

<210> SEQ ID NO 57
<211> LENGTH: 12
<212> TYPE: PRT
<213> ORGANISM: Artificial Sequence
<220> FEATURE:
<223> OTHER INFORMATION: Synthetic

<400> SEQUENCE: 57

Asp Leu Cys Gln Ala Phe Ser Asp Val Ile Leu Ala
1               5                   10

<210> SEQ ID NO 58
<211> LENGTH: 22
<212> TYPE: PRT
<213> ORGANISM: Artificial Sequence
<220> FEATURE:
<223> OTHER INFORMATION: Synthetic

<400> SEQUENCE: 58

Met Ser His Val Ala Val Glu Asn Ala Leu Gly Leu Asp Gln Gln Phe
1               5                   10                  15

Ala Gly Leu Asp Leu Asn
            20

<210> SEQ ID NO 59
<211> LENGTH: 15
<212> TYPE: PRT
<213> ORGANISM: Artificial Sequence
<220> FEATURE:
<223> OTHER INFORMATION: Synthetic

<400> SEQUENCE: 59

Pro Phe Gly Gln Ala Leu Arg Pro Leu Leu Asp Ser Ile Gln Ile
1               5                   10                  15

<210> SEQ ID NO 60
<211> LENGTH: 9
<212> TYPE: PRT
<213> ORGANISM: Artificial Sequence
<220> FEATURE:
<223> OTHER INFORMATION: Synthetic

<400> SEQUENCE: 60

Leu Ser Thr Leu Asp Gln Leu Arg Leu
1               5

-continued

```
<210> SEQ ID NO 61
<211> LENGTH: 13
<212> TYPE: PRT
<213> ORGANISM: Artificial Sequence
<220> FEATURE:
<223> OTHER INFORMATION: Synthetic

<400> SEQUENCE: 61

Ser Leu Glu Gly Ala Val Ser Glu Ile Ser Leu Arg Asp
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Synthetic

<400> SEQUENCE: 62

Leu Tyr Pro Glu Leu Arg Arg Ile Leu Thr Ile
1               5                   10

<210> SEQ ID NO 63
<211> LENGTH: 27
<212> TYPE: PRT
<213> ORGANISM: Artificial Sequence
<220> FEATURE:
<223> OTHER INFORMATION: Synthetic

<400> SEQUENCE: 63

Tyr Leu Ala Glu Ser Ser Gly Pro Ala Arg Gly Arg Gly Arg His Pro
1               5                   10                  15

Gly Lys Gly Val Lys Ser Pro Gly Glu Lys Ser
            20                  25

<210> SEQ ID NO 64
<211> LENGTH: 26
<212> TYPE: PRT
<213> ORGANISM: Artificial Sequence
<220> FEATURE:
<223> OTHER INFORMATION: Synthetic

<400> SEQUENCE: 64

Thr Pro Ser Ala Pro Arg Pro Ala Leu Gly Arg Pro Pro Val Lys Arg
1               5                   10                  15

Arg Leu Asp Leu Glu Thr Asp His Gln Tyr
            20                  25

<210> SEQ ID NO 65
<211> LENGTH: 10
<212> TYPE: PRT
<213> ORGANISM: Artificial Sequence
<220> FEATURE:
<223> OTHER INFORMATION: Synthetic

<400> SEQUENCE: 65

Met Val Leu Thr Arg Glu Glu Leu Val Ile
1               5                   10

<210> SEQ ID NO 66
<211> LENGTH: 20
<212> TYPE: PRT
<213> ORGANISM: Artificial Sequence
<220> FEATURE:
<223> OTHER INFORMATION: Synthetic

<400> SEQUENCE: 66
```

-continued

```
Val Ser Gln Ile Phe Pro Asp Ser Val Met Leu Ala Val Gln Glu Gly
1               5                   10                  15

Ile Asp Leu Leu
            20

<210> SEQ ID NO 67
<211> LENGTH: 19
<212> TYPE: PRT
<213> ORGANISM: Artificial Sequence
<220> FEATURE:
<223> OTHER INFORMATION: Synthetic

<400> SEQUENCE: 67

Phe Asp Ile Asp Glu Ala Glu Glu Gly Val Lys Asp Leu Lys Ile Glu
1               5                   10                  15

Ser Asp Val

<210> SEQ ID NO 68
<211> LENGTH: 24
<212> TYPE: PRT
<213> ORGANISM: Artificial Sequence
<220> FEATURE:
<223> OTHER INFORMATION: Synthetic

<400> SEQUENCE: 68

Arg Ile Asp Arg Asp Val Gln Ile Leu Asn His Ile Leu Asp Asp Ile
1               5                   10                  15

Glu Phe Phe Ile Thr Lys Leu Gln
            20

<210> SEQ ID NO 69
<211> LENGTH: 11
<212> TYPE: PRT
<213> ORGANISM: Artificial Sequence
<220> FEATURE:
<223> OTHER INFORMATION: Synthetic

<400> SEQUENCE: 69

Leu Cys Asn Cys Ala Leu Glu Glu Leu Arg Leu
1               5                   10

<210> SEQ ID NO 70
<211> LENGTH: 10
<212> TYPE: PRT
<213> ORGANISM: Artificial Sequence
<220> FEATURE:
<223> OTHER INFORMATION: Synthetic

<400> SEQUENCE: 70

Leu Trp Glu Phe Ile Arg Asp Ile Leu Ile
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Synthetic

<400> SEQUENCE: 71

Ile His Lys Lys Phe Ser Ser Ile Gln Met
1               5                   10

<210> SEQ ID NO 72
```

```
<211> LENGTH: 19
<212> TYPE: PRT
<213> ORGANISM: Artificial Sequence
<220> FEATURE:
<223> OTHER INFORMATION: Synthetic

<400> SEQUENCE: 72

Arg Leu Ser His Leu Arg Ser Glu Glu Val His Trp Leu His Val Asp
1               5                   10                  15

Met Gly Val

<210> SEQ ID NO 73
<211> LENGTH: 21
<212> TYPE: PRT
<213> ORGANISM: Artificial Sequence
<220> FEATURE:
<223> OTHER INFORMATION: Synthetic

<400> SEQUENCE: 73

Phe Leu Gln Val Arg Lys Tyr Ser Leu Asp Leu Ala Ser Leu Ile Leu
1               5                   10                  15

Tyr Ala Tyr Gln Leu
            20

<210> SEQ ID NO 74
<211> LENGTH: 27
<212> TYPE: PRT
<213> ORGANISM: Artificial Sequence
<220> FEATURE:
<223> OTHER INFORMATION: Synthetic

<400> SEQUENCE: 74

Asp Leu Asn Ala Leu Leu Leu Glu Val Glu Gly Pro Leu Cys Lys Lys
1               5                   10                  15

Leu Ser Leu Ser Lys Val Ile Asp Cys Asp Ser
            20                  25

<210> SEQ ID NO 75
<211> LENGTH: 22
<212> TYPE: PRT
<213> ORGANISM: Artificial Sequence
<220> FEATURE:
<223> OTHER INFORMATION: Synthetic

<400> SEQUENCE: 75

Pro Gln Val Thr Val Asp Val Leu Gln Arg Met Leu Ile Phe Ala Leu
1               5                   10                  15

Asp Ala Leu Ala Ala Gly
            20

<210> SEQ ID NO 76
<211> LENGTH: 17
<212> TYPE: PRT
<213> ORGANISM: Artificial Sequence
<220> FEATURE:
<223> OTHER INFORMATION: Synthetic

<400> SEQUENCE: 76

Leu Ala Asp Leu Lys Val Ser Ile Glu Asn Met Gly Leu Tyr Glu Asp
1               5                   10                  15

Leu

<210> SEQ ID NO 77
<211> LENGTH: 21
```

```
<212> TYPE: PRT
<213> ORGANISM: Artificial Sequence
<220> FEATURE:
<223> OTHER INFORMATION: Synthetic

<400> SEQUENCE: 77

Leu Ser Pro Gly Leu Ile Lys Lys Phe Gln Phe Leu Met Phe Arg Leu
1               5                   10                  15

Phe Ser Glu Ala Arg
            20

<210> SEQ ID NO 78
<211> LENGTH: 31
<212> TYPE: PRT
<213> ORGANISM: Artificial Sequence
<220> FEATURE:
<223> OTHER INFORMATION: Synthetic

<400> SEQUENCE: 78

Gly Asn Glu Asp Ile Ile Ser Arg Leu Gln Glu Met Val Ala Asp Leu
1               5                   10                  15

Glu Leu Gln Gln Asp Leu Ile Val Pro Leu Gly His Thr Pro Ser
            20                  25                  30

<210> SEQ ID NO 79
<211> LENGTH: 10
<212> TYPE: PRT
<213> ORGANISM: Artificial Sequence
<220> FEATURE:
<223> OTHER INFORMATION: Synthetic

<400> SEQUENCE: 79

Leu Val Val Leu Pro Leu Glu Leu Lys Leu
1               5                   10

<210> SEQ ID NO 80
<211> LENGTH: 10
<212> TYPE: PRT
<213> ORGANISM: Artificial Sequence
<220> FEATURE:
<223> OTHER INFORMATION: Synthetic

<400> SEQUENCE: 80

Phe Val Glu Lys Leu Gln Asp Ile Gln Gln
1               5                   10

<210> SEQ ID NO 81
<211> LENGTH: 17
<212> TYPE: PRT
<213> ORGANISM: Artificial Sequence
<220> FEATURE:
<223> OTHER INFORMATION: Synthetic

<400> SEQUENCE: 81

Glu Val Asp Gln Leu Arg Leu Glu Arg Leu Gln Ile Asp Glu Gln Leu
1               5                   10                  15

Arg

<210> SEQ ID NO 82
<211> LENGTH: 10
<212> TYPE: PRT
<213> ORGANISM: Artificial Sequence
<220> FEATURE:
<223> OTHER INFORMATION: Synthetic

<400> SEQUENCE: 82
```

```
Leu His Gly Thr Met Arg Pro Leu Ser Leu
1               5               10

<210> SEQ ID NO 83
<211> LENGTH: 17
<212> TYPE: PRT
<213> ORGANISM: Artificial Sequence
<220> FEATURE:
<223> OTHER INFORMATION: Synthetic

<400> SEQUENCE: 83

Gln Ile Leu Pro Lys Val Leu His Lys Arg Thr Leu Gly Leu Ser Ala
1               5               10              15

Met

<210> SEQ ID NO 84
<211> LENGTH: 33
<212> TYPE: PRT
<213> ORGANISM: Artificial Sequence
<220> FEATURE:
<223> OTHER INFORMATION: Synthetic

<400> SEQUENCE: 84

Met Val Asn Phe Val Ser Val Gly Leu Phe Arg Cys Leu Pro Val Pro
1               5               10              15

Cys Pro Glu Asp Leu Leu Val Glu Glu Leu Val Asp Gly Leu Leu Ser
            20              25              30

Leu

<210> SEQ ID NO 85
<211> LENGTH: 26
<212> TYPE: PRT
<213> ORGANISM: Artificial Sequence
<220> FEATURE:
<223> OTHER INFORMATION: Synthetic

<400> SEQUENCE: 85

Glu Ala Gln Thr Cys Glu Asn Glu Glu Ala Glu Thr Val Thr Ala Met
1               5               10              15

Ala Ser Leu Ser Val Gly Val Lys Pro Ala
            20              25

<210> SEQ ID NO 86
<211> LENGTH: 42
<212> TYPE: PRT
<213> ORGANISM: Artificial Sequence
<220> FEATURE:
<223> OTHER INFORMATION: Synthetic

<400> SEQUENCE: 86

Glu Glu Ala Glu Thr Val Ser Ala Met Ala Leu Leu Ser Val Gly Ala
1               5               10              15

Glu Gln Ala Gln Ala Ala Ala Ala Arg Glu His Ser Pro Arg Pro Ala
            20              25              30

Glu Glu Pro Met Glu Gln Glu Pro Ala Leu
        35              40

<210> SEQ ID NO 87
<211> LENGTH: 15
<212> TYPE: PRT
<213> ORGANISM: Artificial Sequence
<220> FEATURE:
<223> OTHER INFORMATION: Synthetic
```

<400> SEQUENCE: 87

Leu Ser Phe Asp Glu Ser Leu Ala Leu Cys Val Ile Arg Glu Ile
1               5                   10                  15

<210> SEQ ID NO 88
<211> LENGTH: 12
<212> TYPE: PRT
<213> ORGANISM: Artificial Sequence
<220> FEATURE:
<223> OTHER INFORMATION: Synthetic

<400> SEQUENCE: 88

Leu Gln Leu Pro Pro Leu Glu Arg Leu Thr Leu Asp
1               5                   10

<210> SEQ ID NO 89
<211> LENGTH: 10
<212> TYPE: PRT
<213> ORGANISM: Artificial Sequence
<220> FEATURE:
<223> OTHER INFORMATION: Synthetic

<400> SEQUENCE: 89

Leu Val Asp Lys Phe Met Lys Leu Asp Leu
1               5                   10

<210> SEQ ID NO 90
<211> LENGTH: 19
<212> TYPE: PRT
<213> ORGANISM: Artificial Sequence
<220> FEATURE:
<223> OTHER INFORMATION: Synthetic

<400> SEQUENCE: 90

Asp Thr Asp Ile Gln Glu Leu Ser Glu Gln Ile His Arg Leu Leu Leu
1               5                   10                  15

Gln Pro Val

<210> SEQ ID NO 91
<211> LENGTH: 10
<212> TYPE: PRT
<213> ORGANISM: Artificial Sequence
<220> FEATURE:
<223> OTHER INFORMATION: Synthetic

<400> SEQUENCE: 91

Ile Ser Pro Arg Leu Asp Ala Ile Lys Leu
1               5                   10

<210> SEQ ID NO 92
<211> LENGTH: 23
<212> TYPE: PRT
<213> ORGANISM: Artificial Sequence
<220> FEATURE:
<223> OTHER INFORMATION: Synthetic

<400> SEQUENCE: 92

Ala Arg Ser Phe Glu Met Thr Glu Phe Asn Gln Ala Leu Glu Glu Ile
1               5                   10                  15

Lys Gly Gln Val Val Glu Asn
            20

<210> SEQ ID NO 93
<211> LENGTH: 9

```
<212> TYPE: PRT
<213> ORGANISM: Artificial Sequence
<220> FEATURE:
<223> OTHER INFORMATION: Synthetic

<400> SEQUENCE: 93

Asp Ile Glu Leu Thr Leu Arg Leu Asn
1               5

<210> SEQ ID NO 94
<211> LENGTH: 13
<212> TYPE: PRT
<213> ORGANISM: Artificial Sequence
<220> FEATURE:
<223> OTHER INFORMATION: Synthetic

<400> SEQUENCE: 94

Glu Glu Leu Gln Asp Leu Val Asp Gln Leu Gly Phe Leu
1               5                   10

<210> SEQ ID NO 95
<211> LENGTH: 14
<212> TYPE: PRT
<213> ORGANISM: Artificial Sequence
<220> FEATURE:
<223> OTHER INFORMATION: Synthetic

<400> SEQUENCE: 95

Ile Glu Ala Ala Leu Ser Asp Ala Leu Ala Ala Leu Gln Ile
1               5                   10

<210> SEQ ID NO 96
<211> LENGTH: 17
<212> TYPE: PRT
<213> ORGANISM: Artificial Sequence
<220> FEATURE:
<223> OTHER INFORMATION: Synthetic

<400> SEQUENCE: 96

Met Ala Thr Leu Glu Lys Leu Met Lys Ala Phe Glu Ser Leu Lys Ser
1               5                   10                  15

Phe

<210> SEQ ID NO 97
<211> LENGTH: 51
<212> TYPE: PRT
<213> ORGANISM: Artificial Sequence
<220> FEATURE:
<223> OTHER INFORMATION: Synthetic

<400> SEQUENCE: 97

Met Val Ala Glu Met Val Glu Ser Leu Gln Ser Val Leu Ala Leu Gly
1               5                   10                  15

His Lys Arg Asn Ser Gly Val Pro Ala Phe Leu Thr Pro Leu Leu Arg
            20                  25                  30

Asn Ile Ile Ile Ser Leu Ala Arg Leu Pro Leu Val Asn Ser Tyr Thr
            35                  40                  45

Arg Val Pro
        50

<210> SEQ ID NO 98
<211> LENGTH: 55
<212> TYPE: PRT
<213> ORGANISM: Artificial Sequence
<220> FEATURE:
```

-continued

<223> OTHER INFORMATION: Synthetic

<400> SEQUENCE: 98

Met Phe Gln Ala Ala Glu Arg Pro Gln Glu Trp Ala Met Glu Gly Pro
1               5                   10                  15

Arg Asp Gly Leu Lys Lys Glu Arg Leu Leu Asp Asp Arg His Asp Ser
            20                  25                  30

Gly Leu Asp Ser Met Lys Asp Glu Glu Tyr Glu Gln Met Val Lys Glu
        35                  40                  45

Leu Gln Glu Ile Arg Leu Glu
    50                  55

<210> SEQ ID NO 99
<211> LENGTH: 14
<212> TYPE: PRT
<213> ORGANISM: Artificial Sequence
<220> FEATURE:
<223> OTHER INFORMATION: Synthetic

<400> SEQUENCE: 99

Val Ile Asp Tyr Ile Arg Asp Leu Gln Leu Glu Leu Asn Ser
1               5                   10

<210> SEQ ID NO 100
<211> LENGTH: 17
<212> TYPE: PRT
<213> ORGANISM: Artificial Sequence
<220> FEATURE:
<223> OTHER INFORMATION: Synthetic

<400> SEQUENCE: 100

Leu Thr Thr Leu Asn Thr Asp Ile Ser Ile Leu Ser Leu Gln Ala Ser
1               5                   10                  15

Glu

<210> SEQ ID NO 101
<211> LENGTH: 26
<212> TYPE: PRT
<213> ORGANISM: Artificial Sequence
<220> FEATURE:
<223> OTHER INFORMATION: Synthetic

<400> SEQUENCE: 101

Val Ser Lys Tyr Pro Leu Met Glu Glu Ile Gly Phe Leu Val Leu Gly
1               5                   10                  15

Met Arg Val Tyr His Val His Ser Asp Ser
            20                  25

<210> SEQ ID NO 102
<211> LENGTH: 15
<212> TYPE: PRT
<213> ORGANISM: Artificial Sequence
<220> FEATURE:
<223> OTHER INFORMATION: Synthetic

<400> SEQUENCE: 102

Gln Glu Asp Ile Leu Asp Glu Leu Leu Gly Asn Met Val Leu Ala
1               5                   10                  15

<210> SEQ ID NO 103
<211> LENGTH: 11
<212> TYPE: PRT
<213> ORGANISM: Artificial Sequence
<220> FEATURE:

-continued

<223> OTHER INFORMATION: Synthetic

<400> SEQUENCE: 103

Leu Gln Arg Met Leu Pro Ser Leu Ser Leu Thr
1               5                   10

<210> SEQ ID NO 104
<211> LENGTH: 10
<212> TYPE: PRT
<213> ORGANISM: Artificial Sequence
<220> FEATURE:
<223> OTHER INFORMATION: Synthetic

<400> SEQUENCE: 104

Leu Asp Arg Lys Leu Leu Glu Leu Leu Trp
1               5                   10

<210> SEQ ID NO 105
<211> LENGTH: 44
<212> TYPE: PRT
<213> ORGANISM: Artificial Sequence
<220> FEATURE:
<223> OTHER INFORMATION: Synthetic

<400> SEQUENCE: 105

Arg Cys His Ser Leu Thr Pro Asn Phe Leu Gln Met Gln Leu Gln Lys
1               5                   10                  15

Cys Glu Ile Leu Gln Ser Asp Ser Arg Cys Lys Asp Tyr Leu Val Lys
            20                  25                  30

Ile Phe Glu Glu Leu Thr Leu His Lys Pro Thr Gln
        35                  40

<210> SEQ ID NO 106
<211> LENGTH: 31
<212> TYPE: PRT
<213> ORGANISM: Artificial Sequence
<220> FEATURE:
<223> OTHER INFORMATION: Synthetic

<400> SEQUENCE: 106

Ile Pro Tyr Ser Ile Asn Met Asn Val Phe Leu Pro Asp Ile Thr His
1               5                   10                  15

Leu Arg Thr Gly Leu Tyr Lys Ser Gln Arg Pro Cys Val Thr Gln
            20                  25                  30

<210> SEQ ID NO 107
<211> LENGTH: 16
<212> TYPE: PRT
<213> ORGANISM: Artificial Sequence
<220> FEATURE:
<223> OTHER INFORMATION: Synthetic

<400> SEQUENCE: 107

Met Asp Val Leu Pro Met Cys Ser Ile Phe Gln Glu Leu Gln Ile Val
1               5                   10                  15

<210> SEQ ID NO 108
<211> LENGTH: 10
<212> TYPE: PRT
<213> ORGANISM: Artificial Sequence
<220> FEATURE:
<223> OTHER INFORMATION: Synthetic

<400> SEQUENCE: 108

Met Val Pro Leu Val Ile Lys Leu Arg Leu

-continued

```
1               5                    10

<210> SEQ ID NO 109
<211> LENGTH: 25
<212> TYPE: PRT
<213> ORGANISM: Artificial Sequence
<220> FEATURE:
<223> OTHER INFORMATION: Synthetic

<400> SEQUENCE: 109

Phe Lys Pro Asp Met Asn Pro Ala Leu Arg Glu Val Leu Glu Ala Leu
1               5                    10                  15

Glu Asp Glu Ala Tyr Val Val Asn Asp
            20                  25

<210> SEQ ID NO 110
<211> LENGTH: 12
<212> TYPE: PRT
<213> ORGANISM: Artificial Sequence
<220> FEATURE:
<223> OTHER INFORMATION: Synthetic

<400> SEQUENCE: 110

Ala Leu Arg Glu Val Leu Glu Ala Leu Glu Asp Glu
1               5                    10

<210> SEQ ID NO 111
<211> LENGTH: 13
<212> TYPE: PRT
<213> ORGANISM: Artificial Sequence
<220> FEATURE:
<223> OTHER INFORMATION: Synthetic

<400> SEQUENCE: 111

Leu Glu Lys Val Thr Asn Thr Leu Ser Ser Leu Lys Phe
1               5                    10

<210> SEQ ID NO 112
<211> LENGTH: 12
<212> TYPE: PRT
<213> ORGANISM: Artificial Sequence
<220> FEATURE:
<223> OTHER INFORMATION: Synthetic

<400> SEQUENCE: 112

Leu Glu Gln Glu Leu Gln Gln Leu Ser Leu Glu Leu
1               5                    10

<210> SEQ ID NO 113
<211> LENGTH: 12
<212> TYPE: PRT
<213> ORGANISM: Artificial Sequence
<220> FEATURE:
<223> OTHER INFORMATION: Synthetic

<400> SEQUENCE: 113

Leu Phe Gly Asp Thr Ile Ala Tyr Leu Leu Ser Leu
1               5                    10

<210> SEQ ID NO 114
<211> LENGTH: 10
<212> TYPE: PRT
<213> ORGANISM: Artificial Sequence
<220> FEATURE:
<223> OTHER INFORMATION: Synthetic

<400> SEQUENCE: 114
```

```
Leu Leu Tyr Cys Leu Met Val Met Tyr Leu
1               5                   10

<210> SEQ ID NO 115
<211> LENGTH: 14
<212> TYPE: PRT
<213> ORGANISM: Artificial Sequence
<220> FEATURE:
<223> OTHER INFORMATION: Synthetic

<400> SEQUENCE: 115

Gln Leu Leu Gln Glu Lys Leu Glu Lys Leu Thr Lys Leu Lys
1               5                   10

<210> SEQ ID NO 116
<211> LENGTH: 24
<212> TYPE: PRT
<213> ORGANISM: Artificial Sequence
<220> FEATURE:
<223> OTHER INFORMATION: Synthetic

<400> SEQUENCE: 116

Asp Lys Glu Arg Trp Glu Asp Val Lys Glu Glu Met Thr Ser Ala Leu
1               5                   10                  15

Ala Thr Met Arg Val Asp Tyr Glu
            20

<210> SEQ ID NO 117
<211> LENGTH: 13
<212> TYPE: PRT
<213> ORGANISM: Artificial Sequence
<220> FEATURE:
<223> OTHER INFORMATION: Synthetic

<400> SEQUENCE: 117

Ala Leu Gln Lys Lys Leu Glu Glu Leu Glu Leu Asp Glu
1               5                   10

<210> SEQ ID NO 118
<211> LENGTH: 14
<212> TYPE: PRT
<213> ORGANISM: Artificial Sequence
<220> FEATURE:
<223> OTHER INFORMATION: Synthetic

<400> SEQUENCE: 118

Val Pro Glu Val Glu Ala Leu Leu Ala Arg Leu Arg Ala Leu
1               5                   10

<210> SEQ ID NO 119
<211> LENGTH: 9
<212> TYPE: PRT
<213> ORGANISM: Artificial Sequence
<220> FEATURE:
<223> OTHER INFORMATION: Synthetic

<400> SEQUENCE: 119

Asp Leu Val Leu Leu Ser Leu Val Leu
1               5

<210> SEQ ID NO 120
<211> LENGTH: 10
<212> TYPE: PRT
<213> ORGANISM: Artificial Sequence
<220> FEATURE:
<223> OTHER INFORMATION: Synthetic
```

-continued

```
<400> SEQUENCE: 120

Gln Leu Gln Gln Lys Leu Leu Trp Leu Leu
1               5                   10

<210> SEQ ID NO 121
<211> LENGTH: 10
<212> TYPE: PRT
<213> ORGANISM: Artificial Sequence
<220> FEATURE:
<223> OTHER INFORMATION: Synthetic

<400> SEQUENCE: 121

Leu Val Ile Ala Met Asp Gln Leu Asn Leu
1               5                   10

<210> SEQ ID NO 122
<211> LENGTH: 16
<212> TYPE: PRT
<213> ORGANISM: Artificial Sequence
<220> FEATURE:
<223> OTHER INFORMATION: Synthetic

<400> SEQUENCE: 122

Pro Leu Pro Val Leu Gly Leu Gly Gly Leu Arg Ile Ser Ser Asp Ser
1               5                   10                  15

<210> SEQ ID NO 123
<211> LENGTH: 10
<212> TYPE: PRT
<213> ORGANISM: Artificial Sequence
<220> FEATURE:
<223> OTHER INFORMATION: Synthetic

<400> SEQUENCE: 123

Leu Phe Asp Leu Ala Met Leu Ala Leu Asp
1               5                   10

<210> SEQ ID NO 124
<211> LENGTH: 8
<212> TYPE: PRT
<213> ORGANISM: Artificial Sequence
<220> FEATURE:
<223> OTHER INFORMATION: Synthetic

<400> SEQUENCE: 124

Leu His Leu Val Gly Val Asn Val
1               5

<210> SEQ ID NO 125
<211> LENGTH: 20
<212> TYPE: PRT
<213> ORGANISM: Artificial Sequence
<220> FEATURE:
<223> OTHER INFORMATION: Synthetic

<400> SEQUENCE: 125

Ala Ser Leu Thr Lys Leu Phe Glu Cys Met Thr Leu Ala Tyr Ser Gly
1               5                   10                  15

Lys Leu Val Ser
            20

<210> SEQ ID NO 126
<211> LENGTH: 14
<212> TYPE: PRT
<213> ORGANISM: Artificial Sequence
```

```
<220> FEATURE:
<223> OTHER INFORMATION: Synthetic

<400> SEQUENCE: 126

Asp Ile Gln Glu Leu Ser Glu Gln Ile His Arg Leu Leu Leu
1               5                   10

<210> SEQ ID NO 127
<211> LENGTH: 10
<212> TYPE: PRT
<213> ORGANISM: Artificial Sequence
<220> FEATURE:
<223> OTHER INFORMATION: Synthetic

<400> SEQUENCE: 127

Leu Glu Ile Ala Leu Arg Asn Leu Asn Leu
1               5                   10

<210> SEQ ID NO 128
<211> LENGTH: 59
<212> TYPE: PRT
<213> ORGANISM: Artificial Sequence
<220> FEATURE:
<223> OTHER INFORMATION: Synthetic

<400> SEQUENCE: 128

Asp Glu Met Asp Ser Gly Thr Met Val Arg Ala Val Gly Asp Glu Met
1               5                   10                  15

Gly Thr Val Arg Val Ala Ser Thr Met Thr Asp Gly Ala Asn Thr Met
                20                  25                  30

Ile Glu His Asp Asp Thr Leu Pro Ser Gln Leu Gly Thr Met Val Ile
            35                  40                  45

Asn Ala Glu Asp Glu Glu Glu Glu Gly Thr Met
        50                  55

<210> SEQ ID NO 129
<211> LENGTH: 31
<212> TYPE: PRT
<213> ORGANISM: Artificial Sequence
<220> FEATURE:
<223> OTHER INFORMATION: Synthetic

<400> SEQUENCE: 129

Asp Gly Asp Tyr Glu Phe Leu Lys Ser Trp Thr Val Glu Asp Leu Gln
1               5                   10                  15

Lys Arg Leu Leu Ala Leu Asp Pro Met Met Glu Gln Glu Ile Glu
                20                  25                  30

<210> SEQ ID NO 130
<211> LENGTH: 10
<212> TYPE: PRT
<213> ORGANISM: Artificial Sequence
<220> FEATURE:
<223> OTHER INFORMATION: Synthetic

<400> SEQUENCE: 130

Pro Val Ser Lys Ile Thr Phe Val Thr Leu
1               5                   10

<210> SEQ ID NO 131
<211> LENGTH: 10
<212> TYPE: PRT
<213> ORGANISM: Artificial Sequence
<220> FEATURE:
<223> OTHER INFORMATION: Synthetic
```

<400> SEQUENCE: 131

Leu Pro Ser Pro Leu Ala Ser Leu Thr Leu
1               5                   10

<210> SEQ ID NO 132
<211> LENGTH: 9
<212> TYPE: PRT
<213> ORGANISM: Artificial Sequence
<220> FEATURE:
<223> OTHER INFORMATION: Synthetic

<400> SEQUENCE: 132

Leu Cys Leu Ser Asp Leu Ser Leu Leu
1               5

<210> SEQ ID NO 133
<211> LENGTH: 13
<212> TYPE: PRT
<213> ORGANISM: Artificial Sequence
<220> FEATURE:
<223> OTHER INFORMATION: Synthetic

<400> SEQUENCE: 133

Ile Gln Asp Gly Leu Leu Lys Met Leu Ser Leu Val Leu
1               5                   10

<210> SEQ ID NO 134
<211> LENGTH: 10
<212> TYPE: PRT
<213> ORGANISM: Artificial Sequence
<220> FEATURE:
<223> OTHER INFORMATION: Synthetic

<400> SEQUENCE: 134

Ile Thr Phe Ile Phe Lys Ser Leu Gly Leu
1               5                   10

<210> SEQ ID NO 135
<211> LENGTH: 9
<212> TYPE: PRT
<213> ORGANISM: Artificial Sequence
<220> FEATURE:
<223> OTHER INFORMATION: Synthetic

<400> SEQUENCE: 135

Leu Glu Trp Leu Arg Arg Leu Ser Leu
1               5

<210> SEQ ID NO 136
<211> LENGTH: 20
<212> TYPE: PRT
<213> ORGANISM: Artificial Sequence
<220> FEATURE:
<223> OTHER INFORMATION: Synthetic

<400> SEQUENCE: 136

Val Gln Val Val Ala Asp Val Leu Ser Lys Leu Leu Val Val Gly Ile
1               5                   10                  15

Thr Asp Pro Asp
            20

<210> SEQ ID NO 137
<211> LENGTH: 40
<212> TYPE: PRT
<213> ORGANISM: Artificial Sequence

```
<220> FEATURE:
<223> OTHER INFORMATION: Synthetic

<400> SEQUENCE: 137

Leu Ala Pro Asn Val Ala Ala Leu Leu Phe Gly Gly Asn Val Ala Val
1               5                   10                  15

Arg Glu Leu Ala Asp Ser Tyr Glu Ile Thr Tyr Asn Tyr Lys Met Thr
            20                  25                  30

Val Pro Lys Ser Asp Pro Asn Val
        35                  40

<210> SEQ ID NO 138
<211> LENGTH: 34
<212> TYPE: PRT
<213> ORGANISM: Artificial Sequence
<220> FEATURE:
<223> OTHER INFORMATION: Synthetic

<400> SEQUENCE: 138

Cys Thr Leu Ser Asp Ser Gly Arg Ile Ser Tyr Thr Val Glu Phe Ser
1               5                   10                  15

Leu Pro Thr His His Thr Val Arg Leu Ile Arg Val Thr Ala Ser Pro
            20                  25                  30

Ser Ala

<210> SEQ ID NO 139
<211> LENGTH: 28
<212> TYPE: PRT
<213> ORGANISM: Artificial Sequence
<220> FEATURE:
<223> OTHER INFORMATION: Synthetic

<400> SEQUENCE: 139

Gly Leu Pro Lys Asn Val Lys Glu Lys Leu Leu Ser Leu Lys Thr Leu
1               5                   10                  15

Gln Ser Glu Leu Phe Glu Val Glu Lys Glu Phe Gln
            20                  25

<210> SEQ ID NO 140
<211> LENGTH: 26
<212> TYPE: PRT
<213> ORGANISM: Artificial Sequence
<220> FEATURE:
<223> OTHER INFORMATION: Synthetic

<400> SEQUENCE: 140

Lys Lys Thr Ile Ser Pro Glu His Val Ile Gln Ala Leu Glu Ser Leu
1               5                   10                  15

Gly Phe Gly Ser Tyr Ile Ser Glu Val Lys
            20                  25

<210> SEQ ID NO 141
<211> LENGTH: 10
<212> TYPE: PRT
<213> ORGANISM: Artificial Sequence
<220> FEATURE:
<223> OTHER INFORMATION: Synthetic

<400> SEQUENCE: 141

Ile Leu Met Arg Met Ser Lys Met Gln Leu
1               5                   10

<210> SEQ ID NO 142
```

```
<211> LENGTH: 10
<212> TYPE: PRT
<213> ORGANISM: Artificial Sequence
<220> FEATURE:
<223> OTHER INFORMATION: Synthetic

<400> SEQUENCE: 142

Met Val Thr Arg Phe Glu Ser Leu Lys Ile
1               5                   10

<210> SEQ ID NO 143
<211> LENGTH: 12
<212> TYPE: PRT
<213> ORGANISM: Artificial Sequence
<220> FEATURE:
<223> OTHER INFORMATION: Synthetic

<400> SEQUENCE: 143

Tyr Ile Trp Ala Leu Thr Gln Thr Leu Arg Ile Ala
1               5                   10

<210> SEQ ID NO 144
<211> LENGTH: 12
<212> TYPE: PRT
<213> ORGANISM: Artificial Sequence
<220> FEATURE:
<223> OTHER INFORMATION: Synthetic

<400> SEQUENCE: 144

Ser Ala Ile Val Ala Ala Ile Asn Ala Leu Thr Thr
1               5                   10

<210> SEQ ID NO 145
<211> LENGTH: 85
<212> TYPE: PRT
<213> ORGANISM: Artificial Sequence
<220> FEATURE:
<223> OTHER INFORMATION: Synthetic

<400> SEQUENCE: 145

Asp Ala Glu Arg Asn Arg Pro Leu Asn Gly Gly Ser Glu Pro Glu Ser
1               5                   10                  15

Asn Ser Ala Leu Gln Glu Asp Glu Arg Glu Lys Lys Asp Glu Leu Gln
                20                  25                  30

Thr Glu Ser Trp Ser Thr Lys His Glu Ile Ala Asn Ser Asp Gly Leu
            35                  40                  45

Gln Asp Ser Ser Glu Glu Leu Pro Arg Lys Leu Leu Leu Thr Glu Phe
    50                  55                  60

Arg Ser Leu Val Val Ser Asn His Asn Ser Thr Ser Arg Asn Leu Cys
65                  70                  75                  80

Val Asn Glu Cys Gly
                85

<210> SEQ ID NO 146
<211> LENGTH: 50
<212> TYPE: PRT
<213> ORGANISM: Artificial Sequence
<220> FEATURE:
<223> OTHER INFORMATION: Synthetic

<400> SEQUENCE: 146

Lys Glu His Lys Asp Ile Asp Ala Ser Leu Asp Tyr Asn Ser Arg Ala
1               5                   10                  15

Gln Lys Gln Glu Met Glu Arg Ala Glu Lys Asp Tyr Glu Leu Phe Leu
```

-continued

```
              20              25              30

Gln Glu Leu Glu Glu Asp Ala Glu Leu Arg Gln Ser Val Asn Leu Tyr
        35              40              45

Lys Asn
    50

<210> SEQ ID NO 147
<211> LENGTH: 14
<212> TYPE: PRT
<213> ORGANISM: Artificial Sequence
<220> FEATURE:
<223> OTHER INFORMATION: Synthetic

<400> SEQUENCE: 147

Leu Asp Leu Pro Asp Ala Leu Leu Pro Asp Leu Pro Lys Leu
1               5               10

<210> SEQ ID NO 148
<211> LENGTH: 25
<212> TYPE: PRT
<213> ORGANISM: Artificial Sequence
<220> FEATURE:
<223> OTHER INFORMATION: Synthetic

<400> SEQUENCE: 148

Leu Leu Pro Leu Ala Glu Ala Asp Lys Val Arg Leu Ser Tyr Leu His
1               5               10              15

Ile Met Ser Leu Ala Cys Ile Tyr Thr
            20              25

<210> SEQ ID NO 149
<211> LENGTH: 11
<212> TYPE: PRT
<213> ORGANISM: Artificial Sequence
<220> FEATURE:
<223> OTHER INFORMATION: Synthetic

<400> SEQUENCE: 149

Asp Leu Cys Leu Ala Val Glu Glu Val Ser Leu
1               5               10

<210> SEQ ID NO 150
<211> LENGTH: 10
<212> TYPE: PRT
<213> ORGANISM: Artificial Sequence
<220> FEATURE:
<223> OTHER INFORMATION: Synthetic

<400> SEQUENCE: 150

Leu Lys Arg Arg Leu Ser Thr Leu Tyr Leu
1               5               10

<210> SEQ ID NO 151
<211> LENGTH: 10
<212> TYPE: PRT
<213> ORGANISM: Artificial Sequence
<220> FEATURE:
<223> OTHER INFORMATION: Synthetic

<400> SEQUENCE: 151

Leu Arg Asn Gln Leu Thr Ala Leu Arg Ile
1               5               10

<210> SEQ ID NO 152
<211> LENGTH: 11
```

```
<212> TYPE: PRT
<213> ORGANISM: Artificial Sequence
<220> FEATURE:
<223> OTHER INFORMATION: Synthetic

<400> SEQUENCE: 152

Leu Leu Leu Pro Leu Met Arg Asn Leu Glu Met
1               5                   10

<210> SEQ ID NO 153
<211> LENGTH: 11
<212> TYPE: PRT
<213> ORGANISM: Artificial Sequence
<220> FEATURE:
<223> OTHER INFORMATION: Synthetic

<400> SEQUENCE: 153

Leu Val Ser Leu Ile Arg Leu Lys Ser Lys Leu
1               5                   10

<210> SEQ ID NO 154
<211> LENGTH: 27
<212> TYPE: PRT
<213> ORGANISM: Artificial Sequence
<220> FEATURE:
<223> OTHER INFORMATION: Synthetic

<400> SEQUENCE: 154

Asp Glu Met Thr Lys Lys Phe Gly Thr Leu Thr Ile His Asp Thr Glu
1               5                   10                  15

Lys Tyr Ala Ser Gln Pro Glu Leu Cys Asn Asn
            20                  25

<210> SEQ ID NO 155
<211> LENGTH: 10
<212> TYPE: PRT
<213> ORGANISM: Artificial Sequence
<220> FEATURE:
<223> OTHER INFORMATION: Synthetic

<400> SEQUENCE: 155

Leu Cys Pro Asp Leu Pro Glu Leu Asp Leu
1               5                   10

<210> SEQ ID NO 156
<211> LENGTH: 10
<212> TYPE: PRT
<213> ORGANISM: Artificial Sequence
<220> FEATURE:
<223> OTHER INFORMATION: Synthetic

<400> SEQUENCE: 156

Leu Val Asp Ser Leu Gln Gln Leu Arg Leu
1               5                   10

<210> SEQ ID NO 157
<211> LENGTH: 9
<212> TYPE: PRT
<213> ORGANISM: Artificial Sequence
<220> FEATURE:
<223> OTHER INFORMATION: Synthetic

<400> SEQUENCE: 157

Leu Glu Leu Phe Val Leu Arg Leu Ala
1               5
```

```
<210> SEQ ID NO 158
<211> LENGTH: 9
<212> TYPE: PRT
<213> ORGANISM: Artificial Sequence
<220> FEATURE:
<223> OTHER INFORMATION: Synthetic

<400> SEQUENCE: 158

Leu Gln Arg Ile Phe Tyr Leu Lys Leu
1               5

<210> SEQ ID NO 159
<211> LENGTH: 9
<212> TYPE: PRT
<213> ORGANISM: Artificial Sequence
<220> FEATURE:
<223> OTHER INFORMATION: Synthetic

<400> SEQUENCE: 159

Leu Lys Ser Leu Gly Glu Leu Gly Leu
1               5

<210> SEQ ID NO 160
<211> LENGTH: 9
<212> TYPE: PRT
<213> ORGANISM: Artificial Sequence
<220> FEATURE:
<223> OTHER INFORMATION: Synthetic

<400> SEQUENCE: 160

Leu Ser Lys Ile Ala Thr Leu Leu Leu
1               5

<210> SEQ ID NO 161
<211> LENGTH: 9
<212> TYPE: PRT
<213> ORGANISM: Artificial Sequence
<220> FEATURE:
<223> OTHER INFORMATION: Synthetic

<400> SEQUENCE: 161

Leu Leu Leu Ala Gly Leu Pro Leu Leu
1               5

<210> SEQ ID NO 162
<211> LENGTH: 25
<212> TYPE: PRT
<213> ORGANISM: Artificial Sequence
<220> FEATURE:
<223> OTHER INFORMATION: Synthetic

<400> SEQUENCE: 162

His Pro Ser Thr Pro Lys Arg His Thr Val Leu Tyr Ile Ser Pro Pro
1               5                   10                  15

Pro Glu Asp Leu Leu Asp Asn Ser Arg
            20                  25

<210> SEQ ID NO 163
<211> LENGTH: 11
<212> TYPE: PRT
<213> ORGANISM: Artificial Sequence
<220> FEATURE:
<223> OTHER INFORMATION: Synthetic

<400> SEQUENCE: 163

Val Leu Ser Gln Arg Ile Gly Leu Met Asp Val
1               5                   10
```

```
<210> SEQ ID NO 164
<211> LENGTH: 15
<212> TYPE: PRT
<213> ORGANISM: Artificial Sequence
<220> FEATURE:
<223> OTHER INFORMATION: Synthetic

<400> SEQUENCE: 164

Leu Arg His Glu Leu Val Glu Asp Ala Val Tyr Glu Asn Pro Leu
1               5                   10                  15

<210> SEQ ID NO 165
<211> LENGTH: 16
<212> TYPE: PRT
<213> ORGANISM: Artificial Sequence
<220> FEATURE:
<223> OTHER INFORMATION: Synthetic

<400> SEQUENCE: 165

Ser Leu Glu Glu Glu Leu Asp Val Leu Val Leu Asp Asp Glu Gly Gly
1               5                   10                  15

<210> SEQ ID NO 166
<211> LENGTH: 18
<212> TYPE: PRT
<213> ORGANISM: Artificial Sequence
<220> FEATURE:
<223> OTHER INFORMATION: Synthetic

<400> SEQUENCE: 166

Leu Thr Glu Leu Glu Ile Ser Ser Ile Phe Ser His Cys Cys Ser Leu
1               5                   10                  15

Leu Ile

<210> SEQ ID NO 167
<211> LENGTH: 14
<212> TYPE: PRT
<213> ORGANISM: Artificial Sequence
<220> FEATURE:
<223> OTHER INFORMATION: Synthetic

<400> SEQUENCE: 167

Glu Met Phe Arg Glu Leu Asn Glu Ala Leu Glu Leu Lys Asp
1               5                   10

<210> SEQ ID NO 168
<211> LENGTH: 19
<212> TYPE: PRT
<213> ORGANISM: Artificial Sequence
<220> FEATURE:
<223> OTHER INFORMATION: Synthetic

<400> SEQUENCE: 168

Asn Phe Glu Ile Leu Met Lys Leu Lys Glu Ser Leu Glu Leu Met Glu
1               5                   10                  15

Leu Val Pro

<210> SEQ ID NO 169
<211> LENGTH: 13
<212> TYPE: PRT
<213> ORGANISM: Artificial Sequence
<220> FEATURE:
<223> OTHER INFORMATION: Synthetic

<400> SEQUENCE: 169
```

```
Leu Thr Leu Leu Leu Asp Glu Phe Glu Asn Met Ser Val
1               5                   10

<210> SEQ ID NO 170
<211> LENGTH: 15
<212> TYPE: PRT
<213> ORGANISM: Artificial Sequence
<220> FEATURE:
<223> OTHER INFORMATION: Synthetic

<400> SEQUENCE: 170

Val Val Met Glu Phe Leu Glu Gly Gly Ala Leu Thr Asp Ile Val
1               5                   10                  15

<210> SEQ ID NO 171
<211> LENGTH: 10
<212> TYPE: PRT
<213> ORGANISM: Artificial Sequence
<220> FEATURE:
<223> OTHER INFORMATION: Synthetic

<400> SEQUENCE: 171

Leu Lys Gly Phe Leu Asp Arg Leu Leu Val
1               5                   10

<210> SEQ ID NO 172
<211> LENGTH: 18
<212> TYPE: PRT
<213> ORGANISM: Artificial Sequence
<220> FEATURE:
<223> OTHER INFORMATION: Synthetic

<400> SEQUENCE: 172

Val Tyr Asn Leu Val Cys Val Ala Leu Gly Asn Leu Glu Ile Arg Glu
1               5                   10                  15

Ile Arg

<210> SEQ ID NO 173
<211> LENGTH: 19
<212> TYPE: PRT
<213> ORGANISM: Artificial Sequence
<220> FEATURE:
<223> OTHER INFORMATION: Synthetic

<400> SEQUENCE: 173

Glu Ser Phe Asp Ile Asp Asp Leu Cys Ser Lys Leu Lys Asn Lys Ala
1               5                   10                  15

Lys Cys Ser

<210> SEQ ID NO 174
<211> LENGTH: 18
<212> TYPE: PRT
<213> ORGANISM: Artificial Sequence
<220> FEATURE:
<223> OTHER INFORMATION: Synthetic

<400> SEQUENCE: 174

Met Lys Pro Ala Leu Phe Asn Val Leu Cys Glu Ile Lys Glu Lys Thr
1               5                   10                  15

Val Leu

<210> SEQ ID NO 175
<211> LENGTH: 13
<212> TYPE: PRT
```

-continued

```
<213> ORGANISM: Artificial Sequence
<220> FEATURE:
<223> OTHER INFORMATION: Synthetic

<400> SEQUENCE: 175

Ile Leu Lys Lys Val Leu Glu Ala Leu Lys Asp Leu Ile
1               5                   10

<210> SEQ ID NO 176
<211> LENGTH: 11
<212> TYPE: PRT
<213> ORGANISM: Artificial Sequence
<220> FEATURE:
<223> OTHER INFORMATION: Synthetic

<400> SEQUENCE: 176

Leu Leu Lys Asp Leu Pro Glu Leu Ala Leu Asp
1               5                   10

<210> SEQ ID NO 177
<211> LENGTH: 11
<212> TYPE: PRT
<213> ORGANISM: Artificial Sequence
<220> FEATURE:
<223> OTHER INFORMATION: Synthetic

<400> SEQUENCE: 177

Val Ala Glu Met Leu Arg Asp Leu Asn Leu Gly
1               5                   10

<210> SEQ ID NO 178
<211> LENGTH: 10
<212> TYPE: PRT
<213> ORGANISM: Artificial Sequence
<220> FEATURE:
<223> OTHER INFORMATION: Synthetic

<400> SEQUENCE: 178

Leu Glu Leu Glu Ala Leu Arg Leu Ser Leu
1               5                   10

<210> SEQ ID NO 179
<211> LENGTH: 11
<212> TYPE: PRT
<213> ORGANISM: Artificial Sequence
<220> FEATURE:
<223> OTHER INFORMATION: Synthetic

<400> SEQUENCE: 179

Leu Gln Asp Ala Leu Arg Arg Leu Leu Gly Leu
1               5                   10

<210> SEQ ID NO 180
<211> LENGTH: 11
<212> TYPE: PRT
<213> ORGANISM: Artificial Sequence
<220> FEATURE:
<223> OTHER INFORMATION: Synthetic

<400> SEQUENCE: 180

Phe Gly Glu Thr Leu Arg Ala Ala Val Thr Leu
1               5                   10

<210> SEQ ID NO 181
<211> LENGTH: 9
<212> TYPE: PRT
<213> ORGANISM: Artificial Sequence
```

```
<220> FEATURE:
<223> OTHER INFORMATION: Synthetic

<400> SEQUENCE: 181

Leu Asp Glu Phe Asn Glu Leu Ala Ile
1               5

<210> SEQ ID NO 182
<211> LENGTH: 11
<212> TYPE: PRT
<213> ORGANISM: Artificial Sequence
<220> FEATURE:
<223> OTHER INFORMATION: Synthetic

<400> SEQUENCE: 182

Val Ile Glu Lys Leu Gln His Glu Leu Ser Leu
1               5                   10

<210> SEQ ID NO 183
<211> LENGTH: 50
<212> TYPE: PRT
<213> ORGANISM: Artificial Sequence
<220> FEATURE:
<223> OTHER INFORMATION: Synthetic

<400> SEQUENCE: 183

Arg Val Arg Glu Lys Gln Tyr Gln Asp Thr Ile Gly Lys Leu Gln Lys
1               5                   10                  15

Glu Asn Asn Glu Leu Leu Glu Gln Leu Glu Met Leu Gln Ala Gln Leu
            20                  25                  30

Lys Asn Ser Thr Leu Asp Ser Pro Lys Glu Val Glu Val Asn Ser Glu
        35                  40                  45

Val Val
    50

<210> SEQ ID NO 184
<211> LENGTH: 18
<212> TYPE: PRT
<213> ORGANISM: Artificial Sequence
<220> FEATURE:
<223> OTHER INFORMATION: Synthetic

<400> SEQUENCE: 184

Ser Leu Trp Gly Glu His Ile Leu Ala Leu Lys Asn Leu Lys Leu Asp
1               5                   10                  15

Lys Met

<210> SEQ ID NO 185
<211> LENGTH: 15
<212> TYPE: PRT
<213> ORGANISM: Artificial Sequence
<220> FEATURE:
<223> OTHER INFORMATION: Synthetic

<400> SEQUENCE: 185

Asn Glu Leu Ala Leu Lys Leu Ala Gly Leu Asp Ile Asn Lys Thr
1               5                   10                  15

<210> SEQ ID NO 186
<211> LENGTH: 14
<212> TYPE: PRT
<213> ORGANISM: Artificial Sequence
<220> FEATURE:
<223> OTHER INFORMATION: Synthetic
```

-continued

<400> SEQUENCE: 186

Glu Leu Lys Asp Phe Leu Lys Glu Leu Asn Ile Gln Val Asp
1               5                   10

<210> SEQ ID NO 187
<211> LENGTH: 10
<212> TYPE: PRT
<213> ORGANISM: Artificial Sequence
<220> FEATURE:
<223> OTHER INFORMATION: Synthetic

<400> SEQUENCE: 187

Ile Ser Gly Phe Leu Ala Ala Leu Pro Leu
1               5                   10

<210> SEQ ID NO 188
<211> LENGTH: 19
<212> TYPE: PRT
<213> ORGANISM: Artificial Sequence
<220> FEATURE:
<223> OTHER INFORMATION: Synthetic

<400> SEQUENCE: 188

Arg Glu Glu Leu Trp Lys Lys Leu Glu Glu Leu Lys Leu Lys Lys Ala
1               5                   10                  15

Leu Glu Lys

<210> SEQ ID NO 189
<211> LENGTH: 16
<212> TYPE: PRT
<213> ORGANISM: Artificial Sequence
<220> FEATURE:
<223> OTHER INFORMATION: Synthetic

<400> SEQUENCE: 189

Tyr Glu Glu Gln Leu Val Ala Leu Phe Gly Ser Ser Met Asp Leu Arg
1               5                   10                  15

<210> SEQ ID NO 190
<211> LENGTH: 10
<212> TYPE: PRT
<213> ORGANISM: Artificial Sequence
<220> FEATURE:
<223> OTHER INFORMATION: Synthetic

<400> SEQUENCE: 190

Ile Ile Glu Leu Leu Lys Gly Leu Asp Leu
1               5                   10

<210> SEQ ID NO 191
<211> LENGTH: 10
<212> TYPE: PRT
<213> ORGANISM: Artificial Sequence
<220> FEATURE:
<223> OTHER INFORMATION: Synthetic

<400> SEQUENCE: 191

Leu Ser Leu Asn Leu Phe Ala Leu Arg Ile
1               5                   10

<210> SEQ ID NO 192
<211> LENGTH: 8
<212> TYPE: PRT
<213> ORGANISM: Artificial Sequence
<220> FEATURE:
<223> OTHER INFORMATION: Synthetic

<400> SEQUENCE: 192

Leu Thr Leu Ser Ser Leu Thr Leu
1               5

<210> SEQ ID NO 193
<211> LENGTH: 9
<212> TYPE: PRT
<213> ORGANISM: Artificial Sequence
<220> FEATURE:
<223> OTHER INFORMATION: Synthetic

<400> SEQUENCE: 193

Val Glu Val Leu Arg Glu Ile Gln Leu
1               5

<210> SEQ ID NO 194
<211> LENGTH: 10
<212> TYPE: PRT
<213> ORGANISM: Artificial Sequence
<220> FEATURE:
<223> OTHER INFORMATION: Synthetic

<400> SEQUENCE: 194

Ile Met Ser Gln Phe Arg Lys Leu Leu Met
1               5                   10

<210> SEQ ID NO 195
<211> LENGTH: 16
<212> TYPE: PRT
<213> ORGANISM: Artificial Sequence
<220> FEATURE:
<223> OTHER INFORMATION: Synthetic

<400> SEQUENCE: 195

Glu Val Asp Asn Leu Pro Glu Asp Met Lys Arg Leu His Leu Asp Asp
1               5                   10                  15

<210> SEQ ID NO 196
<211> LENGTH: 18
<212> TYPE: PRT
<213> ORGANISM: Artificial Sequence
<220> FEATURE:
<223> OTHER INFORMATION: Synthetic

<400> SEQUENCE: 196

Lys Val Ala Glu Lys Leu Glu Ala Leu Ser Val Lys Glu Glu Thr Lys
1               5                   10                  15

Glu Asp

<210> SEQ ID NO 197
<211> LENGTH: 16
<212> TYPE: PRT
<213> ORGANISM: Artificial Sequence
<220> FEATURE:
<223> OTHER INFORMATION: Synthetic

<400> SEQUENCE: 197

Glu Glu Ile Leu Lys Leu Leu Met Glu Leu Val Phe Arg Leu Val Cys
1               5                   10                  15

<210> SEQ ID NO 198
<211> LENGTH: 10
<212> TYPE: PRT
<213> ORGANISM: Artificial Sequence
<220> FEATURE:

<223> OTHER INFORMATION: Synthetic

<400> SEQUENCE: 198

Leu Ser Glu Ala Leu Leu Gln Leu Gln Phe
1               5                   10

<210> SEQ ID NO 199
<211> LENGTH: 10
<212> TYPE: PRT
<213> ORGANISM: Artificial Sequence
<220> FEATURE:
<223> OTHER INFORMATION: Synthetic

<400> SEQUENCE: 199

Leu Glu Asp Leu Val Arg His Met Ser Leu
1               5                   10

<210> SEQ ID NO 200
<211> LENGTH: 14
<212> TYPE: PRT
<213> ORGANISM: Artificial Sequence
<220> FEATURE:
<223> OTHER INFORMATION: Synthetic

<400> SEQUENCE: 200

Ala Leu Ser Ala Gln Leu Tyr Ser Ser Leu Ser Leu Asp Ser
1               5                   10

<210> SEQ ID NO 201
<211> LENGTH: 42
<212> TYPE: PRT
<213> ORGANISM: Artificial Sequence
<220> FEATURE:
<223> OTHER INFORMATION: Synthetic

<400> SEQUENCE: 201

Glu Lys Gly Asn Leu Pro Glu Leu Glu Lys Leu Glu Ile Asn Gly Asn
1               5                   10                  15

Arg Leu Asp Glu Asp Ser Asp Ala Leu Asp Leu Leu Gln Ser Lys Phe
            20                  25                  30

Asp Asp Leu Glu Val Asp Asp Phe Glu Glu
        35                  40

<210> SEQ ID NO 202
<211> LENGTH: 37
<212> TYPE: PRT
<213> ORGANISM: Artificial Sequence
<220> FEATURE:
<223> OTHER INFORMATION: Synthetic

<400> SEQUENCE: 202

Gly Asp Val Phe Gly Pro Glu Leu Asp Thr Leu Leu Asp Ser Leu Ser
1               5                   10                  15

Leu Val Gln Gly Gly Leu Ser Gly Ser Gly Val Pro Ser Glu Leu Pro
            20                  25                  30

Gln Leu Ile Pro Val
        35

<210> SEQ ID NO 203
<211> LENGTH: 42
<212> TYPE: PRT
<213> ORGANISM: Artificial Sequence
<220> FEATURE:
<223> OTHER INFORMATION: Synthetic

<400> SEQUENCE: 203

```
Asp Gly Phe Asn Glu Leu Ile Pro Glu Asp Leu Val Thr Val Phe Asp
1               5                   10                  15

Glu Arg Glu Leu Glu Leu Leu Ile Gly Gly Ile Ala Glu Ile Asp Ile
            20                  25                  30

Glu Asp Trp Lys Lys His Thr Asp Tyr Arg
        35                  40
```

<210> SEQ ID NO 204
<211> LENGTH: 23
<212> TYPE: PRT
<213> ORGANISM: Artificial Sequence
<220> FEATURE:
<223> OTHER INFORMATION: Synthetic

<400> SEQUENCE: 204

```
Gln Met Leu Ser Lys Glu Val Asp Ala Cys Val Thr Asp Leu Leu Lys
1               5                   10                  15

Glu Leu Val Arg Phe Gln Asp
            20
```

<210> SEQ ID NO 205
<211> LENGTH: 15
<212> TYPE: PRT
<213> ORGANISM: Artificial Sequence
<220> FEATURE:
<223> OTHER INFORMATION: Synthetic

<400> SEQUENCE: 205

```
Gln Asp Gln Phe His Lys Met Val Glu Leu Thr Val Ala Ala Arg
1               5                   10                  15
```

<210> SEQ ID NO 206
<211> LENGTH: 28
<212> TYPE: PRT
<213> ORGANISM: Artificial Sequence
<220> FEATURE:
<223> OTHER INFORMATION: Synthetic

<400> SEQUENCE: 206

```
Gln Tyr Glu Ser Asn Glu Asn Val Val Leu Val Cys Ser Thr Ile Val
1               5                   10                  15

Cys Ser Phe Gly Lys Gln Val Val Glu Lys Val Glu
            20                  25
```

<210> SEQ ID NO 207
<211> LENGTH: 16
<212> TYPE: PRT
<213> ORGANISM: Artificial Sequence
<220> FEATURE:
<223> OTHER INFORMATION: Synthetic

<400> SEQUENCE: 207

```
Leu Glu Pro Asp Leu Ser Glu Glu Val Ser Ala Arg Leu Arg Leu Gly
1               5                   10                  15
```

<210> SEQ ID NO 208
<211> LENGTH: 16
<212> TYPE: PRT
<213> ORGANISM: Artificial Sequence
<220> FEATURE:
<223> OTHER INFORMATION: Synthetic

<400> SEQUENCE: 208

```
Arg Arg Met Gln Glu Met Ile Thr Arg Met Gln Ala Gln Met Gln Ile
1               5                   10                  15
```

<210> SEQ ID NO 209
<211> LENGTH: 19
<212> TYPE: PRT
<213> ORGANISM: Artificial Sequence
<220> FEATURE:
<223> OTHER INFORMATION: Synthetic

<400> SEQUENCE: 209

```
Thr Gly Glu Gln Glu Leu Glu Ser Leu Val Leu Lys Leu Ser Val Leu
1               5                   10                  15

Lys Asp Phe
```

<210> SEQ ID NO 210
<211> LENGTH: 19
<212> TYPE: PRT
<213> ORGANISM: Artificial Sequence
<220> FEATURE:
<223> OTHER INFORMATION: Synthetic

<400> SEQUENCE: 210

```
Leu Glu Ser Leu Val Leu Lys Leu Ser Val Leu Lys Asp Phe Leu Ser
1               5                   10                  15

Gly Ile Gln
```

<210> SEQ ID NO 211
<211> LENGTH: 54
<212> TYPE: PRT
<213> ORGANISM: Artificial Sequence
<220> FEATURE:
<223> OTHER INFORMATION: Synthetic

<400> SEQUENCE: 211

```
Ser Arg Asp Ala Ala Arg Cys Arg Arg Ser Lys Glu Thr Glu Ile Phe
1               5                   10                  15

Met Glu Leu Ser Ala Ala Leu Pro Leu Lys Thr Asp Asp Val Asn Gln
            20                  25                  30

Leu Asp Lys Ala Ser Val Met Arg Ile Thr Ile Ala Phe Leu Lys Ile
        35                  40                  45

Arg Glu Met Leu Gln Phe
    50
```

<210> SEQ ID NO 212
<211> LENGTH: 19
<212> TYPE: PRT
<213> ORGANISM: Artificial Sequence
<220> FEATURE:
<223> OTHER INFORMATION: Synthetic

<400> SEQUENCE: 212

```
Asp Met Asp Phe Leu Arg Asn Leu Phe Ser Gln Thr Leu Ser Leu Gly
1               5                   10                  15

Ser Gln Lys
```

<210> SEQ ID NO 213
<211> LENGTH: 9
<212> TYPE: PRT
<213> ORGANISM: Artificial Sequence
<220> FEATURE:
<223> OTHER INFORMATION: Synthetic

<400> SEQUENCE: 213

```
Leu Thr Lys Met Cys Thr Ile Arg Met
1               5

<210> SEQ ID NO 214
<211> LENGTH: 10
<212> TYPE: PRT
<213> ORGANISM: Artificial Sequence
<220> FEATURE:
<223> OTHER INFORMATION: Synthetic

<400> SEQUENCE: 214

Gly Ile Asp Leu Ser Gly Leu Thr Leu Gln
1               5                   10

<210> SEQ ID NO 215
<211> LENGTH: 12
<212> TYPE: PRT
<213> ORGANISM: Artificial Sequence
<220> FEATURE:
<223> OTHER INFORMATION: Synthetic

<400> SEQUENCE: 215

Glu Leu Ile Ile Gly Gly Leu Asp Lys Ile Asp Leu
1               5                   10

<210> SEQ ID NO 216
<211> LENGTH: 70
<212> TYPE: PRT
<213> ORGANISM: Artificial Sequence
<220> FEATURE:
<223> OTHER INFORMATION: Synthetic

<400> SEQUENCE: 216

Ser Pro Lys Ala Val Glu Leu Thr Ser Leu Ser Asp Glu Asp Ser Gly
1               5                   10                  15

Lys Ser Ser Gln Pro Pro Ser Pro Ser Pro Ala Pro Ser Ser Phe
            20                  25                  30

Ser Ser Thr Ser Ala Ser Ser Leu Glu Ala Glu Ala Phe Ile Ala Phe
        35                  40                  45

Pro Gly Leu Gly Gln Leu Pro Lys Gln Leu Ala Arg Leu Ser Val Ala
    50                  55                  60

Lys Asp Pro Gln Ser Arg
65                  70

<210> SEQ ID NO 217
<211> LENGTH: 15
<212> TYPE: PRT
<213> ORGANISM: Artificial Sequence
<220> FEATURE:
<223> OTHER INFORMATION: Synthetic

<400> SEQUENCE: 217

Met Glu Glu Leu Ser Gln Ala Leu Ala Ser Ser Phe Ser Val Ser
1               5                   10                  15

<210> SEQ ID NO 218
<211> LENGTH: 32
<212> TYPE: PRT
<213> ORGANISM: Artificial Sequence
<220> FEATURE:
<223> OTHER INFORMATION: Synthetic

<400> SEQUENCE: 218

Glu Ser Asn Gly Pro Val Lys Val Trp Gly Ser Ile Lys Gly Leu Thr
```

-continued

```
1               5              10             15

Glu Gly Leu His Gly Phe His Val His Glu Phe Gly Asp Asn Thr Ala
            20             25             30

<210> SEQ ID NO 219
<211> LENGTH: 12
<212> TYPE: PRT
<213> ORGANISM: Artificial Sequence
<220> FEATURE:
<223> OTHER INFORMATION: Synthetic

<400> SEQUENCE: 219

Leu Ser Lys Thr Leu Gly Lys Leu Trp Arg Leu Leu
1               5              10

<210> SEQ ID NO 220
<211> LENGTH: 15
<212> TYPE: PRT
<213> ORGANISM: Artificial Sequence
<220> FEATURE:
<223> OTHER INFORMATION: Synthetic

<400> SEQUENCE: 220

Glu Ile Ser Lys Gln Leu Gly Lys Arg Trp Lys Asn Leu Thr Glu
1               5              10             15

<210> SEQ ID NO 221
<211> LENGTH: 15
<212> TYPE: PRT
<213> ORGANISM: Artificial Sequence
<220> FEATURE:
<223> OTHER INFORMATION: Synthetic

<400> SEQUENCE: 221

Glu Ile Ser Lys Gln Leu Gly Arg Arg Trp Lys Met Leu Thr Glu
1               5              10             15

<210> SEQ ID NO 222
<211> LENGTH: 14
<212> TYPE: PRT
<213> ORGANISM: Artificial Sequence
<220> FEATURE:
<223> OTHER INFORMATION: Synthetic

<400> SEQUENCE: 222

Glu Leu Ser Lys Thr Leu Gly Lys Leu Trp Arg Leu Leu Asn
1               5              10

<210> SEQ ID NO 223
<211> LENGTH: 12
<212> TYPE: PRT
<213> ORGANISM: Artificial Sequence
<220> FEATURE:
<223> OTHER INFORMATION: Synthetic

<400> SEQUENCE: 223

Leu Glu Lys Gln Ile Asn Asp Leu Gln Ile Asp Lys
1               5              10

<210> SEQ ID NO 224
<211> LENGTH: 19
<212> TYPE: PRT
<213> ORGANISM: Artificial Sequence
<220> FEATURE:
<223> OTHER INFORMATION: Synthetic

<400> SEQUENCE: 224
```

Ser Ala Ser Asp Asp Leu Glu Ala Leu Gly Thr Leu Ser Leu Gly Thr
1               5                   10                  15

Thr Glu Glu

<210> SEQ ID NO 225
<211> LENGTH: 10
<212> TYPE: PRT
<213> ORGANISM: Artificial Sequence
<220> FEATURE:
<223> OTHER INFORMATION: Synthetic

<400> SEQUENCE: 225

Ile Tyr Pro Trp Met Lys Arg Val His Leu
1               5                   10

<210> SEQ ID NO 226
<211> LENGTH: 9
<212> TYPE: PRT
<213> ORGANISM: Artificial Sequence
<220> FEATURE:
<223> OTHER INFORMATION: Synthetic

<400> SEQUENCE: 226

Leu Leu Leu Lys Lys Met Tyr Leu Met
1               5

<210> SEQ ID NO 227
<211> LENGTH: 13
<212> TYPE: PRT
<213> ORGANISM: Artificial Sequence
<220> FEATURE:
<223> OTHER INFORMATION: Synthetic

<400> SEQUENCE: 227

Trp Asp Arg Thr Phe Ser Leu Phe Gln Gln Leu Ile Gln
1               5                   10

<210> SEQ ID NO 228
<211> LENGTH: 22
<212> TYPE: PRT
<213> ORGANISM: Artificial Sequence
<220> FEATURE:
<223> OTHER INFORMATION: Synthetic

<400> SEQUENCE: 228

Met Glu Glu Ser Thr Asn Gly Ser Leu Ala Ala Glu Phe Arg His Leu
1               5                   10                  15

Gln Leu Lys Glu Gln Lys
            20

<210> SEQ ID NO 229
<211> LENGTH: 13
<212> TYPE: PRT
<213> ORGANISM: Artificial Sequence
<220> FEATURE:
<223> OTHER INFORMATION: Synthetic

<400> SEQUENCE: 229

Glu Glu Arg Ile Val Glu Leu Phe Arg Asn Leu Met Lys
1               5                   10

<210> SEQ ID NO 230
<211> LENGTH: 11
<212> TYPE: PRT
<213> ORGANISM: Artificial Sequence -continued
<220> FEATURE:
<223> OTHER INFORMATION: Synthetic

<400> SEQUENCE: 230

Leu Ser Ala Glu Phe Lys His Leu Thr Leu Arg
1               5                   10

<210> SEQ ID NO 231
<211> LENGTH: 14
<212> TYPE: PRT
<213> ORGANISM: Artificial Sequence
<220> FEATURE:
<223> OTHER INFORMATION: Synthetic

<400> SEQUENCE: 231

Gln Leu Thr Thr Leu Ala Glu Lys Leu Leu Gly Pro Gly Val
1               5                   10

<210> SEQ ID NO 232
<211> LENGTH: 11
<212> TYPE: PRT
<213> ORGANISM: Artificial Sequence
<220> FEATURE:
<223> OTHER INFORMATION: Synthetic

<400> SEQUENCE: 232

Ile Asn Gln Met Phe Ser Val Gln Leu Ser Leu
1               5                   10

<210> SEQ ID NO 233
<211> LENGTH: 17
<212> TYPE: PRT
<213> ORGANISM: Artificial Sequence
<220> FEATURE:
<223> OTHER INFORMATION: Synthetic

<400> SEQUENCE: 233

Glu Ala Thr Glu Ala Gln Leu Asn Asn Ser Met Ala Ala Leu Asn Val
1               5                   10                  15

Asn

<210> SEQ ID NO 234
<211> LENGTH: 16
<212> TYPE: PRT
<213> ORGANISM: Artificial Sequence
<220> FEATURE:
<223> OTHER INFORMATION: Synthetic

<400> SEQUENCE: 234

Val Lys Lys Gln Phe Glu Glu Leu Thr Leu Gly Glu Phe Leu Lys Leu
1               5                   10                  15

<210> SEQ ID NO 235
<211> LENGTH: 15
<212> TYPE: PRT
<213> ORGANISM: Artificial Sequence
<220> FEATURE:
<223> OTHER INFORMATION: Synthetic

<400> SEQUENCE: 235

Tyr Lys Arg Ile Glu Glu Leu Leu Tyr Lys Ile Ser Leu Thr Thr
1               5                   10                  15

<210> SEQ ID NO 236
<211> LENGTH: 39
<212> TYPE: PRT

<213> ORGANISM: Artificial Sequence
<220> FEATURE:
<223> OTHER INFORMATION: Synthetic

<400> SEQUENCE: 236

Asn Pro Ala Ser Ala Pro Pro Pro Leu Pro Pro Pro Gly Gln Gln Val
1               5                   10                  15

Ile His Val Thr Gln Asp Leu Asp Thr Asp Leu Glu Ala Leu Phe Asn
                20                  25                  30

Ser Val Met Asn Pro Lys Pro
        35

<210> SEQ ID NO 237
<211> LENGTH: 24
<212> TYPE: PRT
<213> ORGANISM: Artificial Sequence
<220> FEATURE:
<223> OTHER INFORMATION: Synthetic

<400> SEQUENCE: 237

His Val Leu Ser Ser Ser Ala Gly Asn Ser Ala Pro Asn Ser Pro Met
1               5                   10                  15

Ala Met Leu His Ile Gly Ser Asn
            20

<210> SEQ ID NO 238
<211> LENGTH: 40
<212> TYPE: PRT
<213> ORGANISM: Artificial Sequence
<220> FEATURE:
<223> OTHER INFORMATION: Synthetic

<400> SEQUENCE: 238

Met Ala Asn Ser Ala Asn Thr Asn Thr Val Pro Lys Leu Tyr Arg Ser
1               5                   10                  15

Val Ile Glu Asp Val Ile Asn Asp Val Arg Asp Ile Phe Leu Asp Asp
                20                  25                  30

Gly Val Asp Glu Gln Val Leu Met
        35                  40

<210> SEQ ID NO 239
<211> LENGTH: 19
<212> TYPE: PRT
<213> ORGANISM: Artificial Sequence
<220> FEATURE:
<223> OTHER INFORMATION: Synthetic

<400> SEQUENCE: 239

Gln Pro Asp Ala Ser Lys Ala Asp Pro Leu Pro Val Leu Glu Asn Leu
1               5                   10                  15

Thr Leu Lys

<210> SEQ ID NO 240
<211> LENGTH: 11
<212> TYPE: PRT
<213> ORGANISM: Artificial Sequence
<220> FEATURE:
<223> OTHER INFORMATION: Synthetic

<400> SEQUENCE: 240

Ile Leu Arg Asp Phe Phe Glu Leu Arg Leu Lys
1               5                   10

```
<210> SEQ ID NO 241
<211> LENGTH: 13
<212> TYPE: PRT
<213> ORGANISM: Artificial Sequence
<220> FEATURE:
<223> OTHER INFORMATION: Synthetic

<400> SEQUENCE: 241

Phe Ile Leu Glu Lys Ile Asp Gly Lys Ile Ile Ile Glu
1               5               10

<210> SEQ ID NO 242
<211> LENGTH: 11
<212> TYPE: PRT
<213> ORGANISM: Artificial Sequence
<220> FEATURE:
<223> OTHER INFORMATION: Synthetic

<400> SEQUENCE: 242

Glu Thr Val Gln Asp Ile Leu Lys Glu Phe Phe
1               5               10

<210> SEQ ID NO 243
<211> LENGTH: 34
<212> TYPE: PRT
<213> ORGANISM: Artificial Sequence
<220> FEATURE:
<223> OTHER INFORMATION: Synthetic

<400> SEQUENCE: 243

Arg Ile Ser Tyr Gln Pro Glu Asn Ile Gln Pro Asn Arg His Val Ala
1               5               10                  15

Asn Ile Val Glu Lys Leu Arg Glu Val Lys Leu Ser Pro Glu Glu Gly
            20                  25                  30

Gln Lys

<210> SEQ ID NO 244
<211> LENGTH: 40
<212> TYPE: PRT
<213> ORGANISM: Artificial Sequence
<220> FEATURE:
<223> OTHER INFORMATION: Synthetic

<400> SEQUENCE: 244

Gln Arg Leu Gln Gly Leu Pro Pro Asp Arg Gly Ile Ile Arg Pro Gly
1               5               10                  15

Ser Leu Asp Ala Glu Ile Asp Ser Leu Thr Ser Met Leu Ala Asp Leu
            20                  25                  30

Asp Gly Gly Arg Ser His Ala Pro
            35                  40

<210> SEQ ID NO 245
<211> LENGTH: 12
<212> TYPE: PRT
<213> ORGANISM: Artificial Sequence
<220> FEATURE:
<223> OTHER INFORMATION: Synthetic

<400> SEQUENCE: 245

Trp Met Ala Ile Ala Gly Lys Ile Arg Ser Asp Leu
1               5               10

<210> SEQ ID NO 246
<211> LENGTH: 10
<212> TYPE: PRT
```

-continued

<213> ORGANISM: Artificial Sequence
<220> FEATURE:
<223> OTHER INFORMATION: Synthetic

<400> SEQUENCE: 246

Cys Ile Leu Cys Gln Leu Leu Leu Leu Tyr
1               5                   10

<210> SEQ ID NO 247
<211> LENGTH: 15
<212> TYPE: PRT
<213> ORGANISM: Artificial Sequence
<220> FEATURE:
<223> OTHER INFORMATION: Synthetic

<400> SEQUENCE: 247

Thr Thr Glu Glu Leu Glu Leu Glu Leu Glu Thr Leu Asp Ile Asn
1               5                   10                  15

<210> SEQ ID NO 248
<211> LENGTH: 39
<212> TYPE: PRT
<213> ORGANISM: Artificial Sequence
<220> FEATURE:
<223> OTHER INFORMATION: Synthetic

<400> SEQUENCE: 248

Thr Asp Pro Phe Leu Ala Met Gln Val Gln Glu Leu Thr Arg Ser Met
1               5                   10                  15

Ala Asn Leu Thr Phe Lys Gln Arg Arg Asp Ala Pro Pro Glu Gly Pro
            20                  25                  30

Ser Ala Lys Lys Pro Lys Lys
        35

<210> SEQ ID NO 249
<211> LENGTH: 14
<212> TYPE: PRT
<213> ORGANISM: Artificial Sequence
<220> FEATURE:
<223> OTHER INFORMATION: Synthetic

<400> SEQUENCE: 249

Glu Leu Asp Thr Asn Phe Phe Thr Leu Tyr Val Ala Gln Gly
1               5                   10

<210> SEQ ID NO 250
<211> LENGTH: 10
<212> TYPE: PRT
<213> ORGANISM: Artificial Sequence
<220> FEATURE:
<223> OTHER INFORMATION: Synthetic

<400> SEQUENCE: 250

Leu Glu Arg Leu Phe Gly Arg Leu Arg Ile
1               5                   10

<210> SEQ ID NO 251
<211> LENGTH: 19
<212> TYPE: PRT
<213> ORGANISM: Artificial Sequence
<220> FEATURE:
<223> OTHER INFORMATION: Synthetic

<400> SEQUENCE: 251

Met Asp Gly Ala Ile Ala Ser Gly Val Ser Lys Phe Ala Thr Leu Ser
1               5                   10                  15

Leu His Asp

<210> SEQ ID NO 252
<211> LENGTH: 12
<212> TYPE: PRT
<213> ORGANISM: Artificial Sequence
<220> FEATURE:
<223> OTHER INFORMATION: Synthetic

<400> SEQUENCE: 252

Ile Glu Val Glu Ala Ser Asp Leu Ser Leu Ser Leu
1               5                   10

<210> SEQ ID NO 253
<211> LENGTH: 19
<212> TYPE: PRT
<213> ORGANISM: Artificial Sequence
<220> FEATURE:
<223> OTHER INFORMATION: Synthetic

<400> SEQUENCE: 253

Ser Ser Leu Gln Glu Leu Val Gln Gln Phe Glu Ala Leu Pro Gly Asp
1               5                   10                  15

Leu Val Gly

<210> SEQ ID NO 254
<211> LENGTH: 15
<212> TYPE: PRT
<213> ORGANISM: Artificial Sequence
<220> FEATURE:
<223> OTHER INFORMATION: Synthetic

<400> SEQUENCE: 254

Glu Gln Leu Glu Arg Leu Arg Lys Asp Met Gly Ser Val Ala Leu
1               5                   10                  15

<210> SEQ ID NO 255
<211> LENGTH: 9
<212> TYPE: PRT
<213> ORGANISM: Artificial Sequence
<220> FEATURE:
<223> OTHER INFORMATION: Synthetic

<400> SEQUENCE: 255

Leu Arg Leu Gly Ser Gln Ile Phe Ile
1               5

<210> SEQ ID NO 256
<211> LENGTH: 10
<212> TYPE: PRT
<213> ORGANISM: Artificial Sequence
<220> FEATURE:
<223> OTHER INFORMATION: Synthetic

<400> SEQUENCE: 256

Leu Gln Leu Val Val Leu Arg Asp Ser Lys
1               5                   10

<210> SEQ ID NO 257
<211> LENGTH: 10
<212> TYPE: PRT
<213> ORGANISM: Artificial Sequence
<220> FEATURE:
<223> OTHER INFORMATION: Synthetic

<400> SEQUENCE: 257

Leu Phe Gly Pro Ile Ala Asp Ile Ala Leu
1               5                   10

<210> SEQ ID NO 258
<211> LENGTH: 11
<212> TYPE: PRT
<213> ORGANISM: Artificial Sequence
<220> FEATURE:
<223> OTHER INFORMATION: Synthetic

<400> SEQUENCE: 258

Leu Glu Lys Leu Ala Asn Glu Leu Pro Asp Leu
1               5                   10

<210> SEQ ID NO 259
<211> LENGTH: 17
<212> TYPE: PRT
<213> ORGANISM: Artificial Sequence
<220> FEATURE:
<223> OTHER INFORMATION: Synthetic

<400> SEQUENCE: 259

Leu Thr Met Lys Glu Val Glu Glu Leu Glu Leu Leu Thr Gln Lys Leu
1               5                   10                  15

Met

<210> SEQ ID NO 260
<211> LENGTH: 28
<212> TYPE: PRT
<213> ORGANISM: Artificial Sequence
<220> FEATURE:
<223> OTHER INFORMATION: Synthetic

<400> SEQUENCE: 260

Ala Pro Pro Ala Gln Pro Pro Ser Gln Pro Gln Gln His Tyr Ser Glu
1               5                   10                  15

Gly Glu Leu Glu Glu Asp Glu Asp Ser Asp Asp Ala
            20                  25

<210> SEQ ID NO 261
<211> LENGTH: 17
<212> TYPE: PRT
<213> ORGANISM: Artificial Sequence
<220> FEATURE:
<223> OTHER INFORMATION: Synthetic

<400> SEQUENCE: 261

Arg Phe Glu Met Phe Arg Glu Leu Asn Glu Ala Leu Glu Leu Lys Asp
1               5                   10                  15

Ala

<210> SEQ ID NO 262
<211> LENGTH: 24
<212> TYPE: PRT
<213> ORGANISM: Artificial Sequence
<220> FEATURE:
<223> OTHER INFORMATION: Synthetic

<400> SEQUENCE: 262

Lys Arg Lys Arg Lys Arg Lys Arg Lys Arg Lys Arg Lys Arg Lys Arg
1               5                   10                  15

Lys Arg Lys Arg Lys Lys Lys Leu
            20

<210> SEQ ID NO 263
<211> LENGTH: 7
<212> TYPE: PRT
<213> ORGANISM: Artificial Sequence
<220> FEATURE:
<223> OTHER INFORMATION: Synthetic

<400> SEQUENCE: 263

Pro Lys Lys Lys Arg Lys Val
1               5

<210> SEQ ID NO 264
<211> LENGTH: 9
<212> TYPE: PRT
<213> ORGANISM: Artificial Sequence
<220> FEATURE:
<223> OTHER INFORMATION: Synthetic

<400> SEQUENCE: 264

Pro Lys Lys Asn Arg Leu Arg Arg Pro
1               5

<210> SEQ ID NO 265
<211> LENGTH: 20
<212> TYPE: PRT
<213> ORGANISM: Artificial Sequence
<220> FEATURE:
<223> OTHER INFORMATION: Synthetic

<400> SEQUENCE: 265

Pro Lys Arg Pro Arg Asp Arg His Asp Gly Glu Leu Gly Gly Arg Lys
1               5                   10                  15

Arg Ala Arg Gly
            20

<210> SEQ ID NO 266
<211> LENGTH: 8
<212> TYPE: PRT
<213> ORGANISM: Artificial Sequence
<220> FEATURE:
<223> OTHER INFORMATION: Synthetic

<400> SEQUENCE: 266

Pro Leu Leu Lys Lys Ile Lys Gln
1               5

<210> SEQ ID NO 267
<211> LENGTH: 7
<212> TYPE: PRT
<213> ORGANISM: Artificial Sequence
<220> FEATURE:
<223> OTHER INFORMATION: Synthetic

<400> SEQUENCE: 267

Pro Asn Lys Lys Lys Arg Lys
1               5

<210> SEQ ID NO 268
<211> LENGTH: 8
<212> TYPE: PRT
<213> ORGANISM: Artificial Sequence
<220> FEATURE:
<223> OTHER INFORMATION: Synthetic

<400> SEQUENCE: 268

Pro Pro Gln Lys Lys Ile Lys Ser

-continued

```
1               5

<210> SEQ ID NO 269
<211> LENGTH: 13
<212> TYPE: PRT
<213> ORGANISM: Artificial Sequence
<220> FEATURE:
<223> OTHER INFORMATION: Synthetic

<400> SEQUENCE: 269

Pro Pro Arg Ile Tyr Pro Gln Leu Pro Ser Ala Pro Thr
1               5                   10

<210> SEQ ID NO 270
<211> LENGTH: 9
<212> TYPE: PRT
<213> ORGANISM: Artificial Sequence
<220> FEATURE:
<223> OTHER INFORMATION: Synthetic

<400> SEQUENCE: 270

Pro Pro Arg Lys Lys Arg Thr Val Val
1               5

<210> SEQ ID NO 271
<211> LENGTH: 9
<212> TYPE: PRT
<213> ORGANISM: Artificial Sequence
<220> FEATURE:
<223> OTHER INFORMATION: Synthetic

<400> SEQUENCE: 271

Pro Pro Val Lys Arg Glu Arg Thr Ser
1               5

<210> SEQ ID NO 272
<211> LENGTH: 7
<212> TYPE: PRT
<213> ORGANISM: Artificial Sequence
<220> FEATURE:
<223> OTHER INFORMATION: Synthetic

<400> SEQUENCE: 272

Pro Gln Pro Lys Lys Lys Pro
1               5

<210> SEQ ID NO 273
<211> LENGTH: 8
<212> TYPE: PRT
<213> ORGANISM: Artificial Sequence
<220> FEATURE:
<223> OTHER INFORMATION: Synthetic

<400> SEQUENCE: 273

Pro Gln Ser Arg Lys Lys Leu Arg
1               5

<210> SEQ ID NO 274
<211> LENGTH: 14
<212> TYPE: PRT
<213> ORGANISM: Artificial Sequence
<220> FEATURE:
<223> OTHER INFORMATION: Synthetic

<400> SEQUENCE: 274

Pro Arg Gly Arg Arg Gln Pro Ile Pro Lys Ala Arg Gln Pro
1               5                   10
```

```
<210> SEQ ID NO 275
<211> LENGTH: 8
<212> TYPE: PRT
<213> ORGANISM: Artificial Sequence
<220> FEATURE:
<223> OTHER INFORMATION: Synthetic

<400> SEQUENCE: 275

Pro Arg Pro Arg Lys Ile Pro Arg
1               5

<210> SEQ ID NO 276
<211> LENGTH: 6
<212> TYPE: PRT
<213> ORGANISM: Artificial Sequence
<220> FEATURE:
<223> OTHER INFORMATION: Synthetic

<400> SEQUENCE: 276

Pro Arg Arg Gly Pro Arg
1               5

<210> SEQ ID NO 277
<211> LENGTH: 5
<212> TYPE: PRT
<213> ORGANISM: Artificial Sequence
<220> FEATURE:
<223> OTHER INFORMATION: Synthetic

<400> SEQUENCE: 277

Pro Arg Arg Arg Lys
1               5

<210> SEQ ID NO 278
<211> LENGTH: 10
<212> TYPE: PRT
<213> ORGANISM: Artificial Sequence
<220> FEATURE:
<223> OTHER INFORMATION: Synthetic

<400> SEQUENCE: 278

Pro Tyr Leu Asn Lys Arg Lys Gly Lys Pro
1               5                   10

<210> SEQ ID NO 279
<211> LENGTH: 7
<212> TYPE: PRT
<213> ORGANISM: Artificial Sequence
<220> FEATURE:
<223> OTHER INFORMATION: Synthetic

<400> SEQUENCE: 279

Pro Lys Lys Ala Arg Glu Asp
1               5

<210> SEQ ID NO 280
<211> LENGTH: 10
<212> TYPE: PRT
<213> ORGANISM: Artificial Sequence
<220> FEATURE:
<223> OTHER INFORMATION: Synthetic

<400> SEQUENCE: 280

Pro Ala Lys Arg Ala Arg Arg Gly Tyr Lys
1               5                   10
```

-continued

```
<210> SEQ ID NO 281
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (5)..(12)
<223> OTHER INFORMATION: Xaa can be any naturally occurring amino acid
<220> FEATURE:
<221> NAME/KEY: misc_feature
<222> LOCATION: (5)..(12)
<223> OTHER INFORMATION: may not be present

<400> SEQUENCE: 281

Lys Arg Xaa Xaa Xaa Xaa Xaa Xaa Xaa Xaa Xaa Xaa Lys Lys Lys Leu
1               5                   10                  15

<210> SEQ ID NO 282
<211> LENGTH: 7
<212> TYPE: PRT
<213> ORGANISM: Artificial Sequence
<220> FEATURE:
<223> OTHER INFORMATION: Synthetic

<400> SEQUENCE: 282

Lys Ser Lys Lys Lys Ala Gln
1               5

<210> SEQ ID NO 283
<211> LENGTH: 7
<212> TYPE: PRT
<213> ORGANISM: Artificial Sequence
<220> FEATURE:
<223> OTHER INFORMATION: Synthetic

<400> SEQUENCE: 283

Lys Thr Arg Lys His Arg Gly
1               5

<210> SEQ ID NO 284
<211> LENGTH: 21
<212> TYPE: PRT
<213> ORGANISM: Artificial Sequence
<220> FEATURE:
<223> OTHER INFORMATION: Synthetic

<400> SEQUENCE: 284

Lys Val Asn Ser Arg Lys Arg Arg Lys Glu Val Pro Gly Pro Asn Gly
1               5                   10                  15

Ala Thr Glu Glu Asp
            20

<210> SEQ ID NO 285
<211> LENGTH: 18
<212> TYPE: PRT
<213> ORGANISM: Artificial Sequence
<220> FEATURE:
<223> OTHER INFORMATION: Synthetic

<400> SEQUENCE: 285

Lys Val Thr Lys Arg Lys His Asp Asn Glu Gly Ser Gly Ser Lys Arg
1               5                   10                  15
```

-continued

Pro Lys

<210> SEQ ID NO 286
<211> LENGTH: 35
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(11)
<223> OTHER INFORMATION: may not be present
<220> FEATURE:
<221> NAME/KEY: misc_feature
<222> LOCATION: (12)..(23)
<223> OTHER INFORMATION: Xaa can be any naturally occurring amino acid
<220> FEATURE:
<221> NAME/KEY: misc_feature
<222> LOCATION: (24)..(28)
<223> OTHER INFORMATION: may not be present
<220> FEATURE:
<221> NAME/KEY: misc_feature
<222> LOCATION: (24)..(28)
<223> OTHER INFORMATION: Xaa can be any naturally occurring amino acid
<220> FEATURE:
<221> NAME/KEY: misc_feature
<222> LOCATION: (32)..(33)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: may not be present
<220> FEATURE:
<221> NAME/KEY: misc_feature
<222> LOCATION: (34)..(34)
<223> OTHER INFORMATION: Xaa can be any naturally occurring amino acid

<400> SEQUENCE: 286

Lys Arg Lys Arg Lys Arg Lys Arg Lys Arg Lys Xaa Xaa Xaa Xaa Xaa
1               5                   10                  15

Xaa Xaa Xaa Xaa Xaa Xaa Xaa Xaa Xaa Xaa Xaa Xaa Arg Lys Lys Xaa
            20                  25                  30

Xaa Xaa Lys
        35

<210> SEQ ID NO 287
<211> LENGTH: 13
<212> TYPE: PRT
<213> ORGANISM: Artificial Sequence
<220> FEATURE:
<223> OTHER INFORMATION: Synthetic

<400> SEQUENCE: 287

Leu Glu Lys Lys Val Lys Lys Lys Phe Asp Trp Cys Ala
1               5                   10

<210> SEQ ID NO 288
<211> LENGTH: 13
<212> TYPE: PRT
<213> ORGANISM: Artificial Sequence
<220> FEATURE:
<223> OTHER INFORMATION: Synthetic

<400> SEQUENCE: 288

Leu Lys Asp Val Arg Lys Arg Lys Leu Gly Pro Gly His
1               5                   10

<210> SEQ ID NO 289
<211> LENGTH: 7

```
<212> TYPE: PRT
<213> ORGANISM: Artificial Sequence
<220> FEATURE:
<223> OTHER INFORMATION: Synthetic

<400> SEQUENCE: 289

Leu Lys Arg Lys Leu Gln Arg
1               5

<210> SEQ ID NO 290
<211> LENGTH: 9
<212> TYPE: PRT
<213> ORGANISM: Artificial Sequence
<220> FEATURE:
<223> OTHER INFORMATION: Synthetic

<400> SEQUENCE: 290

Leu Lys Arg Pro Arg Ser Pro Ser Ser
1               5

<210> SEQ ID NO 291
<211> LENGTH: 42
<212> TYPE: PRT
<213> ORGANISM: Artificial Sequence
<220> FEATURE:
<223> OTHER INFORMATION: Synthetic

<400> SEQUENCE: 291

Met Ala Pro Ser Ala Lys Ala Thr Ala Ala Lys Lys Ala Val Val Lys
1               5                   10                  15

Gly Thr Asn Gly Lys Lys Ala Leu Lys Val Arg Thr Ser Ala Thr Phe
            20                  25                  30

Arg Leu Pro Lys Thr Leu Lys Leu Ala Arg
        35                  40

<210> SEQ ID NO 292
<211> LENGTH: 13
<212> TYPE: PRT
<213> ORGANISM: Artificial Sequence
<220> FEATURE:
<223> OTHER INFORMATION: Synthetic

<400> SEQUENCE: 292

Met Asn Lys Ile Pro Ile Lys Asp Leu Leu Asn Pro Gly
1               5                   10

<210> SEQ ID NO 293
<211> LENGTH: 18
<212> TYPE: PRT
<213> ORGANISM: Artificial Sequence
<220> FEATURE:
<223> OTHER INFORMATION: Synthetic

<400> SEQUENCE: 293

Met Pro Lys Thr Arg Arg Arg Pro Arg Arg Ser Gln Arg Lys Arg Pro
1               5                   10                  15

Pro Thr

<210> SEQ ID NO 294
<211> LENGTH: 30
<212> TYPE: PRT
<213> ORGANISM: Artificial Sequence
<220> FEATURE:
<223> OTHER INFORMATION: Synthetic

<400> SEQUENCE: 294
```

-continued

Met Pro Thr Glu Glu Arg Val Arg Lys Arg Lys Glu Ser Asn Arg Glu
1               5                   10                  15

Ser Ala Arg Arg Ser Arg Tyr Arg Lys Ala Ala His Leu Lys
        20                  25                  30

<210> SEQ ID NO 295
<211> LENGTH: 38
<212> TYPE: PRT
<213> ORGANISM: Artificial Sequence
<220> FEATURE:
<223> OTHER INFORMATION: Synthetic

<400> SEQUENCE: 295

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
        20                  25                  30

Arg Asn Gln Gly Gly Tyr
        35

<210> SEQ ID NO 296
<211> LENGTH: 9
<212> TYPE: PRT
<213> ORGANISM: Artificial Sequence
<220> FEATURE:
<223> OTHER INFORMATION: Synthetic

<400> SEQUENCE: 296

Pro Ala Ala Lys Arg Val Lys Leu Asp
1               5

<210> SEQ ID NO 297
<211> LENGTH: 6
<212> TYPE: PRT
<213> ORGANISM: Artificial Sequence
<220> FEATURE:
<223> OTHER INFORMATION: Synthetic

<400> SEQUENCE: 297

Gln Arg Lys Arg Gln Lys
1               5

<210> SEQ ID NO 298
<211> LENGTH: 23
<212> TYPE: PRT
<213> ORGANISM: Artificial Sequence
<220> FEATURE:
<223> OTHER INFORMATION: Synthetic

<400> SEQUENCE: 298

Arg Ala Ile Lys Arg Arg Pro Gly Leu Asp Phe Asp Asp Asp Gly Glu
1               5                   10                  15

Gly Asn Ser Lys Phe Leu Arg
            20

<210> SEQ ID NO 299
<211> LENGTH: 13
<212> TYPE: PRT
<213> ORGANISM: Artificial Sequence
<220> FEATURE:
<223> OTHER INFORMATION: Synthetic

<400> SEQUENCE: 299

Arg Glu Lys Lys Glu Lys Glu Gln Lys Glu Lys Cys Ala

```
1               5                   10
```

```
<210> SEQ ID NO 300
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(26)
<223> OTHER INFORMATION: Xaa can be any naturally occurring amino acid
<220> FEATURE:
<221> NAME/KEY: misc_feature
<222> LOCATION: (6)..(26)
<223> OTHER INFORMATION: may not be present

<400> SEQUENCE: 300

Arg Arg Pro Ser Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Arg Arg Lys Arg Gln
            20                  25                  30

<210> SEQ ID NO 301
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(14)
<223> OTHER INFORMATION: Xaa can be any naturally occurring amino acid
<220> FEATURE:
<221> NAME/KEY: misc_feature
<222> LOCATION: (5)..(14)
<223> OTHER INFORMATION: may not be present

<400> SEQUENCE: 301

Arg Arg Arg Xaa Xaa Xaa Xaa Xaa Xaa Xaa Xaa Xaa Xaa Xaa Lys Arg
1               5                   10                  15

Arg Lys

<210> SEQ ID NO 302
<211> LENGTH: 7
<212> TYPE: PRT
<213> ORGANISM: Artificial Sequence
<220> FEATURE:
<223> OTHER INFORMATION: Synthetic

<400> SEQUENCE: 302

Arg Arg Ser Met Lys Arg Lys
1               5

<210> SEQ ID NO 303
<211> LENGTH: 7
<212> TYPE: PRT
<213> ORGANISM: Artificial Sequence
<220> FEATURE:
<223> OTHER INFORMATION: Synthetic

<400> SEQUENCE: 303

Arg Val His Pro Tyr Gln Arg
1               5

<210> SEQ ID NO 304
<211> LENGTH: 26
<212> TYPE: PRT
```

-continued

<213> ORGANISM: Artificial Sequence
<220> FEATURE:
<223> OTHER INFORMATION: Synthetic

<400> SEQUENCE: 304

Ser Ala Asn Lys Val Thr Lys Asn Lys Ser Asn Ser Ser Pro Tyr Leu
1               5                   10                  15

Asn Lys Arg Gly Lys Pro Gly Pro Asp Ser
            20                  25

<210> SEQ ID NO 305
<211> LENGTH: 13
<212> TYPE: PRT
<213> ORGANISM: Artificial Sequence
<220> FEATURE:
<223> OTHER INFORMATION: Synthetic

<400> SEQUENCE: 305

Ser Asp Lys Lys Val Arg Ser Arg Leu Ile Glu Cys Ala
1               5                   10

<210> SEQ ID NO 306
<211> LENGTH: 9
<212> TYPE: PRT
<213> ORGANISM: Artificial Sequence
<220> FEATURE:
<223> OTHER INFORMATION: Synthetic

<400> SEQUENCE: 306

Ser Lys Arg Val Ala Lys Arg Lys Leu
1               5

<210> SEQ ID NO 307
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid

<400> SEQUENCE: 307

Ser Xaa Gly Thr Lys Arg Ser Tyr Xaa Xaa Met
1               5                   10

<210> SEQ ID NO 308
<211> LENGTH: 14
<212> TYPE: PRT
<213> ORGANISM: Artificial Sequence
<220> FEATURE:
<223> OTHER INFORMATION: Synthetic

<400> SEQUENCE: 308

Thr Glu Lys Lys Gln Gly Lys Ser Ile Leu Tyr Asp Cys Ala
1               5                   10

<210> SEQ ID NO 309
<211> LENGTH: 8
<212> TYPE: PRT
<213> ORGANISM: Artificial Sequence
<220> FEATURE:
<223> OTHER INFORMATION: Synthetic -continued

```
<220> FEATURE:
<221> NAME/KEY: misc_feature
<222> LOCATION: (5)..(7)
<223> OTHER INFORMATION: Xaa can be any naturally occurring amino acid

<400> SEQUENCE: 309

Thr Lys Arg Ser Xaa Xaa Xaa Met
1               5

<210> SEQ ID NO 310
<211> LENGTH: 11
<212> TYPE: PRT
<213> ORGANISM: Artificial Sequence
<220> FEATURE:
<223> OTHER INFORMATION: Synthetic

<400> SEQUENCE: 310

Val Asn Glu Ala Phe Glu Thr Leu Lys Arg Cys
1               5                   10

<210> SEQ ID NO 311
<211> LENGTH: 7
<212> TYPE: PRT
<213> ORGANISM: Artificial Sequence
<220> FEATURE:
<223> OTHER INFORMATION: Synthetic

<400> SEQUENCE: 311

Val Ser Arg Lys Arg Pro Arg
1               5

<210> SEQ ID NO 312
<211> LENGTH: 13
<212> TYPE: PRT
<213> ORGANISM: Artificial Sequence
<220> FEATURE:
<223> OTHER INFORMATION: Synthetic

<400> SEQUENCE: 312

Tyr Lys Arg Pro Cys Lys Arg Ser Phe Ile Arg Phe Ile
1               5                   10

<210> SEQ ID NO 313
<211> LENGTH: 28
<212> TYPE: PRT
<213> ORGANISM: Artificial Sequence
<220> FEATURE:
<223> OTHER INFORMATION: Synthetic

<400> SEQUENCE: 313

Tyr Leu Thr Gln Glu Thr Asn Lys Val Glu Thr Tyr Lys Glu Gln Pro
1               5                   10                  15

Leu Lys Thr Pro Gly Lys Lys Lys Gly Lys Pro
            20                  25

<210> SEQ ID NO 314
<211> LENGTH: 15
<212> TYPE: PRT
<213> ORGANISM: Artificial Sequence
<220> FEATURE:
<223> OTHER INFORMATION: Synthetic

<400> SEQUENCE: 314

Tyr Asn Asn Gln Ser Ser Asn Phe Gly Pro Met Lys Gly Gly Asn
1               5                   10                  15
```

```
<210> SEQ ID NO 315
<211> LENGTH: 33
<212> TYPE: PRT
<213> ORGANISM: Artificial Sequence
<220> FEATURE:
<223> OTHER INFORMATION: Synthetic

<400> SEQUENCE: 315

Lys Ala Arg Thr Pro Ile Gln Lys His Trp Arg Pro Thr Val Leu Thr
1               5                   10                  15

Glu Gly Pro Pro Val Lys Ile Arg Ile Glu Thr Gly Glu Trp Glu Lys
            20                  25                  30

Ala

<210> SEQ ID NO 316
<211> LENGTH: 7
<212> TYPE: PRT
<213> ORGANISM: Artificial Sequence
<220> FEATURE:
<223> OTHER INFORMATION: Synthetic

<400> SEQUENCE: 316

Arg Arg Met Lys Trp Lys Lys
1               5

<210> SEQ ID NO 317
<211> LENGTH: 7
<212> TYPE: PRT
<213> ORGANISM: Artificial Sequence
<220> FEATURE:
<223> OTHER INFORMATION: Synthetic

<400> SEQUENCE: 317

Arg Arg Lys Gly Lys Glu Lys
1               5

<210> SEQ ID NO 318
<211> LENGTH: 8
<212> TYPE: PRT
<213> ORGANISM: Artificial Sequence
<220> FEATURE:
<223> OTHER INFORMATION: Synthetic

<400> SEQUENCE: 318

Arg Gly Arg Arg Arg Arg Gln Arg
1               5

<210> SEQ ID NO 319
<211> LENGTH: 7
<212> TYPE: PRT
<213> ORGANISM: Artificial Sequence
<220> FEATURE:
<223> OTHER INFORMATION: Synthetic

<400> SEQUENCE: 319

Arg Ile Arg Lys Lys Leu Arg
1               5

<210> SEQ ID NO 320
<211> LENGTH: 17
<212> TYPE: PRT
<213> ORGANISM: Artificial Sequence
<220> FEATURE:
<223> OTHER INFORMATION: Synthetic

<400> SEQUENCE: 320
```

```
Arg Lys Cys Leu Gln Ala Gly Met Asn Leu Glu Ala Arg Lys Thr Lys
1               5                   10                  15

Lys

<210> SEQ ID NO 321
<211> LENGTH: 17
<212> TYPE: PRT
<213> ORGANISM: Artificial Sequence
<220> FEATURE:
<223> OTHER INFORMATION: Synthetic

<400> SEQUENCE: 321

Arg Lys Glu Trp Leu Thr Asn Phe Met Glu Asp Arg Arg Gln Arg Lys
1               5                   10                  15

Leu

<210> SEQ ID NO 322
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(14)
<223> OTHER INFORMATION: Xaa can be any naturally occurring amino acid
<220> FEATURE:
<221> NAME/KEY: misc_feature
<222> LOCATION: (7)..(14)
<223> OTHER INFORMATION: may not be present

<400> SEQUENCE: 322

Arg Lys Lys Arg Lys Xaa Xaa Xaa Xaa Xaa Xaa Xaa Xaa Xaa Lys Ala
1               5                   10                  15

Lys Lys Ser Lys
            20

<210> SEQ ID NO 323
<211> LENGTH: 9
<212> TYPE: PRT
<213> ORGANISM: Artificial Sequence
<220> FEATURE:
<223> OTHER INFORMATION: Synthetic

<400> SEQUENCE: 323

Arg Lys Lys Arg Arg Gln Arg Arg Arg
1               5

<210> SEQ ID NO 324
<211> LENGTH: 19
<212> TYPE: PRT
<213> ORGANISM: Artificial Sequence
<220> FEATURE:
<223> OTHER INFORMATION: Synthetic

<400> SEQUENCE: 324

Arg Lys Arg Ala Phe His Gly Asp Asp Pro Phe Gly Glu Gly Pro Pro
1               5                   10                  15

Asp Lys Lys

<210> SEQ ID NO 325
<211> LENGTH: 32
<212> TYPE: PRT
<213> ORGANISM: Artificial Sequence
<220> FEATURE:
<223> OTHER INFORMATION: Synthetic
```

-continued

<400> SEQUENCE: 325

Arg Lys Arg Ile Arg Glu Asp Arg Lys Ala Thr Thr Ala Gln Lys Val
1               5                   10                  15

Gln Gln Met Lys Gln Arg Leu Asn Glu Asn Glu Arg Lys Arg Lys Arg
            20                  25                  30

<210> SEQ ID NO 326
<211> LENGTH: 5
<212> TYPE: PRT
<213> ORGANISM: Artificial Sequence
<220> FEATURE:
<223> OTHER INFORMATION: Synthetic

<400> SEQUENCE: 326

Arg Lys Arg Lys Lys
1               5

<210> SEQ ID NO 327
<211> LENGTH: 17
<212> TYPE: PRT
<213> ORGANISM: Artificial Sequence
<220> FEATURE:
<223> OTHER INFORMATION: Synthetic

<400> SEQUENCE: 327

Arg Lys Arg Lys Lys Met Pro Ala Ser Gln Arg Ser Lys Arg Arg Lys
1               5                   10                  15

Thr

<210> SEQ ID NO 328
<211> LENGTH: 5
<212> TYPE: PRT
<213> ORGANISM: Artificial Sequence
<220> FEATURE:
<223> OTHER INFORMATION: Synthetic

<400> SEQUENCE: 328

Arg Lys Arg Arg Arg
1               5

<210> SEQ ID NO 329
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(28)
<223> OTHER INFORMATION: Xaa can be any naturally occurring amino acid
<220> FEATURE:
<221> NAME/KEY: misc_feature
<222> LOCATION: (11)..(28)
<223> OTHER INFORMATION: may not be present

<400> SEQUENCE: 329

Arg Leu Lys Lys Leu Lys Cys Ser Lys Xaa Xaa Xaa Xaa Xaa Xaa Xaa
1               5                   10                  15

Xaa Xaa Xaa Xaa Xaa Xaa Xaa Xaa Xaa Xaa Xaa Xaa Lys Thr Lys Arg
            20                  25                  30

<210> SEQ ID NO 330
<211> LENGTH: 5
<212> TYPE: PRT
<213> ORGANISM: Artificial Sequence -continued

```
<220> FEATURE:
<223> OTHER INFORMATION: Synthetic

<400> SEQUENCE: 330

Arg Pro Arg Arg Lys
1               5

<210> SEQ ID NO 331
<211> LENGTH: 12
<212> TYPE: PRT
<213> ORGANISM: Artificial Sequence
<220> FEATURE:
<223> OTHER INFORMATION: Synthetic

<400> SEQUENCE: 331

Arg Gln Ala Arg Arg Asn Arg Arg Arg Trp Arg
1               5               10

<210> SEQ ID NO 332
<211> LENGTH: 17
<212> TYPE: PRT
<213> ORGANISM: Artificial Sequence
<220> FEATURE:
<223> OTHER INFORMATION: Synthetic

<400> SEQUENCE: 332

Arg Arg Glu Arg Asn Lys Met Ala Ala Ala Lys Cys Arg Asn Arg Arg
1               5               10              15

Arg

<210> SEQ ID NO 333
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(8)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: may not be present

<400> SEQUENCE: 333

Arg Arg Glu Arg Xaa Xaa Xaa Xaa Arg Pro Arg Lys Ile Pro Arg
1               5               10              15

<210> SEQ ID NO 334
<211> LENGTH: 38
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(32)
<223> OTHER INFORMATION: Xaa can be any naturally occurring amino acid
<220> FEATURE:
<221> NAME/KEY: misc_feature
<222> LOCATION: (29)..(31)
<223> OTHER INFORMATION: may not be present
<220> FEATURE:
<221> NAME/KEY: misc_feature
<222> LOCATION: (32)..(35)
<223> OTHER INFORMATION: may not be present
<220> FEATURE:
<221> NAME/KEY: misc_feature
<222> LOCATION: (37)..(37)
```

<223> OTHER INFORMATION: Xaa can be any naturally occurring amino acid

<400> SEQUENCE: 334

Lys Arg Lys Arg Lys Arg Lys Arg Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Lys Lys Lys Lys Xaa Lys
        35

<210> SEQ ID NO 335
<211> LENGTH: 8
<212> TYPE: PRT
<213> ORGANISM: Artificial Sequence
<220> FEATURE:
<223> OTHER INFORMATION: Synthetic

<400> SEQUENCE: 335

Lys Lys Lys Arg Glu Arg Leu Asp
1               5

<210> SEQ ID NO 336
<211> LENGTH: 6
<212> TYPE: PRT
<213> ORGANISM: Artificial Sequence
<220> FEATURE:
<223> OTHER INFORMATION: Synthetic

<400> SEQUENCE: 336

Lys Arg Lys Arg Arg Pro
1               5

<210> SEQ ID NO 337
<211> LENGTH: 10
<212> TYPE: PRT
<213> ORGANISM: Artificial Sequence
<220> FEATURE:
<223> OTHER INFORMATION: Synthetic

<400> SEQUENCE: 337

Ile Lys Tyr Phe Lys Lys Phe Pro Lys Asp
1               5                   10

<210> SEQ ID NO 338
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(15)
<223> OTHER INFORMATION: Xaa can be any naturally occurring amino acid

<400> SEQUENCE: 338

His Arg Lys Tyr Glu Ala Pro Arg His Xaa Xaa Xaa Xaa Xaa Xaa Pro
1               5                   10                  15

Arg Lys Arg

<210> SEQ ID NO 339
<211> LENGTH: 20
<212> TYPE: PRT
<213> ORGANISM: Artificial Sequence
<220> FEATURE:
<223> OTHER INFORMATION: Synthetic
<220> FEATURE:

```
<221> NAME/KEY: misc_feature
<222> LOCATION: (4)..(14)
<223> OTHER INFORMATION: Xaa can be any naturally occurring amino acid

<400> SEQUENCE: 339

Lys Arg Lys Xaa Xaa Xaa Xaa Xaa Xaa Xaa Xaa Xaa Xaa Xaa Lys Lys
1               5                   10                  15

Lys Ser Lys Lys
            20

<210> SEQ ID NO 340
<211> LENGTH: 17
<212> TYPE: PRT
<213> ORGANISM: Artificial Sequence
<220> FEATURE:
<223> OTHER INFORMATION: Synthetic

<400> SEQUENCE: 340

His Arg Ile Glu Glu Lys Arg Lys Arg Thr Tyr Glu Thr Phe Lys Ser
1               5                   10                  15

Ile

<210> SEQ ID NO 341
<211> LENGTH: 34
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(25)
<223> OTHER INFORMATION: Xaa can be any naturally occurring amino acid

<400> SEQUENCE: 341

Lys Arg Lys Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Lys Glu Leu Gln Lys Gln Ile
            20                  25                  30

Thr Lys

<210> SEQ ID NO 342
<211> LENGTH: 17
<212> TYPE: PRT
<213> ORGANISM: Artificial Sequence
<220> FEATURE:
<223> OTHER INFORMATION: Synthetic

<400> SEQUENCE: 342

Lys Arg Met Arg Asn Arg Ile Ala Ala Ser Lys Cys Arg Lys Arg Lys
1               5                   10                  15

Leu

<210> SEQ ID NO 343
<211> LENGTH: 16
<212> TYPE: PRT
<213> ORGANISM: Artificial Sequence
<220> FEATURE:
<223> OTHER INFORMATION: Synthetic

<400> SEQUENCE: 343

Lys Arg Pro Ala Ala Thr Lys Lys Ala Gly Gln Ala Lys Lys Lys Lys
1               5                   10                  15

<210> SEQ ID NO 344
```

```
<211> LENGTH: 12
<212> TYPE: PRT
<213> ORGANISM: Artificial Sequence
<220> FEATURE:
<223> OTHER INFORMATION: Synthetic

<400> SEQUENCE: 344

Glu Glu Asp Gly Pro Gln Lys Lys Lys Arg Arg Leu
1               5                   10

<210> SEQ ID NO 345
<211> LENGTH: 24
<212> TYPE: PRT
<213> ORGANISM: Artificial Sequence
<220> FEATURE:
<223> OTHER INFORMATION: Synthetic

<400> SEQUENCE: 345

Lys Arg Pro Ala Cys Thr Leu Lys Pro Glu Cys Val Gln Gln Leu Leu
1               5                   10                  15

Val Cys Ser Gln Glu Ala Lys Lys
            20

<210> SEQ ID NO 346
<211> LENGTH: 17
<212> TYPE: PRT
<213> ORGANISM: Artificial Sequence
<220> FEATURE:
<223> OTHER INFORMATION: Synthetic

<400> SEQUENCE: 346

Lys Arg Pro Ala Glu Asp Met Glu Glu Glu Gln Ala Phe Lys Arg Ser
1               5                   10                  15

Arg

<210> SEQ ID NO 347
<211> LENGTH: 17
<212> TYPE: PRT
<213> ORGANISM: Artificial Sequence
<220> FEATURE:
<223> OTHER INFORMATION: Synthetic

<400> SEQUENCE: 347

Lys Arg Pro Met Asn Ala Phe Ile Val Trp Ser Arg Asp Gln Arg Arg
1               5                   10                  15

Lys

<210> SEQ ID NO 348
<211> LENGTH: 17
<212> TYPE: PRT
<213> ORGANISM: Artificial Sequence
<220> FEATURE:
<223> OTHER INFORMATION: Synthetic

<400> SEQUENCE: 348

Lys Arg Pro Met Asn Ala Phe Met Val Trp Ala Gln Ala Ala Arg Arg
1               5                   10                  15

Lys

<210> SEQ ID NO 349
<211> LENGTH: 18
<212> TYPE: PRT
<213> ORGANISM: Artificial Sequence
<220> FEATURE:
<223> OTHER INFORMATION: Synthetic
```

<400> SEQUENCE: 349

Lys Arg Lys Lys Glu Met Ala Asn Lys Ser Ala Pro Glu Ala Lys Lys
1               5                   10                  15

Lys Lys

<210> SEQ ID NO 350
<211> LENGTH: 11
<212> TYPE: PRT
<213> ORGANISM: Artificial Sequence
<220> FEATURE:
<223> OTHER INFORMATION: Synthetic

<400> SEQUENCE: 350

Ala Pro Lys Arg Lys Ser Gly Val Ser Lys Cys
1               5                   10

<210> SEQ ID NO 351
<211> LENGTH: 18
<212> TYPE: PRT
<213> ORGANISM: Artificial Sequence
<220> FEATURE:
<223> OTHER INFORMATION: Synthetic

<400> SEQUENCE: 351

Lys Arg Ala Ala Glu Asp Asp Glu Asp Asp Val Asp Thr Lys Lys
1               5                   10                  15

Gln Lys

<210> SEQ ID NO 352
<211> LENGTH: 9
<212> TYPE: PRT
<213> ORGANISM: Artificial Sequence
<220> FEATURE:
<223> OTHER INFORMATION: Synthetic

<400> SEQUENCE: 352

Lys Lys Lys Arg Arg Ser Arg Glu Lys
1               5

<210> SEQ ID NO 353
<211> LENGTH: 14
<212> TYPE: PRT
<213> ORGANISM: Artificial Sequence
<220> FEATURE:
<223> OTHER INFORMATION: Synthetic

<400> SEQUENCE: 353

Lys Lys Lys Lys Lys Glu Glu Glu Gly Glu Gly Lys Lys Lys
1               5                   10

<210> SEQ ID NO 354
<211> LENGTH: 7
<212> TYPE: PRT
<213> ORGANISM: Artificial Sequence
<220> FEATURE:
<223> OTHER INFORMATION: Synthetic

<400> SEQUENCE: 354

Lys Lys Lys Tyr Lys Leu Lys
1               5

<210> SEQ ID NO 355
<211> LENGTH: 17
<212> TYPE: PRT

-continued

<213> ORGANISM: Artificial Sequence
<220> FEATURE:
<223> OTHER INFORMATION: Synthetic

<400> SEQUENCE: 355

Lys Lys Gln Thr Thr Leu Ala Phe Lys Pro Ile Lys Lys Gly Lys Lys
1               5                   10                  15

Arg

<210> SEQ ID NO 356
<211> LENGTH: 13
<212> TYPE: PRT
<213> ORGANISM: Artificial Sequence
<220> FEATURE:
<223> OTHER INFORMATION: Synthetic

<400> SEQUENCE: 356

Cys Lys Arg Lys Thr Thr Asn Ala Asp Arg Arg Lys Ala
1               5                   10

<210> SEQ ID NO 357
<211> LENGTH: 9
<212> TYPE: PRT
<213> ORGANISM: Artificial Sequence
<220> FEATURE:
<223> OTHER INFORMATION: Synthetic

<400> SEQUENCE: 357

Lys Lys Glu Lys Lys Lys Ser Lys Lys
1               5

<210> SEQ ID NO 358
<211> LENGTH: 7
<212> TYPE: PRT
<213> ORGANISM: Artificial Sequence
<220> FEATURE:
<223> OTHER INFORMATION: Synthetic

<400> SEQUENCE: 358

Lys His Arg Lys His Pro Gly
1               5

<210> SEQ ID NO 359
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(11)
<223> OTHER INFORMATION: Xaa can be any naturally occurring amino acid

<400> SEQUENCE: 359

Lys Arg Xaa Xaa Xaa Xaa Xaa Xaa Xaa Xaa Xaa Lys Thr Lys Lys
1               5                   10                  15

<210> SEQ ID NO 360
<211> LENGTH: 17
<212> TYPE: PRT
<213> ORGANISM: Artificial Sequence
<220> FEATURE:
<223> OTHER INFORMATION: Synthetic

<400> SEQUENCE: 360

Cys Tyr Gly Ser Lys Asn Thr Gly Ala Lys Lys Arg Lys Ile Asp Asp
1               5                   10                  15

Ala

<210> SEQ ID NO 361
<211> LENGTH: 17
<212> TYPE: PRT
<213> ORGANISM: Artificial Sequence
<220> FEATURE:
<223> OTHER INFORMATION: Synthetic

<400> SEQUENCE: 361

Lys Lys Ser Lys Lys Gly Arg Gln Glu Ala Leu Glu Arg Leu Lys Lys
1               5                   10                  15

Ala

<210> SEQ ID NO 362
<211> LENGTH: 20
<212> TYPE: PRT
<213> ORGANISM: Artificial Sequence
<220> FEATURE:
<223> OTHER INFORMATION: Synthetic

<400> SEQUENCE: 362

Lys Asp Cys Val Ile Asn Lys His His Arg Asn Arg Cys Gln Tyr Cys
1               5                   10                  15

Arg Leu Gln Arg
            20

<210> SEQ ID NO 363
<211> LENGTH: 6
<212> TYPE: PRT
<213> ORGANISM: Artificial Sequence
<220> FEATURE:
<223> OTHER INFORMATION: Synthetic

<400> SEQUENCE: 363

Lys Ala Lys Arg Gln Arg
1               5

<210> SEQ ID NO 364
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(17)
<223> OTHER INFORMATION: Xaa can be any naturally occurring amino acid

<400> SEQUENCE: 364

Lys Lys Xaa Xaa Xaa Xaa Xaa Xaa Xaa Xaa Xaa Xaa Xaa Xaa Xaa Xaa
1               5                   10                  15

Xaa Lys Lys Arg Lys
            20

<210> SEQ ID NO 365
<211> LENGTH: 11
<212> TYPE: PRT
<213> ORGANISM: Artificial Sequence
<220> FEATURE:
<223> OTHER INFORMATION: Synthetic

<400> SEQUENCE: 365

Glu Tyr Leu Ser Arg Lys Gly Lys Leu Glu Leu
1               5                   10

-continued

```
<210> SEQ ID NO 366
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(24)
<223> OTHER INFORMATION: Xaa can be any naturally occurring amino acid

<400> SEQUENCE: 366

Lys Arg Gln Arg Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Lys Lys Ser Lys Lys
            20                  25

<210> SEQ ID NO 367
<211> LENGTH: 17
<212> TYPE: PRT
<213> ORGANISM: Artificial Sequence
<220> FEATURE:
<223> OTHER INFORMATION: Synthetic

<400> SEQUENCE: 367

Lys Arg Ser Ala Glu Gly Gly Asn Pro Pro Lys Pro Leu Lys Lys Leu
1               5                   10                  15

Arg

<210> SEQ ID NO 368
<211> LENGTH: 8
<212> TYPE: PRT
<213> ORGANISM: Artificial Sequence
<220> FEATURE:
<223> OTHER INFORMATION: Synthetic

<400> SEQUENCE: 368

Ala Pro Thr Lys Arg Lys Gly Ser
1               5

<210> SEQ ID NO 369
<211> LENGTH: 9
<212> TYPE: PRT
<213> ORGANISM: Artificial Sequence
<220> FEATURE:
<223> OTHER INFORMATION: Synthetic

<400> SEQUENCE: 369

Lys Lys Lys Lys Arg Lys Arg Glu Lys
1               5

<210> SEQ ID NO 370
<211> LENGTH: 5
<212> TYPE: PRT
<213> ORGANISM: Artificial Sequence
<220> FEATURE:
<223> OTHER INFORMATION: Synthetic

<400> SEQUENCE: 370

Lys Arg Pro Arg Pro
1               5

<210> SEQ ID NO 371
<211> LENGTH: 8
<212> TYPE: PRT
```

```
<213> ORGANISM: Artificial Sequence
<220> FEATURE:
<223> OTHER INFORMATION: Synthetic

<400> SEQUENCE: 371

Gly Arg Lys Arg Lys Lys Arg Thr
1               5

<210> SEQ ID NO 372
<211> LENGTH: 40
<212> TYPE: PRT
<213> ORGANISM: Artificial Sequence
<220> FEATURE:
<223> OTHER INFORMATION: Synthetic

<400> SEQUENCE: 372

His Lys Lys Lys Lys Ile Arg Thr Ser Pro Thr Phe Thr Thr Pro Lys
1               5                   10                  15

Thr Leu Arg Leu Arg Arg Gln Pro Lys Tyr Pro Arg Lys Ser Ala Pro
            20                  25                  30

Arg Arg Asn Lys Leu Asp His Tyr
        35                  40

<210> SEQ ID NO 373
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(6)
<223> OTHER INFORMATION: Xaa can be any naturally occurring amino acid
<220> FEATURE:
<221> NAME/KEY: misc_feature
<222> LOCATION: (11)..(16)
<223> OTHER INFORMATION: Xaa can be any naturally occurring amino acid

<400> SEQUENCE: 373

Gly Gly Gly Xaa Xaa Xaa Lys Asn Arg Arg Xaa Xaa Xaa Xaa Xaa Xaa
1               5                   10                  15

Arg Gly Gly Arg Asn
            20

<210> SEQ ID NO 374
<211> LENGTH: 7
<212> TYPE: PRT
<213> ORGANISM: Artificial Sequence
<220> FEATURE:
<223> OTHER INFORMATION: Synthetic

<400> SEQUENCE: 374

Gly Lys Lys Arg Ser Lys Ala
1               5

<210> SEQ ID NO 375
<211> LENGTH: 9
<212> TYPE: PRT
<213> ORGANISM: Artificial Sequence
<220> FEATURE:
<223> OTHER INFORMATION: Synthetic

<400> SEQUENCE: 375

Gly Lys Lys Lys Tyr Lys Leu Lys His
1               5
```

```
<210> SEQ ID NO 376
<211> LENGTH: 16
<212> TYPE: PRT
<213> ORGANISM: Artificial Sequence
<220> FEATURE:
<223> OTHER INFORMATION: Synthetic

<400> SEQUENCE: 376

Asp Glu Lys Asn Ile Phe Arg Arg Asp Glu Lys Ser Thr Met Asn Gln
1               5                   10                  15

<210> SEQ ID NO 377
<211> LENGTH: 12
<212> TYPE: PRT
<213> ORGANISM: Artificial Sequence
<220> FEATURE:
<223> OTHER INFORMATION: Synthetic

<400> SEQUENCE: 377

Asp Glu Lys Arg Met Gln Asn Arg Met Gln Asn Arg
1               5                   10

<210> SEQ ID NO 378
<211> LENGTH: 11
<212> TYPE: PRT
<213> ORGANISM: Artificial Sequence
<220> FEATURE:
<223> OTHER INFORMATION: Synthetic

<400> SEQUENCE: 378

Asp Glu Lys Lys Pro Leu Gly Leu Lys Gly Leu
1               5                   10

<210> SEQ ID NO 379
<211> LENGTH: 26
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(9)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: may not be present
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (17)..(19)
<223> OTHER INFORMATION: Xaa can be any naturally occurring amino acid
<220> FEATURE:
<221> NAME/KEY: misc_feature
<222> LOCATION: (18)..(19)
<223> OTHER INFORMATION: may not be present

<400> SEQUENCE: 379

Arg Arg Lys Xaa Xaa Xaa Xaa Xaa Xaa Arg Lys Arg Lys Xaa Arg Lys
1               5                   10                  15

Xaa Xaa Xaa Arg Lys Arg Lys Pro Leu Gln
            20                  25

<210> SEQ ID NO 380
<211> LENGTH: 17
<212> TYPE: PRT
<213> ORGANISM: Artificial Sequence
```

-continued

```
<220> FEATURE:
<223> OTHER INFORMATION: Synthetic
<220> FEATURE:
<221> NAME/KEY: misc_feature
<222> LOCATION: (6)..(9)
<223> OTHER INFORMATION: may not be present

<400> SEQUENCE: 380

Arg Arg Lys Arg Lys Arg Lys Arg Lys Pro Leu Arg Lys Met Asn Gln
1               5                   10                  15

Arg

<210> SEQ ID NO 381
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(9)
<223> OTHER INFORMATION: may not be present
<220> FEATURE:
<221> NAME/KEY: misc_feature
<222> LOCATION: (10)..(28)
<223> OTHER INFORMATION: Xaa can be any naturally occurring amino acid
<220> FEATURE:
<221> NAME/KEY: misc_feature
<222> LOCATION: (25)..(28)
<223> OTHER INFORMATION: may not be present
<220> FEATURE:
<221> NAME/KEY: misc_feature
<222> LOCATION: (31)..(36)
<223> OTHER INFORMATION: may not be present

<400> SEQUENCE: 381

Arg Arg Lys Arg Lys Arg Lys Arg Lys Xaa Xaa Xaa Xaa Xaa Xaa Xaa
1               5                   10                  15

Xaa Xaa Xaa Xaa Xaa Xaa Xaa Xaa Xaa Xaa Xaa Xaa Arg Lys Arg Lys
            20                  25                  30

Arg Lys Arg Lys Gln Leu Met Lys
        35                  40

<210> SEQ ID NO 382
<211> LENGTH: 10
<212> TYPE: PRT
<213> ORGANISM: Artificial Sequence
<220> FEATURE:
<223> OTHER INFORMATION: Synthetic

<400> SEQUENCE: 382

Arg Arg Lys Arg Lys Arg Lys Asp Glu Lys
1               5                   10

<210> SEQ ID NO 383
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa can be any naturally occurring amino acid

<400> SEQUENCE: 383

Asp Glu Lys Xaa Arg Arg Lys Met Asn Gln
1               5                   10
```

-continued

```
<210> SEQ ID NO 384
<211> LENGTH: 11
<212> TYPE: PRT
<213> ORGANISM: Artificial Sequence
<220> FEATURE:
<223> OTHER INFORMATION: Synthetic

<400> SEQUENCE: 384

Asp Glu Arg Lys Arg Arg Asp Glu Pro Leu Gln
1               5                   10

<210> SEQ ID NO 385
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa can be any naturally occurring amino acid

<400> SEQUENCE: 385

Asp Glu Arg Xaa Lys Lys Lys Lys
1               5

<210> SEQ ID NO 386
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(10)
<223> OTHER INFORMATION: may not be present

<400> SEQUENCE: 386

Asp Glu Arg Lys Arg Lys Arg Lys Arg Lys Gly Ala Arg Pro Leu Gly
1               5                   10                  15

Ala

<210> SEQ ID NO 387
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid

<400> SEQUENCE: 387

Arg Pro Leu Xaa Xaa Lys Arg Lys Arg Xaa Xaa Lys Arg Val
1               5                   10

<210> SEQ ID NO 388
<211> LENGTH: 11
<212> TYPE: PRT
<213> ORGANISM: Artificial Sequence
<220> FEATURE:
<223> OTHER INFORMATION: Synthetic

<400> SEQUENCE: 388
```

-continued

```
Asp Glu Lys Arg Arg Arg Lys Arg Phe Tyr Trp
1               5               10

<210> SEQ ID NO 389
<211> LENGTH: 10
<212> TYPE: PRT
<213> ORGANISM: Artificial Sequence
<220> FEATURE:
<223> OTHER INFORMATION: Synthetic

<400> SEQUENCE: 389

Arg Gln Met Pro Leu Arg Arg Asp Glu Arg
1               5               10

<210> SEQ ID NO 390
<211> LENGTH: 8
<212> TYPE: PRT
<213> ORGANISM: Artificial Sequence
<220> FEATURE:
<223> OTHER INFORMATION: Synthetic

<400> SEQUENCE: 390

Arg Arg Lys Lys Arg Lys Lys Arg
1               5

<210> SEQ ID NO 391
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 391

Arg Arg Lys Xaa Lys Arg Xaa Arg Lys Arg Lys Asp Glu
1               5               10

<210> SEQ ID NO 392
<211> LENGTH: 16
<212> TYPE: PRT
<213> ORGANISM: Artificial Sequence
<220> FEATURE:
<223> OTHER INFORMATION: Synthetic

<400> SEQUENCE: 392

Arg Ser Thr Cys Met Asn Gln Arg Ser Thr Cys Met Asn Gln Lys Arg
1               5               10                  15

<210> SEQ ID NO 393
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(6)
<223> OTHER INFORMATION: may not be present
<220> FEATURE:
<221> NAME/KEY: misc_feature
<222> LOCATION: (7)..(7)
<223> OTHER INFORMATION: Xaa can be any naturally occurring amino acid
```

-continued

```
<400> SEQUENCE: 393

Asp Glu Arg Arg Arg Arg Xaa Arg Lys Pro Leu
1               5                   10

<210> SEQ ID NO 394
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid

<400> SEQUENCE: 394

Arg Xaa Lys Lys Lys Lys Asp Glu
1               5

<210> SEQ ID NO 395
<211> LENGTH: 6
<212> TYPE: PRT
<213> ORGANISM: Artificial Sequence
<220> FEATURE:
<223> OTHER INFORMATION: Synthetic

<400> SEQUENCE: 395

Arg Arg Pro Arg Arg Arg
1               5

<210> SEQ ID NO 396
<211> LENGTH: 7
<212> TYPE: PRT
<213> ORGANISM: Artificial Sequence
<220> FEATURE:
<223> OTHER INFORMATION: Synthetic

<400> SEQUENCE: 396

Thr Pro Leu Val Lys Arg Cys
1               5

<210> SEQ ID NO 397
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: may not be present
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: may not be present

<400> SEQUENCE: 397

Arg Arg Arg Xaa Lys Lys Lys Arg Ser Thr
1               5                   10

<210> SEQ ID NO 398
<211> LENGTH: 13
<212> TYPE: PRT
<213> ORGANISM: Artificial Sequence
```

-continued

```
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: may not be present
<220> FEATURE:
<221> NAME/KEY: misc_feature
<222> LOCATION: (11)..(12)
<223> OTHER INFORMATION: may not be present

<400> SEQUENCE: 398

Asp Lys Arg Xaa Gln Leu Arg Lys Arg Lys Arg Lys Arg
1               5                   10

<210> SEQ ID NO 399
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: may not be present
<220> FEATURE:
<221> NAME/KEY: misc_feature
<222> LOCATION: (7)..(7)
<223> OTHER INFORMATION: may not be present

<400> SEQUENCE: 399

Arg Arg Arg Lys Lys Lys Lys Pro Leu Arg Lys Glu
1               5                   10

<210> SEQ ID NO 400
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: may not be present

<400> SEQUENCE: 400

Arg Xaa Xaa Xaa Arg Arg Arg Arg Arg Arg
1               5                   10

<210> SEQ ID NO 401
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: may not be present
<220> FEATURE:
<221> NAME/KEY: misc_feature
```

```
<222> LOCATION: (6)..(10)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: may not be present

<400> SEQUENCE: 401

Arg Xaa Xaa Xaa His Xaa Xaa Xaa Xaa Xaa Arg Arg Arg Arg
1               5                   10

<210> SEQ ID NO 402
<211> LENGTH: 9
<212> TYPE: PRT
<213> ORGANISM: Artificial Sequence
<220> FEATURE:
<223> OTHER INFORMATION: Synthetic

<400> SEQUENCE: 402

Asp Arg Met Asn Lys Lys Lys Lys Glu
1               5

<210> SEQ ID NO 403
<211> LENGTH: 8
<212> TYPE: PRT
<213> ORGANISM: Artificial Sequence
<220> FEATURE:
<223> OTHER INFORMATION: Synthetic

<400> SEQUENCE: 403

Trp Lys Gln Lys Arg Arg Lys Phe
1               5

<210> SEQ ID NO 404
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid

<400> SEQUENCE: 404

Arg Xaa Lys Arg Lys Arg Lys Arg Xaa Xaa Arg Lys Lys Arg
1               5                   10

<210> SEQ ID NO 405
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid

<400> SEQUENCE: 405

Arg Xaa Lys Arg Lys Arg Lys Pro Leu Gln Met Arg
1               5                   10

<210> SEQ ID NO 406
<211> LENGTH: 10
```

```
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 406

Arg Xaa Arg Arg Gln Leu Xaa Ser Thr Arg
1               5                   10

<210> SEQ ID NO 407
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 407

Arg Xaa Arg Xaa Arg Xaa Arg Xaa Arg Xaa Arg Xaa Lys
1               5                   10

<210> SEQ ID NO 408
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
```

```
<221> NAME/KEY: misc_feature
<222> LOCATION: (10)..(10)
<223> OTHER INFORMATION: Xaa can be any naturally occurring amino acid

<400> SEQUENCE: 408

Arg Xaa Arg Xaa Arg Xaa Arg Xaa Arg Xaa Arg
1               5                   10

<210> SEQ ID NO 409
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: may not be present
<220> FEATURE:
<221> NAME/KEY: misc_feature
<222> LOCATION: (9)..(9)
<223> OTHER INFORMATION: Xaa can be any naturally occurring amino acid

<400> SEQUENCE: 409

Arg Xaa Arg Ser Arg Ser Xaa Arg Xaa Arg
1               5                   10

<210> SEQ ID NO 410
<211> LENGTH: 8
<212> TYPE: PRT
<213> ORGANISM: Artificial Sequence
<220> FEATURE:
<223> OTHER INFORMATION: Synthetic

<400> SEQUENCE: 410

Asp Lys Gln Leu Lys Lys Gln Leu
1               5

<210> SEQ ID NO 411
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(10)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: may not be present

<400> SEQUENCE: 411

Arg Xaa Arg Arg Xaa Xaa Xaa Xaa Xaa Xaa Arg Lys Lys
1               5                   10

<210> SEQ ID NO 412
<211> LENGTH: 8
```

```
<212> TYPE: PRT
<213> ORGANISM: Artificial Sequence
<220> FEATURE:
<223> OTHER INFORMATION: Synthetic

<400> SEQUENCE: 412

Arg Arg Gln Met Asn Arg Arg Arg
1               5

<210> SEQ ID NO 413
<211> LENGTH: 12
<212> TYPE: PRT
<213> ORGANISM: Artificial Sequence
<220> FEATURE:
<223> OTHER INFORMATION: Synthetic

<400> SEQUENCE: 413

Thr Ser Arg Lys Lys Lys Val Leu Ile Arg Pro Leu
1               5                   10

<210> SEQ ID NO 414
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 414

Gln Leu Xaa Lys Arg Xaa Lys Xaa Lys Lys
1               5                   10

<210> SEQ ID NO 415
<211> LENGTH: 28
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(6)
<223> OTHER INFORMATION: may not be present
<220> FEATURE:
<221> NAME/KEY: misc_feature
<222> LOCATION: (7)..(15)
<223> OTHER INFORMATION: Xaa can be any naturally occurring amino acid
<220> FEATURE:
<221> NAME/KEY: misc_feature
<222> LOCATION: (15)..(18)
<223> OTHER INFORMATION: may not be present

<400> SEQUENCE: 415

Gln Leu Lys Lys Lys Lys Xaa Xaa Xaa Xaa Xaa Xaa Xaa Xaa Xaa Xaa
1               5                   10                  15

Xaa Xaa Arg Lys Gln Leu Arg Lys Gln Leu Lys Arg
            20                  25

<210> SEQ ID NO 416
<211> LENGTH: 18
```

```
<212> TYPE: PRT
<213> ORGANISM: Artificial Sequence
<220> FEATURE:
<223> OTHER INFORMATION: Synthetic

<400> SEQUENCE: 416

Pro Val Leu Ile Arg Lys Arg Lys Arg Lys Arg Lys Arg Lys Gln Met
1               5                   10                  15

Asn Lys

<210> SEQ ID NO 417
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(4)
<223> OTHER INFORMATION: Xaa can be any naturally occurring amino acid

<400> SEQUENCE: 417

Pro Leu Xaa Xaa Lys Arg Ile Val Lys Pro Leu Asp Glu
1               5                   10

<210> SEQ ID NO 418
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(8)
<223> OTHER INFORMATION: may not be present
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 418

Pro Leu Arg Lys Arg Lys Arg Lys Lys Pro Leu Ile Arg Lys Xaa Pro
1               5                   10                  15

Leu Ile Xaa Lys
            20

<210> SEQ ID NO 419
<211> LENGTH: 18
<212> TYPE: PRT
<213> ORGANISM: Artificial Sequence
<220> FEATURE:
<223> OTHER INFORMATION: Synthetic

<400> SEQUENCE: 419

Pro Leu Arg Lys Arg Lys Lys Arg Gly Ala Pro Leu Arg Lys Ser Thr
1               5                   10                  15

Gln Met

<210> SEQ ID NO 420
<211> LENGTH: 15
<212> TYPE: PRT
<213> ORGANISM: Artificial Sequence
<220> FEATURE:
<223> OTHER INFORMATION: Synthetic
```

<400> SEQUENCE: 420

Pro Leu Arg Lys Arg Lys Asp Glu Pro Arg Arg Lys Phe Tyr Trp
1               5                   10                  15

<210> SEQ ID NO 421
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be any naturally occurring amino acid

<400> SEQUENCE: 421

Pro Leu Pro Leu Xaa Lys Arg Arg Asp Glu Lys Arg Gln Ser Thr
1               5                   10                  15

<210> SEQ ID NO 422
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (13)..(16)
<223> OTHER INFORMATION: may not be present

<400> SEQUENCE: 422

Pro Leu Lys Arg Lys Arg Lys Arg Lys Arg Lys Arg Lys Arg Lys Arg
1               5                   10                  15

Pro Leu

<210> SEQ ID NO 423
<211> LENGTH: 9
<212> TYPE: PRT
<213> ORGANISM: Artificial Sequence
<220> FEATURE:
<223> OTHER INFORMATION: Synthetic

<400> SEQUENCE: 423

Pro Leu Arg Asp Glu Lys Asp Glu Arg
1               5

<210> SEQ ID NO 424
<211> LENGTH: 8
<212> TYPE: PRT
<213> ORGANISM: Artificial Sequence
<220> FEATURE:
<223> OTHER INFORMATION: Synthetic

<400> SEQUENCE: 424

Pro Leu Arg Lys Arg Lys Pro Leu
1               5

<210> SEQ ID NO 425
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(8)
<223> OTHER INFORMATION: Xaa can be any naturally occurring amino acid

```
<220> FEATURE:
<221> NAME/KEY: misc_feature
<222> LOCATION: (13)..(14)
<223> OTHER INFORMATION: may not be present
<220> FEATURE:
<221> NAME/KEY: misc_feature
<222> LOCATION: (15)..(15)
<223> OTHER INFORMATION: Xaa can be any naturally occurring amino acid

<400> SEQUENCE: 425

Arg Lys His Arg Lys Xaa Xaa Xaa Arg Lys Arg Lys Arg Lys Xaa Arg
1               5                   10                  15

<210> SEQ ID NO 426
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(6)
<223> OTHER INFORMATION: may not be present
<220> FEATURE:
<221> NAME/KEY: misc_feature
<222> LOCATION: (7)..(7)
<223> OTHER INFORMATION: Xaa can be any naturally occurring amino acid

<400> SEQUENCE: 426

Arg Lys Lys Lys Lys Lys Xaa Arg Lys Gln Leu Arg Lys Pro Leu
1               5                   10                  15

<210> SEQ ID NO 427
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 427

Arg Lys Arg Met Ser Lys Xaa Lys Lys Arg
1               5                   10

<210> SEQ ID NO 428
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(6)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: may not be present
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: may not be present

<400> SEQUENCE: 428

Ser Thr Gly Xaa Xaa Xaa Gly Gly Gly Xaa Xaa Gly Gly Gly Ser Thr
```

-continued

```
1               5               10              15

<210> SEQ ID NO 429
<211> LENGTH: 12
<212> TYPE: PRT
<213> ORGANISM: Artificial Sequence
<220> FEATURE:
<223> OTHER INFORMATION: Synthetic

<400> SEQUENCE: 429

Ser Thr Gln Met Arg Arg Arg Lys Ser Thr Gln Met
1               5               10

<210> SEQ ID NO 430
<211> LENGTH: 12
<212> TYPE: PRT
<213> ORGANISM: Artificial Sequence
<220> FEATURE:
<223> OTHER INFORMATION: Synthetic

<400> SEQUENCE: 430

Ser Thr Gln Met Arg Lys Arg Arg Ser Thr Gln Met
1               5               10

<210> SEQ ID NO 431
<211> LENGTH: 12
<212> TYPE: PRT
<213> ORGANISM: Artificial Sequence
<220> FEATURE:
<223> OTHER INFORMATION: Synthetic

<400> SEQUENCE: 431

Ser Thr Gln Met Arg Lys Arg Lys Ser Thr Gln Met
1               5               10

<210> SEQ ID NO 432
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (16)..(19)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: may not be present

<400> SEQUENCE: 432

Arg Lys Arg Lys Arg Lys Arg Lys Gln Met Asn Pro Leu Arg Lys Xaa
1               5               10              15

Xaa Xaa Xaa Arg Lys Arg Lys
            20

<210> SEQ ID NO 433
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(22)
<223> OTHER INFORMATION: Xaa can be any naturally occurring amino acid
<220> FEATURE:
<221> NAME/KEY: misc_feature
<222> LOCATION: (15)..(22)
```

<223> OTHER INFORMATION: may not be present

<400> SEQUENCE: 433

Arg Lys Arg Lys Arg Lys Xaa Xaa Xaa Xaa Xaa Xaa Xaa Xaa Xaa Xaa
1               5                   10                  15

Xaa Xaa Xaa Xaa Xaa Xaa Arg Lys Arg Lys Arg Lys Arg Lys
            20                  25                  30

<210> SEQ ID NO 434
<211> LENGTH: 27
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (13)..(21)
<223> OTHER INFORMATION: Xaa can be any naturally occurring amino acid
<220> FEATURE:
<221> NAME/KEY: misc_feature
<222> LOCATION: (17)..(21)
<223> OTHER INFORMATION: may not be present

<400> SEQUENCE: 434

Arg Lys Arg Lys Arg Lys Xaa Arg Lys Xaa Arg Lys Xaa Xaa Xaa Xaa
1               5                   10                  15

Xaa Xaa Xaa Xaa Xaa Arg Lys Arg Lys Arg Lys
            20                  25

<210> SEQ ID NO 435
<211> LENGTH: 25
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(8)
<223> OTHER INFORMATION: may not be present
<220> FEATURE:
<221> NAME/KEY: misc_feature
<222> LOCATION: (9)..(12)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: may not be present
<220> FEATURE:
<221> NAME/KEY: misc_feature
<222> LOCATION: (20)..(21)
<223> OTHER INFORMATION: may not be present

<400> SEQUENCE: 435

Arg Lys Arg Lys Arg Lys Arg Lys Xaa Xaa Xaa Xaa Gln Leu Met Arg
1               5                   10                  15

Lys Arg Lys Arg Lys Arg Lys Lys Arg
            20                  25

<210> SEQ ID NO 436
<211> LENGTH: 45
<212> TYPE: PRT
<213> ORGANISM: Artificial Sequence

```
<220> FEATURE:
<223> OTHER INFORMATION: Synthetic
<220> FEATURE:
<221> NAME/KEY: misc_feature
<222> LOCATION: (5)..(8)
<223> OTHER INFORMATION: may not be present
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: may not be present
<220> FEATURE:
<221> NAME/KEY: misc_feature
<222> LOCATION: (11)..(14)
<223> OTHER INFORMATION: may not be present
<220> FEATURE:
<221> NAME/KEY: misc_feature
<222> LOCATION: (21)..(24)
<223> OTHER INFORMATION: may not be present
<220> FEATURE:
<221> NAME/KEY: misc_feature
<222> LOCATION: (25)..(29)
<223> OTHER INFORMATION: Xaa can be any naturally occurring amino acid
<220> FEATURE:
<221> NAME/KEY: misc_feature
<222> LOCATION: (28)..(29)
<223> OTHER INFORMATION: may not be present
<220> FEATURE:
<221> NAME/KEY: misc_feature
<222> LOCATION: (32)..(33)
<223> OTHER INFORMATION: Xaa can be any naturally occurring amino acid
<220> FEATURE:
<221> NAME/KEY: misc_feature
<222> LOCATION: (32)..(33)
<223> OTHER INFORMATION: may not be present
<220> FEATURE:
<221> NAME/KEY: misc_feature
<222> LOCATION: (40)..(43)
<223> OTHER INFORMATION: may not be present

<400> SEQUENCE: 436

Arg Lys Arg Lys Arg Lys Arg Lys Xaa Xaa Arg Lys Arg Lys Arg Lys
1               5                   10                  15

Arg Lys Arg Lys Arg Lys Arg Lys Xaa Xaa Xaa Xaa Xaa Arg Lys Xaa
            20                  25                  30

Xaa Arg Lys Arg Lys Arg Lys Arg Lys Arg Lys Pro Leu
        35                  40                  45

<210> SEQ ID NO 437
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(14)
<223> OTHER INFORMATION: Xaa can be any naturally occurring amino acid
<220> FEATURE:
<221> NAME/KEY: misc_feature
<222> LOCATION: (13)..(14)
<223> OTHER INFORMATION: may not be present

<400> SEQUENCE: 437
```

```
Arg Lys Xaa Arg Lys Xaa Lys Arg Xaa Xaa Xaa Xaa Xaa Xaa Arg Lys
1               5                   10                  15

Lys

<210> SEQ ID NO 438
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (13)..(16)
<223> OTHER INFORMATION: may not be present

<400> SEQUENCE: 438

Arg Lys Pro Leu Ile Val Lys Arg Arg Lys Arg Lys Arg Lys Arg Lys
1               5                   10                  15

Pro Leu Val Ile Arg
            20

<210> SEQ ID NO 439
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: Xaa can be any naturally occurring amino acid

<400> SEQUENCE: 439

Pro Leu Lys Xaa Xaa Lys Arg Arg
1               5

<210> SEQ ID NO 440
<211> LENGTH: 11
<212> TYPE: PRT
<213> ORGANISM: Artificial Sequence
<220> FEATURE:
<223> OTHER INFORMATION: Synthetic

<400> SEQUENCE: 440

Pro Leu Val Arg Lys Ser Thr Arg Asp Glu Lys
1               5                   10

<210> SEQ ID NO 441
<211> LENGTH: 9
<212> TYPE: PRT
<213> ORGANISM: Artificial Sequence
<220> FEATURE:
<223> OTHER INFORMATION: Synthetic

<400> SEQUENCE: 441

Tyr Phe Trp Arg Arg Arg Arg Pro Leu
1               5

<210> SEQ ID NO 442
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(10)
```

-continued

```
<223> OTHER INFORMATION: Xaa can be any naturally occurring amino acid

<400> SEQUENCE: 442

Lys Arg Asp Glu Lys Arg Asp Glu Xaa Xaa Lys Arg Lys Arg Lys Arg
1               5                   10                  15

Lys Arg

<210> SEQ ID NO 443
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (8)..(15)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: may not be present

<400> SEQUENCE: 443

Lys Arg Xaa Xaa Lys Asn Lys Xaa Xaa Xaa Xaa Xaa Xaa Xaa Xaa Lys
1               5                   10                  15

Lys Arg

<210> SEQ ID NO 444
<211> LENGTH: 6
<212> TYPE: PRT
<213> ORGANISM: Artificial Sequence
<220> FEATURE:
<223> OTHER INFORMATION: Synthetic

<400> SEQUENCE: 444

Lys Arg Lys Arg Lys Lys
1               5

<210> SEQ ID NO 445
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(6)
<223> OTHER INFORMATION: Xaa can be any naturally occurring amino acid

<400> SEQUENCE: 445

Lys Arg Gly Gly Xaa Xaa Gly Gly Gly Arg Lys
1               5                   10

<210> SEQ ID NO 446
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
```

-continued

```
<222> LOCATION: (9)..(9)
<223> OTHER INFORMATION: Xaa can be any naturally occurring amino acid

<400> SEQUENCE: 446

Gln Met Asn Arg Arg Lys Xaa Lys Xaa Arg Lys Arg Lys
1               5                   10

<210> SEQ ID NO 447
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 447

Gly Ala Lys Arg Lys Arg Xaa Lys Arg Gly Ala
1               5                   10

<210> SEQ ID NO 448
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 448

Gly Ala Arg Xaa Arg Lys Xaa Arg Lys Arg Lys Xaa Gln Met
1               5                   10

<210> SEQ ID NO 449
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa can be any naturally occurring amino acid

<400> SEQUENCE: 449

Gly Ala Lys Xaa Lys Lys Lys Met Asn Gln
1               5                   10

<210> SEQ ID NO 450
<211> LENGTH: 11
<212> TYPE: PRT
<213> ORGANISM: Artificial Sequence
<220> FEATURE:
<223> OTHER INFORMATION: Synthetic

<400> SEQUENCE: 450

Gly Ala Pro Leu Val Arg Lys Arg Lys Lys Arg
1               5                   10
```

-continued

```
<210> SEQ ID NO 451
<211> LENGTH: 8
<212> TYPE: PRT
<213> ORGANISM: Artificial Sequence
<220> FEATURE:
<223> OTHER INFORMATION: Synthetic

<400> SEQUENCE: 451

Glu Asp Arg Arg Arg Arg Glu Asp
1               5

<210> SEQ ID NO 452
<211> LENGTH: 11
<212> TYPE: PRT
<213> ORGANISM: Artificial Sequence
<220> FEATURE:
<223> OTHER INFORMATION: Synthetic

<400> SEQUENCE: 452

Asp Glu Ser Thr Pro Leu Lys Arg Ser Thr Cys
1               5                   10

<210> SEQ ID NO 453
<211> LENGTH: 14
<212> TYPE: PRT
<213> ORGANISM: Artificial Sequence
<220> FEATURE:
<223> OTHER INFORMATION: Synthetic

<400> SEQUENCE: 453

Lys Arg Lys Arg Lys Arg Lys Arg Lys Arg Lys Arg Lys Arg
1               5                   10

<210> SEQ ID NO 454
<211> LENGTH: 14
<212> TYPE: PRT
<213> ORGANISM: Artificial Sequence
<220> FEATURE:
<223> OTHER INFORMATION: Synthetic

<400> SEQUENCE: 454

Lys Arg Lys Arg Gln Met Asn Arg Arg Lys Gln Met Asn Arg
1               5                   10

<210> SEQ ID NO 455
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 455

Lys Arg Lys Arg Xaa Lys Arg Lys Arg Lys Arg Xaa Lys Arg Lys Arg
1               5                   10                  15

<210> SEQ ID NO 456
<211> LENGTH: 15
<212> TYPE: PRT
<213> ORGANISM: Artificial Sequence
```

```
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 456

Pro Leu Val Lys Arg Lys Xaa Arg Lys Arg Lys Arg Lys Pro Leu
1               5                   10                  15

<210> SEQ ID NO 457
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 457

Pro Leu Val Lys Arg Lys Xaa Gln Met Asn Arg Lys Arg
1               5                   10

<210> SEQ ID NO 458
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(9)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: may not be present

<400> SEQUENCE: 458

Pro Leu Gln Lys Arg Xaa Xaa Xaa Xaa Lys Lys Arg Lys
1               5                   10

<210> SEQ ID NO 459
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: may not be present
<220> FEATURE:
<221> NAME/KEY: misc_feature
<222> LOCATION: (11)..(16)
<223> OTHER INFORMATION: Xaa can be any naturally occurring amino acid
<220> FEATURE:
<221> NAME/KEY: misc_feature
<222> LOCATION: (14)..(16)
<223> OTHER INFORMATION: may not be present
<220> FEATURE:
<221> NAME/KEY: misc_feature
<222> LOCATION: (21)..(22)
<223> OTHER INFORMATION: Xaa can be any naturally occurring amino acid
<220> FEATURE:
<221> NAME/KEY: misc_feature
```

-continued

```
<222> LOCATION: (22)..(22)
<223> OTHER INFORMATION: may not be present
<220> FEATURE:
<221> NAME/KEY: misc_feature
<222> LOCATION: (25)..(26)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: may not be present

<400> SEQUENCE: 459

Pro Leu Gln Lys Arg Lys Xaa Xaa Arg Lys Xaa Xaa Xaa Xaa Xaa Xaa
1               5                   10                  15

Arg Lys Arg Lys Xaa Xaa Arg Lys Xaa Xaa Arg Lys Arg Lys
            20                  25                  30

<210> SEQ ID NO 460
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: Xaa can be any naturally occurring amino acid

<400> SEQUENCE: 460

Pro Leu Gln Met Asn Lys Arg Lys Lys Arg Lys Arg Arg Xaa Lys Pro
1               5                   10                  15

Leu Gln Met Asn Lys Arg
            20

<210> SEQ ID NO 461
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (15)..(15)
<223> OTHER INFORMATION: Xaa can be any naturally occurring amino acid

<400> SEQUENCE: 461

Pro Leu Gln Met Lys Arg Arg Lys Arg Gln Met Lys Arg Arg Xaa Lys
1               5                   10                  15

<210> SEQ ID NO 462
<211> LENGTH: 13
<212> TYPE: PRT
<213> ORGANISM: Artificial Sequence
<220> FEATURE:
<223> OTHER INFORMATION: Synthetic

<400> SEQUENCE: 462

Met Ile Val Trp Ser Arg Asp His Glu Gln Arg Arg Lys
1               5                   10

<210> SEQ ID NO 463
<211> LENGTH: 20
<212> TYPE: PRT
<213> ORGANISM: Artificial Sequence
<220> FEATURE:
<223> OTHER INFORMATION: Synthetic

<400> SEQUENCE: 463
```

-continued

```
Leu Phe Ser Thr Lys Val Ile Gln Met Lys Arg Arg Gln Met Val Ile
1               5                   10                  15

Ser Thr Lys Leu
            20

<210> SEQ ID NO 464
<211> LENGTH: 54
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: may not be present
<220> FEATURE:
<221> NAME/KEY: misc_feature
<222> LOCATION: (10)..(13)
<223> OTHER INFORMATION: may not be present
<220> FEATURE:
<221> NAME/KEY: misc_feature
<222> LOCATION: (14)..(47)
<223> OTHER INFORMATION: Xaa can be any naturally occurring amino acid
<220> FEATURE:
<221> NAME/KEY: misc_feature
<222> LOCATION: (39)..(47)
<223> OTHER INFORMATION: may not be present
<220> FEATURE:
<221> NAME/KEY: misc_feature
<222> LOCATION: (50)..(51)
<223> OTHER INFORMATION: may not be present
<220> FEATURE:
<221> NAME/KEY: misc_feature
<222> LOCATION: (52)..(53)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: may not be present

<400> SEQUENCE: 464

Lys Arg Lys Arg Xaa Lys Arg Lys Arg Lys Arg Lys Arg Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Lys
        35                  40                  45

Lys Lys Lys Xaa Xaa Lys
    50

<210> SEQ ID NO 465
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(10)
<223> OTHER INFORMATION: Xaa can be any naturally occurring amino acid
<220> FEATURE:
<221> NAME/KEY: misc_feature
<222> LOCATION: (8)..(10)
<223> OTHER INFORMATION: may not be present
<220> FEATURE:
<221> NAME/KEY: misc_feature
<222> LOCATION: (15)..(19)
<223> OTHER INFORMATION: Xaa can be any naturally occurring amino acid
```

```
<220> FEATURE:
<221> NAME/KEY: misc_feature
<222> LOCATION: (16)..(19)
<223> OTHER INFORMATION: may not be present

<400> SEQUENCE: 465

Lys Arg Lys Arg Pro Leu Xaa Xaa Xaa Xaa Lys Arg Lys Arg Xaa Xaa
1               5                   10                  15

Xaa Xaa Xaa Lys Lys Lys
            20

<210> SEQ ID NO 466
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(6)
<223> OTHER INFORMATION: may not be present
<220> FEATURE:
<221> NAME/KEY: misc_feature
<222> LOCATION: (7)..(8)
<223> OTHER INFORMATION: Xaa can be any naturally occurring amino acid

<400> SEQUENCE: 466

Lys Arg Lys Arg Lys Arg Xaa Xaa Lys Arg Lys Arg Gln Leu Met
1               5                   10                  15

<210> SEQ ID NO 467
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: Xaa can be any naturally occurring amino acid

<400> SEQUENCE: 467

Asp Glu Arg Lys Arg Lys Arg Lys Xaa Lys Arg Lys Arg Pro Leu
1               5                   10                  15

<210> SEQ ID NO 468
<211> LENGTH: 6
<212> TYPE: PRT
<213> ORGANISM: Artificial Sequence
<220> FEATURE:
<223> OTHER INFORMATION: Synthetic

<400> SEQUENCE: 468

Lys Lys Arg Lys Arg Thr
1               5

<210> SEQ ID NO 469
<211> LENGTH: 27
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(17)
<223> OTHER INFORMATION: Xaa can be any naturally occurring amino acid
<220> FEATURE:
<221> NAME/KEY: misc_feature
<222> LOCATION: (14)..(17)
<223> OTHER INFORMATION: may not be present
```

```
<220> FEATURE:
<221> NAME/KEY: misc_feature
<222> LOCATION: (24)..(24)
<223> OTHER INFORMATION: Xaa can be any naturally occurring amino acid

<400> SEQUENCE: 469

Lys Arg Lys Xaa Xaa Xaa Xaa Xaa Xaa Xaa Xaa Xaa Xaa Xaa Xaa Xaa
1               5                   10                  15

Xaa Lys Arg Lys Arg Lys Arg Xaa Lys Arg Lys
            20                  25

<210> SEQ ID NO 470
<211> LENGTH: 15
<212> TYPE: PRT
<213> ORGANISM: Artificial Sequence
<220> FEATURE:
<223> OTHER INFORMATION: Synthetic

<400> SEQUENCE: 470

Pro Lys Lys Arg Lys Arg Pro Arg Ala Lys Lys Thr Val Ser Glu
1               5                   10                  15

<210> SEQ ID NO 471
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(12)
<223> OTHER INFORMATION: Xaa can be any naturally occurring amino acid
<220> FEATURE:
<221> NAME/KEY: misc_feature
<222> LOCATION: (10)..(12)
<223> OTHER INFORMATION: may not be present
<220> FEATURE:
<221> NAME/KEY: misc_feature
<222> LOCATION: (14)..(17)
<223> OTHER INFORMATION: Xaa can be any naturally occurring amino acid
<220> FEATURE:
<221> NAME/KEY: misc_feature
<222> LOCATION: (16)..(17)
<223> OTHER INFORMATION: may not be present
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid

<400> SEQUENCE: 471

Pro Lys Arg Pro Xaa Xaa Xaa Xaa Xaa Xaa Xaa Xaa Leu Xaa Xaa Xaa
1               5                   10                  15

Xaa Arg Xaa Lys Xaa Lys
            20

<210> SEQ ID NO 472
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(7)
<223> OTHER INFORMATION: Xaa can be any naturally occurring amino acid
<220> FEATURE:
<221> NAME/KEY: misc_feature
```

-continued

```
<222> LOCATION: (6)..(7)
<223> OTHER INFORMATION: may not be present

<400> SEQUENCE: 472

Lys Arg Lys Xaa Xaa Xaa Xaa Asp Arg Arg Lys
1               5                   10

<210> SEQ ID NO 473
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be any naturally occurring amino acid

<400> SEQUENCE: 473

Pro Lys Lys Lys Xaa Arg Lys
1               5

<210> SEQ ID NO 474
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(13)
<223> OTHER INFORMATION: Xaa can be any naturally occurring amino acid
<220> FEATURE:
<221> NAME/KEY: misc_feature
<222> LOCATION: (9)..(13)
<223> OTHER INFORMATION: may not be present

<400> SEQUENCE: 474

Lys Arg Lys Xaa Xaa Xaa Xaa Xaa Xaa Xaa Xaa Xaa Xaa Lys Lys Pro
1               5                   10                  15

Leu Lys

<210> SEQ ID NO 475
<211> LENGTH: 15
<212> TYPE: PRT
<213> ORGANISM: Artificial Sequence
<220> FEATURE:
<223> OTHER INFORMATION: Synthetic

<400> SEQUENCE: 475

Asn Gln Arg Arg Gln Arg Lys Glu Gly Lys Arg Ile Val Leu Ser
1               5                   10                  15

<210> SEQ ID NO 476
<211> LENGTH: 6
<212> TYPE: PRT
<213> ORGANISM: Artificial Sequence
<220> FEATURE:
<223> OTHER INFORMATION: Synthetic

<400> SEQUENCE: 476

Leu Lys Lys Ile Lys Gln
1               5

<210> SEQ ID NO 477
<211> LENGTH: 15
<212> TYPE: PRT
<213> ORGANISM: Artificial Sequence
```

-continued

```
<220> FEATURE:
<223> OTHER INFORMATION: Synthetic

<400> SEQUENCE: 477

Lys Arg Gly Pro Leu Arg Gly Pro Leu Arg Gly Leu Pro Arg Lys
1               5                   10                  15

<210> SEQ ID NO 478
<211> LENGTH: 12
<212> TYPE: PRT
<213> ORGANISM: Artificial Sequence
<220> FEATURE:
<223> OTHER INFORMATION: Synthetic

<400> SEQUENCE: 478

Lys Arg Met Asn Ser Gln Arg Met Asn Ser Gln Arg
1               5                   10

<210> SEQ ID NO 479
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(11)
<223> OTHER INFORMATION: Xaa can be any naturally occurring amino acid
<220> FEATURE:
<221> NAME/KEY: misc_feature
<222> LOCATION: (4)..(11)
<223> OTHER INFORMATION: may not be present

<400> SEQUENCE: 479

Lys Arg Lys Xaa Xaa Xaa Xaa Xaa Xaa Xaa Xaa Lys Arg Pro Leu Lys
1               5                   10                  15

<210> SEQ ID NO 480
<211> LENGTH: 9
<212> TYPE: PRT
<213> ORGANISM: Artificial Sequence
<220> FEATURE:
<223> OTHER INFORMATION: Synthetic

<400> SEQUENCE: 480

Lys Arg Gly Arg Gly Arg Pro Arg Lys
1               5

<210> SEQ ID NO 481
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(9)
<223> OTHER INFORMATION: Xaa can be any naturally occurring amino acid
<220> FEATURE:
<221> NAME/KEY: misc_feature
<222> LOCATION: (4)..(9)
<223> OTHER INFORMATION: may not be present

<400> SEQUENCE: 481

Lys Lys Xaa Xaa Xaa Xaa Xaa Xaa Xaa Lys Pro Leu Pro Leu Ile Val
1               5                   10                  15

Lys Lys
```

```
<210> SEQ ID NO 482
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(15)
<223> OTHER INFORMATION: Xaa can be any naturally occurring amino acid
<220> FEATURE:
<221> NAME/KEY: misc_feature
<222> LOCATION: (12)..(15)
<223> OTHER INFORMATION: may not be present

<400> SEQUENCE: 482

Arg Glu Arg Met Asn Gln Lys Xaa Xaa Xaa Xaa Xaa Xaa Xaa Xaa Arg
1               5                   10                  15

Met Asn Gln Arg Arg
            20

<210> SEQ ID NO 483
<211> LENGTH: 7
<212> TYPE: PRT
<213> ORGANISM: Artificial Sequence
<220> FEATURE:
<223> OTHER INFORMATION: Synthetic

<400> SEQUENCE: 483

Lys Lys Arg Lys Arg Lys Arg
1               5

<210> SEQ ID NO 484
<211> LENGTH: 7
<212> TYPE: PRT
<213> ORGANISM: Artificial Sequence
<220> FEATURE:
<223> OTHER INFORMATION: Synthetic

<400> SEQUENCE: 484

Lys Lys Arg Lys Arg Ser Thr
1               5

<210> SEQ ID NO 485
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: Xaa can be any naturally occurring amino acid

<400> SEQUENCE: 485

Gln Arg Lys His Arg Lys Arg Lys Xaa Arg Arg
1               5                   10

<210> SEQ ID NO 486
<211> LENGTH: 5
<212> TYPE: PRT
<213> ORGANISM: Artificial Sequence
<220> FEATURE:
<223> OTHER INFORMATION: Synthetic

<400> SEQUENCE: 486

Lys Lys Arg Arg Lys
1               5
```

```
<210> SEQ ID NO 487
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 487

Gln Asn Arg Arg Xaa Lys Xaa Arg Lys Arg Lys Asp Gln Glu
1               5                   10

<210> SEQ ID NO 488
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (13)..(14)
<223> OTHER INFORMATION: may not be present
<220> FEATURE:
<221> NAME/KEY: misc_feature
<222> LOCATION: (15)..(15)
<223> OTHER INFORMATION: Xaa can be any naturally occurring amino acid

<400> SEQUENCE: 488

Pro Xaa Pro Gln Leu Val Met Asn Lys Arg Lys Arg Lys Arg Xaa Lys
1               5                   10                  15

Gln

<210> SEQ ID NO 489
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be any naturally occurring amino acid

<400> SEQUENCE: 489

Lys Lys Arg Arg Xaa Lys
1               5

<210> SEQ ID NO 490
<211> LENGTH: 22
<212> TYPE: PRT
<213> ORGANISM: Artificial Sequence
<220> FEATURE:
<223> OTHER INFORMATION: Synthetic

<400> SEQUENCE: 490

Lys Lys Met Asn Gln Ser Thr Cys Arg Met Asn Gln Ser Thr Cys Lys
1               5                   10                  15

Met Asn Gln Ser Thr Cys
```

20

```
<210> SEQ ID NO 491
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(9)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: may not be present

<400> SEQUENCE: 491

Lys Lys Xaa Arg Xaa Xaa Xaa Xaa Xaa Arg Pro Val Leu Lys
1               5                   10

<210> SEQ ID NO 492
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: may not be present
<220> FEATURE:
<221> NAME/KEY: misc_feature
<222> LOCATION: (7)..(7)
<223> OTHER INFORMATION: may not be present

<400> SEQUENCE: 492

Lys Lys Lys Lys Arg Arg Arg
1               5

<210> SEQ ID NO 493
<211> LENGTH: 7
<212> TYPE: PRT
<213> ORGANISM: Artificial Sequence
<220> FEATURE:
<223> OTHER INFORMATION: Synthetic

<400> SEQUENCE: 493

Lys Arg Arg Gln Met Arg Arg
1               5

<210> SEQ ID NO 494
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
```

```
<223> OTHER INFORMATION: Xaa can be any naturally occurring amino acid
<220> FEATURE:
<221> NAME/KEY: misc_feature
<222> LOCATION: (9)..(13)
<223> OTHER INFORMATION: Xaa can be any naturally occurring amino acid

<400> SEQUENCE: 494

Lys Xaa Xaa Lys Xaa Lys Xaa Lys Xaa Xaa Xaa Xaa Xaa Arg Lys Lys
1               5                   10                  15

<210> SEQ ID NO 495
<211> LENGTH: 10
<212> TYPE: PRT
<213> ORGANISM: Artificial Sequence
<220> FEATURE:
<223> OTHER INFORMATION: Synthetic

<400> SEQUENCE: 495

Lys Gly Ala Lys Ala Gly Lys Lys Ala Gly
1               5                   10

<210> SEQ ID NO 496
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(10)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: may not be present
<220> FEATURE:
<221> NAME/KEY: misc_feature
<222> LOCATION: (13)..(14)
<223> OTHER INFORMATION: may not be present
<220> FEATURE:
<221> NAME/KEY: misc_feature
<222> LOCATION: (13)..(14)
<223> OTHER INFORMATION: Xaa can be any naturally occurring amino acid
<220> FEATURE:
<221> NAME/KEY: misc_feature
<222> LOCATION: (16)..(20)
<223> OTHER INFORMATION: Xaa can be any naturally occurring amino acid
<220> FEATURE:
<221> NAME/KEY: misc_feature
<222> LOCATION: (19)..(20)
<223> OTHER INFORMATION: may not be present
<220> FEATURE:
<221> NAME/KEY: misc_feature
<222> LOCATION: (23)..(24)
<223> OTHER INFORMATION: Xaa can be any naturally occurring amino acid
<220> FEATURE:
<221> NAME/KEY: misc_feature
<222> LOCATION: (23)..(24)
<223> OTHER INFORMATION: may not be present
<220> FEATURE:
<221> NAME/KEY: misc_feature
<222> LOCATION: (27)..(28)
<223> OTHER INFORMATION: Xaa can be any naturally occurring amino acid
<220> FEATURE:
<221> NAME/KEY: misc_feature
<222> LOCATION: (27)..(28)
<223> OTHER INFORMATION: may not be present

<400> SEQUENCE: 496

Lys Arg Arg Lys Arg Lys Xaa Xaa Xaa Xaa Arg Lys Xaa Xaa Arg Xaa
1               5                   10                  15

Xaa Xaa Xaa Xaa Arg Lys Xaa Xaa Arg Lys Xaa Xaa Arg Lys Arg Lys
        20                  25                  30
```

-continued

Lys

```
<210> SEQ ID NO 497
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: may not be present

<400> SEQUENCE: 497

Lys Arg Ser Thr Arg Xaa Xaa Arg Arg Arg Arg Gln Leu Lys
1               5                   10

<210> SEQ ID NO 498
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(12)
<223> OTHER INFORMATION: Xaa can be any naturally occurring amino acid
<220> FEATURE:
<221> NAME/KEY: misc_feature
<222> LOCATION: (9)..(12)
<223> OTHER INFORMATION: may not be present

<400> SEQUENCE: 498

Lys Arg Xaa Arg Xaa Arg Xaa Xaa Xaa Xaa Xaa Xaa Arg Lys Arg Lys
1               5                   10                  15

<210> SEQ ID NO 499
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 499

Lys Arg Xaa Arg Xaa Xaa Arg Arg Leu Lys
1               5                   10

<210> SEQ ID NO 500
<211> LENGTH: 7
<212> TYPE: PRT
<213> ORGANISM: Artificial Sequence
```

```
<220> FEATURE:
<223> OTHER INFORMATION: Synthetic

<400> SEQUENCE: 500

Lys Arg Arg Arg Leu Val Ile
1               5

<210> SEQ ID NO 501
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: may not be present
<220> FEATURE:
<221> NAME/KEY: misc_feature
<222> LOCATION: (6)..(11)
<223> OTHER INFORMATION: Xaa can be any naturally occurring amino acid
<220> FEATURE:
<221> NAME/KEY: misc_feature
<222> LOCATION: (9)..(11)
<223> OTHER INFORMATION: may not be present
<220> FEATURE:
<221> NAME/KEY: misc_feature
<222> LOCATION: (16)..(19)
<223> OTHER INFORMATION: may not be present
<220> FEATURE:
<221> NAME/KEY: misc_feature
<222> LOCATION: (20)..(23)
<223> OTHER INFORMATION: Xaa can be any naturally occurring amino acid
<220> FEATURE:
<221> NAME/KEY: misc_feature
<222> LOCATION: (20)..(22)
<223> OTHER INFORMATION: may not be present

<400> SEQUENCE: 501

Lys Arg Arg Arg Arg Xaa Xaa Xaa Xaa Xaa Xaa Arg Lys Arg Lys Arg
1               5                   10                  15

Lys Arg Lys Xaa Xaa Xaa Lys Arg
            20

<210> SEQ ID NO 502
<211> LENGTH: 7
<212> TYPE: PRT
<213> ORGANISM: Artificial Sequence
<220> FEATURE:
<223> OTHER INFORMATION: Synthetic

<400> SEQUENCE: 502

Lys Lys Arg Arg Asp Glu Lys
1               5

<210> SEQ ID NO 503
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 503
```

-continued

```
Lys Arg Xaa Asp Glu Lys Arg Lys Arg Xaa Lys
1               5                   10

<210> SEQ ID NO 504
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 504

Lys Arg Xaa Xaa Lys Lys Xaa Lys Asp Glu
1               5                   10

<210> SEQ ID NO 505
<211> LENGTH: 13
<212> TYPE: PRT
<213> ORGANISM: Artificial Sequence
<220> FEATURE:
<223> OTHER INFORMATION: Synthetic

<400> SEQUENCE: 505

Lys Ile Val Gln Met Arg Arg Val Ile Ser Thr Lys Leu
1               5                   10

<210> SEQ ID NO 506
<211> LENGTH: 9
<212> TYPE: PRT
<213> ORGANISM: Artificial Sequence
<220> FEATURE:
<223> OTHER INFORMATION: Synthetic

<400> SEQUENCE: 506

Lys Lys Arg Lys Arg Arg Arg Lys Arg
1               5

<210> SEQ ID NO 507
<211> LENGTH: 13
<212> TYPE: PRT
<213> ORGANISM: Artificial Sequence
<220> FEATURE:
<223> OTHER INFORMATION: Synthetic

<400> SEQUENCE: 507

Lys Lys Arg Gln Met Asn Arg Lys Arg Gln Met Asn Arg
1               5                   10

<210> SEQ ID NO 508
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid

<400> SEQUENCE: 508

Lys Xaa Pro Leu Val Arg Lys Arg Lys Arg Lys
1               5                   10
```

```
<210> SEQ ID NO 509
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(10)
<223> OTHER INFORMATION: Xaa can be any naturally occurring amino acid

<400> SEQUENCE: 509

Lys Xaa Lys Xaa Lys Xaa Xaa Xaa Xaa Xaa Arg Lys Lys
1               5                   10

<210> SEQ ID NO 510
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid

<400> SEQUENCE: 510

Lys Xaa Lys Arg Gln Arg
1               5

<210> SEQ ID NO 511
<211> LENGTH: 12
<212> TYPE: PRT
<213> ORGANISM: Artificial Sequence
<220> FEATURE:
<223> OTHER INFORMATION: Synthetic

<400> SEQUENCE: 511

Lys Arg Pro Leu Val Gly Ala Lys Arg Lys Pro Leu
1               5                   10

<210> SEQ ID NO 512
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(15)
<223> OTHER INFORMATION: Xaa can be any naturally occurring amino acid
<220> FEATURE:
<221> NAME/KEY: misc_feature
<222> LOCATION: (11)..(15)
<223> OTHER INFORMATION: may not be present

<400> SEQUENCE: 512

Lys Arg Lys Arg Lys Gln Leu Xaa Xaa Xaa Xaa Xaa Xaa Xaa Xaa Arg
1               5                   10                  15

Arg Arg
```

-continued

```
<210> SEQ ID NO 513
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(9)
<223> OTHER INFORMATION: may not be present

<400> SEQUENCE: 513

Lys Arg Lys Arg Lys Arg Lys Arg Lys Ser Thr His
1               5                   10

<210> SEQ ID NO 514
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 514

Lys Pro Leu Lys Lys Lys Xaa Lys Lys
1               5

<210> SEQ ID NO 515
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: may not be present
<220> FEATURE:
<221> NAME/KEY: misc_feature
<222> LOCATION: (7)..(9)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: may not be present
<220> FEATURE:
<221> NAME/KEY: misc_feature
<222> LOCATION: (14)..(17)
<223> OTHER INFORMATION: may not be present
<220> FEATURE:
<221> NAME/KEY: misc_feature
<222> LOCATION: (18)..(26)
<223> OTHER INFORMATION: Xaa can be any naturally occurring amino acid
<220> FEATURE:
<221> NAME/KEY: misc_feature
<222> LOCATION: (24)..(26)
<223> OTHER INFORMATION: may not be present

<400> SEQUENCE: 515

Lys Pro Leu Lys Lys Lys Xaa Xaa Xaa Arg Lys Arg Lys Arg Lys Arg
1               5                   10                  15

Lys Xaa Xaa Xaa Xaa Xaa Xaa Xaa Xaa Xaa Lys Lys Arg
            20                  25

<210> SEQ ID NO 516
<211> LENGTH: 11
<212> TYPE: PRT
<213> ORGANISM: Artificial Sequence
```

<220> FEATURE:
<223> OTHER INFORMATION: Synthetic

<400> SEQUENCE: 516

Lys Pro Leu Met Asn Arg Arg Lys Met Asn Gln
1               5                   10

<210> SEQ ID NO 517
<211> LENGTH: 13
<212> TYPE: PRT
<213> ORGANISM: Artificial Sequence
<220> FEATURE:
<223> OTHER INFORMATION: Synthetic

<400> SEQUENCE: 517

Lys Met Asn Gln Arg Arg Pro Leu Val Ile Lys Pro Leu
1               5                   10

<210> SEQ ID NO 518
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: may not be present
<220> FEATURE:
<221> NAME/KEY: misc_feature
<222> LOCATION: (7)..(11)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: may not be present

<400> SEQUENCE: 518

Lys Arg Xaa Xaa Xaa His Xaa Xaa Xaa Xaa Xaa Arg Leu Gln Arg Arg
1               5                   10                  15

<210> SEQ ID NO 519
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 519

Arg Pro Leu Xaa Gly Xaa Lys Arg Lys Arg Xaa Lys
1               5                   10

<210> SEQ ID NO 520
<211> LENGTH: 9
<212> TYPE: PRT

```
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 520

Arg Arg Xaa Arg Xaa Lys Xaa Lys Gln
1               5

<210> SEQ ID NO 521
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid

<400> SEQUENCE: 521

Arg Arg Xaa Arg Pro Val Leu Arg Lys
1               5

<210> SEQ ID NO 522
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid

<400> SEQUENCE: 522

Arg Arg Xaa Arg Arg Arg Arg Arg
1               5

<210> SEQ ID NO 523
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 523

Arg Arg Xaa Lys Arg Xaa Lys Pro Leu Val
1               5                   10

<210> SEQ ID NO 524
<211> LENGTH: 11
```

-continued

```
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be any naturally occurring amino acid

<400> SEQUENCE: 524

Arg Arg Thr Ser Xaa Gln Lys Lys Arg Lys Asn
1               5                   10

<210> SEQ ID NO 525
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be any naturally occurring amino acid

<400> SEQUENCE: 525

Arg Arg Thr Ser Xaa Gln Lys Lys Arg Lys Asn Ser
1               5                   10

<210> SEQ ID NO 526
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Xaa can be any naturally occurring amino acid

<400> SEQUENCE: 526

Arg Arg Pro Leu Gln Met Asn Xaa Arg Arg Arg Arg
1               5                   10

<210> SEQ ID NO 527
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: Xaa can be any naturally occurring amino acid

<400> SEQUENCE: 527

Arg Arg Pro Leu Ile Val Arg Lys Xaa Lys
1               5                   10

<210> SEQ ID NO 528
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(4)
<223> OTHER INFORMATION: may not be present
<220> FEATURE:
<221> NAME/KEY: misc_feature
<222> LOCATION: (7)..(9)
```

```
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: may not be present

<400> SEQUENCE: 528

Gly Gly Gly Gly Arg Lys Xaa Xaa Xaa Gly Gly Gly
1               5                   10

<210> SEQ ID NO 529
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(7)
<223> OTHER INFORMATION: may not be present

<400> SEQUENCE: 529

Arg Arg Arg Arg Arg Arg Arg Thr
1               5

<210> SEQ ID NO 530
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 530

Arg Arg Xaa Arg Xaa Arg Lys Gln
1               5

<210> SEQ ID NO 531
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(4)
<223> OTHER INFORMATION: Xaa can be any naturally occurring amino acid

<400> SEQUENCE: 531

Arg Arg Xaa Xaa Lys Arg Lys
1               5

<210> SEQ ID NO 532
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: may not be present
<220> FEATURE:
<221> NAME/KEY: misc_feature
```

```
<222> LOCATION: (3)..(3)
<223> OTHER INFORMATION: Xaa can be any naturally occurring amino acid

<400> SEQUENCE: 532

Arg Arg Xaa Arg Arg Arg Arg Arg
1               5

<210> SEQ ID NO 533
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(12)
<223> OTHER INFORMATION: Xaa can be any naturally occurring amino acid
<220> FEATURE:
<221> NAME/KEY: misc_feature
<222> LOCATION: (9)..(12)
<223> OTHER INFORMATION: may not be present

<400> SEQUENCE: 533

Arg Met Asn Gln Xaa Xaa Xaa Xaa Xaa Xaa Xaa Xaa Arg Met Asn Gln
1               5                   10                  15

Arg Arg

<210> SEQ ID NO 534
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: Xaa can be any naturally occurring amino acid

<400> SEQUENCE: 534

Arg Met Asn Gln Arg Arg Arg Arg Xaa Arg
1               5                   10

<210> SEQ ID NO 535
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(9)
<223> OTHER INFORMATION: may not be present

<400> SEQUENCE: 535

Arg Lys Arg Lys Arg Lys Arg Lys Arg Lys Asp Glu
1               5                   10

<210> SEQ ID NO 536
<211> LENGTH: 34
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (6)..(7)
```

-continued

```
<223> OTHER INFORMATION: may not be present
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: may not be present
<220> FEATURE:
<221> NAME/KEY: misc_feature
<222> LOCATION: (14)..(18)
<223> OTHER INFORMATION: Xaa can be any naturally occurring amino acid
<220> FEATURE:
<221> NAME/KEY: misc_feature
<222> LOCATION: (17)..(18)
<223> OTHER INFORMATION: may not be present
<220> FEATURE:
<221> NAME/KEY: misc_feature
<222> LOCATION: (21)..(22)
<223> OTHER INFORMATION: may not be present
<220> FEATURE:
<221> NAME/KEY: misc_feature
<222> LOCATION: (21)..(22)
<223> OTHER INFORMATION: Xaa can be any naturally occurring amino acid

<400> SEQUENCE: 536

Arg Lys Arg Arg Lys Xaa Xaa Arg Lys Xaa Xaa Arg Lys Xaa Xaa Xaa
1               5                   10                  15

Xaa Xaa Arg Lys Xaa Xaa Arg Lys Arg Lys Arg Lys Arg Lys Pro Met
            20                  25                  30

Gln Leu

<210> SEQ ID NO 537
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Xaa can be any naturally occurring amino acid

<400> SEQUENCE: 537

Arg Lys Arg Arg Arg Arg Arg Xaa Arg
1               5

<210> SEQ ID NO 538
<211> LENGTH: 12
<212> TYPE: PRT
<213> ORGANISM: Artificial Sequence
<220> FEATURE:
<223> OTHER INFORMATION: Synthetic

<400> SEQUENCE: 538

Arg Ile Val Leu Pro Ile Val Leu Pro Lys Arg Arg
1               5                   10

<210> SEQ ID NO 539
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (11)..(11)
<223> OTHER INFORMATION: Xaa can be any naturally occurring amino acid

<400> SEQUENCE: 539
```

```
Arg Gly Val Leu Ile Pro Arg Arg Arg Xaa Arg
1               5               10

<210> SEQ ID NO 540
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: may not be present
<220> FEATURE:
<221> NAME/KEY: misc_feature
<222> LOCATION: (11)..(11)
<223> OTHER INFORMATION: Xaa can be any naturally occurring amino acid

<400> SEQUENCE: 540

Arg Gly Ala Xaa Xaa Gly Ala Arg Gly Ala Xaa Gly Ala Arg Gly Ala
1               5               10                  15

<210> SEQ ID NO 541
<211> LENGTH: 10
<212> TYPE: PRT
<213> ORGANISM: Artificial Sequence
<220> FEATURE:
<223> OTHER INFORMATION: Synthetic

<400> SEQUENCE: 541

Arg Gly Ala Ile Val Leu Pro Lys Arg Arg
1               5               10

<210> SEQ ID NO 542
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(10)
<223> OTHER INFORMATION: may not be present
<220> FEATURE:
<221> NAME/KEY: misc_feature
<222> LOCATION: (11)..(12)
<223> OTHER INFORMATION: Xaa can be any naturally occurring amino acid

<400> SEQUENCE: 542

Gly Arg Arg Lys Arg Lys Arg Lys Arg Lys Xaa Xaa Arg Lys Gln Leu
1               5               10                  15

<210> SEQ ID NO 543
<211> LENGTH: 7
<212> TYPE: PRT
<213> ORGANISM: Artificial Sequence
<220> FEATURE:
<223> OTHER INFORMATION: Synthetic

<400> SEQUENCE: 543

Arg Arg Arg Pro Leu Arg Lys
1               5

<210> SEQ ID NO 544
<211> LENGTH: 11
```

```
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(7)
<223> OTHER INFORMATION: Xaa can be any naturally occurring amino acid

<400> SEQUENCE: 544

Arg Arg Arg Leu Pro Xaa Xaa Arg Pro Leu Gln
1               5                   10

<210> SEQ ID NO 545
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 545

Arg Arg Arg Arg Arg Xaa Arg Arg
1               5

<210> SEQ ID NO 546
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(7)
<223> OTHER INFORMATION: may not be present

<400> SEQUENCE: 546

Arg Lys Arg Arg Arg Arg Arg Ser Thr
1               5

<210> SEQ ID NO 547
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(19)
<223> OTHER INFORMATION: Xaa can be any naturally occurring amino acid
<220> FEATURE:
<221> NAME/KEY: misc_feature
<222> LOCATION: (16)..(19)
<223> OTHER INFORMATION: may not be present

<400> SEQUENCE: 547

Arg Lys Arg Xaa Xaa Xaa Xaa Xaa Xaa Xaa Xaa Xaa Xaa Xaa Xaa Xaa
1               5                   10                  15

Xaa Xaa Xaa Arg Arg Lys Lys
            20

<210> SEQ ID NO 548
<211> LENGTH: 15
<212> TYPE: PRT
<213> ORGANISM: Artificial Sequence
<220> FEATURE:
<223> OTHER INFORMATION: Synthetic
```

<400> SEQUENCE: 548

Arg Lys Arg Pro Leu Gln Met Asn Arg Pro Leu Gln Met Asn Arg
1               5                   10                  15

<210> SEQ ID NO 549
<211> LENGTH: 7
<212> TYPE: PRT
<213> ORGANISM: Artificial Sequence
<220> FEATURE:
<223> OTHER INFORMATION: Synthetic

<400> SEQUENCE: 549

Arg Lys Arg Lys Arg Lys Arg
1               5

<210> SEQ ID NO 550
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(11)
<223> OTHER INFORMATION: Xaa can be any naturally occurring amino acid
<220> FEATURE:
<221> NAME/KEY: misc_feature
<222> LOCATION: (9)..(11)
<223> OTHER INFORMATION: may not be present

<400> SEQUENCE: 550

Lys Lys Lys Lys Lys Xaa Xaa Xaa Xaa Xaa Xaa Lys Lys
1               5                   10

<210> SEQ ID NO 551
<211> LENGTH: 7
<212> TYPE: PRT
<213> ORGANISM: Artificial Sequence
<220> FEATURE:
<223> OTHER INFORMATION: Synthetic

<400> SEQUENCE: 551

Lys Lys Lys Lys Arg Lys Arg
1               5

<210> SEQ ID NO 552
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 552

Arg Lys Lys Arg Arg Xaa Arg
1               5

<210> SEQ ID NO 553
<211> LENGTH: 9
<212> TYPE: PRT
<213> ORGANISM: Artificial Sequence
<220> FEATURE:
<223> OTHER INFORMATION: Synthetic

<400> SEQUENCE: 553

-continued

```
Lys Lys Lys Arg Lys Arg Val Pro Leu
1               5

<210> SEQ ID NO 554
<211> LENGTH: 6
<212> TYPE: PRT
<213> ORGANISM: Artificial Sequence
<220> FEATURE:
<223> OTHER INFORMATION: Synthetic

<400> SEQUENCE: 554

Arg Lys Lys Arg Lys Arg
1               5

<210> SEQ ID NO 555
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(12)
<223> OTHER INFORMATION: Xaa can be any naturally occurring amino acid
<220> FEATURE:
<221> NAME/KEY: misc_feature
<222> LOCATION: (10)..(12)
<223> OTHER INFORMATION: may not be present
<220> FEATURE:
<221> NAME/KEY: misc_feature
<222> LOCATION: (14)..(16)
<223> OTHER INFORMATION: Xaa can be any naturally occurring amino acid
<220> FEATURE:
<221> NAME/KEY: misc_feature
<222> LOCATION: (15)..(16)
<223> OTHER INFORMATION: may not be present

<400> SEQUENCE: 555

Lys Lys Pro Xaa Xaa Xaa Xaa Xaa Xaa Xaa Xaa Xaa Lys Xaa Xaa Xaa
1               5                   10                  15

Arg Lys

<210> SEQ ID NO 556
<211> LENGTH: 14
<212> TYPE: PRT
<213> ORGANISM: Artificial Sequence
<220> FEATURE:
<223> OTHER INFORMATION: Synthetic

<400> SEQUENCE: 556

Arg Lys Ile Val Glu Trp Met Leu Thr Gln Arg Asn His Phe
1               5                   10

<210> SEQ ID NO 557
<211> LENGTH: 12
<212> TYPE: PRT
<213> ORGANISM: Artificial Sequence
<220> FEATURE:
<223> OTHER INFORMATION: Synthetic

<400> SEQUENCE: 557

Arg Lys Pro Leu Pro Leu Val Lys Lys Arg Lys His
1               5                   10

<210> SEQ ID NO 558
<211> LENGTH: 11
<212> TYPE: PRT
<213> ORGANISM: Artificial Sequence
```

```
<220> FEATURE:
<223> OTHER INFORMATION: Synthetic
<220> FEATURE:
<221> NAME/KEY: misc_feature
<222> LOCATION: (10)..(10)
<223> OTHER INFORMATION: Xaa can be any naturally occurring amino acid

<400> SEQUENCE: 558

Arg Lys Arg Lys Gln Met Leu Arg Lys Xaa Arg
1               5                   10

<210> SEQ ID NO 559
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(8)
<223> OTHER INFORMATION: may not be present

<400> SEQUENCE: 559

Arg Arg Arg Arg Arg Arg Xaa Xaa Arg
1               5

<210> SEQ ID NO 560
<211> LENGTH: 6
<212> TYPE: PRT
<213> ORGANISM: Artificial Sequence
<220> FEATURE:
<223> OTHER INFORMATION: Synthetic

<400> SEQUENCE: 560

Arg Arg Arg Arg Arg Arg
1               5

<210> SEQ ID NO 561
<211> LENGTH: 8
<212> TYPE: PRT
<213> ORGANISM: Artificial Sequence
<220> FEATURE:
<223> OTHER INFORMATION: Synthetic

<400> SEQUENCE: 561

Arg Arg Arg Lys Ser Thr Cys Lys
1               5

<210> SEQ ID NO 562
<211> LENGTH: 6
<212> TYPE: PRT
<213> ORGANISM: Artificial Sequence
<220> FEATURE:
<223> OTHER INFORMATION: Synthetic

<400> SEQUENCE: 562

Arg Arg Arg Lys Lys Arg
1               5

<210> SEQ ID NO 563
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(10)
<223> OTHER INFORMATION: Xaa can be any naturally occurring amino acid
```

```
<220> FEATURE:
<221> NAME/KEY: misc_feature
<222> LOCATION: (9)..(10)
<223> OTHER INFORMATION: may not be present

<400> SEQUENCE: 563

Arg Arg Lys Xaa Xaa Xaa Xaa Xaa Xaa Xaa Arg Arg Arg
1               5                   10

<210> SEQ ID NO 564
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(8)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: may not be present

<400> SEQUENCE: 564

Arg Arg Lys Xaa Xaa Xaa Xaa Xaa Arg Asp Glu Arg Arg Arg Pro Leu
1               5                   10                  15

Val

<210> SEQ ID NO 565
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(16)
<223> OTHER INFORMATION: Xaa can be any naturally occurring amino acid
<220> FEATURE:
<221> NAME/KEY: misc_feature
<222> LOCATION: (13)..(16)
<223> OTHER INFORMATION: may not be present

<400> SEQUENCE: 565

Arg Arg Glu Arg Met Asn Gln Lys Xaa Xaa Xaa Xaa Xaa Xaa Xaa Xaa
1               5                   10                  15

Arg Met Asn Gln Arg Arg Arg
            20

<210> SEQ ID NO 566
<211> LENGTH: 6
<212> TYPE: PRT
<213> ORGANISM: Artificial Sequence
<220> FEATURE:
<223> OTHER INFORMATION: Synthetic

<400> SEQUENCE: 566

Lys His Leu Lys Gly Arg
1               5

<210> SEQ ID NO 567
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
```

-continued

```
<222> LOCATION: (3)..(14)
<223> OTHER INFORMATION: Xaa can be any naturally occurring amino acid
<220> FEATURE:
<221> NAME/KEY: misc_feature
<222> LOCATION: (10)..(14)
<223> OTHER INFORMATION: may not be present

<400> SEQUENCE: 567

Arg Lys Xaa Xaa Xaa Xaa Xaa Xaa Xaa Xaa Xaa Xaa Xaa Xaa Arg Lys
1               5                   10                  15

Ser Thr Met Asn Gln Lys Lys
            20

<210> SEQ ID NO 568
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(8)
<223> OTHER INFORMATION: may not be present
<220> FEATURE:
<221> NAME/KEY: misc_feature
<222> LOCATION: (13)..(23)
<223> OTHER INFORMATION: Xaa can be any naturally occurring amino acid
<220> FEATURE:
<221> NAME/KEY: misc_feature
<222> LOCATION: (20)..(23)
<223> OTHER INFORMATION: may not be present

<400> SEQUENCE: 568

Arg Lys Arg Lys Arg Lys Arg Lys Pro Leu Arg Lys Xaa Xaa Xaa Xaa
1               5                   10                  15

Xaa Xaa Xaa Xaa Xaa Xaa Xaa Arg Lys Gln Leu Lys His
            20                  25

<210> SEQ ID NO 569
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(9)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: may not be present
<220> FEATURE:
<221> NAME/KEY: misc_feature
<222> LOCATION: (14)..(17)
<223> OTHER INFORMATION: may not be present

<400> SEQUENCE: 569

Arg His Arg Lys His Xaa Xaa Xaa Xaa Arg Lys Arg Lys Arg Lys Arg
1               5                   10                  15

Lys Pro Leu Arg
            20

<210> SEQ ID NO 570
<211> LENGTH: 8
<212> TYPE: PRT
<213> ORGANISM: Artificial Sequence
<220> FEATURE:
<223> OTHER INFORMATION: Synthetic
```

-continued

```
<400> SEQUENCE: 570

Pro Lys Lys Lys Arg Ala Val Glu
1               5
```